(12) United States Patent
Martin et al.

(10) Patent No.: US 12,227,805 B2
(45) Date of Patent: Feb. 18, 2025

(54) GENETIC TEST FOR LIVER COPPER ACCUMULATION IN DOGS

(71) Applicant: MARS, INCORPORATED, McLean, VA (US)

(72) Inventors: Alan James Martin, Leicestershire (GB); Paul Glyn Jones, Leicestershire (GB); Adrian Watson, Aimargues (FR); Jan Rothuizen, Utrecht (NL); Hille Fieten, Utrecht (NL); Pieter Antonius Jozef Leegwater, Utrecht (NL)

(73) Assignee: MARS, INCORPORATED, McLean, VA (US)

( * ) Notice: Subject to any disclaimer, the term of this patent is extended or adjusted under 35 U.S.C. 154(b) by 826 days.

(21) Appl. No.: 17/360,692

(22) Filed: Jun. 28, 2021

(65) Prior Publication Data

US 2022/0389506 A1    Dec. 8, 2022

Related U.S. Application Data

(62) Division of application No. 16/181,516, filed on Nov. 6, 2018, now abandoned, which is a division of
(Continued)

(30) Foreign Application Priority Data

Dec. 6, 2011 (GB) ...................................... 1120989

(51) Int. Cl.
*C12Q 1/68* (2018.01)
*A01K 67/02* (2006.01)
(Continued)

(52) U.S. Cl.
CPC ............ *C12Q 1/6883* (2013.01); *A01K 67/02* (2013.01); *G16B 20/00* (2019.02); *G16B 20/10* (2019.02);
(Continued)

(58) Field of Classification Search
None
See application file for complete search history.

(56) References Cited

U.S. PATENT DOCUMENTS 2,859,115 A    11/1958  Rivoche
3,422,182 A    1/1969   Knapp, Jr.
(Continued)

FOREIGN PATENT DOCUMENTS

DE    19703252 A1    5/1998
EP    0579333 B1     3/1997
(Continued)

OTHER PUBLICATIONS

Coronado et al. (The Veterinary Journal, vol. 177, pp. 293-296, 2008) (Year: 2008).*
(Continued)

*Primary Examiner* — Jeanine A Goldberg
(74) *Attorney, Agent, or Firm* — Baker Botts L.L.P.

(57) ABSTRACT

The present disclosure provides methods of determining the susceptibility of a dog to liver copper accumulation, comprising detecting in a biological sample obtained from the dog the presence or absence in the genome of the dog of one or more polymorphisms, and methods of treating or breeding the dog based on such determination.

6 Claims, 7 Drawing Sheets

Specification includes a Sequence Listing.

Related U.S. Application Data application No. 14/363,751, filed as application No. PCT/GB2012/053038 on Dec. 6, 2012, now Pat. No. 10,150,997.

(51) Int. Cl.
| | |
|---|---|
| *C07H 21/04* | (2006.01) |
| *C12Q 1/6883* | (2018.01) |
| *G16B 20/00* | (2019.01) |
| *G16B 20/10* | (2019.01) |
| *G16B 20/20* | (2019.01) |
| *G16B 20/40* | (2019.01) |

(52) U.S. Cl.
CPC ............ *G16B 20/20* (2019.02); *G16B 20/40* (2019.02); *C12Q 2600/124* (2013.01); *C12Q 2600/156* (2013.01)

(56) References Cited

U.S. PATENT DOCUMENTS

| | | |
|---|---|---|
| 3,899,607 A | 8/1975 | Miller et al. |
| 4,039,687 A | 8/1977 | Weyn |
| 4,104,406 A | 8/1978 | Stringer et al. |
| 4,145,447 A | 3/1979 | Fisher et al. |
| 4,247,562 A | 1/1981 | Bernotaviez et al. |
| 4,284,652 A | 8/1981 | Christensen |
| 4,454,164 A | 6/1984 | Gellman et al. |
| 5,000,940 A | 3/1991 | Staples et al. |
| 5,000,943 A | 3/1991 | Scaglione et al. |
| 5,000,944 A | 3/1991 | Prencipe et al. |
| 5,000,973 A | 3/1991 | Scaglione et al. |
| 5,011,679 A | 4/1991 | Spanier et al. |
| 5,015,485 A | 5/1991 | Scaglione et al. |
| 5,047,231 A | 9/1991 | Spanier et al. |
| 5,069,903 A | 12/1991 | Stitt |
| 5,094,870 A | 3/1992 | Scaglione et al. |
| 5,100,651 A | 3/1992 | Boyer |
| 5,114,704 A | 5/1992 | Spanier et al. |
| 5,171,603 A | 12/1992 | Singer et al. |
| 5,186,964 A | 2/1993 | Gierhart et al. |
| 5,296,209 A | 3/1994 | Simone et al. |
| 5,296,217 A | 3/1994 | Stookey et al. |
| 5,300,289 A | 4/1994 | Garlich et al. |
| 5,364,845 A | 11/1994 | Henderson |
| 5,380,530 A | 1/1995 | Hill et al. |
| 5,405,836 A | 4/1995 | Richar et al. |
| 5,407,661 A | 4/1995 | Simone et al. |
| 5,431,927 A | 7/1995 | Hand et al. |
| 5,467,741 A | 11/1995 | O'Rourke |
| 5,501,868 A | 3/1996 | Collings et al. |
| 5,618,518 A | 4/1997 | Stookey |
| 5,879,698 A | 3/1999 | Ellenbogen et al. |
| 5,904,928 A | 5/1999 | Cyr et al. |
| 5,919,499 A | 7/1999 | Lawley |
| 5,922,379 A | 7/1999 | Wang et al. |
| 6,056,991 A | 5/2000 | Axelrod |
| 6,060,100 A | 5/2000 | Koller |
| 6,080,419 A | 6/2000 | Stookey |
| 6,086,940 A | 7/2000 | Axelrod |
| 6,093,441 A | 7/2000 | Axelrod |
| 6,110,521 A | 8/2000 | Axelrod |
| 6,126,978 A | 10/2000 | Axelrod |
| 6,156,355 A | 12/2000 | Shields, Jr. et al. |
| 6,159,508 A | 12/2000 | Wolf |
| 6,159,516 A | 12/2000 | Axelrod et al. |
| 6,159,530 A | 12/2000 | Christiansen et al. |
| 6,180,161 B1 | 1/2001 | Axelrod |
| 6,227,420 B1 | 5/2001 | Jepson |
| 6,228,418 B1 | 5/2001 | Gluck et al. |
| 6,238,726 B1 | 5/2001 | Fischer |
| 6,254,920 B1 | 7/2001 | Brunner |
| 6,261,591 B1 | 7/2001 | Kealy |
| 6,265,011 B1 | 7/2001 | Kelly et al. |
| 6,274,182 B1 | 8/2001 | Axelrod et al. |
| 6,277,435 B1 | 8/2001 | Lacombe et al. |
| 6,350,485 B2 | 2/2002 | Brunner |
| 6,379,725 B1 | 4/2002 | Wang et al. |
| 6,455,083 B1 | 9/2002 | Wang |
| 6,517,877 B2 | 2/2003 | Gannon |
| 6,518,709 B2 | 2/2003 | Iketsu et al. |
| 6,586,027 B2 | 7/2003 | Axelrod et al. |
| 6,841,178 B2 | 1/2005 | Cupp et al. |
| 6,904,870 B2 | 6/2005 | Russell-Maynard et al. |
| 6,911,224 B1 | 6/2005 | May et al. |
| 6,962,718 B2 | 11/2005 | Ramaekers |
| 7,147,888 B2 | 12/2006 | Brown et al. |
| 7,211,280 B1 | 5/2007 | Young et al. |
| 7,258,879 B1 | 8/2007 | Hodge et al. |
| 7,390,520 B2 | 6/2008 | Dempsey et al. |
| 7,592,031 B2 | 9/2009 | Cupp et al. |
| 7,912,650 B2 | 3/2011 | Kato et al. |
| 8,367,144 B2 | 2/2013 | Pater et al. |
| 9,415,067 B2 | 8/2016 | Jones et al. |
| 2002/0119241 A1 | 8/2002 | Speck et al. |
| 2003/0072841 A1 | 4/2003 | Rajaiah et al. |
| 2003/0092019 A1 | 5/2003 | Meyer et al. |
| 2003/0175387 A1 | 9/2003 | English |
| 2004/0037943 A1 | 2/2004 | Saylock et al. |
| 2004/0037944 A1 | 2/2004 | Cupp et al. |
| 2004/0076735 A1 | 4/2004 | Lacombe et al. |
| 2004/0234654 A1 | 11/2004 | Levin |
| 2005/0123585 A1 | 6/2005 | Cox et al. |
| 2006/0141009 A1 | 6/2006 | Huron et al. |
| 2006/0147962 A1 | 7/2006 | Jones et al. |
| 2007/0009899 A1 | 1/2007 | Mounts |
| 2008/0226766 A1 | 9/2008 | Fretwell et al. |
| 2009/0170111 A1 | 7/2009 | Luke et al. |
| 2009/0308324 A1 | 12/2009 | Fretwell et al. |
| 2010/0196400 A1 | 8/2010 | Li et al. |
| 2010/0278938 A1 | 11/2010 | Jones et al. |
| 2011/0117545 A1 | 5/2011 | Stacey et al. |
| 2012/0021928 A1 | 1/2012 | Lindblad-Toh et al. |
| 2012/0040017 A1 | 2/2012 | Jones et al. |
| 2012/0208182 A1 | 8/2012 | Jones et al. |
| 2014/0093584 A1 | 4/2014 | Jones et al. |
| 2014/0351962 A1 | 11/2014 | Martin |
| 2015/0374750 A1 | 12/2015 | Jones et al. |

FOREIGN PATENT DOCUMENTS

| | | |
|---|---|---|
| EP | 1698232 A1 | 9/2006 |
| JP | H10-201428 A | 8/1998 |
| JP | 2001-299234 A | 10/2001 |
| WO | WO 1995/008641 A1 | 3/1995 |
| WO | WO 97/31011 A1 | 8/1997 |
| WO | WO 1999/048384 A2 | 9/1999 |
| WO | WO 2000/032206 A1 | 6/2000 |
| WO | WO 2002/056703 A1 | 7/2002 |
| WO | WO 03/033734 A2 | 4/2003 |
| WO | WO 2003/033734 A2 | 4/2003 |
| WO | WO 2004/113570 A2 | 12/2004 |
| WO | WO 2005/055739 A1 | 6/2005 |
| WO | WO 2009/044152 A2 | 4/2009 |
| WO | WO 2010/038032 A1 | 4/2010 |
| WO | WO 2010/116137 A1 | 10/2010 |
| ZA | 9905557 B | 4/2000 |

OTHER PUBLICATIONS

Genbank Accession DQ016628 (Jun. 2005) (Year: 2005).*
Hoffmann et al. (J. Vet Intern. Medicine, vol. 20, pp. 856-861, 2006). (Year: 2006).*
Wu, J. of Veterinary Internal Medicine, vol. 33, pp. 1646-1652, 2019 (Year: 2019).*
U.S. Appl. No. 16/181,516 (U.S. Pat. No. 2019/0062839), filed Nov. 6, 2018 (Feb. 28, 2019).
U.S. Appl. No. 14/363,751 (U.S. Pat. No. 10,150,997), filed Jun. 6, 2014 (Dec. 11, 2018).
U.S. Appl. No. 16/181,516, filed Jun. 28, 2021 Petition for Extension of Time.
U.S. Appl. No. 16/181,516, filed Feb. 26, 2021 Non-Final Office Action.

(56) References Cited

OTHER PUBLICATIONS

U.S. Appl. No. 16/181,516, filed Jan. 25, 2021 Response after Final Action with Request for Continued Examination (RCE).
U.S. Appl. No. 16/181,516, filed Oct. 27, 2020 Final Office Action.
U.S. Appl. No. 16/181,516, filed Sep. 29, 2020 Response to Non-Final Office Action.
U.S. Appl. No. 16/181,516, filed Jul. 2, 2020 Non-Final Office Action.
U.S. Appl. No. 16/181,516, filed Jun. 17, 2020 Response to Restriction Requirement.
U.S. Appl. No. 16/181,516, filed Mar. 30, 2020 Restriction Requirement.
U.S. Appl. No. 14/363,751, filed Oct. 29, 2018 Issue Fee Payment.
U.S. Appl. No. 14/363,751, filed Jul. 27, 2018 Notice of Allowance.
U.S. Appl. No. 14/363,751, filed Jul. 6, 2018 Request for Continued Examination (RCE).
U.S. Appl. No. 14/363,751, filed Jun. 14, 2018 Notice of Allowance.
U.S. Appl. No. 14/363,751, filed Jun. 4, 2018 Response after Final Action.
U.S. Appl. No. 14/363,751, filed Apr. 3, 2018 Final Office Action.
U.S. Appl. No. 14/363,751, filed Feb. 15, 2018 Response to Non-Final Office Action.
U.S. Appl. No. 14/363,751, filed Sep. 15, 2017 Non-Final Office Action.
U.S. Appl. No. 14/363,751, filed Aug. 21, 2017 Amendment and Request for Continued Examination (RCE).
U.S. Appl. No. 14/363,751, filed May 19, 2017 Final Office Action.
U.S. Appl. No. 14/363,751, filed Apr. 25, 2017 Response to Non-Final Office Action.
U.S. Appl. No. 14/363,751, filed Nov. 25, 2016 Non-Final Office Action.
U.S. Appl. No. 14/363,751, filed Oct. 28, 2016 Response to Non-Final Office Action.
U.S. Appl. No. 14/363,751, filed Apr. 28, 2016 Non-Final Office Action.
U.S. Appl. No. 14/363,751, filed Mar. 16, 2016 Response to Restriction Requirement.
U.S. Appl. No. 14/363,751, filed Jan. 29, 2016 Restriction Requirement.
"Dog's Health", http://55dog.com/doghealth/index.html/, Sep. 30, 2002, 5 pgs.
"Dry Dog Food", http://www.naturalpetmarket.com/category_detail.cfm?categoryid=175 &varpageid=999&uplevel=All%20Natural%20Dog%20Food&level=Dry%20Dog%20Food. Jul. 1, 2002, 7 pgs.
"English Translation of Japanese Office Action dated Sep. 2, 2014, JP Appl. No. 2012-504068"
"Health and Related Issues," Internet <URL http://homepages.rootsweb.ancestry.com/oldmill/chelseaBB/HealthPage.htm>.
"Hill's Pet Nutrition Hills Prescription L/D", Hill's Pet Nutrition, Aug. 26, 2015, 2 pgs.
"Natural Balance," http://www.jbpet.com/natural-balance-dry-dog-food-lid-lamb-meal-and-brown-rice-formula, 7654.html, Feb. 1, 2001, 3 pgs.
"Nutrient Analysis," Hill's Pet Nutrition, Inc., Jan. 19, 1999.
"Premium Nutrition for Dogs, Nature's Recipe Large Breed Recipe, Product Description" Del Monte: Nature's Recipe®, 2007, available online at http://www.naturesrecipe.com/DogProductDisplay.aspx?p=Dogs/Breed_LargeBreed.
"Premium Nutrition for Dogs, Terrier Dogs Canine Recipe Product Description" Del Monte: Nature's Recipe, available online at http://www.naturesrecipe.com/dogproductdisplay.aspx?p=Dogs/Breed_dryTerrier, 2006.
"Prescription Diet Canine l/d (liver disease)," Hills Pet Nutrition, available online at http://www.hillspet.com/media/WEURG/product/prodkeyPDF/en.pdf, accessed Jan. 30, 2008.
"Prescription Diet Canine lid (liver disease)," Hills Pet Nutrition, available online at http://www.hillspet.com/media/WEURG/product/prodkeyPDF/en/PD K9 D d Id_o_0_no WEURG_prodkey_en.pdf, accessed Jan. 30, 2008.

"Regenerative and Fibrotic Pathways in Canine Liver Disease," Faculty of Veterinary Medicine, 2006.
"Royal Canin MINI Canine Health Nutrition Yorshire 28", http://www.petco.com/product/10844/Royal-Canin-MINI-Canine-Health-Nutrition-Yorkshire-28.aspx. Aug. 15, 2003, 6 pgs.
"Small Animal Clinical Nutrition," Mark Morris Institute, 2000, Ed. 4th.
"The Best Foods for Dogs With Chronic Active Hepatitis," A Dog's Life Photography & Art [online], Jun. 29, 2010, [retrieved on Aug. 21, 2013], Internet <URL: http://phoenixdogphotography.com/2010/06/the-best-foods-for-dogs-with-chronic-active-hepatitis/>.
"The Hill's Key to Clinical Nutrition," Hill's Pet Nutrition, Inc., 1999.
"The Merck Veterinary Manual Eighth Edition", AAFCO Nutrient Requirement for Dogs, National Publishing, Inc., Editor Aiello, Copyright Jul. 1998, pp. 1626, 1627, 1630, 1631, 4 pgs.
"Trophy Pet Foods: Trophy Premium Hypo-Allergenic food," Trophy Pet Foods, available online at http://www.trophypettoods.co.uk/products/premiumdog.htm, accessed Jan. 30, 2008.
"University study shows dogs have a lot to gain when they lose weight," GoodNewsforPets.com, recorded on May 12, 2007, Internet Archive Wayback Machine, searched http://goodnewsforpets.com/news/archive/Research/041300_weight_study.htm, Internet: <URL:http://web.archive.org/web/20070512095423/http://www.goodnewsforpets.com/news/archive/research/041300_weight_study.htm>.
"Whole Dog Journal's Food List," Little Dog & Girl on the Prairie, Jun. 27, 2007, Internet <URL:http://blog.livedoor.jp/urea/archives/51627947.html>.
Acland et al., "A Novel Retinal Degeneration Locus Identified by Linkage and Comparative Mapping of Canine Early Retinal Degeneration," Genomics, 59:134-142 (Aug. 1999).
Acland et al., "Linkage Analysis and Comparative Mapping of Canine Progressive Rod-Cone Degeneration (prcd) Establishes Potential Locus Homology with Retinitis Pigmentosa (RP17) in Humans," Proc. Natl. Acad. Sci. USA, 95:3048-3053 (Mar. 1998).
Allen et al., "Tetramine cupruretic agens: A comparison in dogs," Am. J. Vet. Res., 48(1):28-30 (1987).
Altschul et al., "Basic Local Alignment Search Tool," J. Mol. Biol., 215:403-410 (1990).
Altschul, "A Protein Alignment Scoring System Sensitive at All Evolutionary Distances," J. Mo. Evol., 36:290-300 (1993).
Barrett et al., "Haploview: Analysis and Visualization of LD and Haplotype Maps," Bioinformatics 21(2):263-265 (2005).
Bergstrom et al., "The Pharmacokinetics of Penicillamine in a Female Mongrel Dog," Journal of Pharmacokinetics and Biopharmaceutics 9(5):603-621 Plenum Publishing Corporation (Feb. 6, 1981).
Bode, "Instrumental neutron activation analysis in a routine way," Journal of Trace and Microprobe Techniques, 8(1-2):139-154 (1990) (Abstract Only).
Breen et al., "Chromosome specific single locus FISH probes allow anchorage of a 1800 marker integrated Radiation-hydrid/linkage map of the domestic dog genome to all chromosomes," Genome Res., 11(10):1784-1795 (2001).
Burns, "Bums: Developed by a Veterinary Surgeon. The Holistic Approach to Health & Nutrition," Bums Pet Nutrition Ltd., product brochure, available online at http://www.burns-petnutrition.co.ukfcolour_brochure2006_small.pdf, accessed Jan. 30, 2008.
Chinese Search Report dated Mar. 8, 2013, issued during prosecution of China Patent Application No. 2010800254455.
Copper Content in Dog Foods (http:rottndobie.tripod.com/coppercontent.html (Nov. 2004).
Coronado et al., "New Haplotypes in The Bedlington Terrier Indicate Complexity in Copper Toxicosis," Mammalian Genome 14:481-491 (2003).
Coronado et al., "Polymorphisms in canine A TP7B: candidate modifier of copper toxicosis in the Bedlington terrier," Veterinary Journal, 177(2):293-296 (2008).
Database Medline, "dbSNP Short Genetic Variations," US National Library of Medicine (NLM), 2005, XP002696928, Bethesda, MD.
Debenham, Physical and Linkage Mapping of the Canine Phosphate Carrier (SLC25A3) and Apoptotic Activating Factor (APAFI) Genes

(56) References Cited

OTHER PUBLICATIONS to Canine Chromosome 15, Canis familiaris microsatellite, Nov. 24, 2000, retrieved from EBI Database Accession No. AJ299437, Abstract XP002248980, 1 pg.
Devereux et al., "A Comprehensive Set of Sequence Analysis Programs for the VAX," Nucleic Acids Research, 12:387-395 (1984).
Dias Neto et al., Shotgun Sequencing of the Human Transcriptome with ORF Expressed Sequence Tags Homo sapien cDNA mRNA sequence, Jan. 12, 2001, retrieved from EBI Database accession no. BF49428, Abstract No. XP002248981, 2 pgs.
Dietary Survey Study Jun. 5, 2010; Utrecht University.
Dumin et al., "High Efficiency Breeding and Disease Control of Dogs," China Agriculture Press 1st Edition, p. 103, (2003).
Dunn et al., Mouse Whole Genome Scaffolding with Paired End Reads from 10kb Plasmid Inserts, Mouse Library Mus Musculus Genomic Clone, Feb. 18, 2001, retrieved from EBI Database Accession No. Az759124, XP002248979 Abstract, 1 pg.
Dzanis, "The Association of American Feed Control Officials Dog and Cat Food Nutrient Profiles: Substantiation of Nutritional Adequacy of Complete and Balanced Pet Foods in the United States", J. Nutr. 124 (12): 2535S, Dec. 1994, 5 pgs.
European Search Report dated Apr. 21, 2020 in Application No. EP 19206777.
Fieten et al., "Canine models of copper toxicosis for understanding mammalian copper metabolism," Mamm Genome 23:62-75 (2012).
Fieten et al., "Dietary Management of Labrador Retrievers with Subclinical Hepatic Copper Accumulation," J. Vet. Intern. Med. 29:822-827 (2015).
Fieten et al., "The Menkes and Wilson disease genes counteract in copper toxicosis in Labrador retrievers: a new canine model for copper-metabolism disorders," Disease Models and Mechanisms, 9:25-38 (2016).
Flint River Ranch Super Premium Dry Water Kibble Dog Food, product sheet, Downloaded 2014.
Force Dog Food—Gluten Free, The Honest Kitchen, product Sheet, downloaded 2014.
Friedman et al., "Isolation of a ubiquitin-like (UBL5) gene from a screen identifying highly expressed and conserved iris genes," Genomics, 71(2):252-255 (2001).
Fuentealba et al., "Animal models of copper-associates liver disease," Comparative Hepatology, 2(1):5 (Apr. 3, 2003).
Great life Grain/Potato Free Dog Food as evidenced by Great life Rubicon (www.healthyplanetrx.com/Great-LifeRubicon-for-dogs-p, Jul. 5, 2006).
Groot et al., "Identification of Fragments of Human Transcripts from a Defined Chromosomal Region: Representational Difference Analysis of Somatic Cell Hybrids," Nucleic Acids Research, 26(19):4476-4481 (Oct. 1998).
Guggenheim, al., "Validation in biofilm model of supragingival plaque", J. Dent Res, vol. 80(1): 363-370 (Sep. 13, 2000).
Hale, "Dental caries in the dog.", Journal of Veterinary Denistry, vol. 15(2): 79-83 Abstract Only, 1 pg., Jun. 1998.
Han et al., "Construction of a BAC Contig Map of Chromosome 16q by Two-Dimensional Overgo Hybridization," Genome Res., 10:714-721 (May 2000).
Hardy et al., "Chronic Progressive Hepatitis in Bedlington Terriers Associates with Elevated Copper Concentrations," Minn. Vet., 15:13-24 (1975).
Harlow et al., Antibodies: A Laboratory Manual, Cold Spring Harbor Laboratory Press Cold Spring Harbor, NY, 1988 ,2 pgs.
Haywood et al., "Copper toxicosts in the bedlington terrier: a diagnostic dilemma," Journal of Small Animal Practice, 42(4):181-185 (2001).
Henikoff et al., "Amino Acid Substitution Matrices from Protein Blocks," Proc. Natl. Acad. Sci. USA 89:10915-10919 (Nov. 1992).
Hirschhorn et al., "A comprehensive review of genetic association studies," Genetics in Medicine, 4(2):45-61 (2002).

Hoffmann et al., "Copper-associated chronic hepatitis in Labrador retrievers," Journal of Veterinary Internal Medicine, 20(4):856-861 (2006).
Hoffmann et al., "Heritabilities of Copper-Accumulating Traits in Labrador Retrievers," Animal Genetics, 39(4):454 (Aug. 31, 2008).
Hyun et al., "Evaluation of Haplotypes Associated Wth Copper Toxicosis in Bedlington Terriers in Australia," AJVR, 65:1573-1579, 1452, 1453 (Nov. 2004).
Illumina, Canine HD Bead Chip, 170K Chip, Data Sheet: DNA Genotyping, 2010.
Ioannidis et al., "Replication validity of genetic association studies," Nature Genetics, 29:306-309 (2001).
Johnson et al., "Inheritance of Copper Toxicosis in Bedlington Terriers," Am. J. Vet. Res., 41(11):1865-1866 (Nov. 1980).
Jonasdottir et al., "Genetic Mapping of a Naturally Occurring Hereditary Renal Cancer Syndrome in Dogs," Proc. Natl. Acad. Sci. USA 97:4132 (Apr. 2000).
Karlin et al., "Applications and Statistics for Multiple High-Scoring Segments in Molecular Sequences," Proc. Natl. Acad. Sci. USA, 90:5873-5877, Jun. 1993.
Kirk, et al., "Encyclopedia of Chemical Technology", Waxes to Zymosterol, vol. 15, pp. 232-276, 1965.
Kleinberg, et al., "The Biological Basis of Oral Malodor Formation", Department of Oral Biology & Pathology, School of Dental Medicine, State University of New York, Stony Brook, New York, USA 11794-8702, Tel Aviv: Ramot Publishing-Tel Aviv University; 1995, p. 13-39.
Kobayashi et al., Mite Clinical, Japanese Journal of Small Animal Practice, 26(4):232-234 (2007).
Kohler et al., "Continuous Cultures of Fused Cells Secreting Antibody of Predefined Specificity," Journal of Immunology, Nature 256(5517):495-497 (Aug. 1975).
Korstanje et al., "Mapping of Rabbit Chromosome 1 Markers Generated from a Microsatellite-Enriched Chromosome-Specific Library," Animal Genetics, 32:308-312 (Feb. 2001).
Kruitwagen et al. (Annals of Translational Medicine, Suppl 2: S71, 2019) (Year: 2019).
Li et al., "Construction and Characterization of an Eightfold Redundant Dog Genomic Bacterial Artificial Chromosome Library," Genomics, 58:9 (Jan. 1999).
Lin et al., "The Sleep Disorder Canine Narcolepsy is Caused by a Mutation in the Hypocretin (Orexin) Receptor 2 Gene," Cell, 98:365-376 (Aug. 6, 1999).
Lingaas et al., "Genetic Markers Linked to Neuronal Ceroid Lipofuscinosis in English Setter Dogs," Animal Genetics, 29:371-376 (Jun. 1998).
Maddox et al., "Elevated Serum Levels in Human Pregnancy of a Molecule Immunochemically Similar to Eosinophil Granule Major Basic Protein," J Exp. Med. The Rockefeller University Press 158:1211-1226 (Oct. 1983).
Madsen et al., "Zebrafish mutants calamity and catastrophe define critical pathways of gene nutrient interactions in developmental copper metabolism," PLOS Genetics, 4(11):1-11 (2008).
Muller, "Endemic Tyrolean Infantile Cirrhosis: an Ecogenetic Disorder," Lancet 347: 877 (Mar. 1996).
Murphy et al. (Genbank Accession No. AY011436, Feb. 7, 2001).
Nabetani et al., "Mouse U2af1-rs1 is a Neomorphic Imprinted Gene," Molecular and Cellular Biology, 17(2):789-798 (Feb. 1997).
Noaker et al., JAVMA, 214(10):1502-1506 (1999).
Ostrander et al., "Canine Genetics Comes of Age," Trends Genet., 16:117-24 (Mar. 2000).
Ostrander et al., "Insights From Model Systems: Semper Fidelis: What Man's Best Friend Can Teach US about Human Biology and Disease," Am. J. Hum. Genet., 61:475-480 (Jun. 1997).
Ostrander et al., "Unleashing the Canine Genome," Genome Research, 10:1271-1274 (Sep. 2000).
PCI International Report on Patentability issued in International Application No. PCI/GB2008/003351, dated Apr. 7, 2010.
PCI International Report on Patentability issued in International Application No. PCI/GB2009/002355, dated Apr. 14, 2011.
PCI International Report on Patentability issued in International Application No. PCI/GB20IO/000703, dated Jun. 16, 2010.

(56) References Cited

OTHER PUBLICATIONS

PCI International Search Report and Written Opinion issued in International Application No. PCI/GB2008/003351, Dated May 27, 2009.
PCI International Search Report and Written Opinion issued in International Application No. PCI/GB20IO/000703, Dated Jun. 16, 2010.
PCI International Search Report issued in International Application No. PCT/GB2009/002355, dated Nov. 26, 2009.
Pena et al., "A Delicate Balance: Homeostatic Control of Copper Uptake and Distribution," J. Nutr. 129:1251-1260 (May 1999).
Poulsen et al., "X-Linked Recessive Menkes Disease: Carrier Detection in the Case of a Partial Gene Deletion," Denmark—Clinical Genetics—pp. 440-448 (2002).
Proschowsky et al., "Microsatellite Marker C04107 as a Diagnostic Marker for Copper Toxicosis in the Danish Population of Bedlington Terriers," Acta. Vet. Scand., 41(4):345-350 (2000).
Rothuizen et al., "Diagnostic Value of a Microsatellite DNA Marker for Copper Toxicosis in West-European Bedlington Terriers and Incidence of the Disease," Animal Genetics, 30:190-194 (Jan. 1999).
Rothuizen et al., "Tijdschr Diergeneeskrac," 123(8):246-252 (1998) (Abstract Only).
Safra et al. (Veterinary Journal, vol. 189, pp. 220-226, 2011) (Year: 2011).
Search Report issued in United Kingdom Application No. GBI 120989.7, dated Mar. 30, 2012, 5 pgs.
Shih et al., "Chronic hepatitis in Labrador retrievers: clinical presentation and prognostic factors," Journal of Veterinary Internal Medicine, 21(1):33-39 (2007).
Shimizu et al., "Treatment and management of Wilson's disease," Pediatrics International, 41:419-422 (1999).
Spee et al., "Copper metabolism and oxidative stress in chronic inflammatory and cholestatic liver disease in dogs," Journal of Veterinary Internal Medicine, 20(5):1085-1092 (2006).
Spee et al., "Differential Expression of Copper-Associated and Oxidative Stress Related Proteins in a New Variant of Copper Toxicosis in Doberman Pinschers," Comparative Hepatology Mar. 24, 2005, pp. 1-13.
Stuehler et al., "Analysis of the human homologue of the canine copper toxicosis gene MURR1 in Wilson disease patients," Journal of Molecular Medicine (Berlin), 82:629-634 (2004).
Sutherland, "Copper Toxicosis in Sheep," JAVMA, 180(9):984 (Feb. 1982).
Sutter et al., "Extensive and Breed-Specific Linkage disequilibrium in Canis Familiaris," Genome Res. 14:2388-2396 (2004).
Tacher et al. (J. of Heredity, vol. 96, No. 7, pp. 812-816, 2005) (Year: 2005).
Tanner, "Role of Copper in Indian Childhood Cirrhosis," Am. J. Clin. Nutr. 67:1074S-1081S (May 1998).
Teske et al., "Cytological detection of copper for the diagnosis of inherited copper toxicosis in Bedlington terriers," The Veterinary Record 131:30-32 (1992).
Thornburg, "A Perspective on Copper and Liver Disease in the Dog," J. Vet. Diagn. Invest, 12:101-110 (2000).
Tiira, et al., "Environmental Effects on Compulsive Tail Chasing inDogs", PLoS ONE, vol. 7, No. 7, e41684, Jul. 2012, pp. 1-14.
Twedt et al., "Clinical, Morphologic, and Chemical Studies on Copper Toxicosis of Bedlington Terriers," JAVMA, 175(3):269-275 (Aug. 1979).
Van De Sluis et al., "Genetic Mapping of the Copper Toxicosis Locus in Bedlington Terriers to Dog Chromosome 10, in a Region Systemic to Human Chromosome Region 2P13-P16," Human Molecular Genetics, 8(3):501-507 (Mar. 1999).
Van De Sluis et al., "Refined Genetic and Comparative Physical Mapping of the Canine Copper Toxicosis Locus," Mammalian Genome, 11:455-460 (2000).
Van De Sluis, "Identification of a new copper metabolism gene by positional cloning in a purebred dog population," Human Molecular Genetics, 11(2):165-173 (2002).
Van Den Ingh et al., "Chronic Active Hepatitis with cirrhosis in the Dober Pinscher," The Veterinary Quarterly, 10(2):84-89 (1998).
Van Den Ingh et al., "Possible Nutritionally Induced Copper associated Chronic Hepatitis in Two Dogs," The Veterinary Record, 161:728-729 (Nov. 24, 2007).
Wijmenga et al., "Molecular regulation of copper excretion in the liver," Proceedings of the Nutrition Society, 63:31-39 (2004).
Wu et al., "Canin Models for Copper Homeostasis Disorders," International Journal of Molecular Sciences, vol. 17, No. 196, 14 pgs. (2016).
Xia, "High-Quality Dog Breeding Manual," Hebei Science & Technology Press, 1st Ed., Jan. 31, 2009 (1 page).
Xiaoqing et al., English Abstract "Application of D13S301 Label in Diagnosis of Wilson Disease," Journal of Clinical Pediatrics, Oct. 20, 2002, vol. 20, No. 10, pp. 614-616.
Yuxin et al., "Preliminary Study on Mutations of Copper Transporting P-Type ATPase Gene in the Chinese," Journal of Fudan University (Natural Science), 36(5):517-523 Oct. 1997).
Yuzbasiyan-Gurkan et al., "Linkage of Microsatellite Marker to the Canine Copper Toxicosis Locus in Bedlington Terriers," Am. J. Vet. Res. 58:23-27 (1996).
Yuzbasiyan-Gurkan et al., Microsatellite Markers for the Canine Genome, Canis familiaris SIS microsatellite marker, Apr. 14, 1996, retrieved from EBI Database accession No. L7759, XP002248976 Abstract, 1 pg.
Zhao, "Human BAC Ends," Nucleic Acids Research, 28(1):129-132 (2000).
Zhi-Ying et al., "Mutation analysis of 218 Chinese patients with Wilson disease revealed No. correlation between the canine copper toxicosis gene M(JRRI and Wilson disease," J. Mol. Med., 84:438-442 (2006).

* cited by examiner

Fig. 3

```
Bases: TGT-GCC-GCC-CCC-GCC-CCC-GCC-CCA-AGA    SEQ ID No: 240
AA:     C   A   A   P   A   P   A   P   R    SEQ ID No: 241
                            ↑
                         3135287
```

|  |  |  |
|---|---|---|
| SEQ ID NO: 240 | Ensembl<br>TGTGCCGCCCCCGCCCCCGCCCCCAAGA | (4X CGCCCC) SEQ ID NO: 246 |
| SEQ ID NO: 240<br>SEQ ID NO: 242 | NCBI<br>TGTGCCGCCCCCGCCCCCGCCCCCAAGA<br>TGTGCCGCCCCCGCCCCCGCCCC-----AAGA | (4X CGCCCC) SEQ ID NO: 246<br>(3X CGCCCC) SEQ ID NO: 247 |
| SEQ ID NO: 243<br>SEQ ID NO: 242 | Beagle<br>TGTGCCGCCCCCGCCCC-----AAGA<br>TGTGCCGCCCCCGCCCCCGCCCCCAAGA | (2X CGCCCC) SEQ ID NO: 248<br>(3X CGCCCC) SEQ ID NO: 247 |
| SEQ ID NO: 242<br>SEQ ID NO: 240 | Labradors<br>TGTGCCGCCCCCGCCCCCGCCCC-----AAGA<br>TGTGCCGCCCCCGCCCCCGCCCCCAAGA | (3X CGCCCC) SEQ ID NO: 247<br>(4X CGCCCC) SEQ ID NO: 246 |

Fig. 4

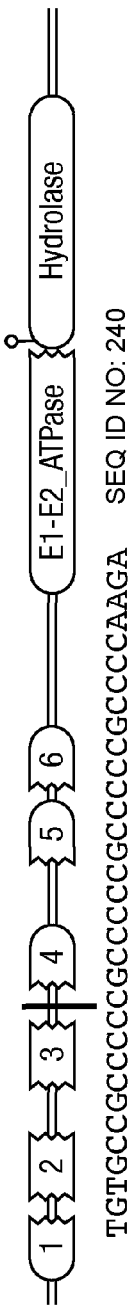

TGTGCCGCCCCCGCCCCCGCCCCCAAGA      SEQ ID NO: 240

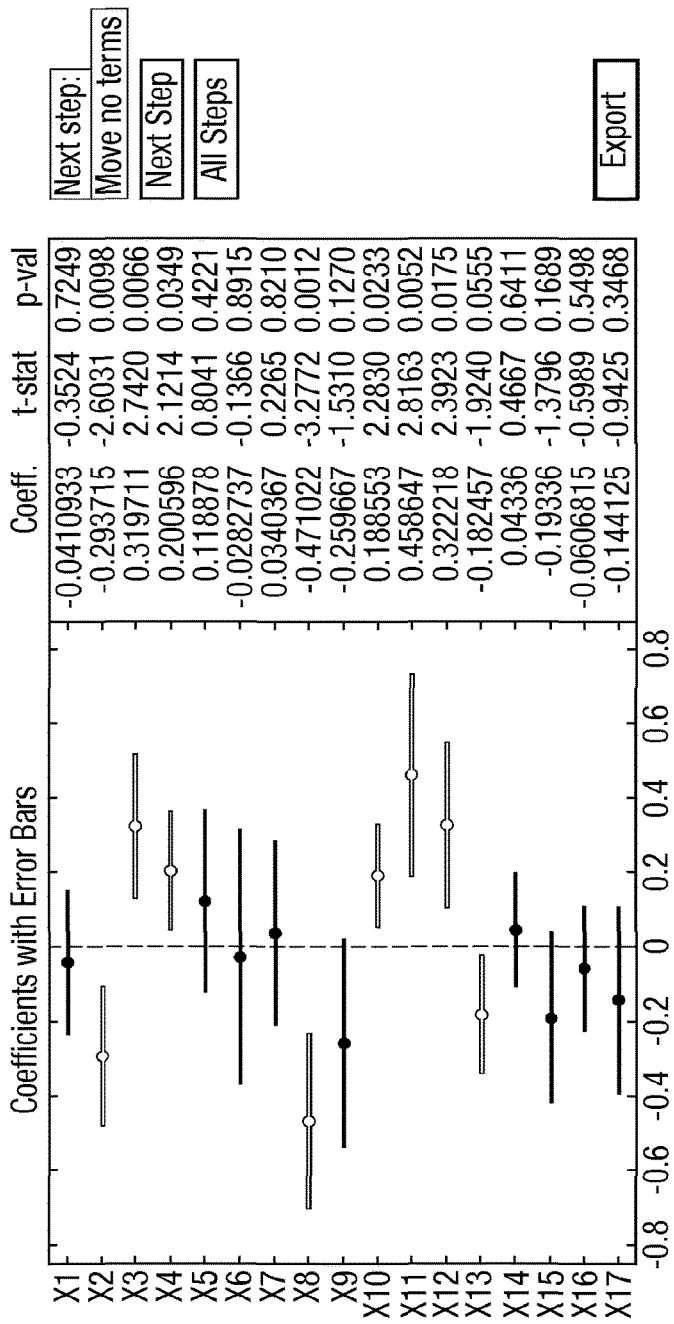
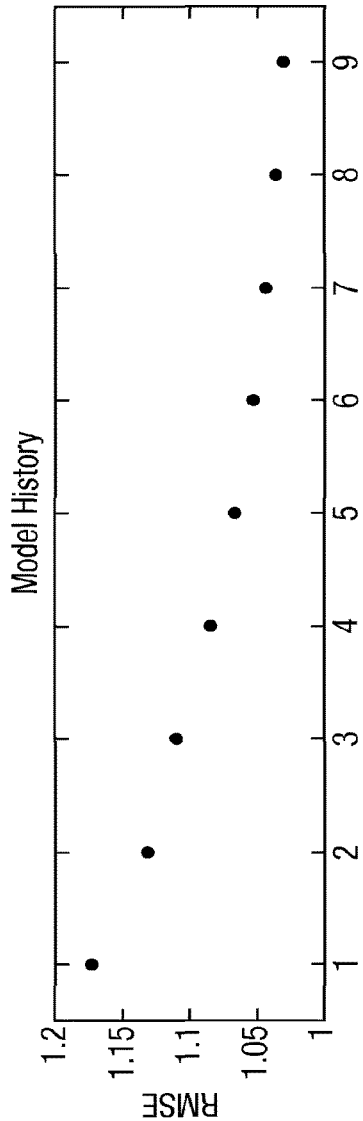
Fig. 8

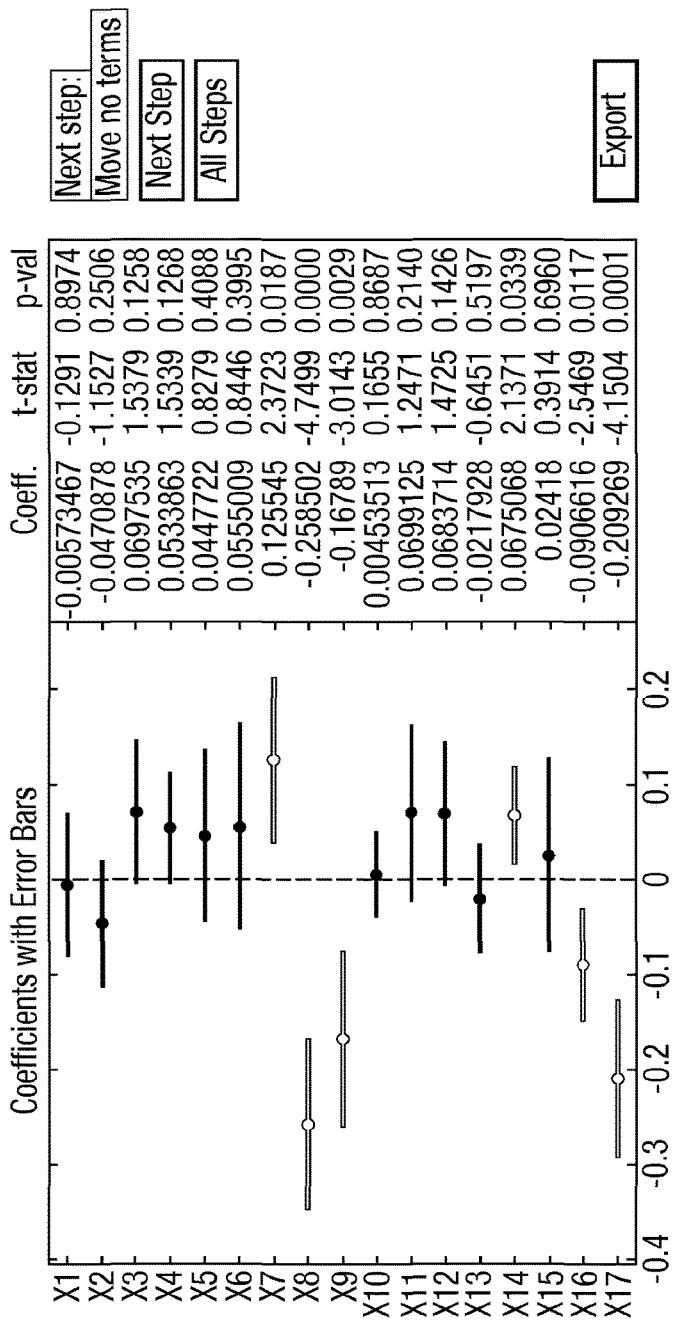
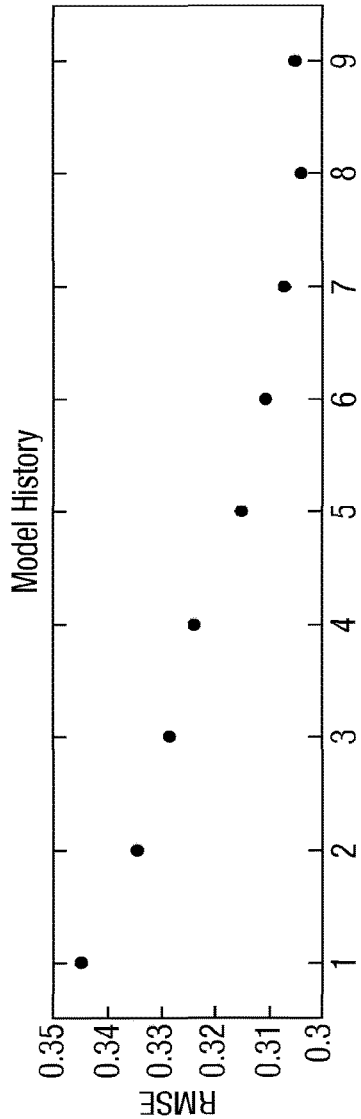
Fig. 9

SEQUENCE LISTING

<160> NUMBER OF SEQ ID NOS: 248

<210> SEQ ID NO 1
<211> LENGTH: 121
<212> TYPE: DNA
<213> ORGANISM: Canis familiaris

<400> SEQUENCE: 1
ctcagaacta gataggctaa taagtgatag gccttgtgtt ttcctagagt gtgctttaaa    60
rgtttcttaa gctaaaaaat tacattcgtg agaaaattga ataaaagga aaacagtcat   120 g                                                                   121

<210> SEQ ID NO 2
<211> LENGTH: 121
<212> TYPE: DNA
<213> ORGANISM: Canis familiaris

<400> SEQUENCE: 2
tctcagatac ttgatagcca gcatttcccc ccattttctt ccaagagcac gaaagcatag    60
raatgatatt acatctcgta tggtgaatgt gacacagccg tcagttgcgt tagctctgct   120
t                                                                   121

<210> SEQ ID NO 3
<211> LENGTH: 121
<212> TYPE: DNA
<213> ORGANISM: Canis familiaris

<400> SEQUENCE: 3
tattaccctg ctctccagcc actcctttac cttccattag cccacacctg ctctacacac    60
yattgctcat ggaagccttg ccacgtccag tcgccactct gaaatgccag catccctccc   120
a                                                                   121

<210> SEQ ID NO 4
<211> LENGTH: 121
<212> TYPE: DNA
<213> ORGANISM: Canis familiaris

<400> SEQUENCE: 4
gacctgacag attatgtaga ctttgttttc aaagggagca cctgctggat atacaacatg    60
rcactaaatt gtgctccaca tccttggcag aggtgggggg cggggcacaa aggaagaaac   120
c                                                                   121

<210> SEQ ID NO 5
<211> LENGTH: 121

```
<212> TYPE: DNA
<213> ORGANISM: Canis familiaris

<400> SEQUENCE: 5
gggcccagca agtggcagaa ctgggaagac ccctcttct tccgcctgga gcagtggtgt    60
rgcagcacac cacaggagtc tgaaagggtg gggagtccaa acgggaacat atacctgaga  120
t                                                                  121

<210> SEQ ID NO 6
<211> LENGTH: 121
<212> TYPE: DNA
<213> ORGANISM: Canis familiaris

<400> SEQUENCE: 6
ggcaacaggg acaggctgct gggccacaca ctcacccaca ctaggagaca agatcctcca   60
yatcctgggt ctctatcagt caatcaccta gaccagtggg ccagaggaca gggtccagct  120
g                                                                  121

<210> SEQ ID NO 7
<211> LENGTH: 121
<212> TYPE: DNA
<213> ORGANISM: Canis familiaris

<400> SEQUENCE: 7
gttgagagag atcatacaga ttcatgtggc aggtgcacac ttttctacc tcttacaacg    60 yattctctct ggccattcct tctcctgggt cccaaagtcg agagcttag cgggagccta   120 g                                                                  121

<210> SEQ ID NO 8
<211> LENGTH: 121
<212> TYPE: DNA
<213> ORGANISM: Canis familiaris

<400> SEQUENCE: 8
ataagttcac attttggtgt ttcaagtgga catgaatgga ggggagggcc ctgttcaatc    60
yactaaagtg tttttcatc ttgttttgt ggaaatcaaa tcaagaagca gagttttatg   120
t                                                                  121

<210> SEQ ID NO 9
<211> LENGTH: 121
<212> TYPE: DNA
<213> ORGANISM: Canis familiaris

<400> SEQUENCE: 9
actctcccga tgtgggcacc atatggtgga ccactttctg tgtgagatgc ctgctcttat    60
ygccatgtcc tgtgaagaca ccatgctggt ggaagcattt gcctttgccc tgggtgttgc  120
c                                                                  121

<210> SEQ ID NO 10
<211> LENGTH: 121
<212> TYPE: DNA
<213> ORGANISM: Canis familiaris

<400> SEQUENCE: 10
aatctaagta gactgagtgg tcaccttcag cgctcagacc tgagcataca aagcatggaa   60
rgttactgtg attcagctga tgtaatgaa tgaaataaat ataagagttt ggtaacctaa   120
```

<210> SEQ ID NO 11
<211> LENGTH: 121
<212> TYPE: DNA
<213> ORGANISM: Canis familiaris

<400> SEQUENCE: 11
tggagagtgc tggcaggcag ggcaggcaa acaacaatag caaagatctc ttccacgctt    60
ytacttcctc aaaagtccaa gccctcttaa gatcgcattt tcttagtgac cttcactcta   120
a                                                                  121

<210> SEQ ID NO 12
<211> LENGTH: 121
<212> TYPE: DNA
<213> ORGANISM: Canis familiaris

<400> SEQUENCE: 12
ttctttgcta ggccaagggc agagaatgca tgcccccct tacctccag ggcccaagag     60 scatcctgag ctgagtctat ggctcctggt gggggcggc tgtgggttgg gggggcacag    120
a                                                                  121

<210> SEQ ID NO 13
<211> LENGTH: 121
<212> TYPE: DNA
<213> ORGANISM: Canis familiaris

<400> SEQUENCE: 13
ggtgtcacca atgccagcga gcaccagctg gagggaacag gacacaggtc ctccgtcctg    60
ygacactcgg atctggggct ttgcctccaa aacggagacc atgcctgtcc atggttctac   120
g                                                                  121

<210> SEQ ID NO 14
<211> LENGTH: 121
<212> TYPE: DNA
<213> ORGANISM: Canis familiaris

<400> SEQUENCE: 14
ctctagaacc cttcaggtag actacattca ctttctacta caacttcatc accacaacca    60
wctcccagta acccccttt tttcttctcc tttttttatt ttttccttct ttttgctcgt    120
c                                                                  121

<210> SEQ ID NO 15
<211> LENGTH: 121
<212> TYPE: DNA
<213> ORGANISM: Canis familiaris

<400> SEQUENCE: 15
tcccatgggt tgaaggatat ctggcagacg gctccaactc cagtaaagcc tcaggcctca    60
rccaggagtt ccccggggct tcattccat cccagacttt gcccagggct gatttgaaag    120
t                                                                  121

<210> SEQ ID NO 16
<211> LENGTH: 121
<212> TYPE: DNA
<213> ORGANISM: Canis familiaris

<400> SEQUENCE: 16

```
tcttccttgc agattggatg gctgtagcct cacctcacac tgttgctggg atctgtccac        60
rcttctgacc tccagcaaga gcctccggga gctaagcctg ggcagcaatg acctgggaga       120
t                                                                      121
```

<210> SEQ ID NO 17
<211> LENGTH: 121
<212> TYPE: DNA
<213> ORGANISM: Canis familiaris

<400> SEQUENCE: 17

```
tattgctagt aaagccaaac tttctattcc acaattataa actcatggag atggtaatta        60
yagtgcatta tttgtcaaat tttattattt tttcaaatcc caaagaaaat gtgatattct       120
a                                                                      121
```

<210> SEQ ID NO 18
<211> LENGTH: 121
<212> TYPE: DNA
<213> ORGANISM: Canis familiaris

<400> SEQUENCE: 18

```
aagaacaagg atacaatcta agtgataatc atccagcatg tacttgtcct gttttcagat        60
katcagctta agtcaagagg aattttagt gcttacaaat atttcaagtg attttttccag       120
a                                                                      121
```

<210> SEQ ID NO 19
<211> LENGTH: 121
<212> TYPE: DNA
<213> ORGANISM: Canis familiaris

<400> SEQUENCE: 19

```
tgaaggggtg ctactcaggg ctcttcattt aaccttccag gatgttttcc tatgtactca        60
ytcttccttt tggttgctcc ttcttcttgc atttctttat ctctttacag aatcatccag       120
g                                                                      121
```

<210> SEQ ID NO 20
<211> LENGTH: 121
<212> TYPE: DNA
<213> ORGANISM: Canis familiaris

<400> SEQUENCE: 20

```
acaaccctaa aatttcagtg attcagtaca acaaaggttt attataacca ttcagggatc        60
saagttggta gaaacttcac tacaatacct gcttccagtc aacaagacag aaaaagaaaa       120
a                                                                      121
```

<210> SEQ ID NO 21
<211> LENGTH: 121
<212> TYPE: DNA
<213> ORGANISM: Canis familiaris

<400> SEQUENCE: 21

```
gcagggttga tatataacta gtatgcatta ggtagacacc tattttgatt actcactatt        60
ktaatatcag cctggtagta agaaccaaat ctattatgta aagtgcatag agaattgaaa       120
g                                                                      121
```

<210> SEQ ID NO 22
<211> LENGTH: 121
<212> TYPE: DNA
<213> ORGANISM: Canis familiaris

<400> SEQUENCE: 22
ctagctagcc acccaactcc ccacatgccc agagtcatcg tttatctttt cacatcagca        60
ytacattttg gcttgcattc aaacattagc ccatttttt tcctttttgtt ttatttatag       120 a                                                                      121

<210> SEQ ID NO 23
<211> LENGTH: 121
<212> TYPE: DNA
<213> ORGANISM: Canis familiaris

<400> SEQUENCE: 23
ttttctcttt ttccataaat gctctgggct tattttcatt atctagtatt tctcttctga        60
rgctaactcc caaagagttt tgtgcatcct tatttccatc acaaggtcaa tgtacgagtt       120
a                                                                      121

<210> SEQ ID NO 24
<211> LENGTH: 121
<212> TYPE: DNA
<213> ORGANISM: Canis familiaris

<400> SEQUENCE: 24
gggcccaagg gctgaggatc tctgtacctt ctgcttcttg gcagcccagg ctgggtagca        60
kttcttggaa gaggatttcc catgagttgt taacagaagg gcgggcttcc aggcgctgct       120
t                                                                      121

<210> SEQ ID NO 25
<211> LENGTH: 121
<212> TYPE: DNA
<213> ORGANISM: Canis familiaris

<400> SEQUENCE: 25
catctttgct tggggcctgg ggttttat t gaggattgtg atctggtgta tgtgtctcct        60
yaggcatcca gaaaccattc agaacaagaa caagcgtcca ggtatcctct gtaagtcact       120
t                                                                      121

<210> SEQ ID NO 26
<211> LENGTH: 121
<212> TYPE: DNA
<213> ORGANISM: Canis familiaris

<400> SEQUENCE: 26
acaaaccctc agacccagat acacagtatc atgtggacac agacatgtaa caccaaaatg        60
mccaacatca tgtgactaca ggccctaagc aactaggtgt aacatcactt gggtatgggc       120
c                                                                      121

<210> SEQ ID NO 27
<211> LENGTH: 121
<212> TYPE: DNA
<213> ORGANISM: Canis familiaris

<400> SEQUENCE: 27
aatgcagtaa tacatgtagc taaacctaac catcagagtc tgttctatcc ttctacaaaa    60
rtagggttgg agctgagcac ataggtagca tacatctagc aaaagttttt gccttcagat   120
t                                                                   121

<210> SEQ ID NO 28
<211> LENGTH: 121
<212> TYPE: DNA
<213> ORGANISM: Canis familiaris

<400> SEQUENCE: 28
ttgtggggtc aggtgagtta tggacccctc cctactcttc tgctatcttg cccctacag    60 kggttgctat tttgatgtaa tcacaaaacg acctggcaat aaaacctttt tctaattagg   120
g                                                                   121

<210> SEQ ID NO 29
<211> LENGTH: 121
<212> TYPE: DNA
<213> ORGANISM: Canis familiaris

<400> SEQUENCE: 29
gatgcaagct gggacagaat aaggtactgg gctgtgtcaa gccccagtaa gagaggagca    60
ytgtagggta gttaggatgg acttaatgga gatgagtcct agggagccac actcagagtt   120
a                                                                   121

<210> SEQ ID NO 30
<211> LENGTH: 121
<212> TYPE: DNA
<213> ORGANISM: Canis familiaris

<400> SEQUENCE: 30
taaacacccc caatcactac catcctcaca cctaaggata cacaatgtgt ctactttatg    60
rtatgtcttt actattcgtt gcttatgaaa ttttattcat tawctaaaac agggaaaaaa   120
g                                                                   121

<210> SEQ ID NO 31
<211> LENGTH: 121
<212> TYPE: DNA
<213> ORGANISM: Canis familiaris

<400> SEQUENCE: 31
tatagytggs caattaaatc tcctattctt ttgtctcaaa ggatatttga aattacatag    60
ytcttttctc atataaaacc taccatacaa tcattagatg atccttctta gttaattttt   120
t                                                                   121

<210> SEQ ID NO 32
<211> LENGTH: 121
<212> TYPE: DNA
<213> ORGANISM: Canis familiaris

<400> SEQUENCE: 32
gatgctgtgg gccagtccag aacccacctg agagaaacaa acaggcctct ttgccagcag    60
rgcagcgtca gtgtcacccc tgtgacatgt cagaacctcc ctgaaagttc atctaacctc   120
t                                                                   121

<210> SEQ ID NO 33
<211> LENGTH: 121
<212> TYPE: DNA
<213> ORGANISM: Canis familiaris

<400> SEQUENCE: 33
ggctcagaag aaaaatcagc ccagttcaca tccaatgttt ccacacatct aatcgtcttg    60
rgttcagagg tagatgtggt atcacttaya tggacacata taacagctgg cccccacctc   120
t                                                                   121

<210> SEQ ID NO 34
<211> LENGTH: 121
<212> TYPE: DNA
<213> ORGANISM: Canis familiaris

<400> SEQUENCE: 34
gtttcagtta attatagtcc ttactggatc cgattgctgt ggcgctaaaa tgaaagaagg    60
yagggtacct gggtggctca ggggttgaga atctgctttt gactcaggtc atgatcccag   120
g                                                                   121

<210> SEQ ID NO 35
<211> LENGTH: 121
<212> TYPE: DNA
<213> ORGANISM: Canis familiaris

<400> SEQUENCE: 35
cagagtagca ttattttctg ctgtatgagg acacttttgt tatatccaca gtggacagaa    60
ractgggttt tagaacatgc tcaattgaaa caagactgag ggctcacaaa ttcctgctcc   120
a                                                                   121

<210> SEQ ID NO 36
<211> LENGTH: 121
<212> TYPE: DNA
<213> ORGANISM: Canis familiaris

<400> SEQUENCE: 36
ttacttattc atctgagacc aaggccactg tggtgaacct acaaagcctt acaaagcagg    60
rccagaaggg cacataaatc acttgactaa catttggtca aaatagctct tgggctcttt   120
t                                                                   121

<210> SEQ ID NO 37
<211> LENGTH: 121
<212> TYPE: DNA
<213> ORGANISM: Canis familiaris

<400> SEQUENCE: 37
ataaaaataa aagagctatt aataagaact cataaaatct acataaatat agtaacaggt    60
yaatattccc agcatatttt tacaaatcat ctataaagag catgagagca tatagggatt   120
a                                                                   121

<210> SEQ ID NO 38
<211> LENGTH: 121
<212> TYPE: DNA
<213> ORGANISM: Canis familiaris

```
<400> SEQUENCE: 38
gcaacaacct ggtttgtgtg tgggaagcta atgcctcccc aaatgcagca aactctcctc      60
ytgattttag aaaagcagtt tagttacagg caaatgcata catgcatgat aaatactact    120
c                                                                     121

<210> SEQ ID NO 39
<211> LENGTH: 121
<212> TYPE: DNA
<213> ORGANISM: Canis familiaris

<400> SEQUENCE: 39
gattttataa aacatgatga ccttggcatt tatatagtag atattactac tctgaaattc      60
saggaagtat gatcataaac tcacacttaa tctggtagaa gtatggacaa tgtatcaaag    120
g                                                                     121

<210> SEQ ID NO 40
<211> LENGTH: 121
<212> TYPE: DNA
<213> ORGANISM: Canis familiaris

<400> SEQUENCE: 40
cttggttgag ttaaaacatt tgcccatgca atttaatgca tgtccctgtg gggttggaac      60
ygacgtacac ccgagccaac agcctttcat ggcagacgcc atcaggcagg tgaccccac     120 c                                                                     121

<210> SEQ ID NO 41
<211> LENGTH: 121
<212> TYPE: DNA
<213> ORGANISM: Canis familiaris

<400> SEQUENCE: 41
ccttccacac gctcaggttg gcacggaggg ggtgtccttg cctgaggggt cctggcacag      60
ycatcagggc acacagctga taacccaagg gagcagtagg caagacctca tgggcgccgg    120
g                                                                     121

<210> SEQ ID NO 42
<211> LENGTH: 121
<212> TYPE: DNA
<213> ORGANISM: Canis familiaris

<400> SEQUENCE: 42
attctctttg ctgtctcctg tatacagaga taaaagcaag agttttcccc ttcaggtttc      60
ygaaacccag cttcctttag attttaaggg gtattctgtg tacccatttc ccaccttctg    120
c                                                                     121

<210> SEQ ID NO 43
<211> LENGTH: 121
<212> TYPE: DNA
<213> ORGANISM: Canis familiaris

<400> SEQUENCE: 43
gcgggttggg acccccccctt ctgctgctcc cacttcagag ttgtggcgtc actaagatga     60
sacctcatgt cgggaacctg agagtccctc gggagttgtg cagggactgt agccgaccta   120
t                                                                     121
```

<210> SEQ ID NO 44
<211> LENGTH: 121
<212> TYPE: DNA
<213> ORGANISM: Canis familiaris

<400> SEQUENCE: 44
acatatgcac agtgaatcgt ggattgttgt gtttgatttc ttacatgata caataaaagg    60
raagtagttg aagcaaaact ttagttttaaa ggaaacaatt tctctatcat aatgttcagt  120
g                                                                  121

<210> SEQ ID NO 45
<211> LENGTH: 121
<212> TYPE: DNA
<213> ORGANISM: Canis familiaris

<400> SEQUENCE: 45
cccacagacc ccaggtgctg accacagcag ccacttgggc ccccaatgca ggagacacct    60
ygggaatgaa ggggacaagg ccagctcagg cacatcgtca gtgcacctga tgggaaggcc  120
g                                                                  121

<210> SEQ ID NO 46
<211> LENGTH: 121
<212> TYPE: DNA
<213> ORGANISM: Canis familiaris

<400> SEQUENCE: 46
atctgatcct agccaatgga aagcaatttg agataggaat catatcttgt tttggtttat    60
rtgctttctt tggagttttg cacatcatag ataactgtaa atttgtagaa taaatgtttg  120
a                                                                  121

<210> SEQ ID NO 47
<211> LENGTH: 121
<212> TYPE: DNA
<213> ORGANISM: Canis familiaris

<400> SEQUENCE: 47
gtcaatgcca ttaacctggc gaagctgctc gagcatccac tgcgatctcc gcacgaacga    60
ygtggagcct tcaaactgtt tgaccttcgt gatggatgct tgtgtgggtt tcttgtttgt  120
c                                                                  121

<210> SEQ ID NO 48
<211> LENGTH: 121
<212> TYPE: DNA
<213> ORGANISM: Canis familiaris

<400> SEQUENCE: 48
actggttaat aagacttcac agattttatc catcatgttg attatctgta tatgtatttt    60
ytaccactta ggataaagtt ctgttatctg taattgattc caaccagcat gtttgctcca  120
a                                                                  121

<210> SEQ ID NO 49
<211> LENGTH: 121
<212> TYPE: DNA
<213> ORGANISM: Canis familiaris

<400> SEQUENCE: 49
cttcttcttt cccattggat tctttcatca atcgtaggta gttcttaatg aagatctgtg    60
rtaaagccat tcatctattc attcaacaaa tggcatcaca gaaaagaaaa ataacctta    120 t    121

<210> SEQ ID NO 50
<211> LENGTH: 121
<212> TYPE: DNA
<213> ORGANISM: Canis familiaris

<400> SEQUENCE: 50
gggacacatt tctggacaga cctctgatca cactcacagg acagcaagag gaagctctgg    60
rtacaagtac agggaaaaaa gaaagaaatg gtcacaggga agctgccgca ggaaaaaggt    120
a    121

<210> SEQ ID NO 51
<211> LENGTH: 121
<212> TYPE: DNA
<213> ORGANISM: Canis familiaris

<400> SEQUENCE: 51
gggcagatcc tcagtgagta ttggctcatg ttctccgagg gaagtagagt cccagaagaa    60
rgatgctaag gtgccaagat tcctgagcct gtgtgtggta cagtcacagc agtactcctg    120
a    121

<210> SEQ ID NO 52
<211> LENGTH: 121
<212> TYPE: DNA
<213> ORGANISM: Canis familiaris

<400> SEQUENCE: 52
tcatctccat ttgtaataga aaccacatat atagagagat tggattatta accactaaaa    60
ygtagccact caaggggagg gggggaatgc atttggttta tttcccatgt caaaacagaa    120
t    121

<210> SEQ ID NO 53
<211> LENGTH: 121
<212> TYPE: DNA
<213> ORGANISM: Canis familiaris

<400> SEQUENCE: 53
aacactgcta ataaatattt ataatggttt gaggaaaata tcaggtgtga gatgtcttca    60
yatcatataa tatatcataa tatcctctaa aaaagctcta agcataggtc tatggaactc    120
a    121

<210> SEQ ID NO 54
<211> LENGTH: 121
<212> TYPE: DNA
<213> ORGANISM: Canis familiaris

<400> SEQUENCE: 54
aagcaatcca ggagtctttc tccgggtagc aggctcgctt tacaggttaa ggctggatga    60
raaggaagaa cctgagcttc aaattatcat ctgagtagag ctgataccca tggttacatt    120
a    121

<210> SEQ ID NO 55
<211> LENGTH: 121
<212> TYPE: DNA
<213> ORGANISM: Canis familiaris

<400> SEQUENCE: 55
gattttattc tttactttga ttttttttaa gttttactat gatattcaat atgattgtgg      60
ytcatgagat tcctcttttt agctgtatca ttaactacag agcgttctca aatattttc     120 t                                                                    121

<210> SEQ ID NO 56
<211> LENGTH: 121
<212> TYPE: DNA
<213> ORGANISM: Canis familiaris

<400> SEQUENCE: 56
gtggccggag ggggtgggcc ctactgtggc ccagcttcac gtcccactgg ccaaacatca     60
rgatgcagac acccaggtcc cttgtgctgc ctgctgaggc taggagcagc gactggaaat    120
g                                                                    121

<210> SEQ ID NO 57
<211> LENGTH: 121
<212> TYPE: DNA
<213> ORGANISM: Canis familiaris

<400> SEQUENCE: 57
gatgggagac ctcatacaca tgcaaagatc actattaaag actctcgagc aaagatcgaa     60
yggactgtgg caagctgccg cgcatgccaa tcaacaaatg cctccgacca tggatctaac    120
c                                                                    121

<210> SEQ ID NO 58
<211> LENGTH: 121
<212> TYPE: DNA
<213> ORGANISM: Canis familiaris

<400> SEQUENCE: 58
caacaaggtt tttaaggttc ttttcactac cttcttcttt ttgtacttgc ttaggacacc     60
ygtatgtctt cacaatatca cctgaaagtc ctttaggaga tatactcaaa aaataaataa    120
a                                                                    121

<210> SEQ ID NO 59
<211> LENGTH: 121
<212> TYPE: DNA
<213> ORGANISM: Canis familiaris

<400> SEQUENCE: 59
caacctgagc tgaaggcaga cactcaactg ttgagctacc caggtgtacc aaacacatct     60
rctcttaacc aagcttattc tttgctatat ttggcaaatt gtggcatgtc tacagtactc    120
a                                                                    121

<210> SEQ ID NO 60
<211> LENGTH: 121
<212> TYPE: DNA
<213> ORGANISM: Canis familiaris

<400> SEQUENCE: 60
attccccatg tttgaggaaa tcacaggagc cactaggaaa tcaaccattt cccaaccaac     60
ytgatgattt cctgatccaa aggttctccc aggacaaata tgaggtagcc tttcacactc    120
t                                                                    121

<210> SEQ ID NO 61
<211> LENGTH: 121
<212> TYPE: DNA
<213> ORGANISM: Canis familiaris

<400> SEQUENCE: 61
cagtcttgta ggagagtaga ttgactcaca gaactggcaa gattgggaat ctgagcattg     60
ycacttgagt cttaaaacgt ttacgatttt atttctagta tttcaataag aaacacattc    120
t                                                                    121

<210> SEQ ID NO 62
<211> LENGTH: 121
<212> TYPE: DNA
<213> ORGANISM: Canis familiaris

<400> SEQUENCE: 62
gaatacattg ccagaataat ttcaagttct caaatctcaa ctaataagat tttcgttaaa     60
kaaggcattc aatcatcact tactgacaac ccacaaaatt aggcactgat gaaaaattag    120
c                                                                    121

<210> SEQ ID NO 63
<211> LENGTH: 121
<212> TYPE: DNA
<213> ORGANISM: Canis familiaris

<400> SEQUENCE: 63
aagttaagat attcaagaaa gagaagagag tgactgagct aaaaagaaaa tcagatctct     60
yccaggcttt aaaataatct ccacaatact gggcaatcca tgtagtctcc ccagttccat    120
t                                                                    121

<210> SEQ ID NO 64
<211> LENGTH: 121
<212> TYPE: DNA
<213> ORGANISM: Canis familiaris

<400> SEQUENCE: 64
ctcaaaagga aaagcctgtg gaaaggcaaa gaggtatgtg aaagaggtaa gttcaaaatg     60
stgacatgac cagtgtacat agattacagg gtacttggag gagcagtgag aaaggagtcc    120
a                                                                    121

<210> SEQ ID NO 65
<211> LENGTH: 121
<212> TYPE: DNA
<213> ORGANISM: Canis familiaris

<400> SEQUENCE: 65
ttctatgaaa tagctaccat tctggttggt atcttctgtt gatttagatg atgaaggaag     60
yataagaagt aaggcttatg agtttataaa gctttagtta aagctttgat tgtgacaaag    120
c                                                                    121

<210> SEQ ID NO 66
<211> LENGTH: 121
<212> TYPE: DNA
<213> ORGANISM: Canis familiaris

<400> SEQUENCE: 66
agaggagaaa acacagctaa aaactttttt acagactgga caaaggtgct tacactttc      60 rtattgggca gaatgagggg atgaaaacac cagtggtctt tttgaagcca cacaaattca    120
g                                                                    121

<210> SEQ ID NO 67
<211> LENGTH: 121
<212> TYPE: DNA
<213> ORGANISM: Canis familiaris

<400> SEQUENCE: 67
aggatgaata tttattaaca gtaaatatac atttttattg ttctatatac tctaaagaca     60
rttgtagaca gtaagatata tcaattttag aaacagaaat aatgttaatt gtataatatg    120
g                                                                    121

<210> SEQ ID NO 68
<211> LENGTH: 121
<212> TYPE: DNA
<213> ORGANISM: Canis familiaris

<400> SEQUENCE: 68
cagggattcc taaagggtga catggtatgg tctaacactt cctcactgtc cttttcccag     60
mtgatataag aggaggacca gagagacaca taaactgtct gagtctttag cattgtgata    120
a                                                                    121

<210> SEQ ID NO 69
<211> LENGTH: 121
<212> TYPE: DNA
<213> ORGANISM: Canis familiaris

<400> SEQUENCE: 69
acactaatgg gtagagaata cacgtccatc agtcatcaat gtaatctact aacagcctca     60
sagtctggca gttttcagtg aaaagaggag tcatctccat ttattcgatc aatcagttga    120
c                                                                    121

<210> SEQ ID NO 70
<211> LENGTH: 121
<212> TYPE: DNA
<213> ORGANISM: Canis familiaris

<400> SEQUENCE: 70 tattccctg ctctccagcc actcctttac cttccattag cccacacctg ctctacacac      60
yattgctcat ggaagccttg ccacgtccag tcgccactct gaaatgccag catccctccc    120
a                                                                    121

<210> SEQ ID NO 71
<211> LENGTH: 121
<212> TYPE: DNA
<213> ORGANISM: Canis familiaris

<400> SEQUENCE: 71
tctcagatac ttgatagcca gcatttcccc ccatttctt ccaagagcac gaaagcatag    60
raatgatatt acatctcgta tggtgaatgt gacacagccg tcagttgcgt tagctctgct   120
t                                                                  121

<210> SEQ ID NO 72
<211> LENGTH: 121
<212> TYPE: DNA
<213> ORGANISM: Canis familiaris

<400> SEQUENCE: 72
acaggaagga gaactgagca tcaagagagt tcagaacatg atcattgggt cagtttgtgg    60
stgcattaac ttttccccaa aacagaaagc aacagagact tctgtaggtc agtcaacagt   120
g                                                                  121

<210> SEQ ID NO 73
<211> LENGTH: 121
<212> TYPE: DNA
<213> ORGANISM: Canis familiaris

<400> SEQUENCE: 73
ttaccattac tataacccaa gttatagtat actataacca agtccttaat tgacttgatg    60
yttgtgcagc tgattttaaa tctatttaga ataatagttt acttgtgaca attcatatta   120
a                                                                  121

<210> SEQ ID NO 74
<211> LENGTH: 121
<212> TYPE: DNA
<213> ORGANISM: Canis familiaris

<400> SEQUENCE: 74
ttggtcgact gactgattgg ttttactgtg gaggaaagaa aagggaatttt cccaaagag    60 racagagaga aaacatggaa ttgagcaaag ggagaataga gagacagggc agccactgaa   120
g                                                                  121

<210> SEQ ID NO 75
<211> LENGTH: 121
<212> TYPE: DNA
<213> ORGANISM: Canis familiaris

<400> SEQUENCE: 75
tgccttatcc tccagctcct ccctcaccat cttggaaact agctcaaatg tcactggtac    60
ktgtctttct tttgatcttt ctgaaagaca aacatgatcc catcacctct gcctttagaa   120
c                                                                  121

<210> SEQ ID NO 76
<211> LENGTH: 121
<212> TYPE: DNA
<213> ORGANISM: Canis familiaris

<400> SEQUENCE: 76
actcctaagt aaaagttaaa ttaacagatt tgccatcaag taccttgccc attttcccta    60
yagatcgact ttttactgga tgatcccctt gataataatc ttgatctatg ttttaattcc   120
a                                                                  121

<210> SEQ ID NO 77
<211> LENGTH: 121
<212> TYPE: DNA
<213> ORGANISM: Canis familiaris

<400> SEQUENCE: 77
ctggtgggct tgtcaggggc aggatgttgt gtggtgagca cagaattaaa actaggagct    60
ygaagcgcct gggggggctca gttggttgac ggactgcctt catctcaggt catgatccct   120
g                                                                   121

<210> SEQ ID NO 78
<211> LENGTH: 121
<212> TYPE: DNA
<213> ORGANISM: Canis familiaris

<400> SEQUENCE: 78
catacagcga agagataaaa acacaggatg ctgggctcac gaccatgacc ggaaaaggac    60
rgcgaggaaa agcaagtatg agcagcccaa agtccttttt ccagcactgg ccataggagg   120
a                                                                   121

<210> SEQ ID NO 79
<211> LENGTH: 121
<212> TYPE: DNA
<213> ORGANISM: Canis familiaris

<400> SEQUENCE: 79
cagagatgag gaatcagact cctcgtcctc tgcttctcta caatggctca tgttctcctt    60 yccctcagc tgttgcatta acagaggtca acccattctt ctaaatttaa atctcccaga    120
a                                                                   121

<210> SEQ ID NO 80
<211> LENGTH: 121
<212> TYPE: DNA
<213> ORGANISM: Canis familiaris

<400> SEQUENCE: 80
aatcaaacaa gtgctagaac atagaacaag tggctcatct tttccccaaa tgtctggata    60
rgaaaaaaaa aatctaaaca aatgctagat gttaagtatc tgaaatgatc agcccatgaa   120
a                                                                   121

<210> SEQ ID NO 81
<211> LENGTH: 121
<212> TYPE: DNA
<213> ORGANISM: Canis familiaris

<400> SEQUENCE: 81
tccataccag tccttgttgt ctaccccgaa cttcacctct ctaggcacag acagctctaa    60
mtttcactca taggtatctt atgctgacct ggcctgcctc ctgttttgtt ttgtttttgtt   120 t                                                                   121

<210> SEQ ID NO 82
<211> LENGTH: 121
<212> TYPE: DNA
<213> ORGANISM: Canis familiaris

<400> SEQUENCE: 82

```
caaaaaattc cctgagccca gcatcaaggt acctggtttg gagtgggtgg gtcctcagaa      60
mgaatgggtg tggtgtacat ttagcaagtt atgtagcatg tgtctgtgta gtctcacctc     120
t                                                                    121
```

<210> SEQ ID NO 83
<211> LENGTH: 121
<212> TYPE: DNA
<213> ORGANISM: Canis familiaris

<400> SEQUENCE: 83

```
gggcccagca agtggcagaa ctgggaagac cccctcttct tccgcctgga gcagtggtgt      60
rgcagcacac cacaggagtc tgaaagggtg gggagtccaa acgggaacat atacctgaga    120
t                                                                    121
```

<210> SEQ ID NO 84
<211> LENGTH: 121
<212> TYPE: DNA
<213> ORGANISM: Canis familiaris

<400> SEQUENCE: 84

```
atataatata acttatttaa aatatttgaa gatatttcta tagttatgct ctaccatttg      60
ytattataag atttccaaca gcttacttct tgtatgaaat taatttacca gccccctcacc   120
t                                                                    121
```

<210> SEQ ID NO 85
<211> LENGTH: 121
<212> TYPE: DNA
<213> ORGANISM: Canis familiaris

<400> SEQUENCE: 85

```
ccctattcta taaacattcc ctctctggcc atcctgtcaa gtgggccctg acagtgtgcc      60
scagaagctc cctagccttt gcccattcca gctatggcta gcctgccacc agccatacac    120
a                                                                    121
```

<210> SEQ ID NO 86
<211> LENGTH: 121
<212> TYPE: DNA
<213> ORGANISM: Canis familiaris

<400> SEQUENCE: 86

```
cactgtgagg tctgaatgga gacattcatg atagactcca ggattttccc agctattaag      60
ycatgggcca taaactggaa cacttggaaa cagtccatag gttcatatta aagaatatgt    120
t                                                                    121
```

<210> SEQ ID NO 87
<211> LENGTH: 121
<212> TYPE: DNA
<213> ORGANISM: Canis familiaris

<400> SEQUENCE: 87

```
gcaaaaggaa catgagttct gatcttctgt aaaggaggct aatttactaa tggtcataac      60
ygtggcctga gggtcaagtt tctaattaaa cgtgcatctt ggggyggact agaatacttt    120
c                                                                    121
```

<210> SEQ ID NO 88
<211> LENGTH: 121
<212> TYPE: DNA
<213> ORGANISM: Canis familiaris

<400> SEQUENCE: 88
caaggsccag gtaccctgaa ggagtccgct tcacccaggc atgatgtgtt tgacagtctt    60
ygtaattgat acagccattg gcatcctctt gcggccaaya tcagctccac ttcaacctcg   120
g                                                                  121

<210> SEQ ID NO 89
<211> LENGTH: 121
<212> TYPE: DNA
<213> ORGANISM: Canis familiaris

<400> SEQUENCE: 89
tgcaatgggt tttgaaatta gaggacatca cagcagagta aatggtttg gaacagggga    60 rtatgattag gattaatgag atgaaagaaa attctggcta gagggctaga agagccatgg   120
a                                                                  121

<210> SEQ ID NO 90
<211> LENGTH: 121
<212> TYPE: DNA
<213> ORGANISM: Canis familiaris

<400> SEQUENCE: 90
ctcagaacta gataggctaa taagtgatag gccttgtgtt ttcctagagt gtgctttaaa    60
rgtttcttaa gctaaaaaat tacattcgtg agaaaattga ataaaagga aaacagtcat    120 g                                                                  121

<210> SEQ ID NO 91
<211> LENGTH: 121
<212> TYPE: DNA
<213> ORGANISM: Canis familiaris

<400> SEQUENCE: 91
gatactttgg gctctgggtg ggagccagca gtggtggggc agggcaggag tccagcaagg    60
ygtctgggca tacatgtctg agagtaggaa aaccacacca ttgcaccttg cctttgactt   120
c                                                                  121

<210> SEQ ID NO 92
<211> LENGTH: 121
<212> TYPE: DNA
<213> ORGANISM: Canis familiaris

<400> SEQUENCE: 92
tcaaggatca gaaaaataaa agcaaagaaa gaggcaaaga agaagaaat gaaataccta    60 rtggcagaag taggcagaga aataaaggct aaaagaaaat ggcagaggat tgtttgaaag   120
g                                                                  121

<210> SEQ ID NO 93
<211> LENGTH: 121
<212> TYPE: DNA
<213> ORGANISM: Canis familiaris

```
<400> SEQUENCE: 93
tatgttatac tattttagta tcttaataaa tatgattagc caaaatagtt ttatcatcct    60
saaaagtgca gcatatatta ttttctatta aattcagaat aggtataaac tagaaagcat   120
t                                                                  121

<210> SEQ ID NO 94
<211> LENGTH: 121
<212> TYPE: DNA
<213> ORGANISM: Canis familiaris

<400> SEQUENCE: 94
acagcagttc tgaggatgga ctcgcagagg ctcctgacaa gcagaatgac caggccgagc    60
rgaaaggtca gtgctgccag tctagccaga agtggggag agaggatgta ggagcagtac   120
t                                                                  121

<210> SEQ ID NO 95
<211> LENGTH: 121
<212> TYPE: DNA
<213> ORGANISM: Canis familiaris

<400> SEQUENCE: 95
actgtactca aaaagttct gtttgcctaa atgggatcag cctctaatgg atgccagtga    60
ygggaggctg ttcatcatcc cttcgggata attcagagcc taggcagagg cccagcgttc   120
a                                                                  121

<210> SEQ ID NO 96
<211> LENGTH: 121
<212> TYPE: DNA
<213> ORGANISM: Canis familiaris

<400> SEQUENCE: 96
tacaggcccc aggaaggagc caccagatgc ccaggactgg gcccaggaat gatggaggct    60
rtacagctgg ctgcctgcac tggctgccgc ccctgtcatc cagtgtcaca gagcagcacc   120
t                                                                  121

<210> SEQ ID NO 97
<211> LENGTH: 121
<212> TYPE: DNA
<213> ORGANISM: Canis familiaris

<400> SEQUENCE: 97
agacattgcc aagaagtatc cacaatgaac agtttgaagg ggatccagaa aagcacaggg    60
yctacttccg ctggatgagc agcagtgaga accacagtca ggtaggtctt aaagcaaagt   120
t                                                                  121

<210> SEQ ID NO 98
<211> LENGTH: 121
<212> TYPE: DNA
<213> ORGANISM: Canis familiaris

<400> SEQUENCE: 98
gctttgaaaa ccaacaggaa atacatccag gaaagctata caactgtggt gaaaggaaag    60
raaaatctgc tcttaaaagg ttgtgtgcag actcacttgc cccagaaacc agtgcgaaaa   120
c                                                                  121
```

```
<210> SEQ ID NO 99
<211> LENGTH: 121
<212> TYPE: DNA
<213> ORGANISM: Canis familiaris

<400> SEQUENCE: 99
gagatgtgta aaatttaata gaaatgaaac ttgccaaaac agacctctgt actcgtcagc    60
rttctaagtc catctttctg tagcatgtaa gtagaataat gttctattaa tttcctctat   120
g                                                                    121

<210> SEQ ID NO 100
<211> LENGTH: 121
<212> TYPE: DNA
<213> ORGANISM: Canis familiaris

<400> SEQUENCE: 100
gttctttcta ttctatcaca cataccaccc ccctgcccac agtacccctt tctgccatgt    60
ytcagactcc tacacaagag gttctctctc ctggcttcca gttagacagg caggtaaagc   120
t                                                                    121

<210> SEQ ID NO 101
<211> LENGTH: 121
<212> TYPE: DNA
<213> ORGANISM: Canis familiaris

<400> SEQUENCE: 101
taaaaaaata caacagtagc attagaagac atgctaagcg gctgtattag agaaggttag    60
ygctggcctg aagtttagaa accttccctt ctcttttttt ttttccttcc cttctcttta   120
a                                                                    121

<210> SEQ ID NO 102
<211> LENGTH: 121
<212> TYPE: DNA
<213> ORGANISM: Canis familiaris

<400> SEQUENCE: 102
tcaagagtac tagagcatct ataatcaatg gtaaattggg gaactagtga aacaagttta    60
yaggacaaat aacataaata aggatttttt tttaaatttg gaaaattgtg gaataatgat   120
a                                                                    121

<210> SEQ ID NO 103
<211> LENGTH: 121
<212> TYPE: DNA
<213> ORGANISM: Canis familiaris

<400> SEQUENCE: 103
agaattcaat tttggggagc caggaaacca gattagtttt ccaaagggaa gtgccatttg    60
yatctatccc ggtggggctg ccaagaattc cctggggtgg gagacggcgc ttctgtggat   120
t                                                                    121

<210> SEQ ID NO 104
<211> LENGTH: 121
<212> TYPE: DNA
<213> ORGANISM: Canis familiaris
```

<400> SEQUENCE: 104
caccagagag ccccgcaaga tcatactgca caagggctcc actggcctgg gcttcaacat    60
ygtaggagga gaggatggag aaggcatttt tgtttccttc atcctggcag gaggcccagc   120
t                                                                  121

<210> SEQ ID NO 105
<211> LENGTH: 121
<212> TYPE: DNA
<213> ORGANISM: Canis familiaris

<400> SEQUENCE: 105
tggtgatgat ttatccccca tgttcaagat ttatcctccc tgtctcaaga aatcatgtca    60
ytacaggcat ccttaaagtc acaagactgg gaagtaaata ctgatgaggt ccaagacctg   120
g                                                                  121

<210> SEQ ID NO 106
<211> LENGTH: 121
<212> TYPE: DNA
<213> ORGANISM: Canis familiaris

<400> SEQUENCE: 106
agcatagtgt acccacatat aaggtcacat ctgaggccag ggagtcgggg tcttgaagat    60
katgactgat catgtgcttg aggatgatga tgatcatgtg cttttcctgg ctgtgcagtt   120
g                                                                  121

<210> SEQ ID NO 107
<211> LENGTH: 121
<212> TYPE: DNA
<213> ORGANISM: Canis familiaris

<400> SEQUENCE: 107
gtgtgtgtgt gtgtgtgtgt gtgtttaatt ctttgtgaga agcccctcat tttgacctaa    60
rtttggtaga ggccccaggg gatctgagag gagaacaaaa ggataaacca tttgctgttc   120
a                                                                  121

<210> SEQ ID NO 108
<211> LENGTH: 121
<212> TYPE: DNA
<213> ORGANISM: Canis familiaris

<400> SEQUENCE: 108
ccaactttca ctagcatcac agcccctatc aatctctgtt ctttttttctg tcagtaccat    60 rtttgctcct actacatcya atctgtgagc tcacaggatg aggaccaaca gctgccctga   120
g                                                                  121

<210> SEQ ID NO 109
<211> LENGTH: 121
<212> TYPE: DNA
<213> ORGANISM: Canis familiaris

<400> SEQUENCE: 109
tgtcttacct ctctctattc ccttgtccat agtagtatta aatatatctt cctgaacaca    60
ratctgatcc agtctctttt tgtaattaaa agcctttgct agctttggtg atcacctcca   120
g                                                                  121

<210> SEQ ID NO 110
<211> LENGTH: 121
<212> TYPE: DNA
<213> ORGANISM: Canis familiaris

<400> SEQUENCE: 110
gacctgacag attatgtaga ctttgttttc aaagggagca cctgctggat atacaacatg    60
rcactaaatt gtgctccaca tccttggcag aggtgggggg cggggcacaa aggaagaaac   120
c                                                                   121

<210> SEQ ID NO 111
<211> LENGTH: 121
<212> TYPE: DNA
<213> ORGANISM: Canis familiaris

<400> SEQUENCE: 111
cagaggaaaa ggagaaggtc ccacttaggg gactggagag gagtggggga acatcaccag    60
mgccttcctg agccaggccc cctgtgggga gaagctctcc ccaggactgg gtgcctttga   120
a                                                                   121

<210> SEQ ID NO 112
<211> LENGTH: 121
<212> TYPE: DNA
<213> ORGANISM: Canis familiaris

<400> SEQUENCE: 112
tcctccctct ccccatcccc attctcatgc aagtgtgctc tctctctaaa acaccccccc    60
mcacacacac acacagacac aaccaaattt gggtctcaat gtcttgacca aggaaaaggc   120
a                                                                   121

<210> SEQ ID NO 113
<211> LENGTH: 121
<212> TYPE: DNA
<213> ORGANISM: Canis familiaris

<400> SEQUENCE: 113
gagaagaagg aggagaaaga ggaaaagtat atttgatgga atgaaaaaca agagttcaat    60
ytcactctgg tctggggtga ccactattag tccttcaaca tcttccttga aggaatttta   120
a                                                                   121

<210> SEQ ID NO 114
<211> LENGTH: 121
<212> TYPE: DNA
<213> ORGANISM: Canis familiaris

<400> SEQUENCE: 114
ctggaattct gtcagatcaa cattcagagc tccatcaaat ctgagggaag cagtgataga    60
rgatacaatt tgacctttca gtctattcag gttcatgtag gttaggcatt caatatcaaa   120
g                                                                   121

<210> SEQ ID NO 115
<211> LENGTH: 121
<212> TYPE: DNA
<213> ORGANISM: Canis familiaris

```
<400> SEQUENCE: 115
ccacatgtgg ttacaccact gtgttatcct tccacctgtc ccatcaaccc acccgcacat    60
rtcacagtgc ctctgtcctc aaagaacact gtatccaaca cctccacatc ctctcagcat   120
g                                                                  121

<210> SEQ ID NO 116
<211> LENGTH: 121
<212> TYPE: DNA
<213> ORGANISM: Canis familiaris

<400> SEQUENCE: 116
attcctatgg tgggcgctgc acatttcctc ccaggggaag ggcaagggtc ctgcatttct    60
rtgctttcca gggcctccgc accaagagca attgctaggt cacgcatgcc cctgcacttc   120
c                                                                  121

<210> SEQ ID NO 117
<211> LENGTH: 121
<212> TYPE: DNA
<213> ORGANISM: Canis familiaris

<400> SEQUENCE: 117
catgtcatca ctaactaatt tattaacaag agttttattc tttgaaaaac aaaatcactc    60
rcattactca gttgcttatt ccttgattca tatacaaatg actgataaca tgagataaaa   120
a                                                                  121

<210> SEQ ID NO 118
<211> LENGTH: 121
<212> TYPE: DNA
<213> ORGANISM: Canis familiaris

<400> SEQUENCE: 118
gatgatttag ttgtttgaat gatctggcat ataaatcttc caaatctgtg tccattggat    60
ygcttacagt ttaatctttt tatttcttcc cagaatcaca ttttttcatt atttatcttt   120
g                                                                  121

<210> SEQ ID NO 119
<211> LENGTH: 121
<212> TYPE: DNA
<213> ORGANISM: Canis familiaris

<400> SEQUENCE: 119
agttaaattc tgtgaataac tagaatccgt tatacttttt ctgaaatgaa gtctgtaggc    60
wtttcaacag caaaaggaat tctgwttttty aaaactatac ataatgcttc ttaaaagccc   120
t                                                                  121

<210> SEQ ID NO 120
<211> LENGTH: 121
<212> TYPE: DNA
<213> ORGANISM: Canis familiaris

<400> SEQUENCE: 120
aatgccaact ttaaaaacgc attcaaggtt ttcctctgta aatgcattcc tcatttttgga    60 ygtgatgtaa aatcttattc agtgttttgt ttttttttcc ccccacaggt ctcaacaatt   120
a                                                                  121
```

<210> SEQ ID NO 121
<211> LENGTH: 121
<212> TYPE: DNA
<213> ORGANISM: Canis familiaris

<400> SEQUENCE: 121
ggtgggaccg gccatcagca ggcgggccag cgcccacag atgttgtcac ggacccgatc    60
rtggcgctcc cgtgccagga ggggcaacag aagccccagc agcttgggga agtatctggt   120
t                                                                  121

<210> SEQ ID NO 122
<211> LENGTH: 121
<212> TYPE: DNA
<213> ORGANISM: Canis familiaris

<400> SEQUENCE: 122
aggggacttg tgctaatcac tgggcaaatt ttatgaactt ctgaattta aagcaaaaga    60 raaggtgaaa gaatggaaag aaggtgtgag tgtttgagga aaacttcttc tttggggttg   120
a                                                                  121

<210> SEQ ID NO 123
<211> LENGTH: 121
<212> TYPE: DNA
<213> ORGANISM: Canis familiaris

<400> SEQUENCE: 123
tacacaagca aggcagtatg ccctgtctcc ttcccttggg ccacctgcac ttagacatgg    60
yaggttccag tgatgtgtct agtctctagc aagcagggct tgcttctgct ctatccatcc   120
a                                                                  121

<210> SEQ ID NO 124
<211> LENGTH: 121
<212> TYPE: DNA
<213> ORGANISM: Canis familiaris

<400> SEQUENCE: 124
ctgtccttgg tctggacctg ctgtgaagac caagtgcttc ctgagatctc tctgagtcta    60
rtttccagag cagtgagtga gaaatgaaat gagccgagga ttgccctccc tcctatggac   120
t                                                                  121

<210> SEQ ID NO 125
<211> LENGTH: 121
<212> TYPE: DNA
<213> ORGANISM: Canis familiaris

<400> SEQUENCE: 125
taagccatca gcatgggctc ctagggtct gttcaactcc cttgtggtgt cttactgctc    60
ragcaaagga acagtctggt acagtgggag caagagctga ggttggagag tggggacaca   120
g                                                                  121

<210> SEQ ID NO 126
<211> LENGTH: 121
<212> TYPE: DNA
<213> ORGANISM: Canis familiaris

<400> SEQUENCE: 126
gaggaggtgg aagtgattaa gtttaaaatt tctggggtgg tttctggcga catgaagctg    60
mgagctagaa tgcctttcaa tctcataatt tctttaattt ggtgattata ccagagccac   120
a                                                                  121

<210> SEQ ID NO 127
<211> LENGTH: 121
<212> TYPE: DNA
<213> ORGANISM: Canis familiaris

<400> SEQUENCE: 127
cctgacaaac actacctctg ctcttcaaaa gcaataagca tttattctgt gacacattta    60
ratacaaagt caattacaat agagtataag tacaatacta gggaaagtac aaagtcatay   120
g                                                                  121

<210> SEQ ID NO 128
<211> LENGTH: 121
<212> TYPE: DNA
<213> ORGANISM: Canis familiaris

<400> SEQUENCE: 128
gcatgatgaa atcagaaaaa gtatgtaagt ttctagaaga agctagatat atggtaactt    60
wggtcaaata gaaccatgta gtgaaaagaa tatgagtttt caagttcaat aaaaaacaaa   120
a                                                                  121

<210> SEQ ID NO 129
<211> LENGTH: 121
<212> TYPE: DNA
<213> ORGANISM: Canis familiaris

<400> SEQUENCE: 129
atgcataagt ttccaaaaga gttcaggatt ccaaaataaa agcttcacta aaagattcat    60
mgcaaaagag taatgaacaa ttaaagtcat aggatatcta aaatgaaaaa ctgttagact   120
g                                                                  121

<210> SEQ ID NO 130
<211> LENGTH: 121
<212> TYPE: DNA
<213> ORGANISM: Canis familiaris

<400> SEQUENCE: 130
agatggctta gttgtttctc tttcctcctg aagtccacag cttagttact tggactctcc    60
raaataggat cgttggacat ttgaggaaag ctctagcatg aaagccatag actaaaaaac   120
a                                                                  121

<210> SEQ ID NO 131
<211> LENGTH: 283
<212> TYPE: DNA
<213> ORGANISM: Canis familiaris

<400> SEQUENCE: 131
ctctcatttt gtgtattgat ttgaggactc tgtccttttt gttctcttag gtgttttgta    60 accattttg tggttcttgc cacaaaaggc cttatgaagt cctgcatatg agtgatgtgc   120
aggacaactt tgactttctg acagccagtt tttgtgtttt gttmccttag ttcccaagtt   180

```
cctatcttgt ttacctcatg atcacatttt aatatcaatg aaatttgtag gaaaacagca      240
gaaggaaaga tataaggtta ctattctcta tggaccttgg ttg                        283
```

<210> SEQ ID NO 132
<211> LENGTH: 223
<212> TYPE: DNA
<213> ORGANISM: Canis familiaris

<400> SEQUENCE: 132

```
ttgcagatta tatgataaat atagttgtag cttcaaaaat gactataacg aacagaaaaa      60
aattaactta tcaaaaactt ttcaaatttc cccatayact taactaggta ggccacagag     120
tatgatagta tgcaagttat taaaatctgt tagcaaggca taacacatat atttctactt    180
aatgaggttt ctataatcaa ggcttgtcaa gtccattatg ttc                       223
```

<210> SEQ ID NO 133
<211> LENGTH: 157
<212> TYPE: DNA
<213> ORGANISM: Canis familiaris

<400> SEQUENCE: 133

```
tcagactgaa tctaaagcca catatatttc ctcagcagct gataacatta gaaatcagaa      60
agccactaty ttagctggca ccgcaaatgt aaaagtaggc tctaggacgc cagtggaggc     120
ttcccatcct attgaaaatg catctgttcc taggcca                              157
```

<210> SEQ ID NO 134
<211> LENGTH: 179
<212> TYPE: DNA
<213> ORGANISM: Canis familiaris

<400> SEQUENCE: 134

```
tcttgtgctt gttctttatc accattcatt cagtacatcc aaattttgaa atccttagag      60
ctctatagcc tctatgtagg agaatgagat ttcatcaaaa ggaaatattt tgagaattta    120
agtgattttt ttatgatatt ttagctatag cagtcacctt gagccaaaag acattctac     179
```

<210> SEQ ID NO 135
<211> LENGTH: 191
<212> TYPE: DNA
<213> ORGANISM: Canis familiaris

<400> SEQUENCE: 135

```
aaaaatatac tctctttctt acagaaacct ctaataattc agattctggc catgaagttc      60
aggaggattc ttcaaaggaa aatgtatcat caagtgctgc ctcyactgac cacaacccaa    120
cacctactca tgatggcaaa tcmcmtraac tgtytawtyt csgattggrr awtmaaykgt    180
traggaatga a                                                          191
```

<210> SEQ ID NO 136
<211> LENGTH: 244
<212> TYPE: DNA
<213> ORGANISM: Canis familiaris

<400> SEQUENCE: 136

```
tttgcccaag aaaaatgaag acctatgacc atggaaagac ttgatacata atgctggagt      60
actagtagtc agacccaccc aagtctttc acgtgttcat tcagtataga tgcggcacac    120
```

```
gttggctgag tccctccgkt gtgtcaggaa ctgttttagg tattggggat gaagtaggga      180
acactgattt agsttctgtt tattcatgtc tcactttgta ggaattycmh tamatagaar      240 aada                                                                  244
```

<210> SEQ ID NO 137
<211> LENGTH: 251
<212> TYPE: DNA
<213> ORGANISM: Canis familiaris

<400> SEQUENCE: 137

```
tctcagtact cacaggtact acaaataca acactaagag gtttcacaaa acagtactct       60
tacatagcac atgctgtact ctctgttcca ttctatttta ttactatttt aaaatatgga     120
ttgtgatytg ccaakttgat tctctggccc attaatagtt tgaaaatctc ttctgtagga    180
gtataggaat taccacagag ttttgagaaa ttgatgaatg ccacgcttta cctgtgggaa    240
cgtagattct a                                                          251
```

<210> SEQ ID NO 138
<211> LENGTH: 191
<212> TYPE: DNA
<213> ORGANISM: Canis familiaris

<400> SEQUENCE: 138

```
cagatgatga gtctggagct ggtgatctgg gctggagata atgaacctgg gagtcatcag      60
ctttggagaa agggtgtctg gcctcactct tgctwgcaca gaaagaaagt gctcattagt     120
gtcaactctc agcaacactt ggtatttgta aactttaatt tttgctgact tcatggagaa    180 ataatgttt t                                                           191
```

<210> SEQ ID NO 139
<211> LENGTH: 206
<212> TYPE: DNA
<213> ORGANISM: Canis familiaris

<400> SEQUENCE: 139

```
taatgataca gaaatgaatt tggcaggaat gtatggaaaa gtccgaaaag ctgctagttc      60
aattgaccag tttaggtaag caagtgcagt actggtgagg aatggkgcat cggctccttc     120
tgtgctattt tccggtggct ccagtcacag ccccatcaag cagagctgat acctaaagtg    180
acatttaccc tacttcctct ctcaat                                           206
```

<210> SEQ ID NO 140
<211> LENGTH: 186
<212> TYPE: DNA
<213> ORGANISM: Canis familiaris

<400> SEQUENCE: 140

```
catcacttaa aatcatctca gcaagtgttg ttgaagatga tttttataa agtatattcc      60 aatcttattc tatacttcag aagcttggaa ttctyatttg ctttgctgga ttgaaaaagt    120
ctggaagtaa ttagaatgac ttctcatact cccaccttga attctcctaa tatcaaaggc    180
tgggag                                                                186
```

<210> SEQ ID NO 141
<211> LENGTH: 171
<212> TYPE: DNA
<213> ORGANISM: Canis familiaris
<220> FEATURE:

<221> NAME/KEY: modified_base
<222> LOCATION: (169)..(169)
<223> OTHER INFORMATION: a, c, t, or g

<400> SEQUENCE: 141

```
atatggagaa atgagctctt atacactttc agtggacatg taaactgtta ttgtcttttt      60
ggagagcatt tggcaggatc tatcaaagtr cacacatcat ttgattgagc aattccactt     120
ccagccatat tctggacata atttacaagt ataaaaagat gcatgtttng a              171
```

<210> SEQ ID NO 142
<211> LENGTH: 213
<212> TYPE: DNA
<213> ORGANISM: Canis familiaris

<400> SEQUENCE: 142

```
aaatattgaa agtgctttat ctacactcca atatgtaagc agcatagtag tttctttaga      60
gaatagatct gccatagtaa agtacaatgc aagcttagtc aytccagaaa ccctgagaaa     120
agcaatagag gccatatcac caggacaata cagagttagt attgctagtg aagttgagag     180
tacctcaaac tctccctcca gctcacctct tca                                  213
```

<210> SEQ ID NO 143
<211> LENGTH: 125
<212> TYPE: DNA
<213> ORGANISM: Canis familiaris

<400> SEQUENCE: 143

```
ttaaataac tacttgcagt gatttctttc ccccagtata aaatgtcagt tttgtctcaa       60
tccacccyct tcaccttaaa aagaaaaaga agtattagt tttcagtgtc atttgcctta     120
aaatg                                                                125
```

<210> SEQ ID NO 144
<211> LENGTH: 201
<212> TYPE: DNA
<213> ORGANISM: Canis familiaris

<400> SEQUENCE: 144

```
gagaggtacg aggcccaggc gcagggccgc atgaagcccc tgacggcgtc ccaggtcagc      60
gtgcacattg gcatggatga ccggcggtgg gactccccgc rggccacgcc ctgggaccag     120
gtcagccgtg tcagccaggt gtctctgtcc tccctgaagt ccgacaagct gtcccgacac     180
agcgccgcgg ccgacgacgg c                                               201
```

<210> SEQ ID NO 145
<211> LENGTH: 201
<212> TYPE: DNA
<213> ORGANISM: Canis familiaris

<400> SEQUENCE: 145

```
cgacggaatg cactgtcagt cttgtgtcct gaacattgaa gagaatatag gccaactccc      60
cggggttcag aatgtgcaag tgtccttgga gaacagaacg rcccaagtac agtacgaccc     120
ttcttgtgtc accgcagggg ccctgcagag ggccattgaa gctctcccac cagggaactt     180
taaagtttct cttcctgccg c                                               201
```

<210> SEQ ID NO 146
<211> LENGTH: 201
<212> TYPE: DNA
<213> ORGANISM: Canis familiaris

```
<220> FEATURE:
<221> NAME/KEY: modified_base
<222> LOCATION: (8)..(8)
<223> OTHER INFORMATION: a, c, t, or g
<220> FEATURE:
<221> NAME/KEY: modified_base
<222> LOCATION: (65)..(65)
<223> OTHER INFORMATION: a, c, t, or g
<220> FEATURE:
<221> NAME/KEY: modified_base
<222> LOCATION: (148)..(148)
<223> OTHER INFORMATION: a, c, t, or g
<220> FEATURE:
<221> NAME/KEY: modified_base
<222> LOCATION: (152)..(152)
<223> OTHER INFORMATION: a, c, t, or g
<220> FEATURE:
<221> NAME/KEY: modified_base
<222> LOCATION: (181)..(181)
<223> OTHER INFORMATION: a, c, t, or g

<400> SEQUENCE: 146
cggggctnga tctcacgacc ctgacatagt gacctgagcc aaaaccaaga gttggacgct    60
caatngactg agcctcccgg gagccccaaa gtcaagagac rctacagatg cgttgggcac   120
aatgacaggg gaggaagctg aggtctgntg gnggaggttc tgcacctccc agcaggaccc   180
ngcacacagc aggtgcctgc t                                              201

<210> SEQ ID NO 147
<211> LENGTH: 201
<212> TYPE: DNA
<213> ORGANISM: Canis familiaris

<400> SEQUENCE: 147
ggggagtccg gcatggcccc ctgtcagccc tgtcccctca gggtgtcttg gccgggttgc    60
tccctgacaa gctctcccte ctctctcttc aggttcagce ygaatctgac accatgcccc   120
tagggaagag cagcgagctt tggaagcagg gagaagacct ataggaggcc gagggcctgg   180
ggatgcccag ctgtctgggg c                                              201

<210> SEQ ID NO 148
<211> LENGTH: 201
<212> TYPE: DNA
<213> ORGANISM: Canis familiaris

<400> SEQUENCE: 148
ccttcagaga gaacccagga caattactaa actaccgtgc cctggaagat gttttgtgac    60
tcctcactcc ctctgccttg cttattggcc attattttt katccctctc tcttctacca   120
ttattaatca aacacaacaa acaaaacact tctaacaagg atattaggtt tgtatacatt   180 tttttttaaaa acagcaactt a                                             201

<210> SEQ ID NO 149
<211> LENGTH: 201
<212> TYPE: DNA
<213> ORGANISM: Canis familiaris

<400> SEQUENCE: 149
acttcctgat tgctactgtc tggacactag gttttgcgat tgttctcccc cttccagtgt    60
ttcacagtct ggtggaactt caggaaacat ttgactccgc rttgctgagc agcaggtatt   120
tatgtgttga gtcgtggcca tctgattcgt acagaatcgc ttttactatc tctttattgc   180
tagtccagta tattcttccc t                                              201
```

<210> SEQ ID NO 150
<211> LENGTH: 201
<212> TYPE: DNA
<213> ORGANISM: Canis familiaris

<400> SEQUENCE: 150

```
cagggaacat tttcaaagat gtagaaaatc ccaagacatg ttaacatagg gaatgcatgt    60
aaagatgcaa tcaaaagcct tgaaatgac aaccacttat rtaagaccta gcaatgtgca    120
cttccaaaca ttaactaaaa gttctatctc ccccctctgg gttccttaaa cattacacct   180
ctctgcctat caaagcacct a                                             201
```

<210> SEQ ID NO 151
<211> LENGTH: 201
<212> TYPE: DNA
<213> ORGANISM: Canis familiaris

<400> SEQUENCE: 151

```
ttcctcatag gaaatttggc cttctctgat attttggttg tgctgttttg ctcaccttt    60 acactgacct ctgtcctgct ggatcagtgg atgtttggca ragtcatgtg tcacattatg   120
ccttttcttc aatgtgtgtc agttctggtt tcaactttaa ttctaatatc aattgccatt   180
gtcaggtatc atatgatcaa g                                             201
```

<210> SEQ ID NO 152
<211> LENGTH: 201
<212> TYPE: DNA
<213> ORGANISM: Canis familiaris

<400> SEQUENCE: 152

```
atccagaaga agtctgctag gggtaactat cttttcgctc tctgtttatg ccaacatttc    60
acaaaagctt gtctcccgtg acttaaatag atacacccag mgtgtatgtt ggggattttt   120
gcaagtatcc ttaggaggcc ctacgtcgta aggcacagtc ataagacctc gcgtccctat   180
tccctcatct gtaaaatggt g                                             201
```

<210> SEQ ID NO 153
<211> LENGTH: 201
<212> TYPE: DNA
<213> ORGANISM: Canis familiaris

<400> SEQUENCE: 153

```
caaggtctgt ggatgtgctt actccgtcct caccacaaac accgatgtct cggacacact    60
cagtgagccc aggttaggaa gccaggattg cagggccaag rgtataagga ggtgtcctgg   120
gagcctcaaa agaaaaatac aaaagtatga agactcagaa taaattctta caaatcttgc   180
tgtgtcttcc cacagatggc a                                             201
```

<210> SEQ ID NO 154
<211> LENGTH: 201
<212> TYPE: DNA
<213> ORGANISM: Canis familiaris

<400> SEQUENCE: 154

```
gaaaggccgt ttcctacctc ggccccaagt agtgagggcc tggaccctga gcccatgatg    60
gaccaaaggg agcaggtggg tgaggcccca gcccttggac rgaatatttc attagctaat   120
gcaaatcatg agttcaggga atcctcacag cccctgaga atacgcagag cactgtgtta   180
tgtctcccag ggtccctttt a                                             201
```

<210> SEQ ID NO 155
<211> LENGTH: 201
<212> TYPE: DNA
<213> ORGANISM: Canis familiaris
<220> FEATURE:
<221> NAME/KEY: modified_base
<222> LOCATION: (56)..(56)
<223> OTHER INFORMATION: a, c, t, or g
<220> FEATURE:
<221> NAME/KEY: modified_base
<222> LOCATION: (100)..(100)
<223> OTHER INFORMATION: a, c, t, or g
<220> FEATURE:
<221> NAME/KEY: modified_base
<222> LOCATION: (130)..(130)
<223> OTHER INFORMATION: a, c, t, or g

<400> SEQUENCE: 155
aaagtatcag cacactgatg cagccagcct agctgaagat ggagttgttg aagcanaggt      60
gttcatgatc cctccccagt gacctgcgat ttttttttn waatcttatt cgcccatttt     120
attaaatccn caaattcaaa tctgtttgtc tcacttgctg agatttcttt tgtctttctc    180
tttcattcat tcttacagtt g                                              201

<210> SEQ ID NO 156
<211> LENGTH: 201
<212> TYPE: DNA
<213> ORGANISM: Canis familiaris
<220> FEATURE:
<221> NAME/KEY: modified_base
<222> LOCATION: (101)..(101)
<223> OTHER INFORMATION: c or absent

<400> SEQUENCE: 156
aagaaaaaga aaacccagc catcaagggt gtgcatgtct gtgaaagctc cagacaggat      60
gatcgaggtt gtttgcaacg acagtctaga gaagaaggtg ngcgttaagt gcaacactga    120
tgacaccatc ggggaccttta agaagctgat tgcagcccag actggcacct gttggaacaa   180
gaccatcctg aagaagtggt a                                              201

<210> SEQ ID NO 157
<211> LENGTH: 201
<212> TYPE: DNA
<213> ORGANISM: Canis familiaris

<400> SEQUENCE: 157
gcctagcatt attcctgaca tgtgttaggt cctcaacaaa tagtagctaa tatactttct     60
ggatttcttt cttttttggct aagtagaaga gctggtgctg ycatccttat agtctgtata   120
gtaggatttc ttttctttcc ttttctttt taaagatttt acttatttac tcatgagaga    180
cacagactga gagagagagg c                                              201

<210> SEQ ID NO 158
<211> LENGTH: 201
<212> TYPE: DNA
<213> ORGANISM: Canis familiaris

<400> SEQUENCE: 158
agagagagga gaagcaggct ctatgcagga agcccgatgt gggactcgat cccaggtctc     60
caggatcatg ccctgagcca aaggcaagac gctcaaccac wtagccaccc aggcgtccct   120

```
tttaccttag tttttgtcct aaagcttcat ataaatggaa tcatgtagta tgtatgtgtg    180
tacactctct tttctgactt c                                              201
```

<210> SEQ ID NO 159
<211> LENGTH: 237
<212> TYPE: DNA
<213> ORGANISM: Canis familiaris

<400> SEQUENCE: 159

```
tgcctctcca ctactcactc ttctcttgaa agattatttc ctgcttaaac tggcccgtga    60
cttcctgctg ccagaaccat ggaatggcct cctgagggag gctccctatg ctgctcccat    120
yagcagatat tgcagcgtca cagtataact cagtggcttg aaatgatggc tatttatcat    180
tgctcagtaa tttgagtggc tcgaagagga tagaatttca tttctttctc agataat      237
```

<210> SEQ ID NO 160
<211> LENGTH: 237
<212> TYPE: DNA
<213> ORGANISM: Canis familiaris

<400> SEQUENCE: 160

```
tgtacagctg actccctgag aaaggacatc ctgggtcacc tttcaagtat ttcctggcat    60
ggaaacccca tatcttcaaa cacaaaaatc agaaaatcac agtccttatc tgtttgggcc    120
yatttatagg agagtctttt tattgcctgg aattgtatat ttttacattt cttagatttc    180
tacaaaataa tatttgtgcc ttctttcaag tataatatta tttattaaag ttgcttt      237
```

<210> SEQ ID NO 161
<211> LENGTH: 237
<212> TYPE: DNA
<213> ORGANISM: Canis familiaris

<400> SEQUENCE: 161

```
attaatacat tcttagtgtc ttctttaaaa atgcaacttc catgctttat aaaataccaa    60
caaatgcttt acatctttat gatggtaatt ttggatcaat actggaggat tttaaaaaaa    120
yctctgcttc ccctgcttgt gtggtctctc acgcgctctc attctcactc tgtcaaataa    180
ataaacaaaa tctttccaaa aagacaaagt ccttgtgaaa actgagaagg cctgtga      237
```

<210> SEQ ID NO 162
<211> LENGTH: 237
<212> TYPE: DNA
<213> ORGANISM: Canis familiaris

<400> SEQUENCE: 162

```
atttgtactt tcttttcact tctcctgcgt ggtgcgtatc tctccagtct gtgttcttta    60
ggcatacatt gctgtatgtg ctttaaatag aatcctacct tatatactgc ttaataacct    120
rtgaccataa gatcaggttc catgtcttca aagattctcc tcatcatttt cacgggtata    180
ggcatagatt acaattgatc cattccccac tttgcacatt tagattgttt tcacttt      237
```

<210> SEQ ID NO 163
<211> LENGTH: 237
<212> TYPE: DNA
<213> ORGANISM: Canis familiaris

<400> SEQUENCE: 163

```
tgcaatgact ctgtttacaa ataaggtcac aatctcaggt accagagctt agggcttcaa    60
cctgtcttgg gggagggtgg gcaggatacc attcagtcca taacagcaga agatcccggt   120
ygtcctcaca gtatggtggg cagtggccag ccctccggac tttcacctcc aggggcagg    180
cggagaagct aaaggggggt ctcatggcct cccagctcct cccttttgccc ctgcaat     237
```

<210> SEQ ID NO 164
<211> LENGTH: 237
<212> TYPE: DNA
<213> ORGANISM: Canis familiaris

<400> SEQUENCE: 164

```
acccacgccc agcatctaag aggccaaccc ctccctgctg tgggctcctg ggcttctcaa    60
ccccccaagga ggggactgca gtccagcgtg ccgacagctg cctccacccc aaggggggcc  120
ratggctggt gagtggagac tgagtgcatg accgactttt ttagccaaga cttttttctta 180
attgttagag atgcaaaact caagcaaatg ggaaactcat ccgctcaagt aaccagc     237
```

<210> SEQ ID NO 165
<211> LENGTH: 237
<212> TYPE: DNA
<213> ORGANISM: Canis familiaris

<400> SEQUENCE: 165

```
gcctcgtggg acagctttct agcactttcc cctttttaag agattgactg caatttctat    60
aataacatca cattagctag aaattaatgt cctcattaag acagcaatta ggcacattag   120
ygcggcaata aaagagaagc ttatgaaata attgctggtt ccgaaatgcc tttaatttag   180
tgttttatat tgcgccatgt tattaatttt ttccctcggc agaagataat aagagaa     237
```

<210> SEQ ID NO 166
<211> LENGTH: 237
<212> TYPE: DNA
<213> ORGANISM: Canis familiaris

<400> SEQUENCE: 166

```
cataaatgcc ccccccacct ctgtgtctgt gcagaaacca aaagtcttgg gcttctatga    60
tccccagtga gtgctaggag caggaccgca atcacagcag cacatcctag aaaggactta  120
rgagccagat actaccatcc tattcactca ggtaatcctc acagtaaacc gcaatggcat  180
aaaaaatatt acctccaggg cccaacggac ggactcttga tctcagggtt gtgagtt     237
```

<210> SEQ ID NO 167
<211> LENGTH: 237
<212> TYPE: DNA
<213> ORGANISM: Canis familiaris

<400> SEQUENCE: 167

```
atgagatatg tctgctcagc cactgtctgg ggccttgtaa ttgaagcctt ataattagca    60
tgaagtcacc agcttggtcc tgctgaaagg gcacagggtg gggtgtgaaa ggaggatggc   120
yaagggctcg tccacaggaa acattttcta aacactagag aggaggcagc caaagagctc   180
ccttcctcat cgcccatgga ccccactgct atgctggcaa ttccccttttt ggttaat     237
```

<210> SEQ ID NO 168
<211> LENGTH: 237
<212> TYPE: DNA

<213> ORGANISM: Canis familiaris

<400> SEQUENCE: 168

| ttcctgtgca gagggacacg tgaaggccct aggtcctcct gggagaaaag atttccctcc | 60 |
| taatgatcca gggactagga tttcattctg aaatggaatg gagaatggca ggtgtggctt | 120 |
| kctggggatt gagaaccaca ggccccagga gattcaggaa aggacagtaa tgccctgctg | 180 |
| ctcaggcccc ggtggaggaa tcatatcctc agctcagcaa caccaccgc cccccta | 237 |

<210> SEQ ID NO 169
<211> LENGTH: 237
<212> TYPE: DNA
<213> ORGANISM: Canis familiaris

<400> SEQUENCE: 169

| acatcggcta aacaaaaaca ggagaatccc attataagac ggttcctgta gtacagatgt | 60 |
| gtctgggtga agcctgggtt gtatcgtggc cccatgtaga gccagcctgg gcagagagct | 120 |
| rgtctaccca ctaagcaact gcaagaggca aagtgcagca ttgatgtcac gaggtccagc | 180 |
| atcaactagg accatcccca tccatgtgag caggctcaca cgtggaatcg cagtgga | 237 |

<210> SEQ ID NO 170
<211> LENGTH: 237
<212> TYPE: DNA
<213> ORGANISM: Canis familiaris

<400> SEQUENCE: 170

| ccgtgcttca caggcgagaa tctgaatgac cgtgatgcca ccacatgtca ccatccccett | 60 |
| ttccactggg aaagggggtcc ttgttgcctt ccagctccag aattgcatcc tcacaatttc | 120 |
| rgaggcccctt cctcctgcta agctctgtgc ttttccagaa agtagagcat aagacaaggg | 180 |
| cttatatgca agtatatttt ttggaaaata tgatcccaga gagcaggagt gagaact | 237 |

<210> SEQ ID NO 171
<211> LENGTH: 237
<212> TYPE: DNA
<213> ORGANISM: Canis familiaris

<400> SEQUENCE: 171

| actccatgaa atggtttatt ttatcctatg aatcgatgtg gagaacaaag gcaaagaaa | 60 |
| tatagaaaaa tattaaattt ccttacaatg tacagcccat tgataatatt ttagacagtg | 120 |
| wgagtgatct tgcttatgga gctcaactgc ctcaatgtta atccttagct aaaggcaaaa | 180 |
| gacaatctta gtttgacatt agcctgaccg cctatgctta ccctaacccc ccgtccc | 237 |

<210> SEQ ID NO 172
<211> LENGTH: 237
<212> TYPE: DNA
<213> ORGANISM: Canis familiaris

<400> SEQUENCE: 172

| aatccaaata ctccatgaaa tggtttattt tatcctatga atcgatgtgg agaacaaagg | 60 |
| caaaagaaat atagaaaaat attaaatttc cttacaatgt acagcccatt gataatattt | 120 |
| kagacagtgt gagtgatctt gcttatggag ctcaactgcc tcaatgttaa tccttagcta | 180 |
| aaggcaaaag acaatcttag tttgacatta gcctgaccgc cttatgctat ccctaac | 237 |

<210> SEQ ID NO 173
<211> LENGTH: 237

<212> TYPE: DNA
<213> ORGANISM: Canis familiaris

<400> SEQUENCE: 173
aggaaaaata tgcttgcttt tgaaggaatc aatttgtggt ttctttttaat gagttatcaa    60
actattaata agcattaatt atttattgtg taaggcaaag tgcttcttaa taggtattct   120
ktccttaact tagaacattc acagattccc aatagcctct agtgcagaag aagtctgccg   180
ctcttctttc ctcctttcac tagtctctcc tatatctgtg atacctccaa tcatagc      237

<210> SEQ ID NO 174
<211> LENGTH: 237
<212> TYPE: DNA
<213> ORGANISM: Canis familiaris

<400> SEQUENCE: 174
cttccatgtt ctgtctccct ttctgatatt tcctactcat tccagaaaat attcttaatg    60
aagcctctga tacggtcttg aggatcctca gagaccatat gtcagtctgt caatgaagca   120
raaatcaaga tgtttggatc cctagtagat atgtaatcaa aatgccatgg gaatacagag   180
aaggggagtc atttgtatca gttagtgtta aaaattatta tcacgctctt gatatta      237

<210> SEQ ID NO 175
<211> LENGTH: 237
<212> TYPE: DNA
<213> ORGANISM: Canis familiaris

<400> SEQUENCE: 175
gagaatactg aagacgtaat gaagttgagt tccacctta taataattcc gttttaccct    60
aaagggaat attcaaaaat gtgacatcgc tctaccagac caccttgcga ctgctctaaa   120
mgattggcag gggcaagaac ttgtgtcact gataggcggg attttttagt cctctctgca   180
aatcattaag aaaatgttcc aacgcaacaa aacaaaatat ggtggcgatc cctgaac      237

<210> SEQ ID NO 176
<211> LENGTH: 237
<212> TYPE: DNA
<213> ORGANISM: Canis familiaris

<400> SEQUENCE: 176
acctgataac accgcctcag tggagaacga gttggcactt caggacagat ttccctgcca    60
gagcctattc ctgtttgaca ctttcatttg aagaaaccca ctcatggttt cttctctcca   120
rggtttaaaa ccgagatcaa gtatatctct ttaataatgt cacattccaa agaatgactc   180
cgataagggg attgttcaag ggcttgggta ttcacataag ggctatcatg cggggag      237

<210> SEQ ID NO 177
<211> LENGTH: 236
<212> TYPE: DNA
<213> ORGANISM: Canis familiaris

<400> SEQUENCE: 177
tcctctagat ctgacctaca tttcaaaaat atatgagtgg gctataacca ggaatgtctt    60
ctcttgctgc cattattcac actgcatttt ctgaagttgt ttttttttt tttttttttt   120
ycccctcggt gactttaatg gccattgagg gaactgtaga cattgggagt ctttatacag   180
ccctagtgaa atggcgagtg ttatcaatag ggtggctgaa tggtacggct ctgggc       236

<210> SEQ ID NO 178

```
<211> LENGTH: 237
<212> TYPE: DNA
<213> ORGANISM: Canis familiaris

<400> SEQUENCE: 178
catctgtgac ccttggattc aaaccaagta ggatgcaaac ctcagaactt ctggcatttc    60
ggatgcactg atctctgcca gcccttgcc ctcttctaat gggatagaag ctgatgatgt    120
ragacaccgc gtgcaccatc tgcccaagac gtcccagttg atgccactca tcctggtttg    180
tgcaaaaaat tctctatttg ccctaattcc accgctcagc aactggaagg acctgag      237

<210> SEQ ID NO 179
<211> LENGTH: 237
<212> TYPE: DNA
<213> ORGANISM: Canis familiaris

<400> SEQUENCE: 179
tcacaatggc ttttttttt taagattta acaggaattt tgtgatcctt tatatgatat    60
gtttcaatga agccttttgg gaaaggttct taatgtgaaa gaattttcac agagaatatc    120
rgaaataaat gtgcaaaagg gagtcgtttt aggattagag atatgcatgg aagagggaaa    180
aagcctactt atattactag aaaataattt tcaatttaga agttatactg aactatt      237

<210> SEQ ID NO 180
<211> LENGTH: 237
<212> TYPE: DNA
<213> ORGANISM: Canis familiaris

<400> SEQUENCE: 180
cccatttttt taggattgat aaactgatca tctaacagat attatataca aaagtcagag    60
aagacacaat agccaaccct gtgtgtaagg aaaatgacag agttggttaa agagaaaaga    120
raaaggaggt acacagagag atgtagaggt cacattaaaa atgaacgttg tccatgtcta    180
tgaaagatgg aagtaattc tatgcctata aggtatgtta taagttaaat taattgt       237

<210> SEQ ID NO 181
<211> LENGTH: 237
<212> TYPE: DNA
<213> ORGANISM: Canis familiaris

<400> SEQUENCE: 181
aacaaaccta ccaaacagga caaaccagtc cggattatat aatatgtaaa tatgccaggg    60
agctggggag catacttgtg ggaggataag ctggagcaat ggttaaatga gctcaatcct    120
yactatactt gaaggtagta gcctcttcat tcacactcca tggctagccc tttgtaacta    180
aaatatggaa aacacaacca atgaagaagt tacatgtatc cctaaaaata ccaccta      237

<210> SEQ ID NO 182
<211> LENGTH: 121
<212> TYPE: DNA
<213> ORGANISM: Canis familiaris

<400> SEQUENCE: 182
cccttggcgt tctaaagtcc agcccctct cttcgcattc tgtgctttct cctgtgtggc    60
rgtctctgtg ctttatctgc acataaacac ttcacaaatt tccgttccag cttagttctc    120
t                                                                    121

<210> SEQ ID NO 183
<211> LENGTH: 237
```

```
<212> TYPE: DNA
<213> ORGANISM: Canis familiaris

<400> SEQUENCE: 183
ttaagtttag aaaaaacaaa ttcaagaaca agcttttat  atttaacatc gatgaatcag        60
aagatacggg gttttttaaa ttattaaact aaaattatta aactggtcct gtttggtata       120
ragttatctt aattatgcta atctggaatc ttaaagcatt tttaaactaa tattttaaga       180
aaccaagttt tagattatt ccaaccttgg gctagaaaag gatgaccttt gtgggcc           237

<210> SEQ ID NO 184
<211> LENGTH: 237
<212> TYPE: DNA
<213> ORGANISM: Canis familiaris

<400> SEQUENCE: 184
tgagccaccc aggtgcccca aacatgatt  agtcttgaaa caaagtgtat cacaataatg        60
attcaattag atgaataaaa tgtagttttt gagaatggta aacactatgt aagagtaaag       120
ytagcctatt tgatcagtaa acctatttaa gtttagaaaa aacaaattca agaacaagct       180
ttttatattt aacatcgatg aatcagaaga tacggggttt tttaaattat taaacta         237

<210> SEQ ID NO 185
<211> LENGTH: 237
<212> TYPE: DNA
<213> ORGANISM: Canis familiaris

<400> SEQUENCE: 185
agatgtcatg ctatgatata tttaaataag ttacagacat gtataatttc catggtatgt        60
tttacattca tataaaaatt aactattcat aaaatataat aaaatgtagt gtttttctta       120
ytgagcttca gtgatcataa tttgtatatt aacttaatga ccagaaataa ttaagtaaag       180
ctagttaaat tcttgggatg ttatggatta tgttatttgg ttggctgttc atgataa         237

<210> SEQ ID NO 186
<211> LENGTH: 120
<212> TYPE: DNA
<213> ORGANISM: Canis familiaris

<400> SEQUENCE: 186
tgttttgaat ttaaggtgtt tttccaggct gagaagaaac gtgagctctt ggaaattatr        60
attaacgtat ctaatgcata taccctagag ggcaaggaaa tttctattca ttccctgtat       120

<210> SEQ ID NO 187
<211> LENGTH: 237
<212> TYPE: DNA
<213> ORGANISM: Canis familiaris

<400> SEQUENCE: 187
cccccaggat ctgtcagtaa tccctgactg cctgcagacc acatggggag agggatccat        60
tcctatgaca gagaatttat actggcttgt gagctgaaca gataccctcag aagatgttca      120 yctgtgagac agagagacat ggtgacaaat acaagtgtca gccaacagca gcaccaagtc      180
caggaatggc tgcctgagct ggatggaacc tcactatcca gagccatcca taggccg         237

<210> SEQ ID NO 188
<211> LENGTH: 121
<212> TYPE: DNA
<213> ORGANISM: Canis familiaris
```

<400> SEQUENCE: 188
agagccaacg ctggatctca gggagaatct agaaggccag ctgaccagaa aaccaactgg      60
rcagacagaa gctgggagca gcgcctgtgg aggcaggcac gagaggcccc ggtgcagccg     120
c                                                                    121

<210> SEQ ID NO 189
<211> LENGTH: 237
<212> TYPE: DNA
<213> ORGANISM: Canis familiaris

<400> SEQUENCE: 189
ctgggtggct gttggagaga gtgtgttgtg ttgttcccag ggttagtcct aggaatggta      60
gagcctgtca agttctccct gaaagtcacg tcactcccca cttcagcagg cccagcctgt     120
sttgtatccc tgcagcactg cctcaggatc cttgctctgc agtgatcaga gtcatctgat     180
aagcctgtcc ctgtctaggc tgatattaat ttcaggttgt caccctctat gcctctt        237

<210> SEQ ID NO 190
<211> LENGTH: 237
<212> TYPE: DNA
<213> ORGANISM: Canis familiaris

<400> SEQUENCE: 190
ggccttatga agacttctct gatctgttga tctgatgtac ccagattctg aatccctaat      60
tagactcaat taggacactc ctggaggtga ctactgcttt cttagacttt gtcactcaaa     120
yatctaatac attcgacttt gacccatgga tttattgagt tcctcttgca cacccagttc     180
agtagatgtg gtccactatt ttggtgcatc gactgctcta gaatttagct tttggaa        237

<210> SEQ ID NO 191
<211> LENGTH: 237
<212> TYPE: DNA
<213> ORGANISM: Canis familiaris

<400> SEQUENCE: 191
atgacacatg caagtgctca ataacgttag acactgtact gttaattaaa ggtctatcgc      60
ccctttaaac aaaatgtcca gaatgttcat gttcaccaaa agtgaaaggc attcatgtct     120
mtgtttctgt tgagttcact gtcacctttg tgcctagaaa ggagaagaca cactggtttt     180
tcctcctcta gagaagtgca gatttgtata ggtgaggagt atacataggt tgtgggc        237

<210> SEQ ID NO 192
<211> LENGTH: 237
<212> TYPE: DNA
<213> ORGANISM: Canis familiaris

<400> SEQUENCE: 192
ctttgggaat gaggcctgtc ccgctagcct gcttcattta ctctcatgat tcttggcaaa      60
gttcttataa gtcacgttca aattatcagg cttcattcct agtctgagca gacttgtccc     120
rtctcccagc ctgtggatgt tcaagaagcg caacttggtt ttatgtttat taatcaaaag     180
ccctttagcc tctgatgaac ctctgagggt ggctttaaag ccccgcgcct gctctga        237

<210> SEQ ID NO 193
<211> LENGTH: 237
<212> TYPE: DNA
<213> ORGANISM: Canis familiaris

<400> SEQUENCE: 193

```
aaagaaaaaa gtaagggtca aaacactagc aaaattaaat taaaaaaata agaaaaacaa      60
gtcacacttt ttttttttt ttggtcattt gggaaaagca caatatttg cttgattact      120
yttcctcact tttcaactag taatatagat tgcatgaaaa ataaacaaaa caagtaaact      180
ttaaatgttt gctggtgtag aggtgaataa gaacaatcca tggattttgc aatcaca       237
```

<210> SEQ ID NO 194
<211> LENGTH: 237
<212> TYPE: DNA
<213> ORGANISM: Canis familiaris

<400> SEQUENCE: 194

```
tctagctcca gtctccttta ttcagtgcca ccttcatttt tccattccag ccaaattagt      60
gttttcattc tctcaagcat tttcatctat gtacttcctg aaccctcttc atggaagaca      120
ycctctactc ttcagcatat tactatccca gcatccctta ccctgatagt ttaacttgat      180
tctttatcta cctgattcag taatatttct ctattcttat catattcagc aatgttc       237
```

<210> SEQ ID NO 195
<211> LENGTH: 237
<212> TYPE: DNA
<213> ORGANISM: Canis familiaris

<400> SEQUENCE: 195

```
tccctactg aaacaaatt cccccatctt caccctacca tggggatttt acatttgtta      60
ccagatttgg ggcaaactca tcctatttc ccttcagtgt ggagaagaga ttttggaaag      120
yagaccatgc aaatctctaa gctcacaata aactgaattg gagaggcata aaacctgaca      180
ggaaaaaaag gtgtgaactt gatctttagc ttgctgttct ggtttaatag gtttctg       237
```

<210> SEQ ID NO 196
<211> LENGTH: 237
<212> TYPE: DNA
<213> ORGANISM: Canis familiaris

<400> SEQUENCE: 196

```
aagggtgaac tgacttttag tcagaatgtt tattttaac agattataaa atagccacct      60
atttagatgg ataaatgtat tgtgattatg gtgttgttta taaaagaat tttcaggatt      120
ktccacaaaa cttaatgtta gtattagtta ttaagagtac aatggaatat cattcagcca      180
tataaaagaa tgaaatcttg ctatttgcaa tgacatagat ggagctagag agtataa       237
```

<210> SEQ ID NO 197
<211> LENGTH: 237
<212> TYPE: DNA
<213> ORGANISM: Canis familiaris

<400> SEQUENCE: 197

```
atgagtttgc aattctagcc ggtgcatgag gacttctccc tttcccgagc cctcccggaa      60
agtttggcca gatccccagc ccaaatggca gcatgtgctc gggaagatga ttaatgttag      120
ygcgaggctc cagagaatct ctcagggccc ttttgtttat taaatagaaa aattcatgtt      180
taaatataat gtcaagggga tgacacggac caacatgatc caagacagac tgccggc       237
```

<210> SEQ ID NO 198
<211> LENGTH: 237
<212> TYPE: DNA

```
<213> ORGANISM: Canis familiaris

<400> SEQUENCE: 198
ctcccactaa ctagcaggta tacatagtta aatttctcta acacagagca atactacctt    60
ccacaccaga aaatggcaaa ggctaaatat aaccacagat ctcaaggcta ctgaactaca   120
ygcaggtaat agattatatt taaaacatat cagatgaatc tgcactaata ctgggggcct   180
ataaaacttt ctaacataca gtagtataag caggatttcc aatcagtgag aaaagga     237

<210> SEQ ID NO 199
<211> LENGTH: 121
<212> TYPE: DNA
<213> ORGANISM: Canis familiaris

<400> SEQUENCE: 199
atgtgtaatt tacaaagagt tcatatatta ctttatcagt taagcttttg taattccata    60
mtctatacta attttaaaga ggagtgattc cttcttgcaa ttagtttatt gcctccgtat   120
g                                                                  121

<210> SEQ ID NO 200
<211> LENGTH: 237
<212> TYPE: DNA
<213> ORGANISM: Canis familiaris

<400> SEQUENCE: 200
atatatcatt ccacctatag taattttcac taatctgccc atttattccc tagtgcatac    60
ccttaatata aatctgcaac aagaatataa cttttctaaa aaaaaaaaaa aagtgtacat   120
rcattagtga tgtgtgtgac caactaaata ccagtgtata agcccatgcc catatttcat   180
tttcacgaat tatgtttgct gcataaataa gacttgtagc ttttttaaact tacctct     237

<210> SEQ ID NO 201
<211> LENGTH: 237
<212> TYPE: DNA
<213> ORGANISM: Canis familiaris

<400> SEQUENCE: 201
gtgtcagtat gttaagccac tagtgcactg ttaactgctg ccatgactaa gaaaaaacac    60
agaagctgct gctgctacta tgtcactctt gtcattttta aggtgaatcc tcatatgaat   120
ragagggagt acatgcttaa tggtcagagt gacagctttt gcttcatggc gagccatcga   180
aaccccacaa atctctttgc cccaacagat tcttcacctt tcttctccag aaatgaa     237

<210> SEQ ID NO 202
<211> LENGTH: 237
<212> TYPE: DNA
<213> ORGANISM: Canis familiaris

<400> SEQUENCE: 202
ttatggatct tacaatctag tgattgaaac acaaattaga tttgggcttg tctataaaac    60
tgggatattt tctgatattg aatgaatac tgggacagtc ccttaattat ggtttcatga   120
rtgattagtc ttatgataca tagtttatgt gtaattgcta tttctaatcc aaaataaatt   180
ggacctttcg tttagattaa acatggagtc tttgatgtaa ataccgtaga aggagtc     237

<210> SEQ ID NO 203
<211> LENGTH: 237
<212> TYPE: DNA
<213> ORGANISM: Canis familiaris
```

<400> SEQUENCE: 203

```
tgctgtctaa acaggagctt gaaggatgag taggaagaga tttcagatag aacagctgtg    60
ctggagcaaa gagggtctga gggagcatgg tatatttagt ggacggcagc tagttgcctg   120
scactggagc atggcgggtg gggagtaaga ggtgggagag aaaactcaat gacaggcaga   180
agccagacca tgaagggcct cacatcctgt gcagaggagt tttgattttt atctcct      237
```

<210> SEQ ID NO 204
<211> LENGTH: 237
<212> TYPE: DNA
<213> ORGANISM: Canis familiaris

<400> SEQUENCE: 204

```
tttgtccttg aaagaagttt ttctctttct ttcccatttt cttttcttc ctatttgctt    60 aattatctgt tgccagataa ttcacaccta agttcataga ggaccaatgt cacagatatt   120
ytcttaaaca aaactggctt tgtaacaata aaatttgtct gtttaaaatg taactaatat   180
cggagatatt tacctaagga agtatttgta aatagtatct agaaatgcaa gaaaata      237
```

<210> SEQ ID NO 205
<211> LENGTH: 237
<212> TYPE: DNA
<213> ORGANISM: Canis familiaris

<400> SEQUENCE: 205

```
gccaacgcta agattcatat gtctattttt actcaacacc aaataaaggt accatttcta    60
atccaagaac ttcactctgc tgtcttctag cacattggca ttttccacag gcatttcttg   120
ytttacttga tgtattttt tccagttttt cttaatatga tatctgagaa attttttgc    180 taagtattga ttcaaaaatt taaaattaag gttaaattgt ggctaatcag catactg      237
```

<210> SEQ ID NO 206
<211> LENGTH: 236
<212> TYPE: DNA
<213> ORGANISM: Canis familiaris

<400> SEQUENCE: 206

```
ttttatcatg ccaggaaatt cttggaatgt agccactgtc tgatatttat ggttccataa    60
gcatttgact ctgaaaagtc tctaattctg gaaaacggcc actgatcagt tgttaatgca   120
yagcagtagg aaaaaagtca ccccttaaaa ggagagagag gacaaaagga acagcttgtg   180
aggctaaaag tatgacaagt atgacgtcta cctatacagg aagtgtatat gcatct       236
```

<210> SEQ ID NO 207
<211> LENGTH: 121
<212> TYPE: DNA
<213> ORGANISM: Canis familiaris

<400> SEQUENCE: 207

```
gctaataaag gatcaacctc tgggctgcag aataacctaa tctattcata cctcagtgac    60
rtcctgaatt agaaccgggg gctgatgaac tccaatgcac cagccaacca accagagtta   120
g                                                                   121
```

<210> SEQ ID NO 208
<211> LENGTH: 237
<212> TYPE: DNA
<213> ORGANISM: Canis familiaris -continued

<400> SEQUENCE: 208
tgaatgactt tttcaacccg aatttcatg acattttgt catgacattt ctcatataac      60
ctaccgcatg taaagcaaga tctcctattg gattctgtct tatttttgt catcttccaa     120 yggtcttagg caaatgaagt ttaagtagta agattatatg cctcctccca ctttggtgca    180
tgcacacaga tgcaggaaca tgcttagtaa ctaatctttg tgggacatag gaatgcc       237

<210> SEQ ID NO 209
<211> LENGTH: 237
<212> TYPE: DNA
<213> ORGANISM: Canis familiaris

<400> SEQUENCE: 209
gccagctcta atgagtttgt ttccaagcgg tgcttccaga aattgttagt ggttggtagt     60
tgcaatgggt tttgaaatta gaggacatca cagcagagta gaatggtttg gaacagggga   120
rtatgattag gattaatgag atgaaagaaa attctggcta gagggctaga agagccatgg   180
aagaaaatat acactaaccc tttggagtgt tcctccaagt gaagatttgc aacattt       237

<210> SEQ ID NO 210
<211> LENGTH: 237
<212> TYPE: DNA
<213> ORGANISM: Canis familiaris

<400> SEQUENCE: 210
acgagaagca agattgccat accgttcctg gtaccgggcc atgacgttga ccttcaaaag    60
ccctgaaacg gctgttttcc tggctgctgt gagctgtgga actcaggagt aggtatttcc   120
ygaaaacatt taacatccca tagcaaaggt gttggaggcg tcgtctccat tgtcgtttct   180
cccgggctgt ggttggcctt tctgcgtgag tgcttctccc cgctgcgggc tggctct      237

<210> SEQ ID NO 211
<211> LENGTH: 237
<212> TYPE: DNA
<213> ORGANISM: Canis familiaris

<400> SEQUENCE: 211
taggaaaaaa catctggcct ctgactcgga tccagtcatc ccagcctcat tcacacccac    60
ccatcagctc tcagagaacc ttctgagact tcgataaata gctgagccct taaaatgaca   120
rcattgattt ggcatggttt gggcaataac ttctggctgc tgtgattttt aggttttgaa   180
tatttagttt ctggaaactc tgatagaatg aataactta tatgtttatt taattct       237

<210> SEQ ID NO 212
<211> LENGTH: 237
<212> TYPE: DNA
<213> ORGANISM: Canis familiaris

<400> SEQUENCE: 212
gtctactgaa gccagacagt tggttcatta gattaattaa agtgcaaact aaccccaatc    60
tggtgttttg ataacggcca cagggctctt gaagttggaa tcggccagca tttgacagtg   120
ytctcattaa agccacagtg gaattgcctc tatggtttct cctaaacttt tgaatttacc   180
ttataacaaa gaagtggact ttgagcatcc ctgattgttt tttcagtgtt aactgct       237

<210> SEQ ID NO 213
<211> LENGTH: 237
<212> TYPE: DNA

<400> SEQUENCE: 213

```
tgttgctttc ctgcacacaa gcagttgaac cagagtaggg aggaatcatt tttaggaatg        60
tgttattatt attttttagg aatgcacaaa acccatgcca aaaagcccat ccacgtctaa       120
ygtccttgaa cctctccttc actaccaatt gtattctttt atgttcccaa tcaactggct       180
ggcctgaaat agatttctcc taccaagaaa tgtagataaa atatttatt tctggaa           237
```

<210> SEQ ID NO 214
<211> LENGTH: 237
<212> TYPE: DNA
<213> ORGANISM: Canis familiaris

<400> SEQUENCE: 214

```
gtctcagccc tctattccag aaggtaggac tggccctggg cctgtctacg aggtggtggc        60
tgcgagccct caaggcctgg cattgtcaaa gttctgacaa ccttccccac ctatggcagc       120
kcagtgttag acgctccagg ctgagggttg atgcacactt tttcggcttc caaagtgtgg       180
ccttctcctc agggcttccc atggggtcca caggctggca gcaacctctt ggagaaa          237
```

<210> SEQ ID NO 215
<211> LENGTH: 237
<212> TYPE: DNA
<213> ORGANISM: Canis familiaris

<400> SEQUENCE: 215

```
cagctgtgtc atggaaatgg cactttaaaa attcatatga atcttaacag taaagcacaa        60
gactttggag atatttctcc tgttgaatag ctgcttgggg atgtgccaca gatctgtaga       120
rgtcagcatt cactctaagt tcccgggaac catgagacag cagcaaccat ggccaccaca       180
gcaacacagc aggtgcccat aagcccattt tacagatgga gaaattgggt ccagaga          237
```

<210> SEQ ID NO 216
<211> LENGTH: 237
<212> TYPE: DNA
<213> ORGANISM: Canis familiaris

<400> SEQUENCE: 216

```
cctctggctc cccagaacct cagagcttag gggatgtagt ggttgtaatc ctggatccct        60
ctgtggggtg gcaggtctgg agtggtgagc tactgtgagg gaactggggt aactgtgacc       120
ygagaagaaa ggagcgaggg agtgagtgtg tgtctgtgaa atatgcctct gtgtgtataa       180
acagggctgg agggctcagt gccccccact cccaaagatc cacctgttac atccccg          237
```

<210> SEQ ID NO 217
<211> LENGTH: 237
<212> TYPE: DNA
<213> ORGANISM: Canis familiaris

<400> SEQUENCE: 217

```
ttcttctctt gtgactggtc actaaagaca gagatttcag gagagctgac tttggtagga        60
attctcaccc ttttctggcc taggcctata atttttatac cgacagctgg agtcccagat       120
rgaagagacc ttaaactctt tggactatga agaacctgtt ttttctctct ctctcttttt       180
tttcccctta aaacaaaaat ttattttcct caggcctcat cctgtaccca gtcttgt          237
```

<210> SEQ ID NO 218
<211> LENGTH: 237
<212> TYPE: DNA

<213> ORGANISM: Canis familiaris

<400> SEQUENCE: 218

| agctccaatt tagtcatata ctaaagaatc aggtcatact ctaggcagac tctaggcagt | 60 |
| tagcacatga aaccagttca catgctttat catcatcctt tttgttctca aaacagccaa | 120 |
| maacagttct gtataagata tttcacatgt ttaattcttt cagttcttct agcaagcagg | 180 |
| aagcttagaa caagatttta gtatttggtt tagataacaa ttgcaaatag gagcacc | 237 |

<210> SEQ ID NO 219
<211> LENGTH: 237
<212> TYPE: DNA
<213> ORGANISM: Canis familiaris

<400> SEQUENCE: 219

| gacttttcta gagagaccat ggaagatgca tgtggggcct gcccaggctg ccacagggga | 60 |
| aaggagccgg gaggagggag ctgtcaggcc acttcctctg atggcccctc agcagcagga | 120 |
| rgagagcatt tcctcaccag atcccactca acactgccca cggtcccccT gtggacttca | 180 |
| gaactgactc agaactaacc tgactgactg cgtatgattt gtctttttag gaggacc | 237 |

<210> SEQ ID NO 220
<211> LENGTH: 237
<212> TYPE: DNA
<213> ORGANISM: Canis familiaris

<400> SEQUENCE: 220

| cccgcgccag gccggtcctc tcctcccagc tcctcctctc ccgctcgcag tcagggcagc | 60 |
| cagggagggg agaaattctc atctcaaaac tagtaagaca aggccccgca gcgggtctgc | 120 |
| rgcgcggagg cggctgcctc tcctggtcca tactggacac agctgaccac atttcaacag | 180 |
| gtaagaatca ttttaaatat tacccttaaa ccaaaaaaag ttcttctttt gcttcta | 237 |

<210> SEQ ID NO 221
<211> LENGTH: 237
<212> TYPE: DNA
<213> ORGANISM: Canis familiaris

<400> SEQUENCE: 221

| cagtattccg attcttctat ttgctaattt taaagtgcag atctaagagg acaaccttat | 60 |
| tattatttcc atggtcttag agatcatctt actgttgccc cacaatgtcc atgcttcccg | 120 |
| kgaaagatgt gtgtatccag actcaaagtg aatctaatag ggaaggaaga ctgagaattc | 180 |
| tattagtaag caacccgtat ttaacaacat ggcccagttt gaagatttgc agaaaca | 237 |

<210> SEQ ID NO 222
<211> LENGTH: 237
<212> TYPE: DNA
<213> ORGANISM: Canis familiaris

<400> SEQUENCE: 222

| tcaggagtga gcctgtacgt tatcctgact actgattccc ttgcaccaaa aaagcaacgg | 60 |
| gagcataagg gcaagatatg acctttagct aaagggttgc aagttatatt actagtcgtc | 120 |
| rctgctcaaa cacccagcac cagaccctgc atagaataca gaaaagagtc ctcaccatca | 180 |
| agccactacc acctgaagca tgaaggagag aacaaggaga gatcacctcc taagtgt | 237 |

<210> SEQ ID NO 223
<211> LENGTH: 237

```
<212> TYPE: DNA
<213> ORGANISM: Canis familiaris

<400> SEQUENCE: 223
ctgacctctg ctctagtcaa ttgctctgaa agtacagtcc tctgatccta gactcgaacc    60
ctctcaagca taacagttcc atctactatt cactaatcca tttatttaac tgggagtgtt   120
statgctttg gctctgggat atgaaggaaa ggacattgtg cccgaacata taggaaagtt   180
attgtttaag gagatataca gggaaataat tttaaaacac catggtaatc ttttcct      237

<210> SEQ ID NO 224
<211> LENGTH: 237
<212> TYPE: DNA
<213> ORGANISM: Canis familiaris

<400> SEQUENCE: 224
cgttttcctt ataaattttt agaaaacaga acaggaaaaa aaaaaaaaga aagaaaacag    60
aacagagaac aaaccaacat gtcttgatgc ctccaggaac cagttttctc atagccttag   120
rggaaacaat ttacaaaata tctgaaaagc ctgcagatat cttagatcca agattccaag   180
gcataaaaat gtaagtgatc atgtactacg tattactgaa atacagaaag caaccaa      237

<210> SEQ ID NO 225
<211> LENGTH: 237
<212> TYPE: DNA
<213> ORGANISM: Canis familiaris

<400> SEQUENCE: 225
agcaccttga gaatggtgta gtggaaagaa agttgacttt tagtaactat gcatttgtct    60
cgttaatgca gtttctcacc tgctttgaga taatgggaaa tggaactaac aggtagtggt   120
racacagatg atggacaata taaagatttg agatatatat aaaaaaaatt tgatcattat   180
atgtacactt tgctagtttt gctctacatt ttttatccac acaaaaagta atttgca      237

<210> SEQ ID NO 226
<211> LENGTH: 237
<212> TYPE: DNA
<213> ORGANISM: Canis familiaris

<400> SEQUENCE: 226
taagtagcct ttagtgcaag gaaaagaaaa aggcagtaag gatgaacctt tgtttcaaag    60
gtattaggag tcatttaagg aatttcaaaa aaaaaaaaaa gaagtgacat gattttgaac   120
raagaagtga ctgtcagtac tataaagagc acattgcctc aaggagaaac tgaagttaga   180
gaagccaaat tggctgataa aaatctaggc cggagatgca acacctaaa tgaaaac       237

<210> SEQ ID NO 227
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 227
gttaccctgc agctgagagt                                                20

<210> SEQ ID NO 228
<211> LENGTH: 20
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 228
atggcgagca tcacagtatc                                              20

<210> SEQ ID NO 229
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 229
gttttcccag tcacgacgtt accctgcagc tgagagt                           37

<210> SEQ ID NO 230
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 230
gttttcccag tcacgac                                                 17

<210> SEQ ID NO 231
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 231
gttaccctgc agctgagag                                               19

<210> SEQ ID NO 232
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 232
agggtcgtac tgtacttggg                                              20

<210> SEQ ID NO 233
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 233
cgtctggatg ggaagtttct c                                            21

<210> SEQ ID NO 234
<211> LENGTH: 19
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 234
ttgtcggact tcagggagg                                                  19

<210> SEQ ID NO 235
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 235
ccggcggtgg gactccccgc                                                 20

<210> SEQ ID NO 236
<211> LENGTH: 989
<212> TYPE: DNA
<213> ORGANISM: Canis familiaris

<400> SEQUENCE: 236
tcagcaccca ggaggcagtc atcacttacc agccttatct tattcaaccc caggacctca      60
gggaccatgt aaacgacatg gggtttgaag ctgtcatcaa gaacagagtg gcacccgtaa     120
gcctgggacc cattgatatt gggcggttac agaggaccaa cccaaagatg cctttgactt     180
ctgataacca gaatctcaat aactctgaga ccttgggcca tcagggagc catgtggtta      240 ccctgcagct gagagtcgac ggaatgcact gtcagtcttg tgtcctgaac attgaagaga     300
atataggcca actccccggg gttcagaatg tgcaagtgtc cttggagaac agaacggccc     360
aagtacagta cgacccttct tgtgtcaccg caggggccct gcagagggcc attgaagctc     420
tcccaccagg gaactttaaa gtttctcttc ctgccgcagc agcaggaagt gagacaggta     480
acaggttttc ggcatgtgcc gcccccgccc aagaaccccc ggcaccgggc aggtgcgata     540
ctgtgatgct cgccattgtg ggcatgacct gtgcatcctg cgtccagtcg atcgaaggcc     600
tgatctccca gagggaaggg gtgcagcaaa tatctgtctc tctggctgaa gggaccgcag     660
tggttctcta tgatccctct ataattggcc cggaagaact ccgagctgcc gtcgaggaga     720
tgggatttga gacttcagtc ctctctggta tgtagtggca ccccgggtct tctcctctct     780
ccttgggcct tacggcagag tgcctgcagg gtggcacagg ggagccaccc cagctgctcg     840
cctgtcgggt tggccaagtc ccgcagcgtt ccctgtgtg ttgaatgtgt ccgggtggga     900
gaaagagaac tttctggtgt gtagattttg cctctcatgg ggctgggact acattgctaa     960
attctttgtt gttgttattt ttttaact                                        989

<210> SEQ ID NO 237
<211> LENGTH: 995
<212> TYPE: DNA
<213> ORGANISM: Canis familiaris

<400> SEQUENCE: 237
tcagcaccca ggaggcagtc atcacttacc agccttatct tattcaaccc caggacctca      60
gggaccatgt aaacgacatg gggtttgaag ctgtcatcaa gaacagagtg gcacccgtaa     120
gcctgggacc cattgatatt gggcggttac agaggaccaa cccaaagatg cctttgactt     180
ctgataacca gaatctcaat aactctgaga ccttgggcca tcagggagc catgtggtta      240 ccctgcagct gagagtcgac ggaatgcact gtcagtcttg tgtcctgaac attgaagaga     300

```
atataggcca actccccggg gttcagaatg tgcaagtgtc cttggagaac agaacggccc    360
aagtacagta cgacccttct tgtgtcaccg caggggccct gcagagggcc attgaagctc    420
tcccaccagg gaactttaaa gtttctcttc ctgccgcagc agcaggaagt gagacaggta    480
acaggttttc ggcatgtgcc gccccgccc ccgccccaag aaccccggca ccgggcaggt     540
gcgatactgt gatgctcgcc attgtgggca tgacctgtgc atcctgcgtc cagtcgatcg    600
aaggcctgat ctcccagagg aaggggtgc agcaaatatc tgtctctctg ctgaaggga     660 ccgcagtggt tctctatgat ccctctataa ttggcccgga agaactccga gctgccgtcg    720
aggagatggg atttgagact tcagtcctct ctggtatgta gtggcacccc gggtcttctc    780
ctctctcctt gggccttacg gcagagtgcc tgcagggtgg cacaggggag ccaccccagc    840
tgctcgcctg tcgggttggc caagtcccgc agcgtttccc tgtgtgttga atgtgtccgg    900
gtgggagaaa gagaactttc tggtgtgtag attttgcctc tcatggggct gggactacat    960
tgctaaattc tttgttgttg ttatttttttt taact                              995

<210> SEQ ID NO 238
<211> LENGTH: 1001
<212> TYPE: DNA
<213> ORGANISM: Canis familiaris

<400> SEQUENCE: 238
tcagcaccca ggaggcagtc atcacttacc agccttatct tattcaaccc caggacctca     60
gggaccatgt aaacgacatg gggtttgaag ctgtcatcaa gaacagagtg cacccgtaa    120 gcctgggacc cattgatatt gggcggttac agaggaccaa cccaaagatg cctttgactt    180
ctgataacca gaatctcaat aactctgaga ccttgggcca tcaagggagc catgtggtta    240
ccctgcagct gagagtcgac ggaatgcact gtcagtcttg tgtcctgaac attgaagaga    300
atataggcca actccccggg gttcagaatg tgcaagtgtc cttggagaac agaacggccc    360
aagtacagta cgacccttct tgtgtcaccg caggggccct gcagagggcc attgaagctc    420
tcccaccagg gaactttaaa gtttctcttc ctgccgcagc agcaggaagt gagacaggta    480
acaggttttc ggcatgtgcc gccccgccc ccgccccgc cccaagaacc ccggcaccgg     540
gcaggtgcga tactgtgatg ctcgccattg tgggcatgac ctgtgcatcc tgcgtccagt    600
cgatcgaagg cctgatctcc cagagggaag ggtgcagca aatatctgtc tctctggctg     660
aagggaccgc agtggttctc tatgatccct ctataattgg cccggaagaa ctccgagctg    720
ccgtcgagga gatgggattt gagacttcag tcctctctgg tatgtagtgg caccccgggt    780
cttctcctct ctccttgggc cttacggcag agtgcctgca gggtggcaca ggggagccac    840
cccagctgct cgcctgtcgg gttggccaag tcccgcagcg tttccctgtg tgttgaatgt    900
gtccgggtgg gagaaagaga actttctggt gtgtagattt tgcctctcat ggggctggga    960
ctacattgct aaattctttg ttgttgttat ttttttttaac t                      1001

<210> SEQ ID NO 239
<211> LENGTH: 499
<212> TYPE: DNA
<213> ORGANISM: Canis familiaris

<400> SEQUENCE: 239
tcagcaccca ggaggcagtc atcacttacc agccttatct tattcaaccc caggacctca     60
gggaccatgt aaacgacatg gggtttgaag ctgtcatcaa gaacagagtg cacccgtaa    120
```

```
gcctgggacc cattgatatt gggcggttac agaggaccaa cccaaagatg cctttgactt      180
ctgataacca gaatctcaat aactctgaga ccttgggcca tcaagggagc catgtggtta      240
ccctgcagct gagagtcgac ggaatgcact gtcagtcttg tgtcctgaac attgaagaga      300
atataggcca actccccggg gttcagaatg tgcaagtgtc cttggagaac agaacggccc      360
aagtacagta cgacccttct tgtgtcaccg caggggccct gcagagggcc attgaagctc      420
tcccaccagg gaactttaaa gtttctcttc ctgccgcagc agcaggaagt gagacaggta      480
acaggttttc ggcatgtgc                                                   499
```

<210> SEQ ID NO 240
<211> LENGTH: 33
<212> TYPE: DNA
<213> ORGANISM: Canis familiaris
<220> FEATURE:
<221> NAME/KEY: CDS
<222> LOCATION: (1)..(33)

<400> SEQUENCE: 240

```
tgt gcc gcc ccc gcc ccc gcc ccc gcc cca aga                            33
Cys Ala Ala Pro Ala Pro Ala Pro Ala Pro Arg
1               5                  10
```

<210> SEQ ID NO 241
<211> LENGTH: 11
<212> TYPE: PRT
<213> ORGANISM: Canis familiaris

<400> SEQUENCE: 241

```
Cys Ala Ala Pro Ala Pro Ala Pro Ala Pro Arg
1               5                  10
```

<210> SEQ ID NO 242
<211> LENGTH: 27
<212> TYPE: DNA
<213> ORGANISM: Canis familiaris

<400> SEQUENCE: 242

```
tgtgccgccc ccgccccgc cccaaga                                           27
```

<210> SEQ ID NO 243
<211> LENGTH: 21
<212> TYPE: DNA
<213> ORGANISM: Canis familiaris

<400> SEQUENCE: 243

```
tgtgccgccc ccgccccaag a                                                21
```

<210> SEQ ID NO 244
<211> LENGTH: 5
<212> TYPE: PRT
<213> ORGANISM: Canis familiaris
<220> FEATURE:
<221> NAME/KEY: MOD_RES
<222> LOCATION: (3)..(3)
<223> OTHER INFORMATION: Arg or Gln

<400> SEQUENCE: 244

```
Ser Pro Xaa Ala Thr
1               5
```

<210> SEQ ID NO 245
<211> LENGTH: 15
<212> TYPE: DNA

```
<213> ORGANISM: Canis familiaris
<220> FEATURE:
<221> NAME/KEY: CDS
<222> LOCATION: (1)..(15)

<400> SEQUENCE: 245 tcc ccg crg gcc acg                                              15
Ser Pro Xaa Ala Thr
1               5

<210> SEQ ID NO 246
<211> LENGTH: 24
<212> TYPE: DNA
<213> ORGANISM: Canis familiaris

<400> SEQUENCE: 246
cgcccccgcc cccgccccg cccc                                        24

<210> SEQ ID NO 247
<211> LENGTH: 18
<212> TYPE: DNA
<213> ORGANISM: Canis familiaris

<400> SEQUENCE: 247
cgcccccgcc cccgcccc                                              18

<210> SEQ ID NO 248
<211> LENGTH: 12
<212> TYPE: DNA
<213> ORGANISM: Canis familiaris

<400> SEQUENCE: 248
cgcccccgcc cc                                                    12
```

GENETIC TEST FOR LIVER COPPER ACCUMULATION IN DOGS

CROSS REFERENCE TO RELATED APPLICATIONS

This application is a divisional of and claims priority to U.S. patent application Ser. No. 16/181,516, filed on Nov. 6, 2018, which is a divisional of U.S. patent application Ser. No. 14/363,751, filed Jun. 6, 2014, which is a national phase application under 35 U.S.C. § 371 of International Application No. PCT/GB2012/053038, filed Dec. 6, 2012, which claims the benefit of Great Britain Application No. 1120989.7, filed Dec. 6, 2011, all of which applications are incorporated herein by reference in their entireties.

SEQUENCE LISTING

The specification incorporates by reference the Sequence Listing submitted herewith via EFS on Jun. 28, 2021. Pursuant to 37 C.F.R. § 1.52(e)(5), the Sequence Listing text file, identified as 069269_0466_SL.txt, is 85,750 bytes and was created on Jun. 28, 2021. The Sequence Listing, electronically filed herewith, does not extend beyond the scope of the specification and thus does not contain new matter.

FIELD OF THE INVENTION

The invention relates to a method of determining the susceptibility of a dog to, or the likelihood that a dog is protected from, liver copper accumulation and copper-associated liver disease.

BACKGROUND OF THE INVENTION

Copper is an important trace mineral for a number of metabolic processes within the body and, as such, is an essential part of the diet. Once absorbed through the gut, copper is mainly stored in the liver although it can also be found in other tissues such as bone marrow, muscle and spleen. As well as storing copper, the liver plays a central role in coordinating the transport and excretion of copper via ceruloplasmin and the bile salts respectively. Generally, deficiencies of copper are a more common issue that toxicities. However, toxicities do occur and can have serious implications for an affected animal.

Although liver diseases are uncommon in dogs, one of its most common forms is chronic hepatitis (CH). CH is a histologic diagnosis, characterised by the presence of fibrosis, inflammation, and hepatocellular apoptosis and necrosis. Cirrhosis can result as the end stage of the disease. One of the causes of CH is hepatic copper accumulation.

Hepatic copper accumulation can result from increased uptake of copper, a primary metabolic defect in hepatic copper metabolism, or from altered biliary excretion of copper. In the latter case, copper toxicity is secondary to hepatic inflammation, fibrosis, and cholestasis, although it is unclear to what extent this occurs in the dog. In secondary copper storage disease, copper accumulation is mainly restricted to periportal parenchyma and hepatic copper concentrations are lower than accumulation in familial storage diseases. Whilst, the nature of the initiating factor(s) and of the sensitizing antigen is unknown, immunological abnormalities and morphologic features observed in primary biliary cirrhosis are concurrent with an immune mediated mechanism.

The small intestine is recognized as the main site of dietary copper absorption in mammals. Transport from the intestinal lumen into intestinal mucosa is a carrier-mediated process involving a saturable transport component. Once in mucosal cells, approximately 80% of the newly absorbed copper is in the cytosol, mainly bound to metallothioneins (MT). These are low molecular weight inducible proteins with many functions including homeostasis, storage, transport and detoxification of metals. After passage through the enterocytes, copper enters the portal circulation where it is bound to carrier proteins peptides and amino acids and is transported to the liver with lesser amounts entering the kidney. In most mammals, copper is excreted easily, and the main route of excretion of copper is the bile.

Dogs with excessive hepatic copper accumulation are typically treated with D-penicillamine, a potent copper chelator. Ultimately however, the most successful treatment available for dogs with CH is liver transplantation.

The genetic basis for hepatic copper accumulation is unknown. This is made difficult by the fact that copper is involved in numerous different biological pathways, each of which is highly complex and involves a large number of genes.

WO 2009/044152 A2 discloses a method of determining the susceptibility of a dog to liver copper accumulation comprising detecting the presence or absence of (a) a polymorphism in the GOLGAS, ATP7a or UBLS gene of the dog that is indicative of susceptibility to liver copper accumulation and/or (b) a polymorphism in linkage disequilibrium with a said polymorphism (a), and thereby determining the susceptibility of the dog to liver copper accumulation.

WO 2010/038032 A1 and WO 2010/116137 A1 disclose further polymorphisms for use in a method of determining the susceptibility of a dog to liver copper accumulation. They also disclose polymorphisms for use in a method of determining the likelihood that a dog is protected from liver copper accumulation.

SUMMARY OF THE INVENTION

The inventors have discovered a number of polymorphisms in the genome of the dog that are associated with susceptibility to liver copper accumulation. They have also discovered polymorphisms in the genome of the dog that are associated with protection from liver copper accumulation. The discovery of these polymorphisms provides the basis for a test to predict the susceptibility of a dog to, or the likelihood of protection of a dog from, liver copper accumulation by screening for the polymorphisms. The predictive power of the test can be magnified using models that involve combining the results of detecting one or more of the defined polymorphisms. A genetic test which combines the results of detecting one or more polymorphisms indicative of protection from liver copper accumulation with the results of detecting one or more polymorphisms indicative of susceptibility to liver copper accumulation in dogs would be particularly informative with regards to the likelihood that a dog is at risk of liver copper accumulation.

The accumulation of copper in the liver of a dog may lead to one or more diseases or conditions of the liver that are attributable to high liver copper. For example, high liver copper can lead to chronic hepatitis, liver cirrhosis and ultimately liver failure. The invention thus enables dogs to be identified which are at risk of developing, or are not protected from, such liver diseases or conditions that are associated with high copper. Once the susceptibility of a dog to liver copper accumulation has been identified, or once a dog has been identified as not having one or more mutations indicative of protection from liver copper accumulation, it is possible to identify suitable preventative measures for that dog, with the aim of maintaining the liver copper level at a low or normal level, such as by administering a low copper foodstuff (e.g. the foodstuff disclosed in WO 2009/044152 A2). Furthermore, dogs that are identified as not having mutations associated with susceptibility to liver copper accumulation, or that are identified as having mutations associated with protection from liver copper accumulation, are ideal for use in breeding programs with the aim of producing dogs that are less likely to suffer from liver disease or other conditions associated with high copper.

Thus, the invention provides a method of testing a dog to determine the susceptibility of the dog to liver copper accumulation, comprising detecting in a sample the presence or absence in the genome of the dog of one or more polymorphisms selected from:
  (a) Chr22_3167534 (SEQ ID NO: 144), Chr22_3135144 (SEQ ID NO: 145), Chr20_55461150 (SEQ ID NO: 146), ChrX_120879711 (SEQ ID NO: 147), Chr19_6078084 (SEQ ID NO: 148), Chr15_62625262 (SEQ ID NO: 149), Chr14_39437543 (SEQ ID NO: 150), Chr15_62625024 (SEQ ID NO: 151), Chr3_86838677 (SEQ ID NO: 152), Chr24_4011833 (SEQ ID NO: 153), Chr18_60812198 (SEQ ID NO: 154), Chr10_65209946 (SEQ ID NO: 155), and the CGCCCC repeat at chromosome location 22:3135287;
  (b) one or more polymorphisms in linkage disequilibrium with a said polymorphism (a); and/or
  (c) Chr32_38904515 (SEQ ID NO: 156), Chr8_4892743 (SEQ ID NO: 157) and Chr8_4880518 (SEQ ID NO: 158).

The invention also provides:
a database comprising information relating to one or more polymorphisms as defined herein and their association with the susceptibility of a dog to liver copper accumulation;
a method of determining the susceptibility of a dog to liver copper accumulation, comprising:
  (a) inputting to a computer system data concerning the presence or absence in the genome of the dog of one or more polymorphisms as defined herein;
  (b) comparing the data to a computer database, which database comprises information relating to one or more polymorphisms as defined herein and their association with the susceptibility of a dog to liver copper accumulation; and
  (c) determining on the basis of the comparison the susceptibility of the dog to liver copper accumulation;
a computer program comprising program code means that, when executed on a computer system, instruct the computer system to perform a method of the invention;
a computer storage medium comprising the computer program of the invention and the database of the invention;
a computer system arranged to perform a method of the invention comprising:
  (a) means for receiving data concerning the presence or absence in the genome of the dog of a polymorphism as defined herein;
  (b) a database comprising information relating to one or more polymorphisms as defined herein and their association with the susceptibility of a dog to liver copper accumulation;
  (c) a module for comparing the data with the database; and
  (d) means for determining on the basis of said comparison the susceptibility of the dog to liver copper accumulation;
a method of determining the susceptibility of a dog to liver copper accumulation, comprising detecting in a sample the presence or absence in the genome of the dog of one or more polymorphisms selected from the polymorphisms as defined herein; use of one or more polymorphisms selected from the polymorphisms as defined herein for determining the susceptibility of a dog to liver copper accumulation; and a method of selecting a dog for producing offspring likely to be protected from liver copper accumulation comprising:
  determining whether the genome of a candidate first dog comprises one or more polymorphisms indicative of susceptibility to liver copper accumulation according to the method of the invention and thereby determining whether the candidate first dog is suitable for producing offspring likely to be protected from liver copper accumulation;
  optionally, determining whether the genome of a second dog of the opposite sex to the first dog comprises one or more polymorphisms indicative of susceptibility to liver copper accumulation according to the method of the invention; and
  optionally, mating the first dog with the second dog in order to produce offspring likely to be protected from liver copper accumulation.

The inventors have discovered polymorphisms associated with the protection of a dog from liver copper accumulation. Therefore, the invention provides a method of testing a dog to determine the likelihood that the dog is protected from liver copper accumulation, comprising detecting in a sample the presence or absence in the genome of the dog of one or more polymorphisms selected from (a) Chr22_3135144 (SEQ ID NO: 145) and (b) one or more polymorphisms in linkage disequilibrium with (a).

The invention also provides:
a database comprising information relating to one or more polymorphisms as defined herein and their association with the protection of a dog from, or susceptibility of a dog to, liver copper accumulation;
a method of determining the likelihood that a dog is protected from liver copper accumulation, the method comprising:
  (a) inputting to a computer system data concerning the presence or absence in the genome of the dog of one or more polymorphisms as defined herein;
  (b) comparing the data to a computer database, which database comprises information relating to one or more polymorphisms as defined herein and their association with the protection of a dog from, or susceptibility of a dog to, liver copper accumulation; and
  (c) determining on the basis of the comparison the likelihood that the dog is protected from liver copper accumulation;
a computer program comprising program code means that, when executed on a computer system, instruct the computer system to perform a method of the invention;
a computer storage medium comprising the computer program according to the invention and the database according to the invention;

a computer system arranged to perform a method of the invention comprising:
  (a) means for receiving data concerning the presence or absence in the genome of the dog of one or more polymorphisms as defined herein;
  (b) a database comprising information relating to said polymorphisms and their association with the protection of a dog from, or susceptibility of a dog to, liver copper accumulation;
  (c) a module for comparing the data with the database; and
  (d) means for determining on the basis of said comparison the likelihood that the dog is protected from liver copper accumulation;

a method of determining the likelihood that a dog is protected from liver copper accumulation, comprising detecting the presence or absence in the genome of the dog of one or more polymorphisms selected from (a) Chr22_3135144 (SEQ ID NO: 145) and (b) one or more polymorphisms in linkage disequilibrium with (a);

use of a polymorphism as defined herein for determining the likelihood that a dog is protected from liver copper accumulation; and a method of selecting a dog for producing offspring likely to be protected from liver copper accumulation comprising:
  determining whether the genome of a candidate first dog comprises one or more polymorphisms indicative of protection from liver copper accumulation according to the method of the invention and thereby determining whether the candidate first dog is suitable for producing offspring likely to be protected from liver copper accumulation;
  optionally, determining whether the genome of a second dog of the opposite sex to the first dog comprises one or more polymorphisms indicative of protection from liver copper accumulation according to the invention; and
  optionally, mating the first dog with the second dog in order to produce offspring likely to be protected from liver copper accumulation.

BRIEF DESCRIPTION OF THE FIGURES

FIG. 3 shows the variable length of a coding repeat in ATP7B. Top: The bases and their corresponding amino acids (AA). The chromosomal location of the boxed C is 3135287. Bottom: Ensembl, NCBI and sequencing of a Beagle and a group of Labradors reveal a different number of a CGCCCC repeat. As a consequence, the boxed amino acids alanine (A) and proline (P) are more or less produced. SEQ ID NOs: 236, 237 and 238 are polynucleotide sequences containing two, three and four repeats respectively.

FIG. 4 shows the location of the ATP7B CGCCCC repeat between heavy metal associated domain 3 and 4.

FIG. 8 shows stepwise modelling of the histology copper score. X1 to X17 are the factors in Table 21.

FIG. 9 shows stepwise modelling of the log-quantitative copper score. X1 to X17 are the factors in Table 21.

BRIEF DESCRIPTION OF THE SEQUENCES

Figure 1:
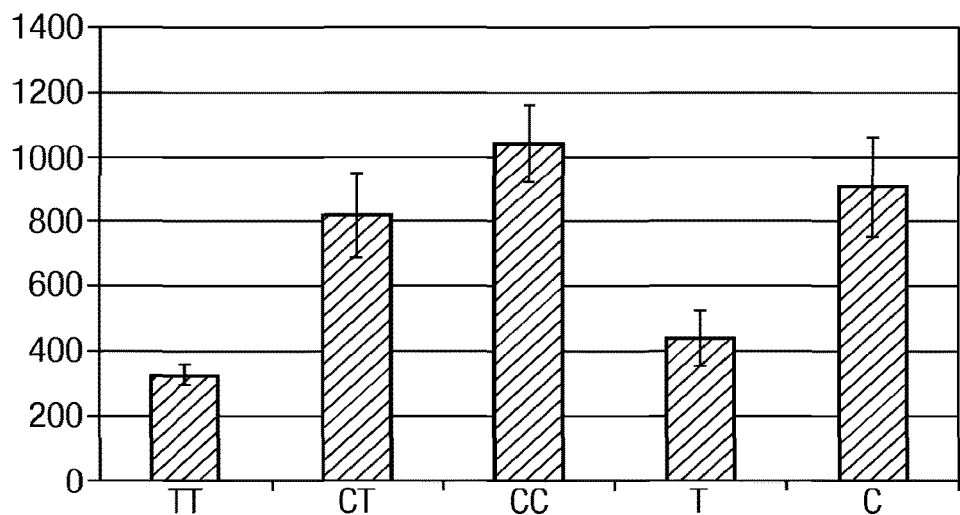
FIG. 1 depicts the average copper levels by gender and ATP7A genotype in Labrador Retrievers (data of Table 9). The y-axis is dry liver weight copper (mg/kg). The x-axis is ATP7A genotype: from left to right, the first three bars are for the female dogs in the study and the last two bars are for the male dogs in the study. Error bars are standard error.

SEQ ID NOs: 1 to 5 show the polynucleotide sequences encompassing the SNPs used in the three region model in Example 2 and are also in Table 4.

SEQ ID NOs: 6 to 141 show the polynucleotide sequences encompassing further SNPs that may be used to determine the susceptibility of a dog to liver copper accumulation. These sequences are also in Tables 5 and 6.

SEQ ID NO: 142 is the polynucleotide sequences of the ATP7A coding region SNP that is associated with the protection of a dog from liver copper accumulation (ChrX_63338063). This sequence is also shown in Table 8.

SEQ ID NO: 143 is the polynucleotide sequence of a SNP (ChrX_63397393 ATP7a Reg16 F 42) that is in linkage disequilibrium with SNP ChrX_63338063. This sequence is also shown in Table 8.

SEQ ID NOs: 144 to 158 show the polynucleotide sequences encompassing the SNPs of the invention. These sequences are also shown in Table 18.

SEQ ID NOs: 159 to 226 show the polynucleotide sequences encompassing SNPs that are in linkage disequilibrium with the SNPs in Table 18. These sequences are also shown in Table 20.

SEQ ID NOs: 227 to 235 are primer sequences.

SEQ ID NOs: 236, 237 and 238 are polynucleotides containing two, three or four CGCCCC repeats respectively for the repeat sequence at genomic location 22:3135287. These sequences are also shown in Table 12.

SEQUENCE LISTING

The instant application contains a Sequence Listing which has been submitted electronically in ASCII format and is hereby incorporated by reference in its entirety. Said ASCII copy, created on Oct. 30, 2018, is named 069269_0297_SL.txt and is 85,712 bytes in size.

DETAILED DESCRIPTION OF THE INVENTION

Identifying Susceptibility to or Protection from Liver Copper Accumulation

Accumulation of copper in the liver leads to liver disease in a number of dog breeds, including the Labrador Retriever, Doberman Pinscher, German Shepherd, Keeshond, Cocker Spaniel, West Highland White Terrier, Bedlington Terrier, and Skye Terrier. The mean copper concentration in the liver of normal dogs of any breed is 200 to 400 mg/kg on a dry weight basis, although newborns generally have higher liver copper concentrations. The amount of copper in the liver of a dog may be measured by biopsy.

A dog that is susceptible to liver copper accumulation has a tendency to accumulate copper such that its liver copper concentration reaches a level above 400 mg/kg on a dry weight basis. Determining the susceptibility of a dog to liver copper accumulation according to the invention involves determining the risk or likelihood that the dog will accumulate liver copper to a level above 400 mg/kg, for example above 600 mg/kg, above 800 mg/kg, above 1000 mg/kg, above 1500 mg/kg, above 2000 mg/kg, above 5000 mg/kg, or above 10000 mg/kg.

A dog that is protected from liver copper accumulation has a low risk or likelihood of accumulating liver copper such that its liver copper concentration is less likely to reach a level above 400 mg/kg on a dry weight basis. The liver copper concentration of a dog that is protected from liver copper accumulation will be below 600 mg/kg, for example below 500 mg/kg, below 400 mg/kg, or below 300 mg/kg. Determining the likelihood that a dog is protected from liver copper accumulation according to the invention involves determining the likelihood that the dog will accumulate liver copper to a level below 600 mg/kg, for example below 500 mg/kg, below 400 mg/kg, or below 300 mg/kg.

The accumulation of liver copper may be assessed by histochemistry. For example, liver copper concentration may be semiquantitatively assessed by histochemistry using the rubeanic acid staining technique for evaluation of copper distribution as previously described (Van den Ingh et al., (1988) Vet Q 10: 84-89). The concentration may be graded in a scale of 0 to 5 as follows: 0=no copper present; 1=solitary liver cells and/or reticulohistiocytic (RHS) cells containing some copper positive granules; 2=small groups of liver cells and/or RHS cells containing small to moderate numbers of copper positive granules; 3=larger groups or areas of liver cells and/or RHS cells containing moderate numbers of copper positive granules; 4=large areas of liver cells and/or RHS cells with many copper positive granules; and 5=diffuse presence of liver cells and/or RHS cells with many copper positive granules. According to this grading system, copper scores above 2 are abnormal.

Therefore determining the likelihood that a dog is protected from liver copper accumulation according to the invention can involve determining the likelihood that the dog would be given a score of less than or equal to 3, for example less than or equal to 2.5, 2, 1.5, or less than or equal to 1, using the grading system described in Van den Ingh et al. Determining the susceptibility of a dog to liver copper accumulation according to the invention can involve determining the risk or likelihood that the dog would be given a score of greater than or equal to 2, for example greater than or equal to 2.5, 3, 3.5, or greater than or equal to 4, using the grading system described in Van den Ingh et al.

The likelihood of protection or susceptibility may for example be expressed as a risk factor, percentage or probability. It may be possible to determine whether or not a dog will accumulate copper to the levels described above. For example, the method of determining the susceptibility of a dog to, or the likelihood of protection of a dog from, liver copper accumulation may comprise determining whether or not a dog will accumulate copper to a level above 400 mg/kg.

Accumulation of liver copper to a level above 400 mg/kg is associated with liver disease and may ultimately lead to liver failure. Therefore, determining whether the genome of a dog comprises one or more polymorphisms indicative of protection from liver copper accumulation indicates that the dog is less likely to develop a disease or condition attributable to liver copper accumulation such as chronic hepatitis, cirrhosis and liver failure. Conversely, determining whether the genome of a dog comprises one or more polymorphisms indicative of susceptibility to liver copper accumulation indicates the susceptibility of the dog to such a disease or condition. Therefore, the invention provides a method of testing for the susceptibility of a dog to, or the likelihood of protection of a dog from, a disease associated with liver copper accumulation, such as chronic hepatitis, cirrhosis and liver failure.

Polymorphisms and Indication of Susceptibility to, or Protection from, Copper Accumulation The inventors have discovered a number of polymorphisms in the genome of the dog that are associated with susceptibility to liver copper accumulation. The present invention therefore relates to a method of determining the susceptibility of a dog to liver copper accumulation using one or more polymorphic markers at these genomic locations.

The present invention therefore provides a method of testing a dog to determine the susceptibility of the dog to liver copper accumulation, comprising detecting in a sample the presence or absence in the genome of the dog of one or more polymorphisms selected from:

(a) Chr22_3167534 (SEQ ID NO: 144), Chr22_3135144 (SEQ ID NO: 145), Chr20_55461150 (SEQ ID NO: 146), ChrX_120879711 (SEQ ID NO: 147), Chr19_6078084 (SEQ ID NO: 148), Chr15_62625262 (SEQ ID NO: 149), Chr14_39437543 (SEQ ID NO: 150), Chr15_62625024 (SEQ ID NO: 151), Chr3_86838677 (SEQ ID NO: 152), Chr24_4011833 (SEQ ID NO: 153), Chr18_60812198 (SEQ ID NO: 154), Chr10_65209946 (SEQ ID NO: 155), and the CGCCCC repeat at chromosome location 22:3135287;

(b) one or more polymorphisms in linkage disequilibrium with a said polymorphism (a); and/or (c) Chr32_38904515 (SEQ ID NO: 156), Chr8_4892743 (SEQ ID NO: 157) and Chr8_4880518 (SEQ ID NO: 158).

The inventors have also discovered polymorphisms in the genome of the dog that are associated with protection from liver copper accumulation. The present invention therefore relates to a method of determining the likelihood that a dog is protected from liver copper accumulation using one or more polymorphic markers at these genomic locations.

The invention therefore also provides a method of testing a dog to determine the likelihood that the dog is protected from liver copper accumulation, comprising detecting in a sample the presence or absence in the genome of the dog of one or more polymorphisms selected from (a) Chr22_3135144 (SEQ ID NO: 145) and (b) one or more polymorphisms in linkage disequilibrium with (a).

The phrase "detecting the presence or absence of a polymorphism" typically means determining whether a polymorphism is present in the genome of the dog. Polymorphisms include Single Nucleotide Polymorphisms (SNPs), microsatellite or repeat polymorphisms, insertion polymorphisms and deletion polymorphisms. Preferably the polymorphism is a SNP. Detecting the presence or absence of a SNP means genotyping the SNP or typing the nucleotide(s) present in the genome of the dog for the SNP. Typically, the nucleotide present at the same position on both homologous chromosomes will be determined. In other words, one or both alleles are genotyped and the identities of one or both alleles are determined based on the genotyping. A dog may be determined to be homozygous for a first allele, heterozygous or homozygous for a second allele of the SNP. When the polymorphism is a microsatellite or repeat sequence, typically the method will involve determining the number of repeats.

Determining a phenotype of an individual, such as the susceptibility of the individual to, or the protection of the individual from, a disease or condition, is not limited to the detection of a polymorphism that is causal for the disease or condition. In genetic mapping studies, genetic variation at a set of marker loci in a sample of individuals is tested for association with a given phenotype. If such an association is found between a particular marker locus and the phenotype, it suggests that either the variation at that marker locus affects the phenotype of interest, or that the variation at that marker locus is in linkage disequilibrium with the true phenotype-related locus, which was not genotyped. In the case of a group of polymorphisms that are in linkage disequilibrium with each other, knowledge of the existence of all such polymorphisms in a particular individual generally provides redundant information. Thus, when determining whether the genome of a dog comprises one or more polymorphisms indicative of susceptibility to, or protection from, liver copper accumulation or to copper-associated liver disease, it is necessary to detect only one polymorphism of such a group of polymorphisms.

As a result of linkage disequilibrium, a polymorphism that is not a functional susceptibility/protective polymorphism, but is in linkage disequilibrium with a functional polymorphism, may act as a marker indicating the presence of the functional polymorphism. A polymorphism that is in linkage disequilibrium with a polymorphism of the invention is indicative of susceptibility to, or protection from, liver copper accumulation.

Accordingly, any one of the polymorphic positions as defined herein may be typed directly, in other words by determining the nucleotide present at that position, or indirectly, for example by determining the nucleotide present at another polymorphic position that is in linkage disequilibrium with said polymorphic position.

Linkage disequilibrium is the non-random gametic association of alleles at different loci in a population. Polymorphisms that have a tendency to be inherited together instead of being inherited independently by random assortment are in linkage disequilibrium. Polymorphisms are randomly assorted or inherited independently of each other if the frequency of the two polymorphisms together is the product of the frequencies of the two polymorphisms individually. For example, if two polymorphisms at different polymorphic sites are present in 50% of the chromosomes in a population, then they would be said to assort randomly if the two alleles are present together on 25% of the chromosomes in the population. A higher percentage would mean that the two alleles are linked. It follows that a first polymorphism is in linkage disequilibrium with a second polymorphism if the frequency of the two polymorphisms together is greater than the product of the frequencies of the two polymorphisms individually in a population. Preferably, a first polymorphism is in linkage disequilibrium with a second polymorphism if the frequency of the two polymorphisms together is more that 10% greater, for example more than 30%, more than 50% or more than 70% greater, than the product of the frequencies of the two polymorphisms individually.

Research has shown that linkage disequilibrium is extensive in dogs (Extensive and breed-specific linkage disequilibrium in *Canis familiaris*, Sutter et al., Genome Research 14: 2388-2396). Polymorphisms which are in linkage disequilibrium are often in close physical proximity, which is why they are co-inherited. Polymorphisms which are in linkage disequilibrium with the polymorphisms mentioned herein are located on the same chromosome. Polymorphisms which are in linkage disequilibrium in dogs are typically within 5 mb, preferably within 2 mb, within 1 mb, within 700 kb, within 600 kb, within 500 kb, within 400 kb, within 200 kb, within 100 kb, within 50 kb, within 10 kb, within 5 kb, within 1 kb, within 500 bp, within 100 bp, within 50 bp or within 10 bp of the polymorphism.

It would be within the capability of the skilled person to use routine techniques to identify polymorphisms that are in linkage disequilibrium with any one of the polymorphic positions as defined herein. Once a potential polymorphism has been selected, the skilled person can readily determine whether this polymorphism, and what version or allele of the polymorphism, is significantly correlated with any of the polymorphisms defined herein.

In more detail, to determine whether a polymorphism is in linkage disequilibrium with any one of the polymorphisms defined herein, the skilled person should genotype the candidate polymorphism and one or more of the polymorphisms defined herein in a panel of dogs. The size of the panel should be adequate enough to achieve a statistically significant result. Typically, samples from at least 100, preferably at least 150 or at least 200, different dogs should be genotyped. The dogs in the panel may be of any breed, but typically will have the same or similar genetic breed background. Once the polymorphisms have been genotyped in the panel of dogs, linkage disequilibrium between one or more pairs of polymorphisms can be measured using any one of a number of readily available statistical packages. An example of a free software package is Haploview (Haploview: analysis and visualisation of LD and haplotype maps, Barrett et al, 2005, Bioinformatics, 21(2): 263-265), downloadable at http://www.broadinstitute.org/haploview/haploview. Another example of software that can be used is PLINK (http://pngu.mgh.harvard.edu/purcell/plink/).

A measure of linkage disequilibrium is D'. A range of 0.5 to 1 for D' is indicative of a pair of polymorphisms being in linkage disequilibrium, with 1 indicating the most significant linkage disequilibrium. Therefore if D' is found to be from 0.5 to 1, preferably from 0.6 to 1, 0.7 to 1, from 0.8 to 1, from 0.85 to 1, from 0.9 to 1, from 0.95 to 1 or most preferably 1, for a candidate polymorphism and a specific polymorphism defined herein, the candidate polymorphism may be said to be predictive of the polymorphism defined herein and will thus indicate susceptibility to or protection from liver copper accumulation. In a preferred method of the invention, a polymorphism that is in linkage disequilibrium with a polymorphism defined herein is within 680 kb and on the same chromosome as the polymorphism defined herein and the calculated measure of linkage disequilibrium between the pair of polymorphisms, D', is greater than or equal to 0.9.

Another measure of linkage disequilibrium is R-squared, where R is the correlation coefficient. R-squared, which is also known as the 'Coefficient of determination', is the fraction of the variance in the genotypes of the first polymorphism which is accounted for in the genotypes of the second polymorphism. Therefore an R-squared of 0.5 for a candidate polymorphism and a specific polymorphism defined herein would mean that the candidate polymorphism accounts for 50% of the variance in the specific polymorphism. R-squared is producible from standard statistical packages such as Haploview. Typically, an R-squared of 0.25 or greater (R of >0.5 or <−0.5) is considered a large correlation. Therefore if R-squared is found to be 0.5 or more, preferably 0.75 or more, 0.8 or more, 0.85 or more, 0.9 or more, or 0.95 or more for a candidate polymorphism and a specific polymorphism defined herein, the candidate polymorphism may be said to be predictive of the polymorphism defined herein and will thus indicate susceptibility to or protection from liver copper accumulation. In a preferred method of the invention, a polymorphism that is in linkage disequilibrium with a polymorphism defined herein is within 680 kb and on the same chromosome as the polymorphism defined herein and the calculated measure of linkage disequilibrium between the pair of polymorphisms, R-squared, is greater than or equal to 0.5.

It is also possible to build a haplotype of polymorphisms in LD with the polymorphisms of the invention. Even if one or more polymorphisms are individually only weakly in LD with the polymorphisms of the invention, they may be in strong LD if they are used in combination. For example, any one polymorphism may have an R-squared value below 0.25. However, two or more mutations individually having an R-squared of below 0.25 may in combination have an R-squared of greater than 0.5. Therefore, these polymorphisms may be used in combination to determine the susceptibility of the dog to, or the likelihood of protection of the dog from, liver copper accumulation.

Therefore, the method of the invention may comprise detecting the presence or absence of two or more polymorphisms in linkage disequilibrium with a polymorphism defined herein, wherein R-squared for each of said two or more polymorphisms individually may be less than or equal to 0.25, but R-squared for the combination of said two or more polymorphisms is greater than or equal to 0.5.

Once a polymorphism has been identified as being in linkage disequilibrium and therefore correlated with a polymorphism defined herein, the skilled person can readily determine which version of the polymorphism, i.e. which allele, is associated with susceptibility to or protection from liver copper accumulation. This could be achieved by phenotyping a panel of dogs for liver copper accumulation and classifying the dogs in terms of the level of liver copper accumulation. The panel of dogs are then genotyped for the polymorphism of interest. The genotypes are then correlated with the level of liver copper in order to determine the association of the genotypes with liver copper level and thereby determine which allele is associated with susceptibility to or protection from liver copper accumulation.

The polymorphisms of the invention that have been found to be indicative of susceptibility of a dog to liver copper accumulation are identified in Tables 17 and 18. Specifically, they are: Chr22_3167534 (SEQ ID NO: 144), Chr20_55461150 (SEQ ID NO: 146), ChrX_120879711 (SEQ ID NO: 147), Chr32_38904515 (SEQ ID NO: 156), Chr19_6078084 (SEQ ID NO: 148), Chr15_62625262 (SEQ ID NO: 149), Chr14_39437543 (SEQ ID NO: 150), Chr15_62625024 (SEQ ID NO: 151), Chr3_86838677 (SEQ ID NO: 152), Chr8_4892743 (SEQ ID NO: 157), Chr24_4011833 (SEQ ID NO: 153), Chr18_60812198 (SEQ ID NO: 154), Chr8_4880518 (SEQ ID NO: 158), Chr10_65209946 (SEQ ID NO: 155) and Chr22_3135144 (SEQ ID NO: 145).

In addition, a microsatellite repeat in the ATP7B gene was found to be associated with susceptibility to liver copper accumulation. This is a CGCCCC repeat on chromosome 22 starting at genomic location 3135287 (22:3135287). The repeat sequence is illustrated in FIG. 3 (SEQ ID NOs: 236 to 238). There may be two (SEQ ID NO: 236), three (SEQ ID NO: 237), four (SEQ ID NO: 238) and potentially more repeats. Therefore the method of the invention may comprise determining the number of CGCCCC repeats in the genome of the dog.

The method of determining susceptibility of a dog to liver copper accumulation comprises detecting in a sample the presence or absence in the genome of the dog of one or more polymorphisms selected from:

(a) Chr22_3167534 (SEQ ID NO: 144), Chr22_3135144 (SEQ ID NO: 145), Chr20_55461150 (SEQ ID NO: 146), ChrX_120879711 (SEQ ID NO: 147), Chr19_6078084 (SEQ ID NO: 148), Chr15_62625262 (SEQ ID NO: 149), Chr14_39437543 (SEQ ID NO: 150), Chr15_62625024 (SEQ ID NO: 151), Chr3_86838677 (SEQ ID NO: 152), Chr24_4011833 (SEQ ID NO: 153), Chr18_60812198 (SEQ ID NO: 154), Chr10_65209946 (SEQ ID NO: 155), and the CGCCCC repeat at chromosome location 22:3135287;

(b) one or more polymorphisms in linkage disequilibrium with a said polymorphism (a); and/or (c) Chr32_38904515 (SEQ ID NO: 156), Chr8_4892743 (SEQ ID NO: 157) and Chr8_4880518 (SEQ ID NO: 158).

Any number and any combination of polymorphisms may be detected to carry out the invention. Preferably at least 2 polymorphisms are detected. Preferably 2 to 5, 3 to 8, 5 to 10 or 8 to 15 polymorphisms are detected.

The DNA of a dog may be typed at the respective positions of:
    (i) one or more polymorphisms (a);
    (ii) one or more polymorphisms (b);
    (iii) one or more polymorphisms (c);
    (iv) one or more polymorphisms (a) and one or more polymorphisms (b);
    (v) one or more polymorphisms (a) and one or more polymorphisms (c); or
    (vi) one or more polymorphisms (b) and one or more polymorphisms (c).

Preferably the method of determining the susceptibility of a dog to liver copper accumulation comprises detecting in a sample the presence or absence in the genome of the dog of:

(a) Chr22_3167534 (SEQ ID NO: 144), Chr22_3135144 (SEQ ID NO: 145), Chr20_55461150 (SEQ ID NO: 146), Chr19_6078084 (SEQ ID NO: 148), Chr3_86838677 (SEQ ID NO: 152), Chr10_65209946 (SEQ ID NO: 155) and ChrX_63338063 (SEQ ID NO: 142); or (b) ChrX_120879711 (SEQ ID NO: 147), Chr15_62625262 (SEQ ID NO: 149), Chr22_3167534 (SEQ ID NO: 144), Chr8_4892743 (SEQ ID NO: 157), Chr24_4011833 (SEQ ID NO: 153) and Chr18_60812198 (SEQ ID NO: 154).

The alleles of the mutations that associated with high copper are provided in Table 18. Thus, the method of determining the susceptibility of a dog to liver copper accumulation of the invention may comprise determining the presence or absence of the A allele for Chr22_3167534 (SEQ ID NO: 144), the A allele for Chr20_55461150 (SEQ ID NO: 146), the C allele for ChrX_120879711 (SEQ ID NO: 147), the C allele for Chr32_38904515 (SEQ ID NO: 156), the T allele for Chr19_6078084 (SEQ ID NO: 148, the A allele for Chr15_62625262 (SEQ ID NO: 149), the G allele for Chr14_39437543 (SEQ ID NO: 150), the A allele for Chr15_62625024 (SEQ ID NO: 151), the C allele for Chr3_86838677 (SEQ ID NO: 152), the T allele for Chr8_4892743 (SEQ ID NO: 157), the G allele for Chr24_4011833 (SEQ ID NO: 153), the A allele for Chr18_60812198 (SEQ ID NO: 154), the A allele for Chr8_4880518 (SEQ ID NO: 158), the T allele for Chr10_65209946 (SEQ ID NO: 155) and/or the G allele for Chr22_3135144 (SEQ ID NO: 145), and thereby determining whether the genome of the dog has a polymorphism indicative of susceptibility to copper accumulation.

Every extra copy of the CGCCCC repeat at chromosome location 22:3135287 was found to increase the risk of copper accumulation. Thus, the method of determining the susceptibility of a dog to liver copper accumulation may comprise determining the number of CGCCCC repeats at chromosome location 22:3135287. The presence of two or more repeats, for example three or four repeats is indicative of susceptibility to liver copper accumulation.

In a preferred method of the invention, a polymorphism in linkage disequilibrium with a polymorphism (a) is a SNP. As a result of being in linkage disequilibrium, the polymorphism will be indicative of susceptibility to liver copper accumulation. Examples of SNPs in linkage disequilibrium with polymorphisms (a) are provided in Table 19 and the sequences surrounding the SNPs are shown in Table 20. These SNPs can either be used on their own, or in combination with one or more polymorphisms (a) and/or (c), to determine the susceptibility of a dog to liver copper accumulation. The method of the invention may therefore comprise detecting in a sample the presence or absence in the genome of the dog of one or more polymorphisms selected from the polymorphisms in Tables 19 and 20.

The inventors previously discovered polymorphisms in the ATP7A gene that are indicative of protection from liver copper accumulation e.g. (ChrX_63338063; SNP ATP7a_Reg3_F_6; SEQ ID NO: 142). Thus, the method of determining the susceptibility of a dog to liver copper accumulation may further comprise detecting in a sample the presence or absence in the genome of the dog of one or more polymorphisms selected from:

(d) ChrX_63338063 (SNP ATP7a_Reg3_F_6; SEQ ID NO: 142); and/or (e) one or more polymorphisms in linkage disequilibrium with a said polymorphism (d).

The A allele of Chr22_3135144 and the T allele of ChrX_63338063 are associated with low copper or protection from liver copper accumulation. Conversely, the G allele of Chr22_3135144 and the C allele of ChrX_63338063 are associated with high copper or susceptibility to liver copper accumulation. Thus, the method of determining the susceptibility of a dog to liver copper accumulation may comprise determining the presence or absence of the A or G allele of Chr22_3135144 and/or the T or C allele of ChrX_63338063. The presence of the A allele of Chr22_3135144 and/or the T allele of ChrX_63338063 indicate that the dog is likely to be protected from liver copper accumulation and the presence of the G allele of Chr22_3135144 and/or the C allele of ChrX_63338063 indicate that the dog is likely to be susceptible to liver copper accumulation.

The polymorphisms that have been found to be associated with protection from liver copper accumulation may be used in a method of determining the likelihood that a dog is protected from liver copper accumulation. Thus, the invention provides a method of testing a dog to determine the likelihood that the dog is protected from liver copper accumulation, comprising detecting in a sample the presence or absence in the genome of the dog of one or more polymorphisms selected from (a) Chr22_3135144 (SEQ ID NO: 145) and (b) one or more polymorphisms in linkage disequilibrium with (a).

Any number and any combination of polymorphisms may be detected to carry out the invention. Preferably at least two polymorphisms are detected. Preferably 2 to 5, 3 to 8, 5 to 10 or 8 to 15 polymorphisms are detected.

Therefore, the DNA of a dog may be typed at the respective positions of (i) polymorphism (a); and/or (ii) one or more polymorphisms (b).

The method of determining the likelihood that a dog is protected from liver copper accumulation may further comprise detecting in a sample the presence or absence in the genome of the dog of (c) ChrX_63338063 (SNP ATP7a_Reg3_F_6; SEQ ID NO:142) and/or (d) one or more polymorphisms in linkage disequilibrium with (c). An example of a polymorphism that is in linkage disequilibrium with ChrX_63338063 (SNP ATP7a_Reg3_F_6; SEQ ID NO: 142) is ChrX_63397393 (SNP ATP7a_Reg16 F 42; SEQ ID NO: 143). Further examples are provided in Tables 19 and 20. Therefore the method of determining the likelihood that a dog is protected from liver copper accumulation may further comprise detecting in a sample the presence or absence in the genome of the dog of (c) ChrX_63338063 (SNP ATP7a_Reg3_F_6; SEQ ID NO:142) and/or (d) ChrX_63397393 (SNP ATP7a_Reg16 F 42; SEQ ID NO: 143).

Preferably the method of determining the likelihood that a dog is protected from liver copper accumulation comprises detecting in a sample the presence or absence in the genome of the dog of: Chr22_3167534 (SEQ ID NO: 144), Chr22_3135144 (SEQ ID NO: 145), Chr20_55461150 (SEQ ID NO: 146), Chr19_6078084 (SEQ ID NO: 148), Chr3_86838677 (SEQ ID NO: 152), Chr10_65209946 (SEQ ID NO: 155) and ChrX_63338063 SEQ ID NO: 142.

As indicated above, the A allele of Chr22_3135144 and the T allele of ChrX_63338063 are associated with low copper or protection from liver copper accumulation. Conversely, the G allele of Chr22_3135144 and the C allele of ChrX_63338063 are associated with high copper or susceptibility to liver copper accumulation. Thus, the method of determining the likelihood that a dog is protected from liver copper accumulation may comprise determining the presence or absence of the A or G allele of Chr22_3135144 and/or the T or C allele of ChrX_63338063. The presence of the A allele of Chr22_3135144 and/or the T allele of ChrX_63338063 indicate that the dog is likely to be protected from liver copper accumulation and the presence of the G allele of Chr22_3135144 and the C allele of ChrX_63338063 indicate that the dog is not likely to be protected from liver copper accumulation.

The polymorphisms that have been found to be associated with high liver copper or susceptibility to liver copper accumulation described herein may also be used in a method of determining the likelihood that a dog is protected from liver copper accumulation. Determining the absence of an allele that is associated with high liver copper can help to determine the likelihood that a dog is protected from liver copper accumulation. The method of determining the likelihood that a dog is protected from liver copper accumulation may therefore comprise detecting in a sample the presence or absence in the genome of the dog of one or more polymorphisms selected from:

(e) Chr22_3167534 (SEQ ID NO: 144), Chr22_3135144 (SEQ ID NO: 145), Chr20_55461150 (SEQ ID NO: 146), ChrX_120879711 (SEQ ID NO: 147), Chr19 6078084 (SEQ ID NO: 148), Chr15_62625262 (SEQ ID NO: 149), Chr14_39437543 (SEQ ID NO: 150), Chr15_62625024 (SEQ ID NO: 151), Chr3_86838677 (SEQ ID NO: 152), Chr24_4011833 (SEQ ID NO: 153), Chr18_60812198 (SEQ ID NO: 154), Chr10_65209946 (SEQ ID NO: 155), and the CGCCCC repeat at chromosome location 22:3135287;

(f) one or more polymorphisms in linkage disequilibrium with a said polymorphism (e); and/or (g) Chr32_38904515 (SEQ ID NO: 156), Chr8_4892743 (SEQ ID NO: 157) and Chr8_4880518 (SEQ ID NO: 158).

The inventors have previously discovered that polymorphisms in or in the region of the canine GOLGAS, ATP7A and UBLS genes are indicative of susceptibility to liver copper accumulation in dogs (Examples 1 and 2). Therefore these polymorphisms could be used in combination with the polymorphisms of the invention to provide an enhanced genetic test for determining the risk or likelihood that a dog is susceptible to or protected from liver copper accumulation. The method of determining the susceptibility of a dog to, or the protection of a dog from, liver copper accumulation of the invention may therefore further comprise detecting the presence or absence of (I) a polymorphism in the GOLGAS, ATP7A or UBLS gene of the dog that is indicative of susceptibility to liver copper accumulation and/or (II) a polymorphism in linkage disequilibrium with a said polymorphism (I). Any number and any combination of these polymorphisms may be detected in addition to the polymorphisms of the invention. Preferably at least 2 of these further polymorphisms are detected. Preferably 2 to 5, 3 to 8 or 5 to 10 polymorphisms are further detected.

Therefore, the DNA of a dog may be further typed at the respective positions of (i) polymorphism (I) and/or (ii) one or more polymorphisms (II). Additionally, the DNA of the dog may be typed at the respective positions of:

(i) two or more polymorphisms (I);
(ii) two or more polymorphisms (II); or
(iii) one or more polymorphisms (I) and one or more polymorphisms (II).

When there are two polymorphisms (I), each polymorphism may be in a separate one of the GOLGAS, ATP7A and UBLS genes or in just one of those genes. When there are three or more polymorphisms (I), for example 3 to 10 such polymorphisms, the polymorphisms may be in the same gene, in two of the genes or in all three genes.

Similarly when there are two polymorphisms (II), each polymorphism may be in linkage disequilibrium with a polymorphism in a separate one of the GOLGAS, ATP7A and UBLS genes or in just one of those genes. When there are three or more polymorphisms (II), for example 3 to 10 such polymorphisms, the polymorphisms may be in linkage disequilibrium with a polymorphism in the same gene, in two of the genes or in all three genes.

A preferred method of the invention further comprises detecting the presence or absence of at least one polymorphism (I) in the GOLGAS, ATP7A or UBLS gene of the dog that is indicative of susceptibility to liver copper accumulation and at least one polymorphism (II) in linkage disequilibrium with a said polymorphism (I).

In a preferred method of the invention, the polymorphism (I) and/or (II) is a SNP. The SNP may be any SNP in or in the region of the GOLGAS, ATP7A or UBLS gene of the dog that is indicative of susceptibility to liver copper accumulation and/or a SNP that is in linkage disequilibrium thereof.

The method of the invention may, therefore, further comprise determining whether the genome of a dog comprises one or more polymorphisms indicative of susceptibility to liver copper accumulation selected from the SNPs identified in Table 4, Table 5 and Table 6. In Tables 4 and 5 each SNP is located at position 61 in the sequence. The first and second alleles are provided for each SNP at that location ([first/second]). In Table 6, the first and second alleles for each SNP are also indicated. Any number of the SNPs may be used from Tables 4, 5 and 6 and in any combination. The SNPs may be combined with a different type of polymorphism.

Preferably, the method of determining the susceptibility of a dog to, or the likelihood of protection of the dog from, liver copper accumulation further comprises detecting the presence or absence of one or more SNPs selected from the SNPs in Table 4 and Table 6 and/or one or more SNPs in linkage disequilibrium thereof. Therefore preferably the one or more SNPs are selected from BICF2P506595 (position 61 of SEQ ID NO:1), BICF2P772765 (position 61 of SEQ ID NO:2), BICF2S2333187 (position 61 of SEQ ID NO:3), BICF2P1324008 (position 61 of SEQ ID NO:4), BICF2P591872 (position 61 of SEQ ID NO:5), ATP7a_Reg4_F_9 (position 164 of SEQ ID NO: 131), UBLS Reg1F_16 (position 97 of SEQ ID NO: 132), golga5_Reg1 24 (position 70 of SEQ ID NO: 133), golga5_26 (position 88 of SEQ ID NO: 134), golga5_27 (position 104 of SEQ ID NO: 135), golga5_28 (position 139 of SEQ ID NO: 136), golga5_29 (position 128 of SEQ ID NO: 137), golga5_30 (position 95 of SEQ ID NO: 138), golga5_31 (position 106 of SEQ ID NO: 139), atp7areg17_32 (position 95 of SEQ ID NO: 140), atp7areg17_33 (position 90 of SEQ ID NO: 141) and one or more SNPs in linkage disequilibrium thereof. Accordingly, any of these 16 SNPs or any SNPs that are in linkage disequilibrium with any if these 16 SNPs may be typed. Preferably at least 2 of these 16 SNPs or SNPs in linkage disequilibrium are typed.

More preferably, the method of the invention further comprises detecting the presence or absence of one or more SNPs selected from the SNPs in Table 4. Accordingly, any of these 5 SNPs or any SNPs that are in linkage disequilibrium with any of these 5 SNPs may be typed. Preferably at least 2 of these 5 SNPs or SNPs in linkage disequilibrium are typed. More preferably all 5 positions are typed. Preferably therefore, the nucleotide(s) that are typed are selected from positions equivalent to:

position 61 of SEQ ID NO: 1 (BICF2P506595, SNP1);
position 61 of SEQ ID NO: 2 (BICF2P772765, SNP 2);
position 61 of SEQ ID NO: 3 (BICF2S2333187, SNP 3);
position 61 of SEQ ID NO: 4 (BICF2P1324008, SNP 4);
position 61 of SEQ ID NO: 5 (BICF2P591872, SNP 5); or
any positions which are in linkage disequilibrium with any one of these positions. Preferably, the method comprises detecting the presence or absence of the SNPs BICF2P506595 (SEQ ID NO:1), BICF2P772765 (SEQ ID NO:2), BICF2S2333187 (SEQ ID NO:3), BICF2P1324008 (SEQ ID NO:4), and BICF2P591872 (SEQ ID NO:5).

SNP 1 is located within an intron of the GOLGAS gene. SNPs 2, 3 and 4 are located in the region of the UBLS gene. SNP 5 is located in the region of the ATP7A gene. The detection method of the invention therefore relates to any SNP that lies within or in the region of one or more of these genes (in coding regions or otherwise), or any other SNP that is in linkage disequilibrium.

Example 2 demonstrates the use of SNPs 1 to 5 to establish a Boolean model of susceptibility to copper accumulation. Table 3 represents the binary conditions of alleles at three genomic locations. The binary values are indicative of a dog having alleles that are indicative of susceptibility to copper accumulation ("bad" alleles). For instance 000 represents not having any of the three bad alleles. 111 represents having all three bad alleles.

The A allele for SNP BICF2P506595 (SNP 1), the G allele for SNP BICF2P772765 (SNP 2), the C allele for SNP BICF2S2333187 (SNP 3), the G allele for SNP BICF2P1324008 (SNP 4) and the A allele for SNP BICF2P591872 (SNP 5) have been determined by the inventors to be indicative of susceptibility to liver copper accumulation. Dogs that are homozygous for these alleles are susceptible to liver copper accumulation. Therefore, a preferred method of the invention further comprises determining the presence or absence of the A allele for SNP BICF2P506595, the G allele for SNP BICF2P772765 (SNP 2), the C allele for SNP BICF2S2333187 (SNP 3), the G allele for SNP BICF2P1324008 (SNP 4) and/or the A allele for SNP BICF2P591872 (SNP 5) and thereby determining whether the genome of the dog comprises a polymorphism indicative of susceptibility to liver copper accumulation. A more preferred method comprises detecting the presence or absence of the AA genotype for SNP BICF2P506595, the GG genotype for SNP BICF2P772765, the CC genotype for SNP BICF2S2333187, the GG genotype for SNP BICF2P1324008 and/or the AA or AG genotype for SNP BICF2P591872.

Therefore, a preferred method of determining the susceptibility of a dog to, or the likelihood that a dog is protected from, liver copper accumulation further comprises detecting the presence or absence of:
(i) An AA genotype for SNP BICF2P506595 (SNP 1);
(ii) A GG genotype for SNP BICF2P772765 (SNP 2);
(iii) A CC genotype for SNP BICF2S2333187 (SNP 3);
(iv) A GG genotype for SNP BICF2P1324008 (SNP 4); and/or
(v) An AA or AG genotype for SNP BICF2P591872 (SNP 5);

and thereby determining whether the genome of the dog comprises one or more polymorphisms indicative of protection from and/or susceptibility to liver copper accumulation. A more preferred method comprises detecting the presence or absence of a genotype (i); a genotype (ii), (iii) and (iv); or a genotype (v). An even more preferable method comprises detecting the presence or absence of all 5 genotypes (i) to (v).

Typing the nucleotide(s) present in the genome of the dog at a position identified in any of Tables 4, 5, 6, 8, 18 and 20 may mean that the nucleotide present at this position in a sequence corresponding exactly with the sequence identified in Tables 4, 5, 6, 8, 18 and 20 is typed. However, it will be understood that the exact sequences presented in SEQ ID NOs: 1 to 5 identified in Table 4, SEQ ID NOs: 6 to 130 in Table 5, SEQ ID NOs: 131 to 141 in Table 6, SEQ ID NO: 142 and SEQ ID NO: 143 in Table 8, SEQ ID NOs: 144 to 158 in Table 18 and SEQ ID NOs: 159 to 226 in Table 20 will not necessarily be present in the dog to be tested. Typing the nucleotide present may therefore be at a position identified in Tables 4, 5, 6, 8, 18 and 20 or at an equivalent or corresponding position in the sequence. The term equivalent as used herein therefore means at or at a position corresponding to that identified in Tables 4, 5, 6, 8, 18 and 20. The sequence and thus the position of the SNP could for example vary because of deletions or additions of nucleotides in the genome of the dog. Those skilled in the art will be able to determine a position that corresponds to or is equivalent to the relevant position in each of SEQ ID NOs: 1 to 226, using for example a computer program such as GAP, BESTFIT, COMPARE, ALIGN, PILEUP or BLAST. The UWGCG Package provides programs including GAP, BESTFIT, COMPARE, ALIGN and PILEUP that can be used to calculate homology or line up sequences (for example used on their default settings). The BLAST algorithm can also be used to compare or line up two sequences, typically on its default settings. Software for performing a BLAST comparison of two sequences is publicly available through the National Center for Biotechnology Information (http://www.ncbi.nlm.nih.gov/). This algorithm is further described below. Similar publicly available tools for the alignment and comparison of sequences may be found on the European Bioinformatics Institute website (http://www.ebi.ac.uk), for example the ALIGN and CLUSTALW programs.

There are a variety of different methods that can be used to determine whether a polymorphism is indicative of either susceptibility to or protection from liver copper accumulation. Typically, the candidate polymorphism is compared to a database of polymorphisms and their association with susceptibility to or protection from liver copper accumulation. Such a database is generated by phenotyping a panel of dogs for liver copper accumulation, for example by liver biopsy, and classifying the dogs in terms of the level of copper accumulation. The dogs in the panel are also genotyped for a panel of polymorphisms. It is then possible to determine the association of each genotype with the level of liver copper. Determining whether a polymorphism is indicative of either susceptibility to or protection from liver copper is therefore achieved by locating the polymorphism in the database.

If a polymorphism of interest is not located in a database as described above, it is still possible to determine whether the polymorphism is indicative of either susceptibility to or protection from liver copper accumulation. This could be achieved by phenotyping a panel of dogs for liver copper accumulation and classifying the dogs in terms of the level of liver copper accumulation. The panel of dogs are then genotyped for the polymorphism of interest. The genotypes are then correlated with the level of liver copper in order to determine the association of the genotypes with liver copper level.

Once the presence or absence of the one or more polymorphisms of the invention have been detected in the genome of the dog, whether the dog is protected from, or susceptible to, liver copper accumulation is thereby determined. The genotype of each polymorphism alone or in combination with other polymorphisms is indicative of the protection from, or susceptibility of the dog to, liver copper accumulation.

To determine whether the susceptibility of a dog to, or the likelihood that a dog is protected from, liver copper accumulation, one may genotype one or more of the polymorphisms defined herein. The presence of one or more alleles that are associated with high copper indicates that the dog is susceptible to liver copper accumulation. Conversely, the presence of one or more alleles associated with low copper indicates that the dog is likely to be protected from liver copper accumulation. For example, to determine whether a dog is protected from liver copper accumulation one may genotype the SNP at Chr22_3135144 in the genome of the dog using a DNA sample from the dog. This functional mutation is located in ATP7B (on the X chromosome) and the A allele is protective. Once the genotype of the SNP has been determined it is possible to determine whether the dog is protected from liver copper accumulation. The presence of the A allele is indicative of protection from liver copper accumulation. A dog that is homozygous for the allele (AA) is most likely to be protected from liver copper accumulation. A preferred method of the invention therefore comprises determining the presence or absence of a A allele of the ATP7B SNP in the genome of the dog. The method may comprise determining whether the dog is homozygous or heterozygous for the A allele of the ATP7B SNP.

If the method comprises testing for the presence or absence of multiple polymorphisms indicative of susceptibility to, or protection from, liver copper accumulation, a model may be used that combines the results to provide an overall assessment of the risk or likelihood that the dog will be susceptible to, or protected from, liver copper accumulation. Example 6 explains how a model can be generated using multiple polymorphisms. Preferably, a stepwise modelling technique is used. A simplified example of model generation is described in Example 2. Table 3 sets out the different possible genotypes of the combination of 5 SNPs in the region of the GOLGAS, UBLS and ATP7A genes and the percentage of dogs with those genotypes that have high copper (liver levels of above 600 mg/kg). In this Example, to determine the susceptibility of a dog to liver copper accumulation one may genotype the 5 SNPs in the genome of the dog using a DNA sample from the dog. Once the genotypes of the SNPs have been determined, these can be converted into binary values based on the key provided in Example 2, i.e. based on the degree of association of the genotype with high copper. Then, Table 3 is used to convert the binary values into a risk factor based on the percentage of dogs that have that genotype pattern and high copper.

A dog may be tested by a method of the invention at any age, for example from 0 to 12, 0 to 6, 0 to 5, 0 to 4, 0 to 3, 0 to 2 or 0 to 1 years old. Preferably the dog is tested at as young an age as possible, for example within the first year, first 6 months or first 3 months of its life. The dog is preferably tested before copper accumulation occurs. The history of the dog may or may not be known. For example, the dog may be a pup of known parents and the history of the parents with respect to copper accumulation may be known. Alternatively, the dog may be a stray or a rescued dog with unknown parentage and history.

The dog to be tested by any method of the present invention may be of any breed. The invention provides a method of determining whether the genome of a mixed or crossbred dog, or a mongrel or out-bred dog comprises one or more polymorphisms indicative of protection from, or susceptibility to, liver copper accumulation.

In the method of the invention, the dog may be one that is suspected of being susceptible to liver copper accumulation. Alternatively, the dog may be suspected of being protected from liver copper accumulation.

Typically the dog will have genetic inheritance of a breed selected from Labrador Retriver, Doberman Pinscher, German Shepherd, Keeshond, Cocker Spaniel, West Highland White Terrier, Bedlington Terrier and Skye Terrier. The dog may be a mixed or crossbred dog, or a mongrel or out-bred dog. The dog may have at least 25%, at least 50%, or at least 100% of its genome inherited from any pure breed or more preferably from any of the breeds described herein. The dog may be a pure-bred. In one embodiment of the invention, one or both parents of the dog to be tested are or were pure-bred dogs. In another embodiment, one or more grandparents are or were purebred dogs. One, two, three or all four of the grandparents of the dog that is tested may be or may have been pure-bred dogs.

Preferably, the dog has genetic breed inheritance of Labrador Retriever. The dog may be a purebred Labrador Retriever. Alternatively, the dog may be a mixed or crossbred dog, or an outbred dog (mongrel). One or both of the parents of the dog may be a pure-bred Labrador Retriever dog. One, two, three or four of the grandparents of the dog may be a pure-bred Labrador Retriever dog. The dog may have at least 50% or at least 75% of the Labrador Retriever breed in its genetic background. Thus, at least 50% or at least 75% of the dog's genome may be derived from the Labrador Retriever breed.

The genetic breed background of a dog may be determined by assessing the allelic frequencies of genetic markers, for example SNPs or microsatellites. The combinations of allelic frequencies of different SNPs or microsatellites in a dog provide a signature that allows the breed of a dog or the breeds that make up a mixed breed dog to be determined. Such a genetic test may be a commercially available test. Alternatively, the dog may not need to be tested for the genetic inheritance of a particular breed because it is suspected of having a particular breed inheritance for example by the dog owner or veterinarian. This could be for example because of knowledge of the dog's ancestry or because of its appearance.

The predictive test of the invention may be carried out in conjunction with one or more other predictive or diagnostic tests such as determining the genetic breed background/inheritance of the dog or susceptibility to one or more other diseases.

Detection of Polymorphisms

The detection of polymorphisms according to the invention may comprise contacting a polynucleotide or protein in a sample from the dog with a specific binding agent for a polymorphism and determining whether the agent binds to the polynucleotide or protein, wherein binding of the agent indicates the presence of the polymorphism, and lack of binding of the agent indicates the absence of the polymorphism.

The method is generally carried out in vitro on a sample from the dog, where the sample contains DNA from the dog. The sample typically comprises a body fluid and/or cells of the dog and may, for example, be obtained using a swab, such as a mouth swab. The sample may be a blood, urine, saliva, skin, cheek cell or hair root sample. The sample is typically processed before the method is carried out, for example DNA extraction may be carried out. The polynucleotide or protein in the sample may be cleaved either physically or chemically, for example using a suitable enzyme. In one embodiment the part of polynucleotide in the sample is copied or amplified, for example by cloning or using a PCR based method prior to detecting the polymorphism.

In the present invention, any one or more methods may comprise determining the presence or absence of one or more polymorphisms in the dog. The polymorphism is typically detected by directly determining the presence of the polymorphic sequence in a polynucleotide or protein of the dog. Such a polynucleotide is typically genomic DNA, mRNA or cDNA. The polymorphism may be detected by any suitable method such as those mentioned below.

A specific binding agent is an agent that binds with preferential or high affinity to the protein or polypeptide having the polymorphism but does not bind or binds with only low affinity to other polypeptides or proteins. The specific binding agent may be a probe or primer. The probe may be a protein (such as an antibody) or an oligonucleotide. The probe may be labelled or may be capable of being labelled indirectly. The binding of the probe to the polynucleotide or protein may be used to immobilise either the probe or the polynucleotide or protein.

Generally, in the method, a polymorphism can be detected by determining the binding of the agent to the polymorphic polynucleotide or protein of the dog. However, in one embodiment the agent is also able to bind the corresponding wild-type sequence, for example by binding the nucleotides or amino acids which flank the variant position, although the manner of binding to the wild-type sequence will be detectably different to the binding of a polynucleotide or protein containing the polymorphism.

The method may be based on an oligonucleotide ligation assay in which two oligonucleotide probes are used. These probes bind to adjacent areas on the polynucleotide that contains the polymorphism, allowing after binding the two probes to be ligated together by an appropriate ligase enzyme. However, the presence of a single mismatch within one of the probes may disrupt binding and ligation. Thus, ligated probes will only occur with a polynucleotide that contains the polymorphism, and therefore the detection of the ligated product may be used to determine the presence of the polymorphism.

In one embodiment the probe is used in a heteroduplex analysis based system. In such a system when the probe is bound to a polynucleotide sequence containing the polymorphism it forms a heteroduplex at the site where the polymorphism occurs and hence does not form a double strand structure. Such a heteroduplex structure can be detected by the use of a single or double strand specific enzyme. Typically, the probe is an RNA probe, the heteroduplex region is cleaved using RNAase H and the polymorphism is detected by detecting the cleavage products.

The method may be based on fluorescent chemical cleavage mismatch analysis which is described for example in PCR Methods and Applications 3, 268-71 (1994) and Proc. Natl. Acad. Sci. 85, 4397-4401 (1998).

In one embodiment a PCR primer is used that primes a PCR reaction only if it binds a polynucleotide containing the polymorphism, for example a sequence-specific PCR system, and the presence of the polymorphism may be determined by detecting the PCR product. Preferably the region of the primer that is complementary to the polymorphism is at or near the 3' end of the primer. The presence of the polymorphism may be determined using a fluorescent dye and quenching agent-based PCR assay such as the Taqman PCR detection system.

The specific binding agent may be capable of specifically binding the amino acid sequence encoded by a polymorphic sequence. For example, the agent may be an antibody or antibody fragment. The detection method may be based on an ELISA system. The method may be an RFLP based system. This can be used if the presence of the polymorphism in the polynucleotide creates or destroys a restriction site that is recognized by a restriction enzyme.

The presence of the polymorphism may be determined based on the change that the presence of the polymorphism makes to the mobility of the polynucleotide or protein during gel electrophoresis. In the case of a polynucleotide, single-stranded conformation polymorphism (SSCP) or denaturing gradient gel electrophoresis (DDGE) analysis may be used. In another method of detecting the polymorphism, a polynucleotide comprising the polymorphic region is sequenced across the region that contains the polymorphism to determine the presence of the polymorphism.

The presence of the polymorphism may be detected by means of fluorescence resonance energy transfer (FRET). In particular, the polymorphism may be detected by means of a dual hybridisation probe system. This method involves the use of two oligonucleotide probes that are located close to each other and that are complementary to an internal segment of a target polynucleotide of interest, where each of the two probes is labelled with a fluorophore. Any suitable fluorescent label or dye may be used as the fluorophore, such that the emission wavelength of the fluorophore on one probe (the donor) overlaps the excitation wavelength of the fluorophore on the second probe (the acceptor). A typical donor fluorophore is fluorescein (FAM), and typical acceptor fluorophores include Texas red, rhodamine, LC-640, LC-705 and cyanine 5 (Cy5).

In order for fluorescence resonance energy transfer to take place, the two fluorophores need to come into close proximity on hybridisation of both probes to the target. When the donor fluorophore is excited with an appropriate wavelength of light, the emission spectrum energy is transferred to the fluorophore on the acceptor probe resulting in its fluorescence. Therefore, detection of this wavelength of light, during excitation at the wavelength appropriate for the donor fluorophore, indicates hybridisation and close association of the fluorophores on the two probes. Each probe may be labelled with a fluorophore at one end such that the probe located upstream (5') is labelled at its 3' end, and the probe located downstream (3') is labelled at its 5' end. The gap between the two probes when bound to the target sequence may be from 1 to 20 nucleotides, preferably from 1 to 17 nucleotides, more preferably from 1 to 10 nucleotides, such as a gap of 1, 2, 4, 6, 8 or 10 nucleotides.

The first of the two probes may be designed to bind to a conserved sequence of the gene adjacent to a polymorphism and the second probe may be designed to bind to a region including one or more polymorphisms. Polymorphisms within the sequence of the gene targeted by the second probe can be detected by measuring the change in melting temperature caused by the resulting base mismatches. The extent of the change in the melting temperature will be dependent on the number and base types involved in the nucleotide polymorphisms.

Polymorphism typing may also be performed using a primer extension technique. In this technique, the target region surrounding the polymorphic site is copied or amplified for example using PCR. A single base sequencing reaction is then performed using a primer that anneals one base away from the polymorphic site (allele-specific nucleotide incorporation). The primer extension product is then detected to determine the nucleotide present at the polymorphic site. There are several ways in which the extension product can be detected. In one detection method for example, fluorescently labelled dideoxynucleotide terminators are used to stop the extension reaction at the polymorphic site. Alternatively, mass-modified dideoxynucleotide terminators are used and the primer extension products are detected using mass spectrometry. By specifically labelling one or more of the terminators, the sequence of the extended primer, and hence the nucleotide present at the polymorphic site can be deduced. More than one reaction product can be analysed per reaction and consequently the nucleotide present on both homologous chromosomes can be determined if more than one terminator is specifically labelled.

The invention further provides primers or probes that may be used in the detection of any of the polymorphisms defined herein for use in the prediction of susceptibility to or protection from liver copper accumulation. Polynucleotides of the invention may also be used as primers for primer extension reactions to detect the SNPs defined herein.

Such primers, probes and other polynucleotide fragments will preferably be at least 10, preferably at least 15 or at least 20, for example at least 25, at least 30 or at least 40 nucleotides in length. They will typically be up to 40, 50, 60, 70, 100 or 150 nucleotides in length. Probes and fragments can be longer than 150 nucleotides in length, for example up to 200, 300, 400, 500, 600, 700 nucleotides in length, or even up to a few nucleotides, such as five or ten nucleotides, short of a full length polynucleotide sequence of the invention.

Primers and probes for genotyping the polymorphisms of the invention may be designed using any suitable design software known in the art using the sequences in Tables 4, 5, 6, 8, 18 and 20. Homologues of these polynucleotide sequences would also be suitable for designing primers and probes. Such homologues typically have at least 70% homology, preferably at least 80, 90%, 95%, 97% or 99% homology, for example over a region of at least 15, 20, 30, 100 more contiguous nucleotides. The homology may be calculated on the basis of nucleotide identity (sometimes referred to as "hard homology").

For example, the UWGCG Package provides the BEST-FIT program that can be used to calculate homology (for example used on its default settings) (Devereux et al (1984) Nucleic Acids Research 12, p387-395). The PILEUP and BLAST algorithms can be used to calculate homology or line up sequences (such as identifying equivalent or corresponding sequences (typically on their default settings), for example as described in Altschul S. F. (1993) J Mol Evol 36:290-300; Altschul, S, F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al, supra). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as default a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two polynucleotide sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologous sequence typically differs by at least 1, 2, 5, 10, 20 or more mutations, which may be substitutions, deletions or insertions of nucleotides.

The polynucleotides of the invention such as primers or probes may be present in an isolated or substantially purified form. They may be mixed with carriers or diluents that will not interfere with their intended use and still be regarded as substantially isolated. They may also be in a substantially purified form, in which case they will generally comprise at least 90%, e.g. at least 95%, 98% or 99%, of polynucleotides of the preparation.

Detector Antibodies

A detector antibody is an antibody that is specific for one polymorphism but does not bind to any other polymorphism as described herein. Detector antibodies are for example useful in purification, isolation or screening methods involving immunoprecipitation techniques.

Antibodies may be raised against specific epitopes of the polypeptides of the invention. An antibody, or other compound, "specifically binds" to a polypeptide when it binds with preferential or high affinity to the protein for which it is specific but does substantially bind not bind or binds with only low affinity to other polypeptides. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

For the purposes of this invention, the term "antibody", unless specified to the contrary, includes fragments that bind a polypeptide of the invention. Such fragments include Fv, F(ab') and F(ab')2 fragments, as well as single chain antibodies. Furthermore, the antibodies and fragment thereof may be chimeric antibodies, CDR-grafted antibodies or humanised antibodies.

Antibodies may be used in a method for detecting polypeptides of the invention in a biological sample (such as any such sample mentioned herein), which method comprises:
I providing an antibody of the invention;
II incubating a biological sample with said antibody under conditions which allow for the formation of an antibody-antigen complex; and
III determining whether antibody-antigen complex comprising said antibody is formed.

Antibodies of the invention can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, NY For example, an antibody may be produced by raising an antibody in a host animal against the whole polypeptide or a fragment thereof, for example an antigenic epitope thereof, hereinafter the "immunogen". The fragment may be any of the fragments mentioned herein (typically at least 10 or at least 15 amino acids long).

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells (Kohler and Milstein (1975) *Nature* 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat, mouse, guinea pig, chicken, sheep or horse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

Detection Kit

The invention also provides a kit that comprises means for typing one or more of the polymorphisms defined herein. In particular, such means may include a specific binding agent, probe, primer, pair or combination of primers, or antibody, including an antibody fragment, as defined herein which is capable of detecting or aiding detection of the polymorphisms defined herein. The primer or pair or combination of primers may be sequence specific primers that only cause PCR amplification of a polynucleotide sequence comprising the polymorphism to be detected, as discussed herein. The primer or pair of primers may alternatively not be specific for the polymorphic nucleotide, but may be specific for the region upstream (5') and/or downstream (3'). These primers allow the region encompassing the polymorphic nucleotide to be copied. A kit suitable for use in the primer-extension technique may specifically include labelled dideoxynucleotide triphosphates (ddNTPs). These may for example be fluorescently labelled or mass modified to enable detection of the extension product and consequently determination of the nucleotide present at the polymorphic position.

The kit may also comprise a specific binding agent, probe, primer, pair or combination of primers, or antibody that is capable of detecting the absence of the polymorphism. The kit may further comprise buffers or aqueous solutions.

The kit may additionally comprise one or more other reagents or instruments that enable any of the embodiments of the method mentioned above to be carried out. Such reagents or instruments may include one or more of the following: a means to detect the binding of the agent to the polymorphism, a detectable label such as a fluorescent label, an enzyme able to act on a polynucleotide, typically a polymerase, restriction enzyme, ligase, RNAse H or an enzyme which can attach a label to a polynucleotide, suitable buffer(s) or aqueous solutions for enzyme reagents, PCR primers which bind to regions flanking the polymorphism as discussed herein, a positive and/or negative control, a gel electrophoresis apparatus, a means to isolate DNA from sample, a means to obtain a sample from the individual, such as swab or an instrument comprising a needle, or a support comprising wells on which detection reactions can be carried out. The kit may be, or include, an array such as a polynucleotide array comprising the specific binding agent, preferably a probe, of the invention. The kit typically includes a set of instructions for using the kit.

Bioinformatics

The sequences of the polymorphisms may be stored in an electronic format, for example in a computer database. Accordingly, the invention provides a database comprising information relating to one or more polymorphisms selected from:

(a) Chr22_3167534 (SEQ ID NO: 144), Chr22_3135144 (SEQ ID NO: 145), Chr20_55461150 (SEQ ID NO: 146), ChrX_120879711 (SEQ ID NO: 147), Chr19_6078084 (SEQ ID NO: 148), Chr15_62625262 (SEQ ID NO: 149), Chr14_39437543 (SEQ ID NO: 150), Chr15_62625024 (SEQ ID NO: 151), Chr3_86838677 (SEQ ID NO: 152), Chr24_4011833 (SEQ ID NO: 153), Chr18_60812198 (SEQ ID NO: 154), Chr10_65209946 (SEQ ID NO: 155), and the CGCCCC repeat at chromosome location 22:3135287;

(b) one or more polymorphisms in linkage disequilibrium with a said polymorphism (a); and/or (c) Chr32_38904515 (SEQ ID NO: 156), Chr8_4892743 (SEQ ID NO: 157) and Chr8_4880518 (SEQ ID NO: 158);

and their association with the susceptibility of a dog to liver copper accumulation. The database may also comprise information relating to any of the other polymorphisms described herein. The database may include further information about the polymorphism, for example the degree of association of the polymorphism with the susceptibility of a dog to liver copper accumulation.

The invention also provides a database comprising information relating to one or more polymorphisms selected from:

(a) Chr22_3135144 (SEQ ID NO: 145); and (b) one or more polymorphisms in linkage disequilibrium with (a);

and their association with the protection of a dog from liver copper accumulation.

The database may also comprise information relating to any of the other polymorphisms described herein. The database may include further information about the polymorphism, for example the degree of association of the polymorphism with the protection of a dog from liver copper accumulation.

A database as described herein may be used to determine whether the genome of a dog comprises one or more polymorphisms indicative of protection from, or susceptibility to, liver copper accumulation. Such a determination may be carried out by electronic means, for example by using a computer system (such as a PC).

Typically, the determination of whether the genome of a dog comprises one or more polymorphisms indicative of susceptibility to or protection from liver copper accumulation will be carried out by inputting to a computer system genetic data from the dog to a computer system; comparing the genetic data to a database as defined herein; and on the basis of this comparison, determining whether the genome of a dog comprises one or more polymorphisms indicative of susceptibility to, or protection from, liver copper accumulation. This information can then be used to guide the management of the liver copper levels of the dog or can be used for informed breeding purposes.

The invention also provides a computer program comprising program code means for performing all the steps of a method of the invention when said program is run on a computer. Also provided is a computer program product comprising program code means stored on a computer readable medium for performing a method of the invention when said program is run on a computer. A computer program product comprising program code means on a carrier wave that, when executed on a computer system, instruct the computer system to perform a method of the invention is additionally provided.

Figure 10:
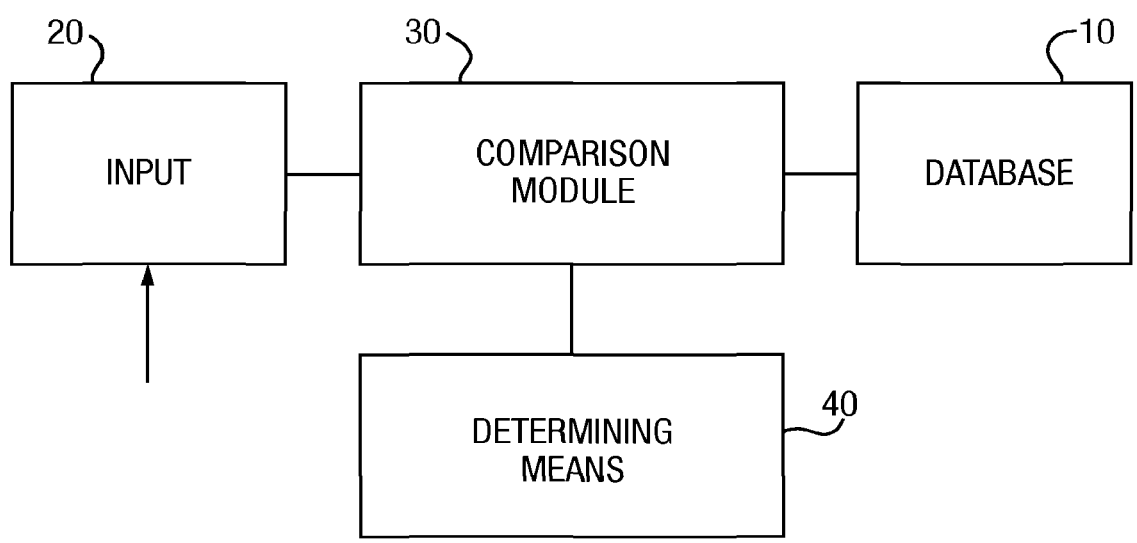
FIG. 10 illustrates schematically embodiments of functional components arranged to carry out the present invention.

As illustrated in FIG. 10, the invention also provides an apparatus arranged to perform a method according to the invention. The apparatus typically comprises a computer system, such as a PC. In one embodiment, the computer system comprises: means 20 for receiving genetic data from the dog; a module 30 for comparing the data with a database 10 comprising information relating to polymorphisms; and means 40 for determining on the basis of said comparison whether the genome of a dog comprises one or more polymorphisms indicative of protection of a dog from, or susceptibility of a dog to, liver copper accumulation.

Breeding Tool

Breeding value is defined as the value of an individual as a parent and is commonly used for improving desirable traits of life-stock in the farming industry. In order to improve the overall copper handling ability of dogs and to reduce the incidence of copper associated diseases, such as chronic hepatitis, it would be advantageous to select dogs for breeding that are protected from, or are not susceptible to, liver copper accumulation. This problem is solved by the use of polymorphisms that can be used to determine whether a dog is protected from, or not susceptible to, liver copper accumulation in order to inform breeding.

For example, the copper handling ability of the offspring of two dogs may be influenced by the genotype of the parents at the ATP7B locus. The transfer of a particular variant at this locus could be beneficial to the offspring. By determining the genotype at this locus it will be possible to assess the breeding value of a prospective parent and thereby make decisions as to whether a given breeding pair are appropriate.

Accordingly, the invention provides a method of selecting a dog for producing offspring protected from liver copper accumulation comprising determining whether the genome of a dog comprises one or more polymorphisms indicative of protection from liver copper accumulation by a method of the invention in a candidate first dog; and thereby determining whether the candidate first dog is suitable for producing offspring protected from liver copper accumulation. The method may further comprise determining whether the genome of a dog comprises one or more polymorphisms indicative of protection from liver copper accumulation by a method of the invention in a second dog of the opposite sex to the first dog. If the results are that the first and/or second dog has a genotype indicative of protection from liver copper accumulation, the first dog may then be mated with the second dog in order to produce offspring protected from liver copper accumulation.

For example, the method may comprise determining the presence or absence of one or more polymorphisms selected from Chr22_3135144 (SEQ ID NO: 145) and one or more polymorphisms in linkage disequilibrium thereof in the genome of the candidate first dog. More preferably the method further comprises determining the presence or absence of the SNP ChrX_63338063 (ATP7a_Reg3 F 6 SNP; SEQ ID NO: 142) or one or more polymorphisms in linkage disequilibrium with said SNP such as ChrX_63397393 (ATP7a_Reg16 F 42 SNP; SEQ ID NO:143). The method of the invention may comprise determining the presence or absence of the A allele of Chr22_3135144 (SEQ ID NO: 145) and/or the T allele of ChrX_63338063 (SEQ ID NO:142). The presence of one or more of these SNPs indicates that the first dog is protected from liver copper accumulation and is therefore a good candidate to be mated with a second dog. Homozygosity in either the first and/or second dog is most preferable as this increases the likelihood that the offspring will be homozygous and thereby protected from liver copper accumulation.

The invention also provides a method of selecting a dog for producing offspring protected from liver copper accumulation by making use of the polymorphisms of the invention that are indicative of susceptibility to copper accumulation. The absence of such polymorphisms in the genome of the dog indicates that the dog is a good candidate for mating. The method of the invention may therefore comprise determining whether the genome of the candidate first dog comprises one or more polymorphisms indicative of susceptibility to liver copper accumulation; and thereby determining whether the candidate first dog is suitable for producing offspring protected from liver copper accumulation.

The method may comprise detecting the presence or absence in the genome of the candidate first dog of one or more polymorphisms selected from:
  (a) Chr22_3167534 (SEQ ID NO: 144), Chr22_3135144 (SEQ ID NO: 145), Chr20_55461150 (SEQ ID NO: 146), ChrX_120879711 (SEQ ID NO: 147), Chr19_6078084 (SEQ ID NO: 148), Chr15_62625262 (SEQ ID NO: 149), Chr14_39437543 (SEQ ID NO: 150), Chr15_62625024 (SEQ ID NO: 151), Chr3_86838677 (SEQ ID NO: 152), Chr24_4011833 (SEQ ID NO: 153), Chr18_60812198 (SEQ ID NO: 154), Chr10_65209946 (SEQ ID NO: 155), and the CGCCCC repeat at chromosome location 22:3135287;
  (b) one or more polymorphisms in linkage disequilibrium with a said polymorphism (a); and/or
  (c) Chr32_38904515 (SEQ ID NO: 156), Chr8_4892743 (SEQ ID NO: 157) and Chr8_4880518 (SEQ ID NO: 158).

The method may further comprise determining whether the genome of a second dog of the opposite sex to the first dog comprises one or more polymorphisms indicative of susceptibility to liver copper accumulation. The method may therefore comprise detecting the presence or absence in the genome of a second dog of one or more polymorphisms selected from:
  (a) Chr22_3167534 (SEQ ID NO: 144), Chr22_3135144 (SEQ ID NO: 145), Chr20_55461150 (SEQ ID NO: 146), ChrX_120879711 (SEQ ID NO: 147), Chr19_6078084 (SEQ ID NO: 148), Chr15_62625262 (SEQ ID NO: 149), Chr14_39437543 (SEQ ID NO: 150), Chr15_62625024 (SEQ ID NO: 151), Chr3_86838677 (SEQ ID NO: 152), Chr24_4011833 (SEQ ID NO: 153), Chr18_60812198 (SEQ ID NO: 154), Chr10_65209946 (SEQ ID NO: 155), and the CGCCCC repeat at chromosome location 22:3135287;
  (b) one or more polymorphisms in linkage disequilibrium with a said polymorphism (a); and/or
  (c) Chr32_38904515 (SEQ ID NO: 156), Chr8_4892743 (SEQ ID NO: 157) and Chr8_4880518 (SEQ ID NO: 158).

If the results are that the genome of the first and/or second dog does not have a genotype indicative of susceptibility to liver copper accumulation, the first dog may then be mated with the second dog in order to produce offspring that is not susceptible to liver copper accumulation.

The method may further comprise detecting the presence or absence in the genome of the candidate first dog of (I) a polymorphism in the GOLGA5, ATP7A or UBL5 gene that is indicative of susceptibility to liver copper accumulation and/or (II) a polymorphism in linkage disequilibrium with a said polymorphism (I). Preferably, the method comprises determining the presence or absence of one or more polymorphisms selected from the SNPs identified in Tables 4 to 6 and one or more polymorphisms in linkage disequilibrium thereof in the genome of the candidate first dog. The presence of one or more of these polymorphisms indicates that the first dog is susceptible to liver copper accumulation and is therefore not a good candidate to be mated with a second dog to produce offspring protected from liver copper accumulation.

The candidate first dog and/or second dog may be of any breed. Preferably the candidate first dog and/or second dog has genetic breed inheritance of a breed selected from Labrador Retriver, Doberman Pinscher, German Shepherd, Keeshond, Cocker Spaniel, West Highland White Terrier, Bedlington Terrier and Skye Terrier. More preferably, the candidate first dog and/or second dog has genetic inheritance of the Labrador Retriever breed. The dog may be a purebred Labrador Retriever. Alternatively, the dog may be a mixed or crossbred dog, or an outbred dog (mongrel). One or both of the parents of the dog may be a pure-bred Labrador Retriever dog. One, two, three or four of the grandparents of the dog may be a pure-bred Labrador Retriever dog. The dog may have at least 50% or at least 75% of the Labrador Retriever breed in its genetic background. Thus, at least 50% or at least 75% of the dog's genome may be derived from the Labrador Retriever breed.

The genetic breed inheritance of a dog may be determined by assessing the allelic frequencies of genetic markers, for example SNPs or microsatellites. The combinations of allelic frequencies of different SNPs or microsatellites in a dog provide a signature that allows the breed of a dog or the breeds that make up a mixed breed dog to be determined. Such a genetic test may be a commercially available test. Alternatively, the dog may not need to be tested for a particular breed inheritance because it is suspected of having a particular breed inheritance for example by the dog owner or veterinarian. This could be for example because of knowledge of the dog's ancestry or because of its appearance.

Most purebred dogs of breeds recognized by all-breed club registries are controlled by "closed studbooks". A studbook is typically the official registry of approved dogs of a given breed kept by, for example, a breed association or kennel club. It is generally termed a "closed" studbook if dogs can only be added if their parents were both registered. Most breeds have closed studbooks, resulting in inbreeding, as genetic diversity cannot be introduced from outside the existing population. In a number of breeds recognized by kennel clubs this has resulted in high incidences of genetic diseases or disorders and other problems such as reduced litter sizes, reduced lifespan and inability to conceive naturally.

In order to avoid the problems associated with inbreeding, it would be advantageous to select dogs for breeding within a particular breed that are more distantly related to each other compared to dogs that are more closely related. Therefore in one aspect of the invention, the genetic breed inheritance of the candidate first dog and of the candidate second dog is determined in order to determine the degree of relatedness of the two dogs. In this aspect of the invention, the term "genetic breed inheritance" relates to the dog's genetic ancestry within a particular breed. The dog's genetic breed inheritance may be determined as described herein. By determining the dogs' genetic inheritance, it is possible to distinguish between dogs within a single breed in order to determine how closely related they are.

Therefore, in one aspect of the invention the degree of relatedness of the candidate first dog and the candidate second dog is determined, which comprises comparing the genetic breed inheritance of the candidate first dog with the candidate second dog of the same breed. Preferably the dogs are purebred dogs. The genetic breed inheritance of each dog may for example be determined by identifying the presence or absence of one or more breed-specific polymorphisms in said dog.

The degree of relatedness may be determined from the number of breed-specific polymorphisms that the dogs have in common. For example, two dogs of the same breed may have from 0 to 100% of the breed-specific polymorphisms tested in common, for example from 10 to 90%, from 20 to 80%, from 30 to 70% or from 40 to 60%. Therefore, two dogs may have at least 10%, 20%, 30%, 40%, 50%, 60%, 70%, 80% or 90% of the breed-specific polymorphisms tested in common. The percentage of tested breed-specific polymorphisms in common between two dogs may be used as a measure of their degree of relatedness. In this aspect of the invention, the two dogs would only be mated together if they are sufficiently genetically unrelated. For example, they may only be mated together if they have less than 60%, 50%, 40%, 30% or less than 20% of the breed-specific polymorphisms tested in common.

The invention also provides a method of selecting one or more dogs for breeding with a subject dog, the method comprising:
  (a) determining for a subject dog and for each dog in a test group of two or more dogs of the opposite sex to the subject dog whether the genome comprises one or more polymorphisms indicative of protection from, and/or one or more polymorphisms indicative of susceptibility to, liver copper accumulation; and
  (b) selecting one or more dogs from the test group for breeding with the subject dog.

The test group may consist of at least 2, 3, 4, 5, 10, 15, 20, 25, 30, 50, 75, 100 or 200 different dogs, for example from 2 to 100, from 5 to 70 or from 10 to 50 dogs. The dogs are typically selected from the test group on the basis of being protected from liver copper accumulation. The dog or dogs selected from the test group may have the same or similar genetic breed inheritance as the subject dog.

The subject dog and each dog in the test group may be of any breed. Preferably the subject dog and/or each dog in the test group has genetic breed inheritance of a breed selected from Labrador Retriver, Doberman Pinscher, German Shepherd, Keeshond, Cocker Spaniel, West Highland White Terrier, Bedlington Terrier and Skye Terrier. More preferably the dog has genetic breed inheritance of the Labrador Retriever breed. The dog may be a purebred Labrador Retriever. Alternatively, the dog may be a mixed or crossbred dog, or an outbred dog (mongrel). One or both of the parents of the dog may be a pure-bred Labrador Retriever dog. One, two, three or four of the grandparents of the dog may be a pure-bred Labrador Retriever dog. The dog may have at least 50% or at least 75% of the Labrador Retriever breed in its genetic background. Thus, at least 50% or at least 75% of the dog's genome may be derived from the Labrador Retriever breed.

The dog within the test group that is most likely to be protected from liver copper accumulation, based on the presence or absence of polymorphisms associated with protection from or susceptibility to liver copper accumulation, may be selected for breeding with the subject dog. Alternatively, a number of the dogs within the test group that are likely to be protected from liver copper accumulation are selected for breeding with the subject dog. For example, at least 2, 3, 4, 5, 10, 15 or 20 dogs in the test group may be selected. A further selection may then be made from the group of selected dogs based on other factors, for example geographical location, age, breeding status, medical history, disease susceptibility or physical characteristics.

As explained above, it is desirable to mate dogs within the same breed that are most genetically unrelated. This is in order to increase or maintain genetic diversity within the breed, and to reduce the likelihood of problems relating to inbreeding arising within the offspring. A further selection of the dogs from the test group may therefore be based on the genetic relatedness of the dogs with the subject dog. Accordingly, the method may further comprise:

(a) comparing the genetic breed inheritance of the subject dog with the genetic breed inheritance of each dog in a test group of two or more dogs of the same breed and of the opposite sex to the subject dog;

(b) determining from the comparison the degree of relatedness between the subject dog and each dog in the test group; and (c) selecting one or more dogs from the test group for breeding with the subject dog.

The dogs may be selected from the test group on the basis of their relatedness to the subject dog (i.e. the dog to be bred from). Preferably the dog or dogs selected from the test group are the most distantly related (i.e. have the lowest degree of relatedness) within the test group of dogs. The genetic breed inheritance of the subject dog and the dogs in the test group may be already known or may be determined e.g. by a commercially available breed test.

The invention thus provides a method of recommending one or more suitable dogs for breeding with a subject dog. The recommendation may be made to the subject dog's owner or carer, a veterinarian, dog breeder, kennel club or breed registry.

The invention also relates to a method of breeding dogs, wherein the protection from, or susceptibility to, liver copper accumulation of at least two dogs of the opposite sex is determined, optionally within the same breed, before breeding them together.

The protection from, or susceptibility to, liver copper accumulation of a dog may be stored in an electronic format, for example in a computer database. Accordingly, the invention provides a database comprising information relating to the susceptibility to, or protection from, liver copper accumulation and sex of one or more dogs. The database may include further information about the dog, for example the dog's genetic breed inheritance, breeding status, age, geographical location, medical history, disease susceptibility or physical characteristics. The database will typically further comprise a unique identifier for each dog, for example the dog's registered name. The database may be accessed remotely, for example using the internet.

The invention is illustrated by the following Examples:

Example 1

Whole Genome Association Study and Identification of Regions Potentially Containing Informative Genes This Example describes the general approach that was taken to develop a genetic predictive test for copper accumulation. It also details the methodology used for a whole genome association study and the identification of regions of the genome potentially containing informative genes.

The general approach used to develop a genetic predictive test for copper accumulation was as follows. First, collected samples from dogs diagnosed as "affected" or "unaffected" by liver copper accumulation were run on a genotyping array with a large number of markers. This is known as a "whole genome association study". Analysis of this data gave an indication of regions potentially containing informative genes. Informative SNPs in regions with interesting genes were then used in model generation. In parallel, the interesting genes were sequenced to look for coding mutations or other mutations that better describe the genetic effect on the disease. These mutations were then used in further model generation. In practice, this process involved loops and parallel tracks because of ongoing improvements in technology.

Patient Recruitment

Data were collected from 254 Labrador retrievers. The dogs were recruited in two ways. Clinically affected dogs were admitted to the Hepatology department of the Faculty of Veterinary Medicine, Utrecht University by a referring veterinarian. First line relatives of affected dogs were actively recruited via registration files of the Dutch Labrador retriever breed club.

Diagnosis

Every dog underwent a physical examination and blood was collected for coagulation testing, determination of liver enzymes (Alkaline phosphatase and Alanine Amino Transferase), bile acids and albumin. An EDTA blood sample was used for DNA isolation.

Liver biopsies were obtained from 239 dogs by Menghini technique, ultrasound guided with a Trucut 14 Gauge needle device, collected during laparoscopy or laparotomy or taken after euthanasia (Teske et al., 1992, Vet. Rec. 131:30-32). Liver biopsies were fixed in 4% buffered formalin for 3 hours, transferred to 70% ethanol and embedded in paraffin. Five micron sections were mounted on slides and stained with Haematoxylin and Eosin (routine evaluation), von Giesson (reticulin staining) and rubeanic acid (copper staining).

Diagnosis was based on histological evaluation of a liver biopsy by our board certified pathologist (TSGAMvdI). Severity of copper accumulation was scored on a scale from 0 to 5 as described previously (Teske et al., 1992, Vet. Rec. 131:30-32). An additional liver biopsy was collected in a copper free container, freeze dried and quantitative copper was determined by Instrumental Neutron Activation Analysis (INAA) in dry weight liver (Bode et al., 2008, Anal. Bioanal. Chem. 390:1653-1658).

The histology score is described below:

Grade 0—no copper.

Grade 1—solitary liver cells contain some copper positive granules.

Grade 2—small groups or area of liver cells contain small to moderate amounts of copper positive granules.

Grade 3—larger groups or areas of liver cells contain moderate amounts of copper positive granules, sometimes associated with copper containing macrophages.

Grade 4—large areas of liver cells with many copper positive granules, usually associated with copper containing macrophages.

Grade 5—diffuse pan-lobular presence of liver cells with many copper positive granules, usually associated with copper containing macrophages.

Sample Phenotyping

Copper-Associated Chronic Hepatitis has previously been phenotypically characterised (Hoffmann et al., 2006, J. Vet. Intern. Med. 20: 856-861). Four phenotypes were defined based on evaluation of the liver biopsies.

For the purposes of the 22 k chip data (see below) we designated liver copper concentrations above 600 mg/kg dry weight as "affected" and below 400 mg/kg dry weight as "unaffected" (quantaff).

A binary phenotype for the most clear copper toxicosis cases and controls was also applied (cutox). A case was defined as having a liver copper level>1200 mg/kg or copper staining>3 and histological signs of hepatitis. A control was defined as having liver copper level<400 mg/kg and staining of <2 and no abnormalities on histology. A more separated phenotype was used to increase the resolution of the genetic mapping.

A semi-quantitative scoring by the pathologist based on rubeanic acid staining was used as a quantitative phenotype (ra) (score 0-5) and was available in all dogs that underwent a liver biopsy.

Quantitative copper level in liver tissue was used as a quantitative phenotype (cuq) and ranged from 65 to 3870 mg/kg.

Genotyping (Illumina 22K Chip)

Genome-wide genotyping was carried out using the first generation Illumina canine genotyping array, which aims to measure approximately 22,000 SNP loci (22K chip). We ran 251 dog DNA samples on this array.

Chi-Squared Analysis

The data were analysed with a collection of chi-squared tests. A two degrees of freedom test was used. Loci were then ranked by p-value to prioritise further investigation.

Pairwise Analysis

Typically genetic mapping is done by genotyping selected samples on markers spread across the whole genome. The samples are phenotyped for a trait such as a disease. The samples are typically selected from a single sub population and selected to be as unrelated within that population as possible. This is done to reduce the risk of getting false positive hits from the population structure.

In previous canine genetic studies it was difficult to satisfy these stringent criteria as dogs are constantly under large amounts of varying genetic selection. This creates population structure in the dataset across subtypes of breeds, geographies, time and social cliques. New methods had to be developed to analyse the canine genetic data in the presence of population structure and closely related samples. Pairwise mapping was the most successful method developed for this purpose.

A method was developed to determine the polymorphisms associated with a genetic trait in a group of individuals, namely "Partition Mapping" (also known as "2D mapping"). The method is currently limited to binary conditions (case/control studies). Complex diseases with a genetic link are generally driven by more than one gene. These genes can interact in non-linear ways, making them more difficult to map using traditional methods. By working on the level of a pair of individuals it is possible to factor out the impact of multiple genes because a locus will either be contributing to the phenotype on that pair of individuals or not. The full working of this process is described below. After running this analysis it is possible to extract the risk alleles in each area and build a model to predict the phenotype using other methods.

The "Partition Mapping" algorithm scans through the genome stopping every 50 kilobases. At each of these points, every pair of individuals is analysed. For each pair, the genotypes for the whole chromosome are analysed comparing the likelihood of the genotypes under three possible scenarios. The first scenario is that there is a recessive mutation driving the phenotype in this pair of individuals. The second scenario is that there is a dominant mutation driving the phenotype in this pair of individuals. The third scenario is that there is no important mutation for the phenotype in the pair of dogs at this location. The likelihoods are calculated using a hidden markov model, described below. By comparing these likelihoods it is possible to derive a Bayes-Factor for this pair of individuals towards or against the presence of a recessive or dominant phenotype-driving mutation at that point. The log of these values is taken; a positive value then represents more weight towards the recessive or dominant mutation scenario, a negative value represents more evidence towards there being no important mutation here.

The pairs of individuals are sorted in order of the Log-Bayes factors at that locus. The pairs' Log-Bayes-Factors are then summed up in descending order taking a record of the cumulative weight of evidence at each percentile of the data. In most cases some Log-Bayes-Factors will be positive and some will be negative. This will give the effect of the recorded value rising for a percentage of the data and then falling. The maximum of this value gives a measure of the weight of evidence towards either the recessive or dominant models. This is referred to as the "peak-value".

In some cases the algorithm has bias towards particularly homozygous areas of the genome or areas with a high density of polymorphisms. This effect is quantified by running the process with every pair permuted across the four possible case/control states (case-case, case-control, control-case, control-control). For any one locus, one subtracts the peak-value under the permuted model from the normal peak-value, and this gives a corrected peak-value. It is then possible to compare the corrected peak-values across the genome giving regions of interest. This method has been used to map a number of locations associated with copper loading in the liver. These locations are marked by haplotype patterns indicative of a trait-linked gene. The locations were then investigated for likely genes.

Region Gene Analysis

Regions identified in the whole genome association study were then analysed for likely genes. The process involved identifying the informative region boundaries; identifying all genes in the region in Ensembl; looking for relevant protein domains related to copper or liver function; looking for membership of pathways linked to copper; and looking for genes expressed in relevant tissues. Based on this information, genes were then prioritised by likelihood of involvement with the disease.

A number of candidate genes associated with copper accumulation or liver disease were identified by this process.

Genotyping (Illumina 170K Chip)

A newer SNP chip than the 22K chip described above became available which has 172,115 markers from more varied sources (170K chip). This chip contains on average more than 70 markers per Mb. We ran the same and further DNA samples on this array as were run on the 22K chip.

Analysis

Using the results from the 170K chip, genome wide association analysis was performed with GenABEL software (Aulchenko et al., 2007, Bioinformatics, 23: 12941296). SNPs that were successfully typed in 98% of individuals and individuals that had 98% of SNPs successfully genotyped were kept in the analysis. SNPs were kept in the analysis when at least 20 carriers were present. Significantly associated SNPs were checked for Hardy Weinberg Equilibrium (HWE) after analysis.

Genetic kinship was estimated based on autosomal genotype information. Heritability for three traits (copper toxicosis, rubeanic acid stain score and quantitative liver copper in mg/kg) was estimated by a polygenic model (Aulchenko et al., 2007, Genetics, 177: 577-585) in which population sub-structuring was accounted for by calculating the genetic kinship matrix. Age and sex were modeled as covariates. Population stratification was checked by a multidimensional scaling plot. Correction for stratification was performed by performing a score test on residuals of the estimates of the polygenic model and genomic control. The functions grammas (Amin et al., 2007, PloS One, 2: e1274) and fasta (Chen et al., 2007, Am. J. Hum. Genetics, 81: 913-926) were used to correct for population stratification. A thousand permutations were used in grammas analysis to obtain genome wide corrected p-values. The X-chromosome was analyzed separately for males and females.

The pairwise method described above was applied here also.

In total, 109496 markers and 253 dogs passed quality control. A summary of phenotypes and calculated heritability (H2) for each trait is depicted in Table 1.

TABLE 1

Summary of phenotypes

| Phenotype | H2 | Nr of individuals | Sex | Nr of individuals | Age in years Mean (Sd) |
|---|---|---|---|---|---|
| Copper toxicosis (cutox) | 0.64 | Cases | Males | 8 | 6.2 (2.2) |
|  |  | 33 | Females | 25 |  |
|  |  | Controls | Males | 30 | 6.0 (2.6) |
|  |  | 62 | Females | 32 |  |
| Rubeanic acid stain score (ra) (0-5) | 0.49 | 235 | Males | 80 | 5 9 (2.6) |
|  |  |  | Females | 155 |  |

The genome wide association analysis resulted in hits that were close to being genome wide significant results. Results of the top 5 significant SNPs for all three analyses are depicted in Table 2.

P-values for Fasta analysis of each of the three phenotypes.

| Phenotype | Chromosome | Location | SNP name | p-value |
|---|---|---|---|---|
| Cutox | 31 | 36465117 | BICF2P124447 | 6.632271e−05 |
|  | 27 | 40245328 | BICF2P154172 | 1.939526e−04 |
|  | 38 | 12095696 | BICF2P981165 | 2.029342e−04 |
|  | 38 | 11652179 | BICF2P514131 | 2.138857e−04 |
|  | 10 | 67858787 | BICF2S23647325 | 2.733150e−04 |

-continued

P-values for Fasta analysis of each of the three phenotypes.

| Phenotype | Chromosome | Location | SNP name | p-value |
|---|---|---|---|---|
| Ra | 22 | 7767302 | BICF2G630316066 | 4.016960e−06 |
|  | 22 | 12463818 | BICF2S23122114 | 1.464354e−05 |
|  | 22 | 12495308 | BICF2S23320612 | 1.464354e−05 |
|  | 22 | 12511354 | BICF2S2417189 | 1.464354e−05 |
|  | 22 | 7548442 | BICF2G630315950 | 1.526836e−05 |
| Cuq | 18 | 38185045 | BICF2G630699136 | 1.514989e−06 |
|  | 27 | 43555866 | BICF2G630153553 | 2.723925e−06 |
|  | 18 | 40278498 | BICF2G630697308 | 3.293349e−06 |
|  | 18 | 40223465 | BICF2G630697352 | 5.019301e−06 |
|  | 18 | 40227604 | BICF2G630697350 | 5.019301e−06 |

A close to genome wide significant region (p-value after 1000 permutations in grammas was 0.11) was identified with the ra genotype on chromosome 22. The associated region was found to span a 15 Mb region at the beginning of the chromosome. The candidate gene ATP7B was located in this region at 3.12-3.16 Mb. The analysis of this gene is described in Example 5.

Example 2

Three Region Model Generation

This Example describes the generation of a three-region model for determining susceptibility to liver copper accumulation. This work is also described in WO 2009/044152 A2, WO 2010/038032 A1 and WO 2010/116137 A1.

SNPs in and around the genes prioritised in the region analysis described in Example 1 were extracted from the dataset. These were analysed singly and in haplotypes looking for informative allele patterns associated with liver copper level.

The most significant (by 1 degree freedom chi-squared test) of these patterns were used in the model. SNPs near three genes (ATP7A, UBLS-ortholog and GOLGAS) were chosen for use in the model. A Boolean model was then generated, with each gene pattern being represented by either a 0 or a 1 (1 being the higher risk genotype or pattern) and the combination of the three patterns by a three number pattern (e.g. 0-0-0 or 0-1-1). 1-1-1 therefore represents the greatest risk of high liver copper.

Table 3 shows the result of the three-region model for predicting copper accumulation. Each region uses either a single SNP or a group of SNPs. The model shows a clear difference in risk of disease depending on the genotype of the dog using this simple model of SNPs in three genomic regions.

TABLE 3

A model predicting copper accumulation using genetic mutations in three regions of the genome.

| Chr 8 location: 4850000 bp (near GOLGA5) | Chr X location: 63000000 bp (near ATP7A) | Chr 32 location: 40000000 bp (near UBL5) | 3 allele pattern | Average of Cu2 conc | % dogs affected | Number of dogs with pattern |
|---|---|---|---|---|---|---|
| 1 | 1 | 1 | 111 | 1253.09 | 81.5% | 27 |
| 1 | 1 | 0 | 110 | 733.40 | 60.0% | 20 |
| 1 | 0 | 1 | 101 | 1138.90 | 77.8% | 9 |
| 1 | 0 | 0 | 100 | 737.84 | 60.7% | 28 |
| 0 | 1 | 1 | 011 | 502.27 | 42.9% | 7 |
| 0 | 1 | 0 | 010 | 670.83 | 63.6% | 11 |
| 0 | 0 | 1 | 001 | 450.00 | 50.0% | 4 |
| 0 | 0 | 0 | 000 | 332.47 | 7.1% | 14 |

The key to the binary values in Table 3 is as set out below
Genomic location Chromosome 8 (CFA8), GOLGA5 gene region:
1=if there is an AA genotype at SNP BICF2P506595
0=if there is any other genotype at SNP BICF2P506595
Genomic location Chromosome 32 (CFA32), UBL5 gene region:
1=if there is a GG at BICF2P772765, a CC at BICF2S2333187 and a GG at BICF2P1324008
0=if any of those SNPs show a different genotype
Genomic location Chromosome X (CFAX), ATP7A gene region:
1=if there is an AA or an AG at BICF2P591872
0=if there is a GG at BICF2P591872

Table 3 represents the binary conditions of alleles at three genomic locations. At genomic location CFA8, one SNP was used (SNP 1). At genomic location CFA32 three SNPs were used (SNPs 2, 3 and 4). At genomic location CFAX one SNP was used (SNP 5). The binary values are indicative of a dog having alleles that are indicative of susceptibility to copper accumulation ("bad" alleles). For instance 000 represents not having any of the three bad alleles. 111 represents having all three bad alleles.

Table 4 shows the position and sequence of the SNPs used for the results in Table 3. The results implicated three genomic locations (in and around the GOLGA5, UBL5 and ATP7A genes) associated with susceptibility to copper accumulation. Further SNPs in these regions that are indicative of susceptibility to copper accumulation are provided in Table 5.

TABLE 4

Position and sequence of SNPs used for results in Table 3

| SNP name (SNP no.) | SEQ ID NO: | Chromosome in cafam 2 | Location in canfam 2 | Gene containing or close to mutation | SNP Sequence SNP = [first allele/second allele] |
|---|---|---|---|---|---|
| BICF2P506595 (SNP 1) | 1 | 8 | 4886813 | GOLGA5 | CTCAGAACTAGATAGGCTAATAAGTGATAGGCCTTGTGTTTTC CTAGAGTGTGCTTTAAA[A/G]GTTTCTTAAGCTAAAAAATTA CATTCGTGAGAAAATTGAAATAAAAGGAAAACAGTCATG |
| BICF2P772765 (SNP 2) | 2 | 32 | 39278300 | UBL5 | TCTCAGATACTTGATAGCCAGCATTTCCCCCCATTTTCTTCCA AGAGCACGAAAGCATAG[A/G]AATGATATTACATCTCGTATG GTGAATGTGACACAGCCGTCAGTTGCGTTAGCTCTGCTT |
| BICF2S2333187 (SNP 3) | 3 | 32 | 39390236 | UBL5 | TATTACCCTGGTCTCCAGCCACTCCTTTACCTTCCATTAGCCC ACACCTGCTCTACACAC[T/C]ATTGCTCATGGAAGCCTTGCC ACGTGCAGTCGCCACTCTGAAATGCCAGCATCGCTCCCA |
| BICF2P1324008 (SNP 4) | 4 | 32 | 40043909 | UBL5 | GACCTGACAGATTATGTAGACTTTGTTTTCAAAGGGAGCACCT GCTGGATATACAACATG[A/G]CACTAAA7TGTGCTCCACATC CTTGGCAGAGGTGGGGGGCGGGGCACAAAGGAAGAAACC |
| BICF2PS91872 (SNP 5) | 5 | X | 62989720 | ATP7A | GGGCCCAGCAAGTGGCAGAACTGGGAAGACCCCCTCTTCTTCC GCCTGGAGCAGTGGTGT[A/G]GCAGCACACCACAGGAGTCTG AAAGGGTGGGGAGTCCAAACGGGAACATATACCTGAGAT |

TABLE 5

Position and sequence of further SNPs indicative of susceptibility to liver copper accumulation

| SNP name (SNP no.) | SEQ ID NO: 2 | Chromosome in canfam 2 | Location in canfam 2 | Allele Frequency | Minor Allele Frequency | SNP Sequence SNP = [first allele/second allele] |
|---|---|---|---|---|---|---|
| BICF2P1246154 (SNP 6) | 6 | X | 47335181 | 0.999507 | 0.000493 | GGCAACAGGGACAGGCTGCTGGGCCACACACTCACCCACACT AGGAGACAAGATCCTCCA[T/C]ATCCTGGGTCTCTATCAGT CAATCACCTAGACCAGTGGGCCAGAGGACAGGGTCCAGCTG |
| BICF2P463335 (SNP 7) | 7 | X | 44401786 | 0.000493 | 0.000493 | GTTGAGAGAGATCATACAGATTCATGTGGCAGGTGCACACTT TTTCTACCTCTTACAACG[T/C]ATTCTCTCTGGCCATTCCT TCTCCTGGGTCCCAAAGTCGGAGAGCTTAGCGGGAGCCTAG |
| BICF2P1246989 (SNP 8) | 8 | 8 | 4149835 | 0.999506 | 0.000494 | ataagttcacattttgGTGTTTCAAGTGGACATGAATGGAGG GGAGGGCCCTGTTCAATC[T/C]ACTAAAGTGTTTTTTCATC TTGTTTTTGTGGAAATCAAATCAAGAAGCAGAGTTTTATGT |
| BICF2P723557 (SNP 9) | 9 | 8 | 3406227 | 0.999014 | 0.000986 | ACTCTCCCGATGTGGGCACCATATGGTGGACCACTTTCTGTG TGAGATGCCTGCTCTTAT[T/C]GCCATGTCCTGTGAAGACA CCATGCTGGTGGAAGCATTTGCCTTTGCCCTGGGTGTTGCC |
| BICF2S23427298 (SNP 10) | 10 | 8 | 5393517 | 0.999014 | 0.000986 | AATCTAAGTAGACTGAGTGGTCACCTTCAGCGCTCAGACCTG AGCATACAAAGCATGAA[A/G]GTTACTGTGATTCAGCTGA TGTAATGGAATGAAATAAATATAAGAGTTTGGTAACCTAAT |

TABLE 5-continued

Position and sequence of further SNPs indicative of susceptibility to liver copper accumulation

| SNP name (SNP no.) | SEQ ID NO: | Chromosome in canfam 2 | Location in canfam 2 | Allele Frequency | Minor Allele Frequency | SNP Sequence SNP = [first allele/second allele] |
|---|---|---|---|---|---|---|
| BICF2P312189 (SNP 11) | 11 | 8 | 5773958 | 0.999014 | 0.000986 | TGGAGAGTGCTGGCAGGCAGGGGCAGGCAAACAACAATAGCA AAGATCTCTTCCACGCTT[T/C]TACTTCCTCAAAAGTCCAA GCCCTCTTAAGATCGCATTTTCTTAGTGACCTTCACTCTAA |
| BICF2S2432154 (SNP 12) | 123 | X | 56410647 | 0.999014 | 0.000986 | TTCTTTGCTAGGCCAAGGGCAGAGAATGCATGCCCCCCCTTA CCTCCCAGGGCCCAAGAG[C/G]CATCCTGAGCTGAGTCTAT GGCTCCTGGTGGGGGGCGGCTGTGGGTTGGGGGGGCACAGA |
| BICF2P1273450 (SNP 13) | 13 | 8 | 3160594 | 0.999013 | 0.000987 | ggtgtcaccaatgccagcgagcaccagctggagggaacagga cacaggtcctccgtcCTG[T/C]GACACTCGGATCTGGGGCT TTGCCTCCAAAACGGAGACCATGCCTGTCCATGGTTCTACG |
| BICF2P1439540 (SNP 14) | 14 | 8 | 3771142 | 0.998521 | 0.001479 | CTCTAGAACCCTTCAGGTAGACTACATTCACTTTCTACTACA ACTTCATCACCACAACCA[A/T]CTCCCAGTAACCCCCtttt tttcttctccttttttttatttttttccttcttttttgctcgtc |
| BICF2P506204 (SNP 15) | 15 | 8 | 4191144 | 0.998521 | 0.001479 | TCCCATGGGTTGAAGGATATCTGGCAGACGGCTCCAACTCCA GTAAAGCCTCAGGCCTCA[A/G]CCAGGAGTTCCCCGGGGCT TCATTCCCATCCCAGACTTTGCCCAGGGCTGATTTGAAAGT |
| BICF2P380732 (SNP 16) | 16 | 8 | 3299879 | 0.998519 | 0.001481 | TCTTCCTTGCAGATTGGATGGCTGTAGCCTCACCTCACACTG TTGCTGGGATCTGTCCAC[A/G]CTTCTGACCTCCAGCAAGA GCCTCCGGGAGCTAAGCCTGGGCAGCAATGACCTGGGAGAT |
| BICF2G63016020 (SNP 17) | 17 | X | 73980557 | 0.004955 | 0.004955 | TATTGCTAGTAAAGCCAAACTTTCTATTCCACAATTATAAAC TCATGGAGATGGTAATTA[T/C]AGTGCATTATTTGTCAAAT TTTATTATTTTTTCAAATCCCAAAGAAAATGTGATATTCTA |
| BICF2S23623569 (SNP 18) | 18 | 32 | 38362784 | 0.994576 | 0.005424 | AAGAACAAGGATACAATCTAAGTGATAATCATCCAGCATGTA CTTGTCCTGTTTTCAGAT[T/G]ATCAGCTTAAGTCAAGAGG AATTTTTAGTGCTTACAAATATTTCAAGTGATTTTTCCAGA |
| BICF2P216837 (SNP 19) | 19 | 8 | 7474389 | 0.012327 | 0.012327 | TGAAGGGGTGCTACTCAGGGCTCTTCATTTAACCTTCCAGGA TGTTTTCCTATGTACTCA[T/C]TCTTCCTTTTGGTTGCTCC TTCTTCTTGCATTTCTTTATCTCTTTACAGAATCATCCAGG |
| BICF2S22922146 (SNP 20) | 20 | X | 75388683 | 0.986193 | 0.013807 | acaaccctaaaatttcagtgattcagtacaacaaaggttttat tATAACCATTCAGGGATC[C/G]AAGTTGGTAGAAACTTCAC TACAATACCTGCTTCCAGTCAACAAGACAGAAAAAGAAAAA |
| BICF2G63015714 (SNP 21) | 21 | X | 74415223 | 0.01382 | 0.01382 | GCAGGGTTGATATATAACTAGTATGCATTAGGTAGACACCTA TTTTGATTACTCACTATT[T/G]TAATATCAGCCTGGTAGTA AGAACCAAATCTATTATGTAAAGTGCATAGAGAATTGaaag |
| BICF2G63015674 (SNP 22) | 22 | X | 74439123 | 0.0143 | 0.0143 | CTAGCTAGCCACCCAACTCCCCACATGCCCAGAGTCATCGTT TATCTTTTCACATCAGCA[T/C]TACATTTTGGCTTGCATTC AAACATTAGCCCATTTTTTTTCCTTTTGTTTTATTTATAGA |
| BICF2P426463 (SNP 23) | 23 | 8 | 5833993 | 0.015286 | 0.015286 | TTTTCTCTTTTTCCATAAATGCTCTGGGCTTATTTTCATTAT CTAGTATTTCTCTTCTGA[A/G]GCTAACTCCCAAAGAGTTT TGTGCATCCTTATTTCCATCACAAGGTCAATGTACGAGTTA |
| BICF2S22926688 (SNP 24) | 24 | 8 | 7502279 | 0.015779 | 0.015779 | GGGCCCAAGGGCTGAGGATCTCTGTACCTTCTGCTTCTTGGC AGCCCAGGCTGGGTAGCA[T/G]TTCTTGGAAGAGGATTTCC CATGAGTTGTTAACAGAAGGGCGGGCTTCCAGGCGCTGCTT |
| BICF2P1113947 (SNP 25) | 25 | 32 | 38074100 | 0.981169 | 0.018831 | CATCTTTGCTTGGGGCCTGGGGTTTTTATTGAGGATTGTGAT CTGGTGTATGTGTCTCCT[T/C]AGGCATCCAGAGAAACCATTC AGAACAAGACAAGCGTCCAGGTATCCTCTGTAAGTCACTT |
| BICF2P342874 (SNP 26) | 26 | X | 44861101 | 0.020217 | 0.020217 | ACAAACCCTCAGACCCAGATACACAGTATCATGTGGACACAG ACATGTAACACCAAAATG[A/C]CCAACATCATGTGACTACA GGCCCTAAGCAACTAGGTGTAACATCACTTGGTTATGGGCC |
| BICF2P1171925 (SNP 27) | 27 | 32 | 36457625 | 0.022189 | 0.022189 | AATGCAGTAATACATGTAGCTAAACCTAACCATCAGAGTCTG TTCTATCCTTCTACAAAA[A/G]TAGGGTTGGAGCTGAGCAC ATAGGTAGCATACATCTAGCAAAAGTTTTTGCCTTCAgatt |
| BICF2G63017200 (SNP 28) | 28 | X | 71984532 | 0.025641 | 0.025641 | ttgtggggtcaggtgagttatggaccccctccctactcttctg ctatcttgccccCTACAG[T/G]GGTTGCTATTTTGATGTAA TCACAAAACGACCTGGCAATAAAACCTTTTTCTAATTAggg |

TABLE 5-continued

Position and sequence of further SNPs indicative of susceptibility to liver copper accumulation

| SNP name (SNP no.) | SEQ ID NO: | Chromosome in canfam 2 | Location in canfam 2 | Allele Frequency | Minor Allele Frequency | SNP Sequence SNP = [first allele/second allele] |
|---|---|---|---|---|---|---|
| BICF2P1286548 (SNP 29) | 29 | X | 57448138 | 0.026423 | 0.026423 | GATGCAAGCTGGGACAGAATAAGGTACTGGGCTGTGTCAAGC CCCAGTAAGAGAGGAGCA[T/C]TGTAGGGTAGTTAGGATGG ACTTAATGGAGATGAGTCCTAGGGAGCCACACTCAGAGTTA |
| BICF2P790089 (SNP 30) | 30 | 32 | 38885957 | 0.0286 | 0.0286 | TAAACACCCCCAATCACTACCATCCTCACACCTAAGGATACA CAATGTGTCTACTTTATG[A/G]TATGTCTTTACTATTCGTT GCTTATGAAATTTTATTCATTAWCTAAAACAGGGAAAAAAG |
| BICF2G63016713 (SNP 31) | 31 | X | 72619011 | 0.9714 | 0.0286 | TATAGYTGGSCAATTAAATCTCCTATTCTTTTGTCTCAAGG ATATTTGAAATTACATAG[T/C]TCTTTTCTCATATAAAACC TACCATACAATCATTAGATGATCCTTCTTAGTTAATTTTTT |
| BICF2P276536 (SNP 32) | 32 | 8 | 3149437 | 0.966436 | 0.033564 | GATGCTGTGGGCCAGTCCAGAACCCACCTGAGAGAAACAAAC AGGCCTCTTTGCCAGCAG[A/G]GCAGCGTCAGTGTCACCCC TGTGACATGTCAGAACCTCCCTGAAAGTTCATCTAACCTCT |
| BICF2G63015658 (SNP 33) | 33 | X | 74531965 | 0.963018 | 0.036982 | GGCTCAGAAGAAAAATCAGCCCAGTTCACATCCAATGTTTCC ACACATCTAATCGTCTTG[A/G]GTTCAGAGGTAGATGTGGT ATCACTTAYATGGACACATATAACAGCTGGCCCCCACCTCT |
| BICF2P308749 (SNP 34) | 34 | 8 | 7325380 | 0.962032 | 0.037968 | gtttcagttaattatagtccttactggatccgattgctgtgg cgctaaaatgaAAGAAGG[T/C]Agggtacctgggtggctca ggggttgagaatctgcttttgactcaggtcatgatcccagg |
| BICF2P872820 (SNP 35) | 35 | 8 | 6388554 | 0.956114 | 0.043886 | CAGAGTAGCATTATTTTCTGCTGTATGAGGACACTTTTGTTA TATCCACAGTGGACAGAA[A/G]ACTGGGTTTTAGAAGATGC TCAATTGAAACAAGACTGAGGGCTCACAAATTCCTGCTCCA |
| BICF2G63016210 (SNP 36) | 36 | X | 73592920 | 0.955084 | 0.044916 | TTACTTATTCATCTGAGACCAAGGCCACTGTGGTGAACCTAC AAAGCCTTACAAAGCAGG[A/G]CCAGAAGGGCACATAAATC ACTTGACTAACATTTGGTCAAAATAGCTCTTGGGCTCTTTT |
| BICF2G63016209 (SNP 37) | 37 | X | 73593955 | 0.049456 | 0.049456 | ATAAAAATAAAAGAGCTATTAATAAGAACTCATAAAATCTAC ATAAATATAGTAACAGGT[T/C]AATATTCCCAGCATATTTT TACAAATCATCTATAAAGAGCATGAGAGCATATAGGGATTA |
| BICF2P1149405 (SNP 38) | 38 | 32 | 41212550 | 0.941321 | 0.058679 | GCAACAACCTGGTTTGTGTGTGGGAAGCTAATGCCTCCCCAA ATGCAGCAAACTCTCCTC[T/C]TGATTTTAGAAAAGCAGTT TAGTTACAGGCAAATGCATACATGCATGATAAATACTACTC |
| BICF2G63016173 (SNP 39) | 39 | X | 73672050 | 0.940828 | 0.059172 | GATTTTATAAAACATGATGACCTTGGCATTTATATAGTAGAT ATTACTACTCTGAAATTC[C/G]AGGAAGTATGATCATAAAC TCACACTTAATCTGGTAGTAAGTATGGACAATGTATCAAAGG |
| BICF2P401962 (SNP 40) | 40 | 8 | 4495597 | 0.935897 | 0.064103 | CTTGGTTGAGTTAAAACATTTGCCCATGCAATTTAATGCATG TCCCTGTGGGGTTGAAC[T/C]GACGTACACCCGAGCCAAC AGCCTTTCATGGCAGACGCCATCAGGCAGGTGACCCCCACC |
| BICF2P991264 (SNP 41) | 41 | 8 | 3165755 | 0.071992 | 0.071992 | CCTTCCACACGCTCAGGTTGGCACGGAGGGGGTGTCCTTGCC TGAGGGGTCCTGGCACAG[T/C]CATCAGGGCACACAGCTGA TAACCCAAGGGAGCAGTAGGCAAGACCTCATGGGCGCCGGG |
| BICF2S23230847 (SNP 42) | 42 | X | 58531292 | 0.079389 | 0.079389 | ATTCTCTTTGCTGTCTCCTGTATACAGAGATAAAAGCAAGAG TTTTCCCCTTCAGGTTTC[T/C]GAAACCCAGCTTCCTTTAG ATTTTAAGGGGTATTCTGTGTACCCATTTCCCACCTTCTGC |
| BICF2P1252842 (SNP 43) | 43 | 8 | 4618608 | 0.919132 | 0.080868 | GCGGGTTGGGACCCCCCCCTTCTGCTGCTCCCACTTCAGAGTT GTGGCGTCACTAAGATGA[C/G]ACCTCATGTCGGGAACCTG AGAGTCCCTCGGGAGTTGTGcagggactgtagccgacctat |
| BICF2G63017198 (SNP 44) | 44 | X | 71984983 | 0.913947 | 0.086053 | ACATATGCACAGTGAATCGTGGATTGTTGTGTTTGATTTCTT ACATGATACAATAAAGG[A/G]AAGTAGTTGAAGCAAAACT TTAGTTTAAAGGAAACAATTTCTCTATCATAATGTTCAGTG |
| BICF2P1364202 (SNP 45) | 45 | 8 | 3175135 | 0.910256 | 0.089744 | CCCACAGACCCCAGGTGCTGACCACAGCAGCCACTTGGGCCC CCAATGCAGGAGACACCT[T/C]GGGAATGAAGGGGACAAGG CCAGCTCAGGCACATCGTCAGTGCACCTGATGGGAAGGCCG |
| BICF2P963708 (SNP 46) | 46 | 8 | 5472668 | 0.095945 | 0.095945 | ATCTGATCCTAGCCAATGGAAAGCAATTTGAGATAGGAATCA TATCTTGTTTTGGTTTAT[A/G]TGCTTTCTTTGGAGTTTTG CACATCATAGATAACTGTAAATTTGTAGAATAAATGTTTGA |

TABLE 5-continued

Position and sequence of further SNPs indicative of susceptibility to liver copper accumulation

| SNP name (SNP no.) | SEQ ID NO: 2 | Chromosome in canfam 2 | Location in canfam 2 | Allele Frequency | Minor Allele Frequency | SNP Sequence SNP = [first allele/second allele] |
|---|---|---|---|---|---|---|
| BICF2S2293948 (SNP 47) | 47 | 8 | 7696228 | 0.098619 | 0.098619 | GTCAATGCCATTAACCTGGCGAAGCTGCTCGAGCATCCACTG CGATCTCCGCACGAACGA[T/C]GTGGAGCCTTCAAACTGTT TGACCTTCGTGATGGATGCTTGTGTGGGTTTCTTGTTTGTC |
| BICF2P1028186 (SNP 48) | 48 | 32 | 40758922 | 0.107495 | 0.107495 | ACTGGTTAATAAGACTTCACAGATTTTATCCATCATGTTGAT TATCTGTATATGTATTTT[T/C]TACCACTTAGGATAAAGTT CTGTTATCTGTAATTGATTCCAACCAGCATGTTTGCTCCAA |
| BICF2P19238 (SNP 49) | 49 | 32 | 40849057 | 0.897012 | 0.107988 | CTTCTTCTTTCCCATTGGATTCTTTCATCAATCGTAGGTAGT TCTTAATGAAGATCTGTG[A/G]TAAAGCCATTCATCTATTC ATTCAACAAATGGCATCACAGAAAAGAAAAATAACCTTTAT |
| BICF2P247312 (SNP 50) | 50 | 8 | 7825200 | 0.112426 | 0.112426 | GGGACACATTTCTGGACAGACCTCTGATCACACTCACAGGAC AGCAAGAGGAAGCTCTGG[A/G]TACAAGTACAGGGAAAAAA GAAAGAAATGGTCACAGGGAAGCTGCCGCAGGAAAAAGGTA |
| BICF2S2301711 (SNP 51) | 51 | 8 | 7615543 | 0.881164 | 0.118836 | GGGCAGATCCTCAGTGAGTATTGGCTCATGTTCTCCGAGGGA AGTAGAGTCCCAGAAGAA[A/G]GATGCTAAGGTGCCAAGAT TCCTGAGCCTGTGTGTGGTACAGTCACAGCAGTACTCCTGA |
| BICF2P132419 (SNP 52) | 52 | 32 | 35699747 | 0.874506 | 0.125494 | TCATCTCCATTTGTAATAGAAACCACATATATAGAGAGATTG GATTATTAACCACTAAAA[T/C]GTAGCCACTCAAGGGGAGG GGGGAATGCATTTGGTTTATTTCCCATGTCAAAACAGAAT |
| BICF2S2311591 (SNP 53) | 53 | 32 | 40712955 | 0.873393 | 0.126607 | AACACTGCTAATAAATATTTATAATGGTTTGAGGAAAATATC AGGTGTGAGATGTCTTCA[T/C]ATCATATAATATATCATAA TATCCTCTAAAAAAGCTCTAAGCATAGGTCTATGGAACTCA |
| BICF2G6305317 (SNP 54) | 54 | X | 43502595 | 0.127219 | 0.127219 | AAGCAATCCAGGAGTCTTTCTCCGGGTAGCAGGCTCGCTTTA CAGGTTAAGGCTGGATGA[A/G]AAGGAAGAACCTGAGCTTC AAATTATCATCTGAGTAGAGCTGATACCCATGGTTACATTA |
| BICF2G6305878 (SNP 55) | 55 | 32 | 38771348 | 0.127838 | 0.127838 | GATTTTATTCTTTACTTTGATTTTTTTTAAGTTTTACTATGA TATTCAATATGATTGTGG[T/C]TCATGAGATTCCTCTTTTT AGCTGTATCATTAACTACAGAGCGTTCTCAAATATTTTTCT |
| BICF2P1007047 (SNP 56) | 56 | 8 | 4812890 | 0.87092 | 0.12908 | GTGGCCGGAGGGGGTGGGCCCTACTGTGCCCAGCTTCACGT CCCACTGGCCAAACATCA[A/G]GATGCAGACACCCAGGTCC CTTGTGCTGCCTGCTGAGGCTAGGAGCAGCGACTGGAAATG |
| BICF2G6305318 (SNP 57) | 57 | X | 43317221 | 0.869329 | 0.130671 | GATGGGAGACCTCATACACATGCAAAGATCACTATTAAAGAC TCTCGAGCAAAGATCGAA[T/C]GGACTGTGGCAAGCTGCCG CGCATGCCAATCAACAAATGCCTCCGACCATGGATCTAACC |
| BICF2S2363287 (SNP 58) | 58 | 8 | 5056863 | 0.866371 | 0.133629 | CAACAAGGTTTTTAAGGTTCTTTTCACTACCTTCTTCTTTTT GTACTTGCTTAGGACACC[T/C]GTATGTCTTCACAATATCA CCTGAAAGTCCTTTAGGAGATATACTCAAAAAATAAATAAA |
| BICF2G6301558 (SNP 59) | 59 | X | 75321307 | 0.865385 | 0.134615 | caacctgagctgaaggcagacactcaactgttgagctaccca ggtgtaccAAACACATCT[A/G]CTCTTAACCAAGCTTATTC TTTGCTATATTTGGCAAATTGTGGCATGTCTACAGTACTCA |
| BICF2P482693 (SNP 60) | 60 | X | 43587959 | 0.804897 | 0.135108 | ATTCCCCATGTTTGAGGAAATCACAGGAGCCACTAGGAAATC AACCATTTCCCAACCAAC[T/C]TGATGATTTCCTGATCCAA AGGTTCTCCCAGGACAAATATGAGGTAGCCTTTCACACTCT |
| BICF2P940430 (SNP 61) | 61 | 32 | 40921126 | 0.136364 | 0.136364 | CAGTCTTGTAGGAGAGTAGATTGACTCACAGAACTGGCAAGA TTGGGAATCTGAGCATTG[T/C]CACTTGAGTCTTAAAACGT TTACGATTTTATTTCTAGTATTTCAATAAGAAACACATTCT |
| BICF2P786384 (SNP 62) | 62 | 32 | 36389913 | 0.136723 | 0.136723 | GAATACATTGCCAGAATAATTTCAAGTTCTCAAATCTCAACT AATAAGATTTTCGTTAAA[T/G]AAGGCATTCAATCATCACT TACTGACAACCCACAAAATTAGGCACTGATGAAAAATTAGC |
| BICF2P1340243 (SNP 63) | 63 | 32 | 41050914 | 0.150394 | 0.150394 | AAGTTAAGATATTCAAGAAAGAGAAGAGAGTGACTGAGCTAA AAAGAAAATCAGATCTCT[T/C]CCAGGCTTTAAAATAATCT CCACAATACTGGGCAATCCATGTAGTCTCCCCAGTTCCATT |
| BICF2S2362644 (SNP 64) | 64 | 32 | 36617978 | 0.153846 | 0.153846 | CTCAAAAGGAAAAGCCTGTGGAAAGGCAAAGAGGTATGTGAA AGAGGTAAGTTCAAAATG[C/G]TGACATGACCAGTGTACAT AGATTACAGGGTACTTGGAGGAGCAGTGTAGAAAGGAGTCCA |

TABLE 5-continued

Position and sequence of further SNPs indicative of susceptibility to liver copper accumulation

| SNP name (SNP no.) | SEQ ID NO: 2 | Chromosome in canfam 2 | Location in canfam 2 | Allele Frequency | Minor Allele Frequency | SNP Sequence SNP = [first allele/second allele] |
|---|---|---|---|---|---|---|
| BICF2P161586 (SNP 65) | 65 | 32 | 37795702 | 0.156312 | 0.156312 | TTCTATGAAATAGCTACCATTCTGGTTGGTATCTTCTGTTGA TTTAGATGATGAAGGAAG[T/C]ATAAGAAGTAAGGCTTATG AGTTTATAAAGCTTTAGTTAAAGCTTTGATTGTGACAAAGC |
| BICF2P579617 (SNP 66) | 66 | 32 | 36631235 | 0.162389 | 0.162389 | AGAGGAGAAAACACAGCTAAAAACTTTTTTACAGACTGGACA AAGGTGCTTACACTTTTC[A/G]TATTgggcagaatgagggg atgaaaacaccagtggtcttttgaagccacacaaattcag |
| BICF2G63016280 (SNP 67) | 67 | X | 73386098 | 0.835968 | 0.164032 | AGGATGAATATTTATTAACAGTAAATATACATTTTTATTGTT CTATATACTCTAAAGACA[A/G]TTGTAGACAGTAAGATATA TCAATTTTAGAAACAGAAATAATGTTAATTGTATAATATGG |
| BICF2P721687 (SNP 68) | 68 | 32 | 40771787 | 0.829389 | 0.170611 | CAGGGATTCCTAAAGGGTGACATGGTATGGTCTAACACTTCC TCACTGTCCTTTTCCCAG[A/C]TGATATAAGAGGAGGACCA GAGAGACACATAAACTGTCTGAGTCTTTAGCATTGTGATAA |
| BICF2P504739 (SNP 69) | 69 | 32 | 37328946 | 0.827909 | 0.172091 | ACACTAATGGGTAGAGAATACACGTCCATCAGTCATCAATGT AATCTACTAACAGCCTCA[C/G]AGTCTGGCAGTTTTCAGTG AAAAGAGGAGTCATCTCCATTTATTCGAtcaatcagttgac |
| BICF2S23331874 (SNP 70) | 70 | 32 | 39390236 | 0.825444 | 0.174556 | TATTACCCTGCTCTCCAGCCACTCCTTTACCTTCCATTAGCC CACACCTGCTCTACACAC[T/C]ATTGCTCATGGAAGCCTTG CCACGTCCAGTCGCCACTCTGAAATGCCAGCATCCCTCCCA |
| BICF2P772765 (SNP 71) | 71 | 32 | 3978300 | 0.816075 | 0.183925 | TCTCAGATACTTGATAGCCAGCATTTCCCCCCATTTTCTTCC AAGAGCACGAAAGCATAG[A/G]AATGATATTACATCTCGTA TGGTGAATGTGACACAGCCGTCAGTTGCGTTAGCTCTGCTT |
| BICF2S2318354 (SNP 72) | 72 | 32 | 35849858 | 0.18787 | 0.18737 | ACAGGAAGGAGAACTGAGCATCAAGAGAGTTCAGAACATGAT CATTGGGTCAGTTTGTGG[C/G]TGCATTAACTTTTCCCCAA AACAGAAAGCAACAGAGACTTCTGTAGGTCAGTCAACAGTG |
| BICF2G630588054 (SNP 73) | 73 | 32 | 38521693 | 0.810052 | 0.189948 | TTACCATTACTATAACCCAAGTTATAGTATACTATAACCAAG TCCTTAATTGACTTGATG[T/C]TTGTGCAGCTGATTTTAAA TCTATTTAGAATAATAGTTTACTTGTGACAATTCATATTAA |
| BICF2S23313445 (SNP 74) | 74 | 8 | 6343006 | 0.809665 | 0.190335 | TTGGTCGACTGACTGATTGGTTTTACTGTGGAGGAAAGAAAA GGGAATTTTCCCAAAGAG[A/G]ACAGAGAGAAAACATGGAA TTGAGCAAAGGGAGAATAGAGAGACAGGGCAGCCACTGAAG |
| BICF2P675334 (SNP 75) | 75 | 8 | 4477476 | 0.19428 | 0.19428 | TGCCTTATCCTCCAGCTCCTCCCTCACCATCTTGGAAACTAG CTCAAATGTCACTGGTAC[T/G]TGTCTTTCTTTTGATCTTT CTGAAAGACAAACATGATCCCATCACCTCTGCCTTTAGAAC |
| BICF2G63017409 (SNP 76) | 76 | X | 71722644 | 0.80441 | 0.195759 | ACTCCTAAGTAAAAGTTAAATTAACAGATTTGCCATCAAGTA CCTTGCCCATTTTTCCTA[T/C]AGATCGACTTTTTACTGGA TGATCCCCTTGATAATAATCTTGATCTATGTTTTAATTCCA |
| BICF2P798346 (SNP 77) | 77 | 8 | 4651519 | 0.195759 | 0.195759 | ctggtgggcttgtcaggggcaggatgttgtgtggtgagcaca gaattaaaactaggaGCT[T/C]gaagcgcctgggggggctca gttggttgacggactgccttcatctcaggtcatgatccctg |
| BICF2P1150684 (SNP 78) | 78 | 8 | 7652070 | 0.802761 | 0.197239 | CATACAGCGAAGAGATAAAAACACAGGATGCTGGGCTCACGA CCATGACCGGAAAAGGAC[A/G]GCGAGGAAAAGCAAGTATG AGCAGCCCAAAGTCCTTTTTCCAGCACTGGCCATAGGAGGA |
| BICF2P1348758 (SNP 79) | 79 | 32 | 36083895 | 0.801579 | 0.198421 | CAGAGATGAGGGAATCAGACTCCTCGTCCTCTGCTTCTCTACA ATGGCTCATGTTCTCCTT[T/C]CCCCTCAGCTGTTGCATTA ACAGAGGTCAACCCATTCTTCTAAATTTAAATCTCCCAGAA |
| BICF2G63017599 (SNP 80) | 80 | X | 71555277 | 0.198617 | 0.198617 | AATCAAACAAGTGCTAGAACATAGAACAAGTGGCTCATCTTT TCCCCAAATGTCTGGATA[A/G]GAAAAAAAAAATCTAAACA AATGCTAGATGTTAAGTATCTGAAATGATCAGCCCATGAAA |
| BICF2G63016090 (SNP 81) | 81 | X | 73800072 | 0.200197 | 0.200197 | TCCATACCAGTCCTTGTTGTCTACCCCGAACTTCACCTCTCT AGGCACAGACAGCTCTAA[A/C]TTTCACTCATAGGTATCTT ATGCTGACCTGGCCTGCCTCCtgttttgttttgttttgttt |
| BICF2S23524027 (SNP 82) | 82 | X | 64785623 | 0.79931 | 0.20069 | CAAAAATTCCCTGAGCCCAGCATCAAGGTACCTGGTTTGGA GTGGGTGGGTCCTCAGAA[A/C]GAATGGGTGTGGTGTACAT TTAGCAAGTTATGTAGCATGTGTCTGTGTAGTCTCACCTCT |

TABLE 5-continued

Position and sequence of further SNPs indicative of susceptibility to liver copper accumulation

| SNP name (SNP no.) | SEQ ID NO: | Chromosome in canfam 2 | Location in canfam 2 | Allele Frequency | Minor Allele Frequency | SNP Sequence SNP = [first allele/second allele] |
|---|---|---|---|---|---|---|
| BICF2P591872 (SNP 83) | 83 | X | 62989720 | 0.795252 | 0.204748 | GGGCCCAGCAAGTGGCAGAACTGGGAAGACCCCCTCTTCTTC CGCCTGGAGCAGTGGTGT[A/G]GCAGCACACCACAGGAGTC TGAAAGGGTGGGGAGTCCAAACGGGAACATATACCTGAGAT |
| BICF2G630587712 (SNP 84) | 84 | 32 | 38968302 | 0.794379 | 0.205621 | atataatataacttatttaaaatatttGAAGATATTTCTATA GTTATGCTCTACCATTTG[T/C]TATTATAAGATTTCCAACA GCTTACTTCTTGTATGAATTAATTTACCAGCCCCTCACCT |
| BICF2G630587722 (SNP 85) | 85 | 32 | 38964413 | 0.792899 | 0.207101 | CCCTATTCTATAAACATTCCCTCTCTGGCCATCCTGTCAAGT GGGCCCTGACAGTGTGCC[C/G]CAGAAGCTCCCTAGCCTTT GCCCATTCCAGCTATGGCTAGCCTGCCACCAGCCATACACA |
| BICF2G63018557 (SNP 86) | 86 | X | 66396513 | 0.218164 | 0.218164 | CACTGTGAGGTCTGAATGGAGACATTCATGATAGACTCCAGG ATTTTCCCAGCTATTAAG[T/C]CATGGGCCATAAACTGGAA CACTTGGAAACAGTCCATAGGTTCATATTAAAGAATATGTT |
| BICF2P652606 (SNP 87) | 87 | 32 | 37855796 | 0.776134 | 0.223866 | GCAAAAGGAACATGAGTTCTGATCTTCTGTAAAGGAGGCTAA TTTACTAATGGTCATAAC[T/C]GTGGcctgagggtcaagtt tctaattaaacgtgcatcttggggYggactagaatactttc |
| BICF2S23312799 (SNP 88) | 88 | 32 | 36791310 | 0.224852 | 0.224852 | CAAGGSCCAGGTACCCTGAAGGAGTCCGCTTCACCCAGGCAT GATGTGTTTGACAGTCTT[T/C]GTAATTGATACAGCCATTG GCATCCTCTTGCGGCCAAYATCAGCTCCACTTCAACCTCGG |
| BICF2S2303948 (SNP 89) | 89 | 8 | 5896281 | 0.773669 | 0.226331 | TGCAATGGGTTTTGAAATTAGAGGACATCACAGCAGAGTAGA ATGGTTTGGAACAGGGGA[A/G]TATGATTAGGATTAATGAG ATGAAAGAAAATTCTGGCTAGAGGGCTAGAAGAGCCATGGA |
| BICF2P506595 (SNP 90) | 90 | 8 | 4886813 | 0.228304 | 0.228304 | CTCAGAACTAGATAGGCTAATAAGTGATAGGCCTTGTGTTTT CCTAGAGTGTGCTTTAAA[A/G]GTTTCTTAAGCTAAAAAAT TACATTCGTGAGAAAATTGAAATAAAAGGAAAACAGTCATG |
| BICF2S23130600 (SNP 91) | 91 | 8 | 5180802 | 0.228304 | 0.228304 | GATACTTTGGGCTCTGGGTGGGAGCCAGCAGTGGTGGGGCAG GGCAGGAGTCCAGCAAGG[T/C]GTCTGGGCATACATGTCTG AGAGTAGGAAAACCACACCATTGCACCTTGCCTTTGACTTC |
| BICF2P1270451 (SNP 92) | 92 | 8 | 5580117 | 0.229783 | 0.229783 | TCAAGGATCAGAAAAATAAAAGCAAAGAAAGAGGCAAAGAAA GAAGAAATGAAATACCTA[A/G]TGGCAGAAGTAGGCAGAGA AATAAAGGCTAAAAGAAAATGGCAGAGGATTGTTTGAAAGG |
| BICF2G63058826 7 (SNP 93) | 93 | 32 | 37876000 | 0.23001 | 0.23001 | TATGTTATACTATTTTAGTATCTTAATAAAATATGATTAGCCA AAATAGTTTTATCATCCT[C/G]AAAAGTGCAGCATATATTA TTTTCTATTAAATTCAGAATAGGTATAAACTAGAAAGCATT |
| BICF2S23122074 (SNP 94) | 94 | 8 | 4965974 | 0.76999 | 0.23001 | ACAGCAGTTCTGAGGATGGACTCGCAGAGGCTCCTGACAAGC AGAATGACCAGGCCGAGC[A/G]GAAAGGTCAGTGCTGCCAG TCTAGCCAGAAGTGGGGAGAGAGGATGTAGGAGCAGTACT |
| BICF2P555643 (SNP 95) | 95 | 32 | 40258722 | 0.230769 | 0.230769 | ACTGTACTCAAAAAAGTTCTGTTTGCCTAAATGGGATCAGCC TCTAATGGATGCCAGTGA[T/C]GGGAGGCTGTTCATCATCC CTTCGGGATAATTCAGAGCCTAGGCAGAGGCCCAGCGTTCA |
| BICF2S23259999 (SNP 96) | 96 | 8 | 4990277 | 0.231732 | 0.231732 | TACAGGCCCCAGGAAGGAGCCACCAGATGCCCAGGACTGGGC CCAGGAATGATGGAGGCT[A/G]TACAGCTGGCTGCCTGCAC TGGCTGCCGCCCCTGTCATCCAGTGTCACAGAGCAGCACCT |
| BICF2G63016525 (SNP 97) | 97 | X | 72989415 | 0.251482 | 0.251482 | AGACATTGCCAAGAAGTATCCACAATGAACAGTTTGAAGGGG ATCCAGAAAAGCACAGGG[T/C]CTACTTCCGCTGGATGAGC AGCAGTGAGAACCACAGTCAGGTAGGTCTTAAAGCAAAGTT |
| BICF2G63019552 (SNP 98) | 98 | X | 60108249 | 0.737179 | 0.262821 | GCTTTGAAAACCAACAGGAAATACATCCAGGAAAGCTATACA ACTGTGGTGAAAGGAAAG[A/G]AAAATCTGCTCTTAAAAGG TTGTGTGCAGACTCACTTGCCCCAGAAAACAGTGCGAAAAC |
| BICF2G63017884 (SNP 99) | 99 | X | 70145192 | 0.271019 | 0.271019 | GAGATGTGTAAAATTTAATAGAAATGAAACTTGCCAAAACAG ACCTCTGTACTCGTCAGC[A/G]TTCTAAGTCCATCTTTCTG TAGCATGTAAGTAGAATAATGTTCTATTAATTTCCTCTATG |
| BICF2G630587598 (SNP 100) | 100 | 32 | 39023585 | 0.706931 | 0.293069 | GTTCTTTCTATTCTATCACACATACCACCCCCCTGCCCACAG TACCCCTTTCTGCCATGT[T/C]TCAGACTCCTACACAAGAG GTTCTCTCTCCTGGCTTCCAGTTAGACAGGCAGGTAAAGCT |

TABLE 5-continued

Position and sequence of further SNPs indicative of susceptibility to liver copper accumulation

| SNP name (SNP no.) | SEQ ID NO: 2 | Chromosome in canfam 2 | Location in canfam 2 | Allele Frequency | Minor Allele Frequency | SNP Sequence SNP = [first allele/second allele] |
|---|---|---|---|---|---|---|
| BICF2P285901 (SNP 101) | 101 | 8 | 6743491 | 0.70069 | 0.29931 | TAAAAAAATACAACAGTAGCATTAGAAGACATGCTAAGCGGC TGTATTAGAGAAGGTTAG[T/C]GCTGGCCTGAAGTTTAGAA ACCTTCCCTTCTCTTTTTTTTTTCCTTCCCTTCTCTTTAA |
| BICF2P811511 (SNP 102) | 102 | 32 | 36167454 | 0.30583 | 0.30583 | TCAAGAGTACTAGAGCATCTATAATCAATGGTAAATTGGGGA ACTAGTGAAACAAGTTTA[T/C]AGGACAAATAACATAAATA AGGATTTTTTTTAAATTTGGAAAATTGTGGAATAATGATA |
| BICF2P1146265 (SNP 103) | 103 | X | 63433179 | 0.693725 | 0.306275 | AGAATTCAATTTTGGGGAGCCAGGAAACCAGATTAGTTTTCC AAAGGGAAGTGCCATTTG[T/C]ATCTATCCCGGTGGGGCTG CCAAGAATTCCCTGGGGTGGGAGACGGCGCTTCTGTGGATT |
| BICF2P243607 (SNP 104) | 104 | X | 57821508 | 0.690523 | 0.309477 | CACCAGAGAGCCCCGCAAGATCATACTGCACAAGGGCTCCAC TGGCCTGGGCTTCAACAT[T/C]GTAGGAGGAGAGGATGGAG AAGGCATTTTTGTTTCCTTCATCCTGGCAGGAGGCCCAGCT |
| BICF2P382932 (SNP 105) | 105 | X | 64010327 | 0.690335 | 0.309665 | TGGTGATGATTTATCCCCCATGTTCAAGATTTATCCTCCCTG TCTCAAGAAATCATGTCA[T/C]TACAGGCATCCTTAAAGTC ACAAGACTGGGAAGTAAATACTGATGAGGTCCAAGACCTGG |
| BICF2P1061734 (SNP 106) | 106 | X | 57654632 | 0.69003 | 0.30997 | AGCATAGTGTACCCACATATAAGGTCACATCTGAGGCCAGGG AGTCGGGGTCTTGAAGAT[T/G]ATGACTGATCATGTGCTTG AGGATGATGATGATCATGTGCTTTTCCTGGCTGTGCAGTTG |
| BICF2S2293723 (SNP 107) | 107 | X5 | 57492668 | 0.310158 | 0.310158 | gtgtgtgtgtgtgtgtgtgtgtgtTTAATTCTTTGTGAGAAG CCCCTCATTTTGACCTAA[A/G]TTTGGTAGAGGCCCCAGGG GATCTGAGAGGAGAACAAAAGGATAAACCATTTGCTGTTCA |
| BICF2S2293748 (SNP 108) | 108 | X9 | 73723672 | 0.687068 | 0.312932 | CCAACTTTCACTAGCATCACAGCCCCTATCAATCTCTGTTCT TTTTTCTGTCAGTACCAT[A/G]TTTGCTCCTACTACATCYA ATCTGTGAGCTCACAGGATGAGGACCAACAGCTGCCCTGAG |
| BICF2P903726 (SNP 109) | 109 | 32 | 40883681 | 0.329389 | 0.329389 | TGTCTTACCTCTCTCTATTCCCTTGTCCATAGTAGTATTAAA TATATCTTCCTGAACACA[A/G]ATCTGATCCAGTCTCTTTT TGTAATTAAAAGCCTTTGCTAGCTTTGGTGATCACCTCCAG |
| BICF2P1324008 (SNP 110) | 110 | 32 | 40043909 | 0.664179 | 0.335821 | GACCTGACAGATTATGTAGACTTTGTTTTCAAAGGGAGCACC TGCTGGATATACAACATG[A/G]CACTAAATTGTGCTCCACA TCCTTGGCAGAGGTGGGGGCGGGCACAAAGGAAGAAACC |
| BICF2P320425 (SNP 111) | 111 | 8 | 7105593 | 0.336283 | 0.336283 | CAGAGGAAAAGGAGAAGGTCCCACTTAGGGGACTGGAGAGGA GTGGGGAACATCACCAG[A/C]GCCTTCCTGAGCCAGGCCC CCTGTGGGAGAAGCTCTCCCCAGGACTGGGTGCCTTTGAA |
| BICF282321071 (SNP 112) | 112 | 8 | 6397309 | 0.634615 | 0.365385 | tcctccctctccccatccccattctcatgcaagtgtgctctc tctctAAAACACCCCCC[A/C]CACACACACACACAGACAC AACCAAAtttgggtctcaatgtcttgaccaaggaaaaggca |
| BICF2G6301842 (SNP 113) | 113 | X4 | 66756995 | 0.367793 | 0.367793 | gagaagaaggaggagaaagaggaaaagTATATTTGATGGAAT GAAAAACAAGAGTTCAAT[T/C]TCACTCTGGTCTGGGGTGA CCACTATTAGTCCTTCAACATCTTCCTTGAAGGAATTTTAA |
| BICF2G6301589 (SNP 114) | 114 | X7 | 74179959 | 0.631164 | 0.368836 | CTGGAATTCTGTCAGATCAACATTCAGAGCTCCATCAAATCT GAGGGAAGCAGTGATAGA[A/G]GATACAATTTGACCTTTCA GTCTATTCAGGTTCATGTAGGTTAGGCATTCAATATCAAAG |
| BICF2P305287 (SNP 115) | 115 | 8 | 3258209 | 0.371175 | 0.371175 | CCACATGTGGTTACACCACTGTGTTATCCTTCCACCTGTCCC ATCAACCCACCCGCACAT[A/G]TCACAGTGCCTCTGTCCTC AAAGAACACTGTATCCAACACCTCCACATCCTCTCAGCATG |
| BICF2G6301666 (SNP 116) | 116 | X2 | 7264720 | 0.615878 | 0.384122 | ATTCCTATGGTGGGCGCTGCACATTTCCTCCCAGGGGAAGGG CAAGGGTCCTGCATTTCT[A/G]TGCTTTCCAGGGCCTCCGC ACCAAGAGCAATTGCTAGGTCACGCATGCCCCTGCACTTCC |
| BICF2G6301785 (SNP 117) | 117 | X4 | 70302610 | 0.606541 | 0.393459 | CATGTCATCACTAACTAATTTATTAACAAGAGTTTTATTCTT TGAAAAACAAAATCACTC[A/G]CATTACTCAGTTGCTTATT CCTTGATTCATATACAAATGACTGATAACATGAGATAAAAA |
| BICF2P170917 (SNP 118) | 118 | 32 | 38039478 | 0.600592 | 0.399408 | GATGATTTAGTTGTTTGAATGATCTGGCATATAAATCTTCCA AATCTGTGTCCATTGGAT[T/C]GCTTACAGTTTAATCTTTT TATTTCTTCCCAGAATCACATTTTTTCATTATTTATCTTTG |

TABLE 5-continued

Position and sequence of further SNPs indicative of susceptibility to liver copper accumulation

| SNP name (SNP no.) | SEQ ID NO: 2 | Chromo- some in canfam 2 | Loca- tion in canfam 2 | Allele Fre- quency | Minor Allele Fre- quency | SNP Sequence SNP = [first allele/second allele] |
|---|---|---|---|---|---|---|
| BICF2G630588207 (SNP 119) | 119 | 32 | 38333881 | 0.425201 | 0.425201 | AGTTAAATTCTGTGAATAACTAGAATCCGTTATACTTTTTCT GAAATGAAGTCTGTAGGC[A/T]TTTCAACAGCAAAAGGAAT TCTGWTTTTYAAAACTATACATAATGCTTCTTAAAAGCCCT |
| BICF2P702899 (SNP 120) | 120 | 32 | 39207136 | 0.428854 | 0.428854 | AATGCCAACTTTAAAAACGCATTCAAGGTTTTCCTCTGTAAA TGCATTCCTCATTTTGGA[T/C]GTGATGTAAAATCTTATTC AGTGTTTTGTTTTTTTTCCCCCCACAGGTCTCAACAATTA |
| BICF2P1388432 (SNP 121) | 121 | 8 | 7178740 | 0.446203 | 0.446203 | GGTGGGACCGGCCATCAGCAGGCGGGCCAGCGCCCCACAGAT GTTGTCACGGACCCGATC[A/G]TGGCGCTCCCGTGCCAGGA GGGGCAACAGAAGCCCCAGCAGCTTGGGGAAGTATCTGGTT |
| BICF2P588571 (SNP 122) | 122 | 32 | 37214320 | 0.454635 | 0.454635 | AGGGGACTTGTGCTAATCACTGGGCAAATTTTATGAACTTCT GAATTTTAAAGCAAAAGA[A/G]AAGGTGAAAGAATGGAAAG AAGGTGTGAGTGTTTGAGGAAAACTTCTTCTTTGGGGTTGA |
| BICF2S2291251 (SNP 123) | 123 | 8 | 6934693 | 0.544872 | 0.455128 | TACACAAGCAAGGCAGTATGCCCTGTCTCCTTCCCTTGGGCC ACCTGCACTTAGACATGG[T/C]AGGTTCCAGTGATGTGTCT AGTCTCTAGCAAGCAGGGCTTGCTTCTGCTCTATCCATCCA |
| BICF2P223099 (SNP 124) | 124 | 8 | 7427438 | 0.53002 | 0.469398 | CTGTCCTTGGTCTGGACCTGCTGTGAAGACCAAGTGCTTCCT GAGATCTCTCTGAGTCTA[A/G]TTTCCAGAGCAGTGAGTGA GAAATGAAATGAGCCGAGGATTGCCCTCCCTCCTATGGACT |
| BICF2P568891 (SNP 125) | 125 | 8 | 7938712 | 0.475321 | 0.475321 | TAAGCCATCAGCATGGGCTCCTAGGGGTCTGTTCAACTCCCT TGTGGTGTCTTACTGCTC[A/G]AGCAAAGGAACAGTCTGGT ACAGTGGGAGCAAGAGCTGAGGTTGGAGAGTGGGGACACAG |
| BICF2G6301950 (SNP 126) | 126 | X | 60714796 | 0.521308 | 0.478692 | GAGGAGGTGGAAGTGATTAAGTTTAAAATTTCTGGGGTGGTT TCTGGCGACATGAAGCTG[A/C]GAGCTAGAATGCCTTTCAA TCTCATAATTTCTTTAATTTGGTGATTATACCAGAGCCACA |
| BICF2P814468 (SNP 127) | 127 | 32 | 37551101 | 0.517787 | 0.482213 | CCTGACAAACACTACCTCTGCTCTTCAAAAGCAATAAGCATT TATTCTGTGACACATTTA[A/G]ATACAAAGTCAATTACAAT AGAGTATAAGTACAATACTAGGGAAAGTACAAAGTCATAYG |
| BICF2P948321 (SNP 128) | 128 | 32 | 37526448 | 0.511834 | 0.488166 | GCATGATGAAATCAGAAAAAGTATGTAAGTTTCTAGAAGAAG CTAGATATATGGTAACTT[A/T]GGTCAAATAGAACCATGTA GTGAAAAGAATATGAGTTTTCAAGTTCAATAAAAAACAAAA |
| BICF2P807378 (SNP 129) | 129 | 32 | 37648000 | 0.510848 | 0.489152 | ATGCATAAGTTTCCAAAAGAGTTCAGGATTCCAAAATAAAAG CTTCACTAAAAGATTCAT[A/C]GCAAAAGAGTAATGAACAA TTAAAGTCATAGGATATCTAAAATGAAAAACTGTTAGACTG |
| BICF2P175415 (SNP 130) | 130 | 8 | 6494289 | 0.489645 | 0.489645 | AGATGGCTTAGTTGTTTCTCTTTCCTCCTGAAGTCCACAGCT TAGTTACTTGGACTCTCC[A/G]AAATaggatcgttggacat ttgaggaaagctctagcatgaaagccatagactaaaaaaca |

Example 3

Identification of Further SNPs Associated with Susceptibility to Liver Copper Accumulation and Protective SNPs This Example describes the identification of further SNPs associated with susceptibility to liver copper accumulation and also some protective SNPs in the ATP7A gene. This work is also described in WO 2010/038032 A1 and WO 2010/116137 A1.

The three genes identified in Example 2 were investigated to identify further SNPs associated with susceptibility to liver copper accumulation. Thirty-three amplicons covering every exon of the three identified genes were chosen. These were amplified in 72 samples of genomic DNA from dogs of the Labrador Retriever breed. The samples were taken from dogs with either high copper (liver levels of copper above 600 mg/kg) or normal copper liver levels (below 400 mg/kg). The amplified product was sequenced in both directions by the Sanger method. The software 'Seqman 4.0' supplied by DNASTAR was used to assemble the sequence in each amplicon. The assembly was then examined to find single base variations (SNPs). These variations were then genotyped by examining the base-intensity at the SNP in the sequence from both directions. If the genotypes of a SNP from the two directions disagreed in more than 10 samples the SNP was classed as an artefact and ignored. The identified susceptibility SNPs are set out in Table 6.

Discovery of a Protective SNP in the Coding Region of ATP7A

A protective SNP was discovered (ATP7A Reg3 F 6; ChrX_63338063). This is provided in Table 7 and the sequence surrounding the SNP is provided in Table 8. This SNP is in the coding region of the ATP7A gene (an X chromosome-linked gene) and results in a change in the coding sequence. A study of average liver copper levels by gender and ATP7A genotype was conducted (Table 9). FIG.

Figure 2:
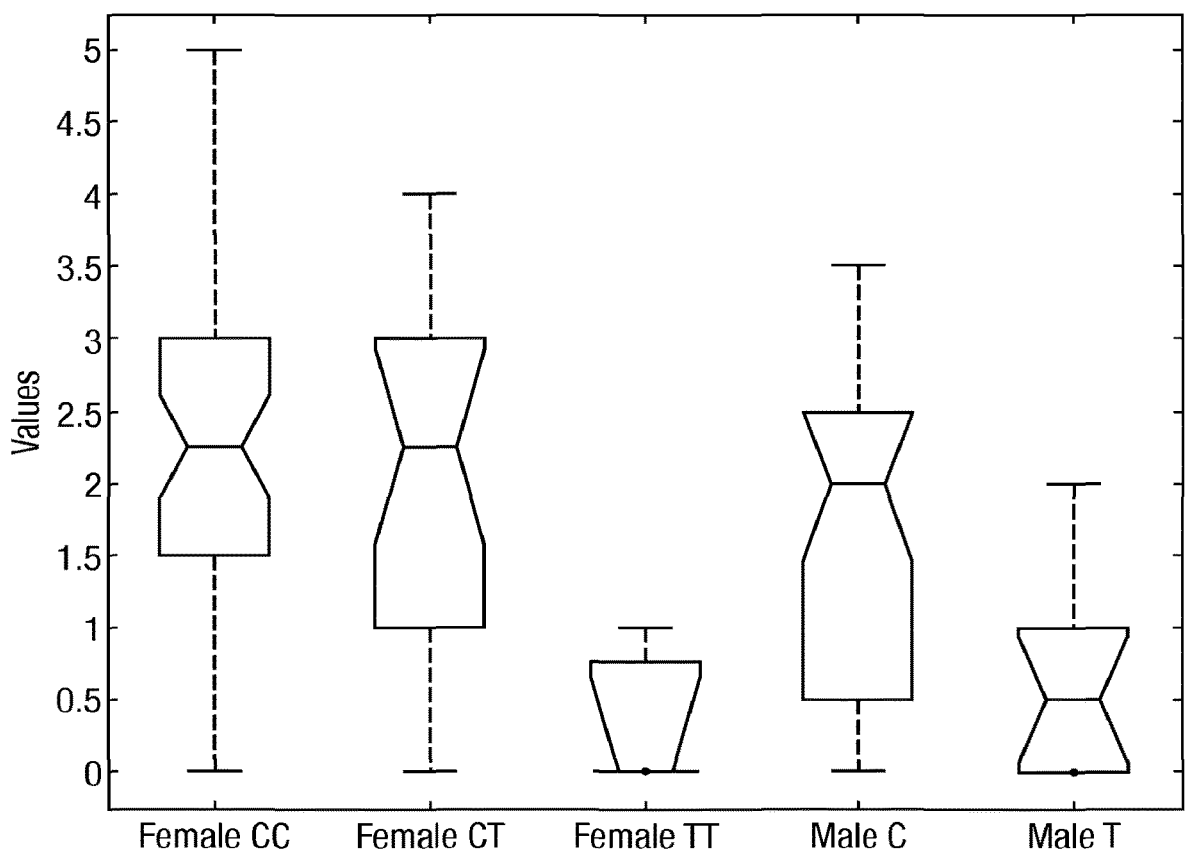
FIG. 2 is a box-plot of copper-histological scores by gender and ATP7A genotype in Labrador Retrievers (data of Table 9). The y-axis is the copper histological score values. The x-axis is ATP7A genotype: from left to right, the first three are for the female dogs in the study and the last two are for the male dogs in the study. The kruskal-walis p-value is 0.000396.

1 illustrates the data from Table 9 graphically. FIG. 2 illustrates the same data as copper-histological scores. The p-value (0.000396) was determined from a Kruskal-Wallis test on the histological score with gender-genotype as the groups. It is clear from the data that the presence of the T allele is indicative of a dog being protected from high liver copper.

The results may explain the female bias of chronic hepatitis. Male dogs have only one copy of the X chromosome and so are hemizygous at the ATP7A locus. An X-linked recessive gene-effect is more likely to be seen in males than females because of the hemizygous state of the male X chromosome. The protective effect here is recessive so we see more cases in the female population.

The protective SNP results in a change of a Threonine to Isoleucine at amino acid 328 of ATP7A leading to a decrease in the number of potential hydrogen bonds from 3 to 0 and an increase in hydrophobicity, potentially altering the shape of the protein. The Threonine at this position is conserved across many mammals, including horse, human, chimpanzee and dolphin, indicating the importance of this amino acid in the function of the protein.

Discovery of a Further Protective, but Non-Coding SNP, in ATP7A

Sequencing the ATP7A gene revealed an intronic SNP that is almost in complete linkage disequilibrium with coding SNP ATP7a_Reg3 F 6 (ChrX_63338063). Like the coding SNP, the intronic SNP (ATP7a_Reg 16_F42) is significantly associated with protection from liver copper accumulation (Table 7). The significance of both was measured using a chi-squared with two degrees of freedom on the independence of genotype and disease status. Disease status was positive for >600 mg/kg dry liver weight copper quantification and >=2.5 histology score; negative for <400 mg/kg dry liver weight copper quantification and <2.5 histology score. The expected table was based upon a Bayesian estimate of genotype frequencies and disease frequency within the sample assuming independence of the two variables.

The calculated measures of linkage disequilibrium between the non-coding SNP and the coding SNP are: D'=0.93 and R-squared=0.86. The SNPs are therefore almost in complete disequilibrium.

The sequence surrounding ATP7a_Reg 16_F42 is shown in Table 8.

Example 4

Investigation into Breed and Geographic Diversity of the ATP7A Protective SNP

This Example describes an investigation into breed and geographic diversity of the ATP7A protective coding region SNP.

The ATP7A coding region SNP (ATP7A Reg3 F 6; ChrX_63338063) was genotyped in samples of DNA from dogs of other breeds in addition to Labrador Retriever to determine whether the SNP is present in other breeds. Table 10 shows the results, with the number of dogs of each genotype. The 'T' column refers to homozygote females (TT) and hemizygote males (T). The results demonstrate that the SNP is present in diverse dog breeds and therefore may be used as in indicator of protection from copper accumulation in a wide variety of different breeds, mixed bred dogs and mongrels. The T allele of the SNP has also been found in US and Japanese Labrador populations, demonstrating that geographical location of the dog is not a hindrance to the utility of the SNP.

TABLE 6

Sequence of further SNPs indicative of susceptibility to liver copper accumulation.

| SNP name (SNP no.) | SEQ ID NO: | Sequence to the Left of the SNP | First Allele | Second Allele | Sequence to Right of the SNP |
|---|---|---|---|---|---|
| ATP7a_Reg4_F_9 | 131 | CTCTCATTTTGTGTATTGATTTGAGGACTCTGTCCTTTTTGTTCTCTTAGGTGTTTTGTAACCATTTTTGTGGTTCTTGCCACAAAAGGCCTTATGAAGTCCTGCATATGAGTGATGTGCAGGACAACTTTGACTTTCTGACAGCCAGTTTTTGTGTTTTGTT | A | C | CCTTAGTTCCCAAGTTCCTATCTTGTTTACCTCATGATCACATTTTAATATCAATGAAATTTGTAGGAAAACAGCAGAAGGAAAGATATAAGGTTACTATTCTCTATGGACCTTGGTTG |
| UBL5_Reg1F_16 (SNP 132) | 132 | TTGCAGATTATATGATAAATATAGTTGTAGCTTCAAAAATGACTATAACGAACAGAAAAAAATTAACTTATCAAAAACTTTTCAAATTTCCCCATA | T | C | ACTTAACTAGGTAGGCCACAGAGTATGATAGTATGCAAGTTATTAAAATCTGTTAGCAAGGCATAACACATATATTTCTACTTAATGAGGTTTCTATAATCAAGGCTTGTCAAGTCCATTATGTTC |
| golga5_Reg1_24 (SNP 133) | 133 | TCAGACTGAATCTAAAGCCACATATATTTCCTCAGCAGCTGATAACATTAGAAATCAGAAAGCCACTAT | C | T | TTAGCTGGCACCGCAAATGTAAAAGTAGGCTCTAGGACGCCAGTGGAGGCTTCCCATCCTATTGAAAATGCATCTGTTCCTAGGCCA |
| golga5_26 (SNP 134) | 134 | TCTTGTGCTTGTTCTTTATCACCATTCATTCAGTACATCCAAATTTTGAAATCCTTAGAGCTCTATAGCCTCTATGTAGGAGAATGA | G | A | ATTTCATCAAAAGGAAATATTTTGAGAATTTAAGTGATTTTTTTATGATATTTTAGCTATAGCAGTCACCTTGAGCCAAAAGACATTCTAC |
| golga5_27 (SNP 135) | 135 | AAAAATATACTCTCTTTCTTACAGAAACCTCTAATAATTCAGATTCTGGCCATGAAGTTCAGGAGGATTCTTCAAAGGAAAATGTATCATCAAGTGCTGCCTC | T | C | ACTGACCACAACCCAACACCTACTCATGATGGCAAATCMCMTRAACTGTYTAWTYTCSGATTGGRRAWTMAAYKGTTRAGGAATGAA |

TABLE 6-continued

Sequence of further SNPs indicative of susceptibility to liver copper accumulation.

| SNP name (SNP no.) | SEQ ID NO: | Sequence to the Left of the SNP | First Allele | Second Allele | Sequence to Right of the SNP |
|---|---|---|---|---|---|
| golga5_28 (SNP 136) | 136 | TTTGCCCAAGAAAAATGAAGACCTA TGACCATGGAAAGACTTGATACATA ATGCTGGAGTACTAGTAGTCAGACC CACCCAAGTCTTTTCACGTGTTCAT TCAGTATAGATGCGGCACACGTTGG CTGAGTCCCTCCG | T | G | TGTGTCAGGAACTGTTTTAGGTATT GGGGATGAAGTAGGGAACACTGATT TAGSTTCTGTTTATTCATGTCTCAC TTTGTAGGAATTYCMHTAMATAGAA RAADA |
| golga5_29 (SNP 137) | 137 | TCTCAGTACTCACAGGTACTTACAA ATACAACACTAAGAGGTTTCACAAA ACAGTACTCTTACATAGCACATGCT GTACTCTCTGTTCCATTCTATTTTA TTACTATTTTAAAATATGGATTGTG AT | C | T | TGCCAAKTTGATTCTCTGGCCCATT AATAGTTTGAAAATCTCTTCTGTAG GAGTATAGGAATTACCACAGAGTTT TGAGAAATTGATGAATGCCACGCTT TACCTGTGGGAACGTAGATTCTA |
| golga5_30 (SNP 138) | 138 | CAGATGATGAGTCTGGAGCTGGTGA TCTGGGCTGGAGATAATGAACCTGG GAGTCATCAGCTTTGGAGA- AAGGGTGTCTGGCCTCACTCTTGCT | T | A | GCACAGAAAGAAAGTGCTCATTAGT GTCAACTCTCAGCAACACTTGGTAT TTGTAAACTTTAATTTTTGCTGACT TCATGGAGAAATAATGTTTTT |
| golga5_31 (SNP 139) | 139 | TAATGATACAGAAATGAATTTGGCA GGAATGTATGGAAAAGTCCGAAAAG CTGCTAGTTCAATTGACCAGTTTAG GTAAGCAAGTGCAGTACTGGTGAGG AATGG | G | T | GCATCGGCTCCTTCTGTGCTATTTT CCGGTGGCTCCAGTCACAGCCCCAT CAAGCAGAGCTGATACCTAAAGTGA CATTTACCCTACTTCCTCTCTCAAT |
| atp7areg17_32 (SNP 140) | 140 | CATCACTTAAAATCATCTCAGCAAG TGTTGTTGAAGATGATTTTTTATAA AGTATATTCCAATCTTATTCTATAC TTCAGAAGCTTGGAATTCT | T | C | ATTTGCTTTGCTGGATTGAAAAAGT CTGGAAGTAATTAGAATGACTTCTC ATACTCCCACCTTGAATTCTCCTAA TATCAAAGGCTGGGAG |
| atp7areg17_33 (SNP 141) | 141 | ATATGGAGAAATGAGCTCTTATACA CTTTCAGTGGACATGTAAACTGTTA TTGTCTTTTTGGAGAGCATTTGGCA GGATCTATCAAAGT | G | A | CACACATCATTTGATTGAGCAATTC CACTTCCAGCCATATTCTGGACATA ATTTACAAGTATAAAAAGATGCATG TTT-GA |

TABLE 7

| Amplicon name | SNP position | Exonic or intronic | Coding change | Amino acid number | Base in Genbank | Base change to | Amino Acid in Genbank | Amino Acid change to | Association with phenotype |
|---|---|---|---|---|---|---|---|---|---|
| ATP7A Reg 3 | ATP7A 30,374 | Exonic | Yes | 328 | C | T | T | I | 0.001669996 |
| ATP7A Reg 16 | ATP7A 89,705 | Intronic | No | NA | C | T | NA | NA | 0.001796187 |

TABLE 8

Sequences or SNPs indicative of protection from liver copper accumulation.

| SNP name (SNP no.) | SEQ ID NO: | Comment | Sequence to the Left of the SNP | Wild type Allele | Alternative Allele | Sequence to Right of the SNP |
|---|---|---|---|---|---|---|
| ATP7a_Reg3_F_6; ChrX_63338063 (SNP 142) | 142 | coding change, protective T | AAATATTGAAAGTGCTTTATCTACA CTCCAATATGTAAGCAGCATAGTAG TTTCTTTAGAGAATAGATCTGCCAT AGTAAAGTACAATGCAAGCTTAGTC A | C | T | TCCAGAAACCCTGAGAAAAGCAATA GAGGCCATATCACCAGGACAATACA GAGTTAGTATTGCTAGTGAAGTTGA GAGTACCTCAAACTCTCCCTCCAGC TCACCTCTTCA |

TABLE 8-continued

Sequences or SNPs indicative of protection from liver copper accumulation.

| SNP name (SNP no.) | SEQ ID NO: | Comment | Sequence to the Left of the SNP | Wild type Allele | Alternative Allele | Sequence to Right of the SNP |
|---|---|---|---|---|---|---|
| ATP7a_Reg16_F_42 (SNP 143) | 143 | Intronic, protective T | TTAAAATAACTACTTGCAGTGATTT CTTTCCCCCAGTATAAAATGTCAGT TTTGTCTCAATCCACCC | C | T | CTTCACCTTAAAAAGAAAAAGAAAG TATTAGTTTTCAGTGTCATTTGCCT TAAAATG |

TABLE 9

| Gender | Genotype | Average Copper Level | Count |
|---|---|---|---|
| Females | TT | 323.3 | 3 |
| | CT | 818.3 | 22 |
| | CC | 1041.3 | 45 |

TABLE 9-continued

| Gender | Genotype | Average Copper Level | Count |
|---|---|---|---|
| Males | T | 437.5 | 13 |
| | C | 905.8 | 34 |

TABLE 10

| Breed | C | CT | T (Mutant associated with low copper levels) |
|---|---|---|---|
| Labrador Retriever | 31 | 13 | 28 |
| Miniature Poodle | 3 | 2 | 8 |
| Golden Retriever | 0 | 0 | 1 |

Example 5

ATP7B Sequencing

This Example describes the sequencing of ATP7B (cDNA and gDNA) and the elucidation of mutations associated with copper accumulation.

ATP7B Sequencing—cDNA

Amplicon Choice and Primer Sequences

Primers were developed with Perl Primer and checked for specificity using NCBI Primer Blast. Primers needed to be designed that were specific for the active ATP7B, rather than the pseudogene of ATP7B (a 1106 bp fragment at genomic position (4:38596510-38597615). The primers (Table 11) were secured by developing primers that mismatch the pseudogene of ATP7B. According to the NCBI database the fragment of main focus was located in exon 2 of ATP7B. However, Ensemble states this fragment is both exon 2 (ENSCAFE00000046065) and exon 3 (ENSCAFE00000046071) with a 33 base pair intron in between.

TABLE 11

Primer information

| Gene | Exon | Forward primer sequence 5' → 3' | Reverse primer sequence 5' → 3' | Size of amplicon |
|---|---|---|---|---|
| ATP7B chr 22 | NCBI: 2 Ensembl: 2 & 3 | GTTACCCTGCAGCTG AGAGT Location: 790G > A 5024- 790G > A 5043 (SEQ ID NO: 227) | ATGGCGAGCATCAC AGTATC Location: 790G > A 5355- 790G > A 5336 (SEQ ID NO: 228) | 332 bp |

Sequencing

Polymerase chain reaction (PCR) was performed using Pfx polymerase (Invitrogen, Carlsbad, USA). Results of the sequencing were analyzed using SeqMan (DNAstar8.1). Results were compared with NCBI (Build2.1) and Ensembl (CanFam 2.0 May 2005, database version 62.2r). The Labrador pedigrees were checked for Mendelian inconsistencies.

Results

Sequencing of Beagle cDNA prepared from liver RNA for primer optimization had revealed an interesting fragment and, due to the simultaneous gDNA sequencing of ATP7B, only this part of DNA was eventually sequenced in our Labrador subset. The sequencing results revealed two interesting coding, non-synonymous mutations: a SNP and a repeat. Furthermore we were able to resolve one of the discrepancies between the two genomic browsers NCBI and Ensembl. Because the sequence of exon 1 of ATP7B is not yet elucidated, the numbering of the exons starts with exon 2.

ATP7B Coding Repeat (Chr22_3135287)

There is a discrepancy between two online genome databases (NCBI and Ensembl) in predicting the exon structure of the ATP7B gene. According to NCBI, exon 2 is 1237 base pairs (bp) in length. However, Ensembl states that these 1237 bp are two exons, namely exon 2 (971 bp), intron 2-3 (33 bp) and exon 3 (233 bp). Our sequencing results show that exon two is indeed 1237 base pairs long and there is no intronic sequence.

Another remarkable discovery was that the 33 bp coding fragment is variable in length (FIG. 3). Ensemble shows four repeats, while NCBI shows heterozygosity (3 and 4 repeats). The Beagle we sequenced is also heterozygous but with two and three repeats. In our Labrador subset we found homozygous (3 repeats), heterozygous (3 and 4 repeats) and homozygous (4 repeats) dogs. The chromosomal location of the first C in the repeat is 22:3135287. The repeat is located between the third and fourth heavy metal associated domain of ATP7B (FIG. 4). Multi species alignment among eutherian mammals shows that this particular region is not well conserved. The dog is the only species in which a CGCCCC repeat at this position is found.

The sequence surrounding the repeat from NCBI is shown in Table 12.

TABLE 12

Sequence upstream and downstream of the CGCCCC repeat (SEQ ID NOs 236, 237, 238, and 239).

| 500 bp upstream | CGCCCC repeat (two, three or four repeats) | 500 bp downstream |
|---|---|---|
| tcagcacccaggaggcagtcatcacttaccagc cttatcttattcaaccccaggacctcagggacc atgtaaacgacatgggtttgaagctgtcatca agaacagagtggcacccgtaagcctgggaccca ttgatattgggcggttacagaggaccaacccaa agatgcctttgacttctgataaccagaatctca ataactctgagaccttgggccatcaagggagcc atgtggttaccctgcagctgagagtcgacggaa tgcactgtcagtcttgtgtcctgaacattgaag agaatataggccaactccccggggttcagaatg tgcaagtgtccttggagaacagaacggcccaag tacagtacgaccctt cttgtgtcaccgcagggg ccctgcagagggccattgaagctctcccaccag ggaactttaaagtttctcttcctgccgcagcag caggaagtgagacaggtaacaggttttcggcat gtgc (SEQ ID NO: 239) | CGCCCCCGCCCC; CGCCCCCGCCCCCGCCCC; or CGCCCCCGCCCCCGCCCC CGCCCC | aagaaccccggcaccgggcaggtgcgatactg tgatgctcgccattgtgggcatgacctgtgca tcctgcgtccagtcgatcgaaggcctgatctc ccagagggaaggggtgcagcaaatatctgtct ctctggctgaagggaccgcagtggttctctat gatccctctataattggcccggaagaactccg agctgccgtcgaggagatgggatttgagactt cagtcctctctggtatgtagtggcaccccggg tcttctcctctctccttgggccttacggcaga gtgcctgcagggtggcacaggggagccacccc agctgctcgcctgtcgggttggccaagtcccg cagcgtttccctgtgtgttgaatgtgtccggg tgggagaaagagaactttctggtgtgtagatt ttgcctctcatggggctgggactacattgcta aattctttgttgttgttatttttttttaact |

ATP7B 790G>A (Chr22_3135144)

Approximately 144 bp upstream of the repeat we found a non-synonymous mutation (ATP7B 790 G>A). This SNP is also located in exon 2 on chromosomal position 3135144. It is a G>A substitution and as a consequence the amino acid alanine is substituted by threonine. The SNP is located in the third heavy metal associated domain.

ATP7B Sequencing—Genomic

Resequencing (Sanger) of ATP7B was performed by Beckmann Coulter in 98 dogs from which complete phenotypic data was available. Exons and exon-intron boundaries were sequenced.

Results of the sequencing were analyzed using SeqMan (DNAstar8.1). Results were compared with NCBI (Build2.1) and Ensembl (CanFam 2.0 May 2005, database version 62.2r). The Labrador pedigrees were checked for Mendelian inconsistencies.

Results

Analysis of whole gDNA sequencing of ATP7B in 98 Labradors revealed 2 exonic non-synonymous mutations (including SNP ATP7B 790 G>A; Chr22_3135144) and 4 exonic synonymous mutations. Nine single base-pair substitutions in introns were detected. Further, 3 single base-pair indels and a 7 bp deletion were detected in intronic regions. The coding repeat of 6 base pairs (described above) was also found. Statistical analysis of relation with the phenotype was performed. Only the repeat and the 2 non-synonymous SNPs had a significant association with the phenotype in this group of 98 Labradors. These three mutations were studied in an extended set of dogs (see next section) and evidence for functional effects was searched for.

ATP7B 4145G>A

Figure 5:
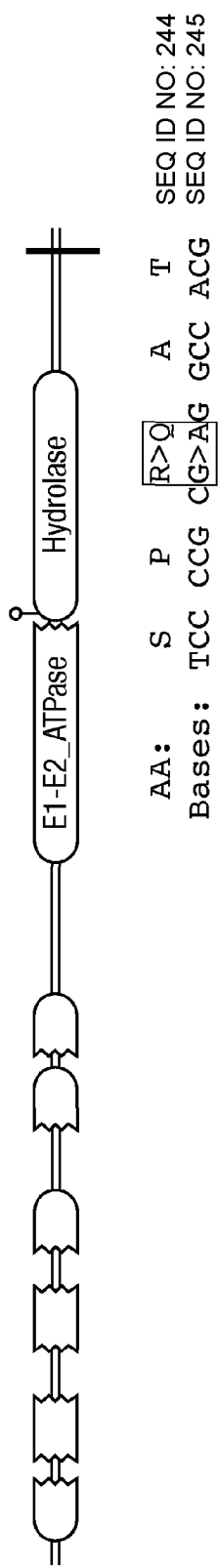
FIG. 5 shows the ATP7B 4145G>A SNP (Chr22_3167534). The vertical line on the far right shows the approximate position of the mutation. The G>A substitution leads to a glutamine amino acid (AA).

The ATP7B 4145G>A SNP is located at the end of ATP7B, approximately 154 bp upstream of the stop codon (exon 21, chromosomal position 3167534). It is a non-synonymous mutation in which a G>A substitution leads to the amino acid glutamine instead of arginine (FIG. 5).

Typing Mutations in Extended Set of Labradors and Effect Prediction

Two interesting SNPs (SNP790G>A and SNP4145G>A) and a repeat found in ATP7B were further analyzed in a larger subset of Labrador retrievers. For SNP790G>A, 267 Labradors and 1 Beagle (control) were typed and for SNP4145G>A a total of 242 Labradors were typed by SNaPshot. For the repeat, 216 dogs were typed by Genescan. The protocols used for typing the mutations are described in more detail below.

Genescan

Genescan was performed to type the DNA fragment length polymorphism in ATP7B using a 3-primer protocol. The Pfx polymerase was used for PCR amplification of the amplicon because Platinum Taq polymerase is not able to detect shot tandem GC-repeats. The same primers as used for sequencing were also used for the Genescan, except that there was a M13-tail added to the forward primer. Primer sequences are listed in Table 13.

TABLE 13

Primer sequences for Genescan

| Primer | Sequence (5' → 3') |
|---|---|
| M13-tailed forward primer | <u>GTTTTCCCAGTCACGACGTTACCCTGCAGCT</u>-GAGAGT (SEQ ID NO: 229) |
| Reverse primer | ATGGCGAGCATCACAGTATC (SEQ ID NO: 228) |
| 6-FAM-labeled M13 primer | <u>GTTTTCCCAGTCACGAC</u> (SEQ ID NO: 230) |

The underlined sequence is the M13-tail added to the forward primer.

Genescan results were analyzed with the Applied Biosystems GeneMapper Software Version 4.0. Focus was on the length and the differences in length of the microsatellite and if the individuals were homozygous or heterozygous at this locus for the microsatellite. Peaks were compared with each other and with the size standard to determine reliability of the peak.

SNaPshot

SNaPshot was performed for a precise SNP analysis in an extended group of Labrador retrievers.

For 790G>A the (functional ATP7B specific) primers used for sequencing were also used for the PCR reaction of the SNaPshot protocol. PCR primers for SNP 4145G>A were developed with Perl Primer and checked with NCBI Primer Blast. These primers were specific for the functional ATP7B gene because an intronic sequence was also incorporated. In addition, for both SNPs a SNaPshot primer was designed. The primer sequences are provided in Table 14.

TABLE 14

Primer information

| | SNP 790G > A | | | SNP 4145G > A | |
|---|---|---|---|---|---|
| Primer | Sequence (5'→3') | Location | Primer | Sequence (5'→3') | Location |
| PCR forward primer | GTTACCCTGCAGC TGAGAG (SEQ ID NO 231) | 3135024-3135043 | PCR forward primer | CGTCTGGATGGGAA GTTTCTC (SEQ ID NO: 233) | 3167222-3167242 |
| PCR reverse primer | ATGGCGAGCATCA CAGTATC (SEQ ID NO 228) | 3135355-3135336 | PCR reverse primer | TTGTCGGACTTCAGG GAGG (SEQ ID NO: 234) | 3167600-3167582 |
| SNaPshot primer (Rv) | AGGGTCGTACTGT ACTTGGG (SEQ ID NO 232) | 3135164-3135145 | SNaPshot primer (Fw) | CCGGCGGTGGGACT CCCCGC (SEQ ID NO 235) | 3167514-3167533 |

The SNaPshot protocol was the same for both SNPs, except for the PCR step. The template of SNP 4145G>A was created using standard Platinum Taq polymerase. In contrast, the template of SNP 790G>A was created using the Pfx polymerase, which is able to amplify GC-rich stretches more accurately.

Results were analyzed with the Applied Biosystems GeneMapper Software Version 4.0. Focus was on the different colors, with each color representing another base, and on the heterozygosity or homozygosity of the individuals. Peaks were compared with each other and with the size standard to determine reliability of a peak.

Multi Species Alignment

To check the conservation of the regions of the mutations among other species, a multi-species alignment was performed using the Ensemble multispecies alignment tool Both the single bases are highly conserved over different species, whereas the coding repeat is not. The dog is the only species with a repeat at that position.

Prediction of Mutations Effect

Both SNPs were evaluated for possible predicted deleterious effects on protein function with several prediction programs:

Align-GVGD (http://agvgd.iarc.fr/index.php).

The tool combines the biophysical characteristics of amino acids and protein multiple sequence alignments to predict where missense substitutions in genes of interest fall in a spectrum from enriched deleterious to enriched neutral.

PolyPhen (http://genetics.bwh.harvard.edu/pph/index.html).

Prediction of the possible impact of an amino acid substitution on the structure and function of a human protein using straightforward physical and comparative considerations.

PhD-SNP (http://gper.biocomp.unibo.it/cgi/predictors/PhD-SNP.cgi).

The tool is used as a predictor of human deleterious Single Nucleotide Polymorphisms.

SNAP (http://rostlab.org/services/snap/).

This is a method for evaluating effects of single amino acid substitutions on protein function.

Because the prediction programs are predominantly based on human data input, not all the programs could predict the effect of canine amino acid substitutions. According to the used prediction programs, ATP7B 790 G>A is suspected to have the most deleterious effects on protein function.

LD Calculations

Figure 6:
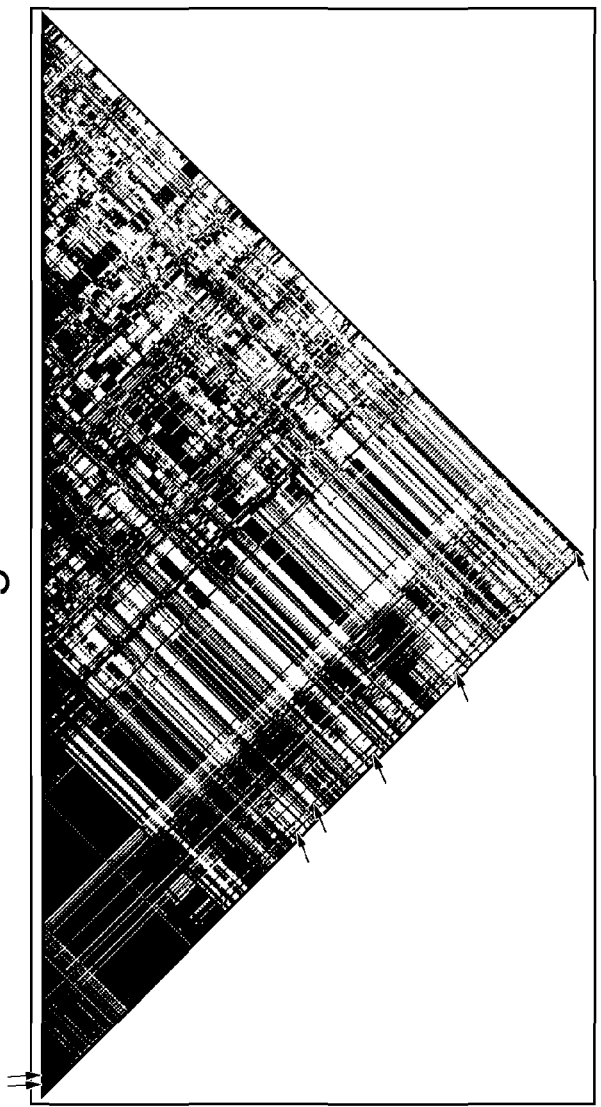
FIG. 6 shows the LD structure in the first 15 Mb of chr 22. Arrows at the top of the triangle indicate the location of the coding mutations. The line pointed at by the arrows depicts high LD of the coding mutations with several SNPs in the area.

Two measures of LD (D' with confidence interval and R-squared) were calculated using the program Haploview for the coding mutations in ATP7B and 672 SNPs in the first part of ATP7B. Results for the top three most associated SNPs from the GWAS are depicted in Table 15. High D' and low R-squared indicate a difference in allele frequencies of any combination of mutations measured. LD structure in the region (first 15 Mb of Chr 22) is depicted in FIG. 6. High LD between the mutations and several SNPs in this region is present, resulting in a large area that is associated in the GWAS analysis.

TABLE 15

Measures of LD for 3 coding mutations in ATP7B and top 3 SNPs from GWAS analysis

| | | 933_938Dup CGCCCC 3135287 | | 4145G > A 3167534 | | BICF2G6303159 50 7548442 | | BICF2G6303160 66 7767302 | | BICF2S23122114 12463818 |
|---|---|---|---|---|---|---|---|---|---|---|
| 790 G > A 3135144 | D' | 1.0 | D' | 1.0 | D' | 1.0 | D' | 1.0 | D' | 0.819 |
| | CLD' | 0.42-1.0 | CLD' | 0.64-1.0 | CLD' | 0.15-0.99 | CLD' | 0.58-1.0 | CLD' | 0.35-0.95 |
| | $R^2$ | 0.018 | $R^2$ | 0.085 | $R^2$ | 0.021 | $R^2$ | 0.044 | $R^2$ | 0.031 |

TABLE 15-continued

Measures of LD for 3 coding mutations in ATP7B and top 3 SNPs from GWAS analysis

|  | 933_938Dup CGCCCC 3135287 | | 4145G > A 3167534 | | BICF2G6303159 50 7548442 | | BICF2G6303160 66 7767302 | | BICF2S23122114 12463818 | |
|---|---|---|---|---|---|---|---|---|---|---|
| 933_938Dup CGCCCC 3135287 | D' CLD' $R^2$ | 1.0 0.32-1.0 0.043 | D' CLD' $R^2$ | 1.0 0.08-0.98 0.01 | D' CLD' $R^2$ | 1.0 0.89-1.0 0.4 | D' CLD' $R^2$ | 1.0 0.89-1.0 0.376 | | |
| 4145G > A 3167534 | | | | | D' CLD' $R^2$ | 0.93 0.79-0.98 0.213 | D' CLD' $R^2$ | 0.35 0.21-0.48 0.065 | D' CLD' $R^2$ | 0.31 0.17-0.44 0.31 |

Statistical Associations of the Coding Mutations with the Phenotype

The coding mutations in ATP7B were typed in an extended set of Labradors and a linear model was used to determine the magnitude and direction of effect of a mutation (beta) and the significance of association (p-value) for the single mutations and with all mutations in the same model. For 211 Labradors all three mutations in ATP7B and the mutation in ATP7A were typed. In this set, the number of risk alleles of each dog was determined and the effect of the number of risk alleles on liver copper based on RA staining was calculated.

Linear modeling with ra-scoring for copper as outcome variable was performed with age, sex and mutations as covariates for the ATP7B coding mutations. Both single allelic effects as well as effects of each mutation corrected for the other two were calculated and results are summarized in Table 16. Mutations were modeled in an additive way, so effect was estimated for every extra copy of the allele.

The 790 G/A (Chr22_3135144) mutation was found to be protective, whereas every extra copy of the repeat (Chr22_3135287) and every extra A in at position 4145 (Chr22_3167534) resulted in significantly higher RA scoring for liver copper.

TABLE 16

Linear modelling for RA phenotype and coding mutations in ATP7B

|  | Single alleles in the model | | | All alleles in the model | | |
|---|---|---|---|---|---|---|
| Mutation | Beta | 95% CI | p-value | Beta | 95% CI | p-value |
| 790 G > A | −0.46 | −0.75-0.17 | 0.00216 | −0.26 | −0.56-0.05 | 0.099 |
| 933_938Dup CGCCCC | 0.42 | 0.02-0.81 | 0.0398 | 0.51 | 0.12-0.91 | 0.012 |
| 4145G > A | 0.48 | 0.26-0.70 | 3.53e−05 | 0.51 | 0.27-0.75 | 3.62e−05 |

Figure 7:
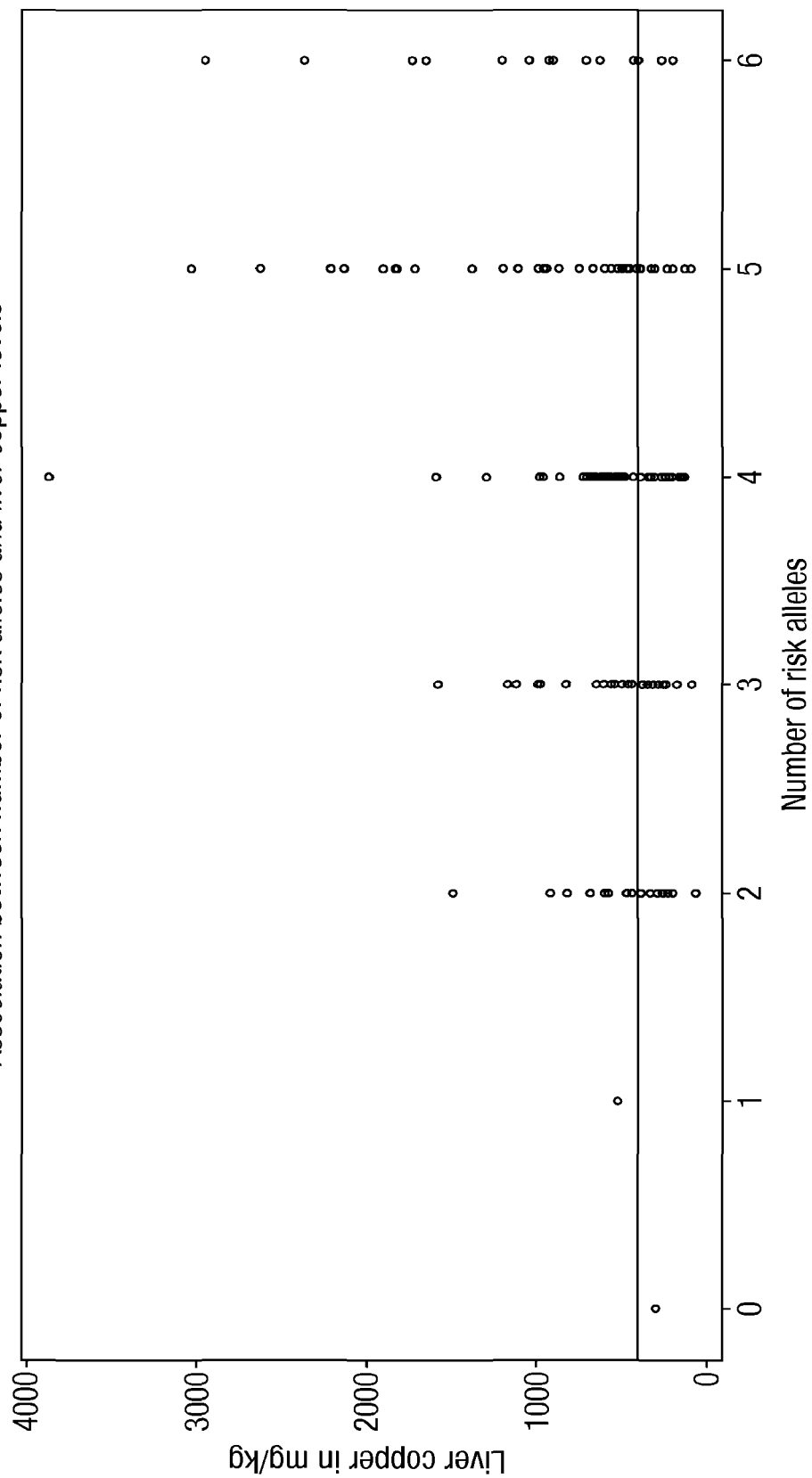
FIG. 7 shows the effect of the number of risk alleles on quantitative liver copper levels. The x-axis is the number of risk alleles and the y-axis is liver copper in mg/kg. The horizontal line indicates normal liver copper level of 400 mg/kg.

To study the effect of all known coding mutations contributing to the disease phenotype, linear modeling was performed in 211 Labradors for which the three mutations in ATP7B were typed successfully as well as the previously discovered ATP7A coding mutation. The number of risk alleles for each individual dog was counted. The risk alleles were: C for the ATP7A coding mutation, G for ATP7B 790, G/A (Chr22_3135144), 3 repeats for the ATP7B repeat at chromosome location 22:3135287, and A for ATP7B 4145 G/A (Chr22_3167534). Outcome variable was liver copper level based on RA copper staining (levels 0-5) and number of risk alleles was modeled as covariate. Every extra risk allele resulted in a significant increase in RA staining score of 0.33 with a very significant p-value of 3.5 e-08. FIG. 7 shows the effect of the number of risk alleles on quantitative liver copper levels.

Example 6

SNP Genotyping and Model Generation

This Example describes genotyping of SNPs and model generation.

SNPs were identified by SOLID sequencing (using the SOLID 3 sequencing platform) of CACH-phenotyped DNA samples. In addition, SNPs from previous work and sequencing of the ATP7A, COMMD1, ATOX1 and ATP7B genes were included in the analysis.

The SNPs were genotyped by GeneSeek on all available phenotyped DNA samples. SNPs were analysed with a collection of chi-squared tests. A two degrees of freedom test was used with a null hypothesis of independence between phenotype and genotype. Phenotypes used were:
  Histology score>=2.5 vs. histology score<2.5
  Quantitative copper>600 vs. Quantitative copper<400
  As well as the chi-squared tests a correlation co-efficient test was applied against quantitative copper and histology score. The test was performed in MATLAB using the corrcoef function producing a p-value and a correlation coefficient.

Loci were then ranked by p-value to prioritise further investigation. Genomic regions beyond a significance of 0.001 were investigated for potential candidate genes as described in the section headed "Region gene analysis" in Example 1.

Genotypes were then inspected for the selected SNPs. Because the corrcoef function can sometimes provide false positives in ordinal data (like genotypes) with low membership of groups the SNPs were filtered for only those that contain ten or more samples in at least two groups that have a difference in the phenotype. The remaining SNPs were used in model generation.

The final data consists of 386 SNPs genotyped on 260 samples. Analysis identified many SNPs that are significantly associated with susceptibility to, or protection from, liver copper accumulation. This analysis is shown in Table 17. Further information on the SNPs, including the surrounding sequences, is provided in Table 18.

Examples of SNPs in linkage disequilibrium with the SNPs, and which are therefore also associated with susceptibility to, or protection from, liver copper accumulation are provided in Tables 19 and 20.

TABLE 17

Results of the analysis of the GeneSeek data. Mutations indicative of "protection" from liver copper accumulation are in bold.

| SNP name | corrcoef pvalue - cuquant | corrcoef R - cuquant | corrcoef pvalue - log cuquant | corrcoef R - log cuquant | corrcoef pvalue - cuhist | corrcoef R - cuhist | chisquared pval - quantaff | chisquared pval - hist_aff | chr | Loc | Info | genes |
|---|---|---|---|---|---|---|---|---|---|---|---|---|
| Chr22_3167534 | 0.00828 | 0.297627 | 0.007077 | 0.241694 | 6.00E-05 | 0.298521 | 1.66E-01 | 2.22E-03 | chr22 | 3167534 | Exonic coding | ATP7B-coding |
| Chr20_55461150 | 0.164589 | -0.10583 | 0.014631 | -0.18482 | 0.009595 | -0.16689 | 3.46E-03 | 2.88E-01 | chr20 | 55461150 | Nearby | STXB2 bile acid gene) |
| ChrX_120879711 | 0.04194 | -0.15439 | 0.003159 | -0.22257 | 0.42838 | -0.05136 | 3.91E-03 | 2.39E-01 | chrX | 1.21E+08 | Nearby | MTMR1 |
| Chr32_38904515 | 0.043678 | -0.15139 | 0.049299 | -0.14759 | 0.141384 | -0.09501 | 4.95E-03 | 2.72E-01 | chr32 | 38904515 | Exonic coding | UBL5 ortholog - coding |
| Chr19_6078084 | 0.015583 | 0.193361 | 0.000449 | 0.277662 | 8.69E-06 | 0.298791 | 1.11E-02 | 3.94E-03 | chr19 | 6078084 | Nearby | microsomal glutathione S-transferase 2 (GST) |
| Chr15_62625262 | 0.000339 | -0.26857 | 0.000306 | -0.27052 | 0.01002 | -0.16628 | 1.13E-02 | 7.12E-02 | chr15 | 62625262 | Exonic noncoding | unknown |
| Chr14_39437543 | 0.007167 | 0.203766 | 0.00359 | 0.220272 | 0.007118 | 0.174397 | 2.33E-02 | 7.37E-02 | chr14 | 39437543 | Nearby | Interleukin-6 Precursor (IL-6) |
| Chr15_62625024 | 0.023044 | -0.17375 | 0.002611 | -0.22881 | 0.000993 | -0.21255 | 3.14E-02 | 2.27E-02 | chr15 | 62625024 | Exonic coding | Unknown |
| ChrX_63338063 | 0.034843 | -0.15568 | 0.040425 | -0.15124 | 0.000895 | -0.2084 | 3.85E-02 | 2.38E-02 | chrX | 63338063 | Exonic coding | ATP7A |
| Chr3_86838677 | 0.000256 | 0.276149 | 0.000973 | 0.25003 | 0.000456 | 0.226406 | 1.63E-01 | 4.69E-02 | chr3 | 86838677 | Nearby | KRT18 (Indian childhood cirrhosis - keratin 18 ortholog) |
| Chr8_482743 | 0.004603 | 0.328072 | 0.005334 | 0.322881 | 0.287162 | 0.113417 | 1.96E-01 | 5.76E-01 | chr8 | 4892743 | intronic | GOLGA5 |
| Chr24_4011833 | 0.030795 | -0.15758 | 0.048763 | -0.14394 | 0.005057 | -0.17472 | 2.20E-01 | 8.27E-02 | chr24 | 4011833 | Nearby | FOXA2 |
| Chr18_60812198 | 0.005568 | -0.02432 | 0.021119 | 0.058831 | 0.562541 | -0.0378 | 4.31E-01 | 5.25E-01 | chr18 | 60812198 | Potentially URT | ATOX1 |
| Chr8_4880518 | 0.00302 | 0.224225 | 0.073156 | 0.136583 | 0.58772 | 0.035242 | 4.78E-01 | 4.03E-01 | chr8 | 4880518 | intronic | GOLGA5 |
| Chr10_65209946 | 0.108151 | 0.120486 | 0.047767 | 0.14817 | 0.00069 | 0.215782 | 5.07E-01 | 2.77E-01 | chr10 | 65209946 | UTR | COMMD1 |
| Chr22_3135144 | 0.019406 | 0.184089 | 0.026966 | 0.174352 | 0.00047 | 0.232303 | 5.21E-01 | 5.61E-01 | chr22 | 3135144 | Exonic coding | ATP7B - coding |

TABLE 18

Sequences of the mutations in Table 17

| SNP (SEQ ID NO:) | canfam2 chromosome | canfam2 location | base1 | base2 | Rsq-histology | High copper allele | Sequence |
|---|---|---|---|---|---|---|---|
| Chr22_3167534 (SEQ ID NO: 144) | chr22 | 3167534 | G | A | 0.298521 | A | GAGAGGTACGAGGCCCAGGCGCAGGGCCGCATGAAGCCCCT GACGGCGTCCCAGGTCAGCGTGCACATTGGCATGGATGACC GGCGGTGGGACTTCCCCGC[G/A]GGCCACGCCTGGGACCA GGTCAGCCGTGTCAGCCAGGTGTCTGTCCTCCCTGAAGT CCGACAAGCTGTCCGACACAGCGCCGGGCCCGACGACGGC |
| Chr20_55461150 (SEQ ID NO: 146) | chr20 | 55461150 | A | G | -0.16689 | A | CGGGGCTNGATCTCACGACCCTGACATAGTGACCTGAGCCA AAACCAAGAGTTGGACGCTCAATNGACTGAGCCTCCGGGA GCCCAAAGTCAAGAGAC[A/G]CTACACAGATGCGTTGGGCA CAATGACAGGGGAGGAAGCTGAGGTCTGNTGNGGAGGTTC TGCACCTTCCCAGCAGGACCCNGCACAGCCAGGTGCCTGCT |
| ChrX_120879711 (SEQ ID NO: 147) | chrX | 120879711 | C | T | -0.05136 | C | GGGGAGTCCGGCATGGCCCCCTGTCAGCCCTGTCCCCTCAG GGTGTCTTGGCCGGTTGCTCCCTGACAAGCTCTCCCTCCT CTCTCTTCAGGTTCAGCC[C/T]GAATCTGACACCATGCCC CTAGGGAAGGAGCGAGCTTTGGAAGCAGGAGAAGACCT ATAGGAGCCGAGGGCCTGGGGATGCCCAGCTGTCTGGGGC |
| Chr32_38904515 (SEQ ID NO: 156) | chr32 | 38904515 | C | - | -0.09501 | C | AAGAAAAAGAAAAAACCCAGCCATCAAGGGTGTGCATGTCTG TGAAGCTCCAGACAGGATGATCGAGGTTGTTTGCAACGAC AGTCTAGAGAAGAGGTG[C/-]GCGTTAAGTGCAACTG ATGCACCCATCGGGGACCTTAAGAAGCTGATTGCAGCCCAG ACTGGCACCTGTTGGACAAGACCATCCTGAGAAGTGGTA |
| Chr19_6078084 (SEQ ID NO: 148) | chr19 | 6078084 | G | T | 0.298791 | T | CCTTCAGAGAGAACCCAGGACAATTACTAAACTACCGTGCC CTGGAAGATGTTTTGTGACTCCTCCACTCCCTCGCCTTGCT TATTGGCCATTATTTTT[G/T]ATCCCTCTCTCTTCTACC ATTATTAATCAAACACACACAAACAAAACACTTCTAACAAGG ATATTAGGTTTGTATACATTTTTTTAAAAACAGCAACTTA |
| Chr15_62625262 (SEQ ID NO: 149) | chr15 | 62625262 | A | G | -0.16628 | A | ACTTCCTGATTGCTACTGTCTGGACACTAGGTTTGCGATT TGTTCCCCCTTCCAGTGTTTCACAGTCTGGTGGAACTTCA GGAAACATTTGACTCCGC[A/G]TTGCTGAGCAGCAGGTAT TTATGTGTTGAGTCGTGCCATCTGATTCGTACAGAATCGC TTTTACTATCTCTTATTGCTAGTCCAGTATATTCTTCCCT |
| Chr14_39437543 (SEQ ID NO: 150) | chr14 | 39437543 | A | G | 0.174397 | G | CAGGGAACATTTTCAAAGATGTAGAAAATCCCAAGACATGT TAACATAGGAATGCATGTAAAGATGCAATCAAAAGCCTTT GAAATGACAACCACTTAT[A/G]TAAGACCTAGCAATGTGC ACTTCCAAACATTAACTAAAAGTTCTATCTCCCCCCTCTGG GTTCCTTAAACATTACACCTCTCGCCTATCAAAGCACCTA |
| Chr15_62625024 (SEQ ID NO: 151) | chr15 | 62625024 | A | G | -0.21255 | A | TTCCTCATAGGAAATTTGGCCTTCTCTTGATATTTTGTTGT GCTGTTTTGCTCACCTTTACACTGACCTCTGTCCTGCTGG ATCAGTGGATGTTTGGCA[A/G]AGTCATGTCACATTAT |

TABLE 18-continued

Sequences of the mutations in Table 17

| SNP (SEQ ID NO:) | canfam2 chromosome | canfam2 location | base1 | base2 | Rsq-histology | High copper allele | Sequence |
|---|---|---|---|---|---|---|---|
| ChrX_63338063 (SEQ ID NO: 142) | chrX | 63338063 | C | T | -0.2084 | C | GCCTTTCTCAATGTGTCAGTTCTGGTTTCAACTTTAA TTCTAATATCAATTGCCATTGTCAGTTATCATATGATCAAG |
| Chr3_86838677 (SEQ ID NO: 152) | chr3 | 86838677 | A | C | 0.226406 | C | See Table 8 |
| Chr8_4892743 (SEQ ID NO: 157) | chr8 | 4892743 | C | T | 0.113417 | T | ATCCAGAGAAGAAGTCTGCTAGGGGTAACTATCTTTCGCTCT CTGTTTATGCCAACATTTCACAAAGCTTGTCTCCCGTGAC TTAAATAGATACACCCAG[A/C]GTGTATGTTGGGATTTT TGCAAGTATCCTTAGGAGGCCCTACGTCGTAAGGCACAGTC ATAAGACCTCGCGTCCCTATTCCCTCATCTGTAAAATGGTG |
| Chr24_4011833 (SEQ ID NO: 153) | chr8 | 4892743 | C | T | 0.113417 | T | GCCTAGACATTATTCCTGACATGTGTTAGGTCCTCAACAAAT AGTAGCTAATATATACTTTCTGGATTTCTTTCTTTTGGCTAA GTAGAAGAGCTGGTGCTG[C/T]CATCCTTATAGTCTGTAT AGTAGGATTTCTTTTTCTTTCTTTTTTTTAAAGATTTT ACTTATTTACTCATGAGAGACACCAGACTGAGAGAGGAGGC |
| Chr24_4011833 (SEQ ID NO: 153) | chr24 | 4011833 | G | A | -0.17472 | G | CAAGGTCTGTGATGTCTTACTCCGTCCTCCACCACAAACA CCGATGTCTCGGACACACTCAGTGAGCCCAGGTTAGGAAGC CAGGATTGCAGGGCCAAG[G/A]GTATAAGGAGGTGTCCTG GGAGCCTCAAAAGAAAATACAAAAGTATGAAGACTCAGAA TAAATTCTTACAAATCTTGCTGTGTCTTCCCACAGATGGCA |
| _60812198 (SEQ ID NO: 154) | chr18 | 60812198 | A | G | -0.0378 | A | Gaaaggccgttctcctacctcggcccaagtagtgaggcct Ggacccctagcctcgatgaccaaagggagcaggtgggtg aggccccagccctggac[A/G]gaatatttcattagctaa tgcaaatcatgagtcaggaatcctcacagcccctgaga atacgcagagcactgtgttatgtctcccagggtccctttta |
| Chr8_4880518 (SEQ ID NO: 158) | chr8 | 4880518 | T | A | 0.035242 | A | AGAGAGAGGAGAAGCAGGCTCTATGCAGGAAGCCCGATGTG GGACTCGATCCCAGGTCTCCAGGATCATGCCCTGAGCCAAA GGCAAGACGCTCAACCAC[T/A]TAGCCACCCAGGCGTCCC TTTTACCTTAGTTTTGTCCTAAAGCTTCATATAAATGGAA TCATGTAGTATGTATGTGTACACTCTCTTTTCTGACTTC |
| Chr10_65209946 (SEQ ID NO: 155) | chr10 | 65209946 | A | T | 0.215782 | T | AAAGTATCAGCACACTGATGCAGCCAGCCTAGCTGAAG ATGGAGTGTTGAAGCANAGGTGTTCATGATCCCTCCC CAGTGACCTGCGATTTTTTTTTTN[A/T]AATCTTATT CGCCCATTTATTAAATCCNCAAATTCAAATCTGTTTG TCTCACTTGCTGAGATTTCTTTTGTCTTTCTCTTTCAT TCATTCTTACAGTTG |
| Chr22_3135144 (SEQ ID NO: 145) | chr22 | 3135144 | G | A | 0.232303 | G | CGACGGAATGCACTGTCAGTCTTGTGTCCTGAACATTG AAGAGAATATAGGCCAACTCCCCGGGGTTCAGAATGTG CAAGTGTCCTTGGAGAACAGAACG[G/A]CCCAAGTAC AGTACGACCCTTCTTGTGTCACCGACCAGGGCCCTGCAG |

TABLE 18-continued

Sequences of the mutations in Table 17

| SNP (SEQ ID NO:) | canfam2 chromosome | canfam2 location | base1 | base2 | Rsq-histology | High copper allele | Sequence |
|---|---|---|---|---|---|---|---|
| | | | | | | | AGGGCCATTGAAGCTCTCCCACCAGGGAACTTTAAAGT TTCTCTTCCTGCCGC |

TABLE 19

SNPs that are in LD with SNPs in Tables 17 and 18

| SNP in Table 17/18 (1st SNP) | SNP in LD with 1st SNP (2nd SNP) | Distance between 1st and 2nd SNPs | D' | R-squared | P value, histology phenotype, 1st SNP | P value, histology phenotype, 2nd SNP | P value, quantitative copper phenotype, 1st SNP | P value, quantitative copper phenotype, 2nd SNP |
|---|---|---|---|---|---|---|---|---|
| Chr22_3167534 | Chr22_9075014 | 5907480 | 0.826688 | 0.658336 | 0.000102 | 0.838726 | 0.011219 | 0.662255 |
| Chr22_3167534 | Chr22_9110499 | 5942965 | 0.826688 | 0.658336 | 0.000102 | 0.838726 | 0.011219 | 0.662255 |
| Chr22_3167534 | Chr22_12226464 | 9058930 | 0.775399 | 0.506036 | 0.000102 | 0.961949 | 0.011219 | 0.822992 |
| Chr22_3167534 | Chr22_12167150 | 8999616 | 0.776521 | 0.519594 | 0.000102 | 0.935438 | 0.011219 | 0.815249 |
| Chr20_55461150 | Chr20_55413165 | 47985 | 1 | 0.618847 | 0.013353 | 0.002002 | 0.02121 | 0.006836 |
| Chr20_55461150 | Chr_55722677 | 261527 | 0.981609 | 0.604767 | 0.013353 | 0.001949 | 0.02121 | 0.006911 |
| Chr20_55461150 | Chr20_51285925 | 4175225 | 0.864011 | 0.516789 | 0.013353 | 0.019014 | 0.02121 | 0.003384 |
| Chr20_55461150 | Chr20_51293507 | 4167643 | 0.864011 | 0.516789 | 0.013353 | 0.019014 | 0.02121 | 0.003384 |
| ChrX_120879711 | ChrX_121658683 | 778972 | 1 | 0.614854 | 0.439138 | 0.122152 | 0.003469 | 0.006726 |
| ChrX_120879711 | ChrX_121460633 | 580922 | 1 | 0.614854 | 0.439138 | 0.122152 | 0.003469 | 0.006726 |
| ChrX_120879711 | ChrX_122098973 | 1219262 | 0.985408 | 0.597007 | 0.439138 | 0.14357 | 0.003469 | 0.007408 |
| ChrX_120879711 | ChrX_121686983 | 807272 | 1 | 0.614854 | 0.439138 | 0.122152 | 0.003469 | 0.006726 |
| Chr32_38904515 | Chr32_38901362 | 3153 | 1 | 1 | 0.203207 | 0.096572 | 0.095103 | 0.012416 |
| Chr32_38904515 | Chr32_41530572 | 2626057 | 0.918132 | 0.746623 | 0.203207 | 0.478783 | 0.095103 | 0.067148 |
| Chr32_38904515 | Chr32_41464680 | 2560165 | 0.930789 | 0.775057 | 0.203207 | 0.40641 | 0.095103 | 0.053666 |
| Chr32_38904515 | Chr_39410526 | 506011 | 0.974846 | 0.897803 | 0.203207 | 0.101671 | 0.095103 | 0.004032 |
| Chr32_38904515 | Chr32_39400223 | 495708 | 0.975 | 0.94828 | 0.203207 | 0.092261 | 0.095103 | 0.009802 |
| Chr19_6078084 | Chr19_6118863 | 40779 | 1 | 1 | 1.44E-05 | 1.12E-06 | 0.000718 | 0.000995 |
| Chr19_6078084 | Chr19_5955685 | 122399 | 1 | 0.962909 | 1.44E-05 | 7.35E-07 | 0.000718 | 0.000352 |
| Chr19_6078084 | Chr19_11224079 | 5145995 | 0.904645 | 0.519971 | 1.44E-05 | 2.03E-05 | 0.000718 | 0.015058 |
| Chr19_6078084 | Chr19_11219212 | 5141128 | 0.904645 | 0.519971 | 1.44E-05 | 2.03E-05 | 0.000718 | 0.015058 |
| Chr19_6078084 | Chr19_3103155 | 2974929 | 0.985272 | 0.948479 | 1.44E-05 | 3.27E-07 | 0.000718 | 0.000352 |
| Chr19_6078084 | Chr19_3132042 | 2946042 | 0.98518 | 0.948389 | 1.44E-05 | 2.84E-07 | 0.000718 | 0.000352 |
| Chr15_62625262 | Chr15_62710768 | 85506 | 0.982189 | 0.931938 | 0.013595 | 0.028102 | 0.000506 | 0.000519 |
| Chr15_62625262 | Chr15_62710622 | 85360 | 0.955267 | 0.866969 | 0.013595 | 0.037358 | 0.000503 | 0.000281 |
| Chr15_62625262 | Chr15_60266576 | 2358686 | 0.799649 | 0.50462 | 0.013595 | 0.097143 | 0.000503 | 0.02112 |
| Chr15_62625262 | Chr15_61996961 | 628301 | 0.861755 | 0.708941 | 0.013595 | 0.148755 | 0.000503 | 0.002744 |
| Chr14_39437543 | Chr14_39362812 | 74731 | 1 | 1 | 0.010528 | 0.012587 | 0.005583 | 0.006317 |
| Chr14_39437543 | Chr14_39525972 | 88429 | 1 | 0.983673 | 0.010528 | 0.026677 | 0.005583 | 0.006317 |
| Chr14_39437543 | Chr14_34279412 | 5158131 | 0.761669 | 0.537724 | 0.010528 | 0.00068 | 0.005583 | 0.01334 |
| Chr14_39437543 | Chr14_34385007 | 5052536 | 0.903595 | 0.547279 | 0.010528 | 0.000433 | 0.005583 | 0.035825 |
| Chr14_39437543 | Chr14_39185668 | 251875 | 0.965622 | 0.901263 | 0.010528 | 0.007561 | 0.005583 | 0.006455 |
| Chr15_62625024 | Chr15_62564157 | 60867 | 0.977671 | 0.497765 | 0.001012 | 0.000129 | 0.002747 | 0.002696 |
| Chr15_62625024 | Chr15_62596216 | 28808 | 0.79665 | 0.466377 | 0.001012 | 0.002047 | 0.002747 | 0.006061 |
| ChrX_63338063 | ChrX_64356804 | 1018741 | 0.989019 | 0.946875 | 0.001246 | 0.000247 | 0.034731 | 0.005983 |
| ChrX_63338063 | ChrX_64247356 | 909293 | 0.989019 | 0.946875 | 0.001246 | 0.000247 | 0.034731 | 0.005983 |
| ChrX_63338063 | ChrX_64596205 | 1258142 | 0.989019 | 0.946875 | 0.001246 | 0.000247 | 0.034731 | 0.005983 |
| ChrX_63338063 | ChrX_64318806 | 980743 | 0.989019 | 0.946875 | 0.001246 | 0.000247 | 0.034731 | 0.005983 |
| Chr3_86838677 | Chr3_86858401 | 19724 | 1 | 1 | 0.000661 | 0.000937 | 0.001572 | 0.003251 |
| Chr3_86838677 | Chr3_86974042 | 135365 | 0.949195 | 0.870279 | 0.000661 | 0.000305 | 0.001572 | 0.00148 |
| Chr3_86838677 | Chr3_86397551 | 441126 | 0.739619 | 0.527699 | 0.000661 | 0.004155 | 0.001572 | 0.023787 |
| Chr3_86838677 | Chr3_86403839 | 434838 | 0.739619 | 0.527699 | 0.000661 | 0.004155 | 0.001572 | 0.023787 |
| Chr3_86838677 | Chr3_86948527 | 109850 | 0.949195 | 0.870279 | 0.000661 | 0.000305 | 0.001527 | 0.00148 |
| Chr8_4892743 | Chr8_4892196 | 547 | 1 | 1 | 0.274005 | 0.098475 | 0.004869 | 0.014759 |
| Chr8_4892743 | Chr8_4889521 | 3222 | 1 | 1 | 0.274005 | 0.238005 | 0.004869 | 0.026988 |
| Chr8_4892743 | Chr8_11618239 | 6725496 | 0.845679 | 0.650159 | 0.274005 | 0.013872 | 0.004869 | 0.034342 |
| Chr8_4892743 | Chr8_11613479 | 6720736 | 0.845679 | 0.650159 | 0.274005 | 0.013872 | 0.004869 | 0.034342 |
| Chr8_4892743 | Chr8_9064669 | 4171926 | 0.966276 | 0.825462 | 0.274005 | 0.013109 | 0.004869 | 0.006045 |
| Chr8_4892743 | Chr8_9054168 | 4161425 | 0.966699 | 0.825173 | 0.274005 | 0.012575 | 0.004869 | 0.006045 |
| Chr8_4892743 | Chr8_5938207 | 1045464 | 1 | 1 | 0.274005 | 0.177173 | 0.004869 | 0.018788 |
| Chr8_4892743 | Chr8_5896281 | 1003538 | 1 | 1 | 0.274005 | 0.255392 | 0.004869 | 0.025001 |
| Chr24_4011833 | Chr24_9568995 | 5557162 | 0.968436 | 0.770885 | 0.002878 | 0.005212 | 0.028429 | 0.018937 |
| Chr24_4011833 | Chr24_9311101 | 5299268 | 0.968436 | 0.770885 | 0.002878 | 0.005212 | 0.028429 | 0.018937 |
| Chr24_4011833 | Chr24_9391376 | 5379543 | 0.968436 | 0.770885 | 0.002878 | 0.005212 | 0.028429 | 0.018937 |
| Chr18_60812198 | Chr18_42897855 | 17914343 | 0.687167 | 0.073112 | 0.447897 | 0.198618 | 0.047887 | 0.125786 |
| Chr18_60812198 | Chr18_45266899 | 15545299 | 0.781952 | 0.069095 | 0.447897 | 0.218449 | 0.047887 | 0.624226 |
| Chr8_4880518 | Chr8_19298728 | 14418210 | 0.69073 | 0.065351 | 0.579649 | 0.317402 | 0.066075 | 0.937917 |
| Chr8_4880518 | Chr8_6295891 | 1415373 | 0.385029 | 0.059849 | 0.579649 | 0.369191 | 0.066075 | 0.205044 |
| Chr10_65209946 | Chr10_65089416 | 120530 | 1 | 0.459482 | 0.003119 | 0.009497 | 0.141706 | 0.192725 |
| Chr10_65209946 | Chr10_65142039 | 67907 | 1 | 0.459482 | 0.003119 | 0.009497 | 0.141706 | 0.192725 |
| Chr22_3135144 | Chr22_3067105 | 68039 | 0.984428 | 0.879056 | 0.00026 | 0.000877 | 0.015303 | 0.012789 |
| Chr22_3135144 | Chr22_3349188 | 214044 | 0.969246 | 0.864914 | 0.00026 | 0.000456 | 0.015303 | 0.004781 |
| Chr22_3135144 | Chr22_13256436 | 10121292 | 0.943853 | 0.667922 | 0.00026 | 0.000326 | 0.015303 | 0.089054 |
| Chr22_3135144 | Chr22_13202693 | 10067549 | 0.953395 | 0.53079 | 0.00026 | 0.00268 | 0.015303 | 0.090825 |
| Chr22_3135144 | Chr22_10985753 | 7850609 | 0.984186 | 0.864323 | 0.00026 | 0.000905 | 0.015303 | 0.014708 |
| Chr22_3135144 | Chr22_10587732 | 7452588 | 0.984186 | 0.864323 | 0.00026 | 0.000905 | 0.015303 | 0.014708 |
| Chr22_3135144 | Chr22_14998527 | 11863383 | 0.776007 | 0.405128 | 0.00026 | 0.000216 | 0.015303 | 0.000397 |
| Chr22_3135144 | Chr22_11895473 | 8760329 | 0.962141 | 0.676774 | 0.00026 | 0.004793 | 0.015303 | 0.019903 |

TABLE 20

Sequences of the SNPs (2$^{nd}$ SNPs) in Table 19

| SNP in Table 19 (2$^{nd}$ SNP) | base1 | base2 | High copper allele | Sequence |
|---|---|---|---|---|
| Chr22_9075014 (SEQ ID NO: 159) | T | C | C | TgcctctccactactcactcttctcttgaaagattatttcCTgcttaaactggcccgtgactt cctgctgcCAGAACCATGGAATGGCCTCCTGAGGGAGGCTCCCTATGCTGCTCCCAT[T/C]A GCAGATATTGCAGCGTCACAGTATAACTCAGTGGCTTGAAATGATGGCTATTTATCATTGCTC AGTAATTTGagtggctcgaagaggatagaaatttcatttctttctcagataat |
| Chr22_9110499 (SEQ ID NO: 160) | T | C | C | TGTACAGCTGACTCCCTGAGAAAGGACATCCTGGGTCACCTTTCAAGTATTTCCTGGCATGGA AACCCCATATCTTCAAACACAAAAATCAGAAAATCACAGTCCTTATCTGTTTGGGCC[T/C]A TTTATAGGAGAGTCTTTTTATTGCCTGGAATTGTATATTTTTACATTTCTTAGATTTCTACAA AATAATATTTGTGCCTTCTTTGAAGTATAATATTATTTATTAAAGTTGCTTT |
| Chr22_12226464 (SEQ ID NO: 161) | T | C | T | ATTAATACATTCTTAGTGTCTTCTTTAAAAATGCAACTTCCATGCTTTATAAAATACCAACAA ATGCTTTACATCTTTATGATGGTAATTTTGGATCAATACTGGAGGATTTTAAAAAAA[T/C]C TCTGCTTCCCCTGCTTGTGTGGTCTCTCACGCGCTCTCATTCTCACTCTGTCAAATAAATAAA CAAAATCTTTCCAAAAAGACAAAGTCCTTGTGAAAACTGAGAAGGCCTGTGA |
| Chr22_12167150 (SEQ ID NO: 162) | G | A | G | ATTTGTACTTTCTTTTCACTTCTCCTGCGTGGTGCGTATCTCTCCAGTCTGTGTTCTTTAGGC ATACATTGCTGTATGTGCTTTAAATAGAATCCTACCTTATATACTGCTTAATAACCT[G/A]T GACCATAAGATCAGGttccatgtcttcaaagattctcctcatcattttcacgggtataggcat agattacaattgatccattcccactttgcacatttagattgttttcacttt |
| Chr20_55413165 (SEQ ID NO: 163) | T | C | T | TgcaatgactctgtttacaaataaggtcacaatctcaggtAccagagcttagggcttcaacct gtcttgggggagggtggGcaggataccattcagtccataacaGCAGAAGATCCCGGT[T/C]G TCCTCACAGTATGGTGGGCAGTGGCCAGCCCTCCGGACTTTCACCTCCAGGGGGCAGGCGGAG AAGCTAAAGGGGGGTCTCATGGCCTCCCAGCTCCTCCCTTTGCCCCTGCAAT |
| Chr20_55722677 (SEQ ID NO: 164) | G | A | G | ACCCACGCCCAGCATCTAAGAGGCCAACCCCTCCCTGCTGTGGGCTCCTGGGCTTCTCAACCC CCAAGGAGGGGACTGCAGTCCAGCGTGCCGACAGCTGCCTCCACCCCAAAGGGGGGC[G/A]A TGGCTGGTGGAGTGGAGACTGAGTGCATGACCGACTTTTTAGCCAAGACTTTTTCTTAATTGT TAGAGATGGCAAActcaagcaaatgggaaactcatccgctcaagtaaccagc |
| Chr20_51285925 (SEQ ID NO: 165) | T | C | C | GCCTCGTGGGACAGCTTTCTAGCACTTTCCCCTTTTTAAGAGATTGACTGCAATTTCTATAAT AACATCACATTAGCTAGAAATTAATGTCCTCATTAAGACAGCAATTAGGCACATTAG[T/C]G CGGCAATAAAAGAGAAGCTTATGAAATAATTGCTGGTTCCGAAATGCCTTTAATTTAGTGTTT TATATTGCGCCATGTTATTAATTTTTTCCCTCGGCAGAAGATAATAAGAGAA |
| Chr20_51293507 (SEQ ID NO: 166) | A | G | G | CATAAATGCCCCCCCACCTCTGTGTCTGTGCAGAAACCAAAGTCTTGGGCTTCTATGATCC CCAGTGAGTGCTAGGAGCAGGACCGCAATCACAGCAGCACATCCTAGAAAGGACTTA[A/G]G AGCCAGATACTACCATCCTATTCACTCAGGTAATCCTCACAGTAAACCGCAATGGCATAAAAA ATATTACCTCCAGGGCCCAACGGACGgactcttgatctcagggttgtgagtt |
| ChrX_121658683 (SEQ ID NO: 167) | T | C | C | ATGAGATATGTCTGCTCAGCCACTGTCTGGGGCCTTGTAATTGAAGCCTTATAATTAGCATGA AGTCACCAGCTTGGTCCTGCTGAAAGGGCACAGGGTGGGGTGTGAAAGGAGGATGGC[T/C]A AGGGCTCGTCCACAGGAAACATTTTCTAAACACTAGAGAGGAGGCAGCCAAAGAGCTCCCTTC CTCATCGCCCATGGACCCCACTGCTATGCTGGCAATTCCCCTTTTGGTTAAT |
| ChrX_121460633 (SEQ ID NO: 168) | G | T | T | TTCCTGTGCAGAGGGACACGTGAAGGCCCTAGGTCCTCCTGGGAGAAAAGATTTCCCTCCTAA TGATCCAGGGACTAGGATTTCATTCTGAAATGGAATGGAGAATGGCAGGTGTGGCTT[G/T]C TGGGGATTGAGAACCACAGGCCCCAGGAGATTCAGGAAAGGACAGTAATGCCCTGCTGCTCAG GCCCCGGTGGAGGAATCATATCCTCAGCTCAGCAACACCACCCGCCCCCCTA |
| ChrX_122098973 (SEQ ID NO: 169) | A | G | G | ACATCGGCTAAACAAAAACAGGAGAATCCCATTATAAGACGGTTCCTGTAGTACAGATGTGTC TGGGTGAAGCCTGGGTTGTATCGTGGCCCCATGTAGAGCCAGCCTGGGCAGAGAGCT[A/G]G TCTACCCACTAAGCAACTGCAAGAGGCAAAGTGCAGCATTGATGTCACGAGGTCCAGCATCAA CTAGGACCATCCCCATCCATGTGAGCAGGCTCACACGTGGAATCGCAGTGGA |
| ChrX_121686983 (SEQ ID NO: 170) | G | A | A | CCGTGCTTCACAGGCGAGAATCTGAATGACCGTGATGCCACCACATGTCACCATCCCCTTTTC CACTGGGAAAGGGGTCCTTGTTGCCTTCCAGCTCCAGAATTGCATCCTCACAATTTC[G/A]G AGGCCCTTCCTCCTGCTAAGCtctgtgcttttccagaaagtagagcataagacaagggcttat atgcaagtatatttttggaaaatatgatcccagagagcaggagtgagaact |
| Chr32_38901362 (SEQ ID NO: 171) | T | A | A | ACTCCATGAAATGGTTTATTTTATCCTATGAATCgatgtgGagaacaaaggcaaaagaaatat agaaaaatattaaatttCcttacaatgtacagcccattgataatattttagacagtg[T/A]g agtgatcttgcttatggagctcaactgcctcaatgttaatccttagctaaaggcaaaagacaa tcttagtttgacattagcctgaccgccttatgctatccctaaccccgtccc |
| Chr32_38901353 (SEQ ID NO: 172) | T | G | G | AATCCAAATACTCCATGAAATGGTTTATTTTATCCTATGAATCgatgtggagaacaaaggcaa aagaaatatagaaaaatAttaaatttccttacaatgtacagcccattgataatattt[T/G]a gacagtgtgagtgatcttgcttatggagctcaactgcctcaatgttaatccttagctaaaggc aaaagacaatcttagtttgacattagcctgaccgccttatgctatccctaac |
| Chr32_41530572 (SEQ ID NO: 173) | G | T | T | AGGAAAAATATGCTTGCTTTTGAAGGAATCAATTTGTGGTTTCTTTTAATGAGTTATCAAACT ATTAATAAGCATTAATTATTTATTGTGTAAGGCAAAGTGCTTCTTAATAGGTATTC[G/T]T CCTTAACTTAGAACATTCACAGATTCCCAATAGCCTCTAGTGCAGAAGAAGTCTGCCGCTCTT CTTTCCTCCTTTCACTAGTCTCTCCTATATCTGTGATACCTCCAATCATAGC |

TABLE 20-continued

Sequences of the SNPs (2<sup>nd</sup> SNPs) in Table 19

| SNP in Table 19 (2<sup>nd</sup> SNP) | base1 | base2 | High copper allele | Sequence |
|---|---|---|---|---|
| Chr32_41464680 (SEQ ID NO: 174) | G | A | A | CttccatgttctgtctcccttttctgatatttcctactcatTccAGAAAATATTCTTAATGAAGCCTCTGATACGGTCTTGAGGATCCTCAGAGACCATATGTCAGTCTGTCAATGAAGCA[G/A]AAATCAAGATGTTTGGATCCCAGTAGATATGTAATCAAAATGCCATGGGAATACAGAGAAGGGGAGTCATTTGTATCAGTTAGTGTTAAAAATTATTATCACGCTCTTGATATTA |
| Chr32_39410526 (SEQ ID NO: 175) | C | A | A | GAGAATACTGAAGACGTAATGAAGTTGAGTTCCACCTTTATAATAATTCCGTTTTACCCTAAAGGGGAATATTCAAAAATGTGACATCGCTCTACCAGACCACCTTGCGACTGCTCTAAA[C/A]GATTGGCAGGGGCAAGAACTTGTGTCACTGATAGGCGGGATTTTTTAGTCCTCTCTGCAAATCATTAAGAAAATGTTCCAACGCAACAAAACAAAATATGGTGGCGATCCCTGAAC |
| Chr32_39400223 (SEQ ID NO: 176) | G | A | A | ACCTGATAACACCGCCTCAGTGGAGAACGAGTTGGCACTTCAGGACAGATTTCCCTGCCAGAGCCTATTCCTGTTTGACACTTTCATTTGAAGAAACCCACTCATGGTTTCTTCTCTCCA[G/A]GGTTTAAAACCGAGATCAAGTATATCTCTTTAATAATGTCACATTCCAAAGAATGACTCCGATAAGGGGATTGTTCAAGGGCTTGGGTATTCACATAAGGGCTATCATGCGGGGAG |
| Chr19_6118863 (SEQ ID NO: 177) | T | C | T | TCCTCTAGATCTGACCTACATTTCAAAAATATATGAGTGGGCTATAACCAGGAATGTCTTCTCTTGCTGCCATTATTCACACTGCATTTTCTGAAGTTGtttttttttttttttttttt[T/C]CCCCTCGGTGACTTTAATGGCCATTGAGGGAACTGTAGACATTGGGAGTCTTTATACAGCCCTAGTGAAATGGCGAGTGTTATCAATAGGGTGGCTGAATGGTACGGCTCTGGGC |
| Chr19_5955685 (SEQ ID NO: 178) | A | G | A | CATCTGTGACCCTTGGATTCAAACCAAGTAGGATGCAAACCTCAGAACTTCTGGCATTTCGGATGCACTGATCTCTGCCAGCCCCTTGCCCTCTTCTAATGGGATAGAAGCTGATGATGT[A/G]AGACACCGCGTGCACCATCTGCCCAAGACGTCCCAGTTGATGCCACTCATCCTGGTTTGTGCAAAAAATTCTCTATTTGCCCTAATTCCACCGCTCAGCAACTGGAAGGACCTGAG |
| Chr19_11224079 (SEQ ID NO: 179) | A | G | G | TCACAATGGCTTTTTTTTTTTAAGATTTAACAGGAATTTTGTGATCCTTTATATGATATGTTTCAATGAAGCCTTTTGGGAAAGGTTCTTAATGTGAAAGAATTTTCACAGAGAATATC[A/G]GAAATAAATGTGCAAAAGGGAGTCGTTTTAGGATTAGAGATATGCATGGAAGAGGGAAAAAGCCTACTTATATTACTAGAAAATAATTTTCAATTTAGAAGTTATACTGAACTATT |
| Chr19_11219212 (SEQ ID NO: 180) | G | A | A | CCCATTTTTTTAGGATTGATAAACTGATCATCTAACAGATATTTATATACAAAAGTCAGAGAAGACACAATAGCCAACCCTGTGTGTAAGGAAAATGACAGAGTTGGTTAAAGAGAAAAGA[G/A]AAAGGAGGTACACAGAGAGATGTAGAGGTCACATTAAAAATGAACGTTGTCCATGTCTATGAAAGATGGAAGGTAATTCTATGCCTATAAGGTATGTTATAAGTTAAATTAATTGT |
| Chr19_3103155 (SEQ ID NO: 181) | T | C | C | AACAAACCTACCAAACAGGACAAACCAGTCCGGATTATATAATATGTAAATATGCCAGGGAGCTGGGGAGCATACTTGTGGGAGGATAAGCTGGAGCAATGGTTAAATGAGCTCAATCCT[T/C]ACTATACTTGAAGGTAGTAGCCTCTTCATTCACACTCCATGGCTAGCCCTTTGTAACTAAAATATGGAAAACACAACCAATGAAGAAGTTACATGTATCCCTAAAAATACCACCTA |
| Chr_3132043 (SEQ ID NO: 182) | A | G | G | CCCTTGGCGTTCTAAAGTCCAGCCCCCTCTCTTCGCATTCTGTGCTTTCTCCTGTGTGGC[A/G]GTCTCTGTGCTTTATCTGCACATAAACACTTCACAAATTTCCGTTCCAGCTTAGTTCTCT |
| Chr15_62710768 (SEQ ID NO: 183) | G | A | A | TTAAGTTTAGAAAAAACAAATTCAAGAACAAGCTTTTTATATTTAACATCGATGAATCAGAAGATACGGGGtttttttaaaTtattaaactaaaattattaaaCTGGTCCTGTTTGGGTATA[G/A]GTTATCTTAATTATGCTAATCTGGAATCTTAAAGCATTTTTAAACTAATATTTTAAGAAACCAAGTTTTAGATTTATTCCAACCTTGGGCTAGAAAAGGATGACCTTTGTGGGCC |
| Chr15_62710622 (SEQ ID NO: 184) | C | T | T | TgagccacccaggtgccccAAAAACATGATTAGTCTTGAAACAAAGTGTATCACAATAATGATTCAATTAGATGAATAAAATGTAGTTTTTGAGAATGGTAAACACTATGTAAGAGTAAAG[C/T]TAGCCTATTTGATCAGTAAACCTATTTAAGTTTAGAAAAAACAAATTCAAGAACAAGCTTTTTATATTTAACATCGATGAATCAGAAGATACGGGGtttttttaaattattaaacta |
| Chr15_60266576 (SEQ ID NO: 185) | C | T | T | AGATGTCATGCTATGATATATTTAAATAAGTTACAGACATGTATAATTTCCATGGTATGTTTTACATTCatataaaaattAactattcataaaatataatAaaatGTAGTGTTTTTCTTA[C/T]TGAGCTTCAGTGATCATAATTTGTATATTAACTTAATGACCAGAAATAATTAAGTAAAGCTAGTTAAATTCTTGGGATGTTATGGATTATGTTATTTGGTTGGCTGTTCATGATAA |
| Chr15_61996961 (SEQ ID NO: 186) | A | G | G | TGTTTTGAATTTAAGGTGTTTTTCCAGGCTGAGAAGAAACGTGAGCTCTTGGAAATTAT[A/G]ATTAACGTATCTAATGCATATACCCTAGAGGGCAAGGAAATTTCTATTCATTCCCTGTAT |
| Chr14_39362812 (SEQ ID NO: 187) | C | T | C | CCCCCAGGATCTGTCAGTAATCCCTGACTGCCTGCAGACCACATGGGAGAGGGATCCATTCCTATGACAGAGAATTTATACTGGCTTGTGAGCTGAACAGATACCTCAGAAGATGTTCA[C/T]CTGTGAGACAGAGAGACAGGTGACAAATACAAGTGTCAGCCAACAGCAGCACCAAGTCCAGGAATGGCTGCCTGAGCTGGATGGAACCTCACTATCCAGAGCCATCCATAGGCCG |
| Chr14_39525972 (SEQ ID NO: 188) | A | G | G | AGAGCCAACGCTGGATCTCAGGGAGAATCTAGAAGGCCAGCTGACCAGAAAACCAACTGG[A/G]CAGACAGAAGCTGGGAGCAGCGCCTGTGGAGGCAGGCACGAGAGGCCCCGGTGCAGCCGC |
| Chr14_34279412 (SEQ ID NO: 189) | G | C | C | CTGGGTGGCTGTTGGAGAGAGTGTGTTGTGTTGTTCCCAGGGTTAGTCCTAGGAATGGTAGAGCCTGTCAAGTTCTCCCTGAAAGTCACGTCACTCCCCACTTCAGCAGGCCCAGCCTGT[G/C]TTGTATCCCTGCAGCACTGCCTCAGGATCCTTGCTCTGCAGTGATCAGAGTCATCTGATAAGCCTGTCCCTGTCTAGGCTGATATTAATTTCAGGTTGTCACCCTCTATGCCTCTT |

TABLE 20-continued

Sequences of the SNPs (2$^{nd}$ SNPs) in Table 19

| SNP in Table 19 (2$^{nd}$ SNP) | base1 | base2 | High copper allele | Sequence |
|---|---|---|---|---|
| Chr14_34385007 (SEQ ID NO: 190) | T | C | C | GGCCTTATGAAGACTTCTCTGATCTGTTGATCTGATGTACCCAGATTCTGAATCCCTAATTAG ACTCAATTAGGACACTCCTGGAGGTGACTACTGCTTTCTTAGACTTTGTCACTCAAA[T/C]A TCTAATACATTCGACTTTGACCCATGGATTTATTGAGTTCCTCTTGCACACCCAGTTCAGTAG ATGTGGTCCACTATTTTGGTGCATCGACTGCTCTAGAATTTAGCTTTTGGAA |
| Chr14_39185668 (SEQ ID NO: 191) | C | A | C | AtgacacatgcaagtgctcaataacgttagACACTGTACTGTTAATTAAAGGTCTATCGCCCC TTTAAACAAAATGTCCAGAATGTTCATGTTCACCAAAAGTGAAAGGCATTCATGTCT[C/A]T GTTTCTGTTGAGTTCACTGTCACCTTTGTGCCTAGAAAGGAGAAGACACACTGGTTTTTCCTC CTCTAGAGAAGTGCAGATTTGTATAGGTGAGGAGTATACATAGGTTGTGGGC |
| Chr15_62564157 (SEQ ID NO: 192) | G | A | G | CTTTGGGAATGAGGCCTGTCCCGCTAGCCTGCTTCATTTACTCTCATGATTCTTGGCAAAGTT CTTATAAGTCACGTTCAAATTATCAGGCTTCATTCCTAGTCTGAGCAGACTTGTCCC[G/A]T CTCCCAGCCTGTGGATGTTCAAGAAGCGCAACTTGGTTTTATGTTTATTAATCAAAAGCCCTT TAGCCTCTGATGAACCTCTGAGGGTGGCTTTAAAGCCCCGCGCCTGCTCTGA |
| Chr15_62596216 (SEQ ID NO: 193) | T | C | C | AAAGAAAAAGTAAGGGTCAAAACACTAGCAaaaattaaatTaaaaaaataaGAAAAACAAGTC ACACTTTTTTTTTTTTTTGGTCATTTGGGAAAAGCACAATATTTTGCTTGATTACT[T/C]T TCCTCACTTTTCAACTAGTAATATAGATTGCATGAAAAATAAACAAAACAAGTAAACTTTAAA TGTTTGCTGGTGTAGAGGTGAATAAGAACAATCCATGGATTTTGCAATCACA |
| ChrX_64356804 (SEQ ID NO: 194) | T | C | C | TCTAGCTCCAGTCTCCTTTATTCAGTGCCACCTTCATTTTTCCATTCCAGCCAAATTAGTGTT TTCATTCTCTCAAGCATTTTCATCTATGTACTTCCTGAACCCTCTTCATGGAAGACA[T/C]C CTCTACTCTTCAGCATATTACTATCCCAGCATCCCTTACCCTGATAGTTTAACTTGATTCTTT ATCTACCTGATTCAGTAATATTTCTCTATTCTTATCATATTCAGCAATGTTC |
| ChrX_64247356 (SEQ ID NO: 195) | T | C | C | TCCCCTACTGAAAACAAATTCCCCCATCTTCACCCTACCATGGGGATTTTACATTTGTTACCA GATTTGGGGCAAACTCATCCTATTTTCCCTTCAGTGTGGGAAGAGATTTTGGAAAA[T/C]A GACCATGCAAATCTCTAAGCTCACAATAAACTGAATTGGAGAGGCATAAAACCTGACAGGAAA AAAAGGTGTGAACTTGATCTTTAGCTTGCTGTTCTGGTTTAATAGGTTTCTG |
| ChrX_64596205 (SEQ ID NO: 196) | T | G | G | AAGGGTGAACTGACTTTTAGTCAGAATGTTTATTTTTAACAGATTATAAAATAGCCACCTATT TAGATGGATAAATGTATTGTGATTATGGTGTTGTTTATAAAAGAATTTTCAGGATT[T/G]T CCACAAAACTTAATGTTAGTATTAGTTATTAAGAGtacaatggaatatcattcagccatataa aagaatgaaatcttgctatttgcaatgacatagatggagctagagagtata |
| ChrX_64318806 |  |  | unknown |  |
| Chr3_86858401 (SEQ ID NO: 197) | T | C | T | ATGAGTTTGCAATTCTAGCCGGTGCATGAGGACTTCTCCCTTTCCCGAGCCCTCCCGGAAAGT TTGGCCAGATCCCCAGCCCAAATGGCAGCATGTGCTCGGGAAGATGATTAATGTTAG[T/C]G CGAGGCTCCAGAGAATCTCTCAGGGCCCTTTTGTTTATTAAATAGAAAAATTCATGTTTAAAT ATAATGTCAAGGGGATGACACGGACCAACATGATCCAAGACAGACTGCCGGC |
| Chr3_86974042 (SEQ ID NO: 198) | T | C | C | CTCCCACTAACTAGCAGGTATACATAGTTAAATTTCTCTAACACAGAGCAATACTACCTTCCA CACCAGAAAATGGCAAAGGCTAAATATAACCACAGATCTCAAGGCTACTGAACTACA[T/C]G CAGGTAATAGATTATATTTAAAACATATCAGATGAATCTGCACTAATACTGGGGGCCTATAAA ACTTTCTAACATACAGTAGTATAAGCAGGATTTCCAATCAGTGAGAAAAGGA |
| Chr3_86397551 (SEQ ID NO: 199) | A | C | A | ATGTGTAATTTACAAAGAGTTCATATATTACTTTATCAGTTAAGCTTTTGTAATTCCATA[A/ C]TCTATACTAATTTTAAAGAGGAGTGATTCCTTCTTGCAATTAGTTTATTGCCTCCGTATG |
| Chr3_86403839 (SEQ ID NO: 200) | A | G | A | ATATATCATTCCACCTATAGTAATTTTCACTAATCTGCCCATTTATTCCCTAGTGCATACCCT TAATATAAATCTGCAACAAGAATATAACTTTTCTAAAAAAAAAAAAAAGTGTACAT[A/G]C ATTAGTGATGTGTGACCAACTAAATACCAGTGTATAAGCCCATGCCCATATTTCATTTTCA CGAATTATGTTTGCTGCATAAATAAGACTTGTAGCTTTTTAAACTTACCTCT |
| Chr3_86948527 (SEQ ID NO: 201) | G | A | A | GTGTCAGTATGTTAAGCCACTAGTGCACTGTTAACTGCTGCCATGACTAAGAAAAACACAGA AGCTGCTGCTGCTACTATGTCACTCTTGTCATTTTTAAGGTGAATCCTCATATGAAT[G/A]A GAGGGAGTACATGCTTAATGGTCAGAGTGACAGCTTTTGCTTCATGGCGAGCCATCGAAACCC CACAAATCTCTTTGCCCCAACAGATTCTTCACCTTTCTTCCAGAAATGAA |
| Chr8_4892196 (SEQ ID NO: 202) | A | G | G | TtatggatcttacaatctagtgattgaaacaCAAATTAGATTTGGGCTTGTCTATAAAACTGG GATATTTTCTGATATTGGAATGAATACTGGGACAGTCCCTTAATTTTGGTTTCATGA[A/G]T GATTAGTCTTATGATACATAGTTTATGTGTAATTGCTATTTCTAATCCAAAATAAATTGGACC TTTCGTTTAGATTAAACATGGAGTCTTTGATGTAAATACCGTAGAAGGAGTC |
| Chr8_44889521 (SEQ ID NO: 203) | C | G | G | TgctgtctaaacaggagcttgaaggatgagtaggaagagaTttcagatagaacagctgtgctg gagcaaagagggtctgaGggagcatggtatatttgtggacggcagctagttgcctg[C/G]c actggagcatggcggtggggagtaagaggtgggagagaaaactcaatgacaggcagaagcca gaccatgaagGGCCTCACATCCTGTGCAGAGGAGTTTGATTTTTATCTCCT |

TABLE 20-continued

Sequences of the SNPs (2nd SNPs) in Table 19

| SNP in Table 19 (2nd SNP) | base1 | base2 | High copper allele | Sequence |
|---|---|---|---|---|
| Chr8_11618239 (SEQ ID NO: 204) | T | C | C | TTTGTCCTTGAAAGAAGTTTTTCTCTTTCCTTTCCCATTTTCTTTTCTTCCTATTTGCTTAAT TATCTGTTGCCAGATAATTCACACCTAAGTTCATAGAGGACCAATGTCACAGATATT[T/C]T CTTAAACAAAACTGGCTTTGTAACAATAAAATTTGTCTGTTTAAAATGTAACTAATATCGGAG ATATTTACCTAAGGAAGTATTTGTAAATAGTATCTAGAAATGCAAGAAAATA |
| Chr8_11613479 (SEQ ID NO: 205) | C | T | T | GCCAACGCTAAGATTCATAGTCTATTTTTTACTCAACACCAAATAAAGGTACCATTTCTAATC CAAGAACTTCACTCTGCTGTCTTCTAGCACATTGGCATTTTCCACAGGCATTTCTTG[C/T]T TTACTTGATGTATTTTTTTCCAGTTTTTCTTAATATGATATCTGAGAAATTTTTTGCTAAGT ATTGATTCAAAAATTTAAAATTAAGGTTAAATTGTGGCTAATCAGCATACTG |
| Chr8_9064669 (SEQ ID NO: 206) | C | T | C | TTTTATCATGCCAGGAAATTCTTGGAATGTAGCCACTGTCTGATATTTATGGTTCCATAAGCA TTTGACTCTGAAAAGTCTCTAATTCTGGAAAACGGCCACTGATCAGTTGTTAATGCA[C/T]A GCAGTAGGAAAAAGTCACCCCTTAAAAGGAGAGAGAGGACAAAAGGAACAGCTTGTGAGGCT AAAAGTATGACAAGTATGACGTCTACCTATACAGGAAGTGTATATGCATCT |
| Chr8_9054168 (SEQ ID NO: 207) | A | G | A | GCTAATAAAGGATCAACCTCTGGGCTGCAGAATAACCTAATCTATTCATACCTCAGTGAC[A/ G]TCCTGAATTAGAACCGGGGGCTGATGAACTCCAATGCACCAGCCAACCAACCAGAGTTAG |
| Chr8_5938207 (SEQ ID NO: 208) | T | C | T | TGAATGACTTTTTCAACCCGAATTTTCATGACATTTTTGTCATGACATTTCTCATATAACCTA CCGCATGTAAAGCAAGATCTCCTATTGGATTCTGCTTATTTTTGTCATCTTCCAA[[T/C]G GTCTTAGGCAAATGAAGTTTAAGTAGTAAGATTATATGCCTCCTCCCACTTTGGTGTGCATGCAC ACAGATGCAGGAACATGCTTAGTAACTAATCTTTGTGGGACATAGGAATGCC |
| Chr8_5896281 (SEQ ID NO: 209) | G | A | G | GCCAGCTCTAATGAGTTTGTTTCCAAGCGGTGCTTCCAGAAATTGTTAGTGGTTGGTAGTTGC AATGGGTTTTGAAATTAGAGGACATCACAGCAGAGTAGAATGGTTTGGAACAGGGGG[G/A]T ATGATTAGGATTAATGAGATGAAAGAAAATTCTGGCTAGAGGGCTAGAAGAGCCATGGAAGAA AATATACACTAACCCTTTGGAGTGTTCCTCAAGTGAAGATTTGCAACATTT |
| Chr24_9568995 (SEQ ID NO: 210) | T | C | C | ACGAGAAGCAAGATTGCCATACCGTTCCTGGTACCGGGCCATGACGTTGACCTTCAAAAGCCC TGAAACGGCTGTTTTCCTGGCTGCTGTGAGCTGTGGAACTCAGGAGTAGGTATTTCC[T/C]G AAAACATTTAACATCCCATAGCAAAGGTGTTGGAGGCGTCGTCTCCATTGTCGTTTCTCCCGG GCTGTGGTTGGCCTTTCTGCGTGAGTGCTTCTCCCCGCTGCGGGCTGGCTCT |
| Chr24_9311101 (SEQ ID NO: 211) | G | A | G | TAGGAAAAAACATCTGGCCTCTGACTCGGATCCAGTCATCCCAGCCTCATTCACACCCACCCA TCAGCTCTCAGAGAACCTTCTGAGACTTCGATAAATAGCTGAGCCCCTTAAAATGACA[G/A]C ATTGATTTGGCATGGTTTGGGCAATAACTTCTGGCTGCTGTGATTTTTAGGTTTTGAATATTT AGTTTCTGGAAACTCTGATAGAATGAATAACTTTATATGTTTATTTAATTCT |
| Chr24_9391376 (SEQ ID NO: 212) | T | C | C | GTCTACTGAAGCCAGACAGTTGGTTCATTAGATTAATTAAAGTGCAAACTAACCCCAATCTGG TGTTTTGATAACGGCCACAGGGCTCTTGAAGTTGGAATCGGCCAGCATTTGACAGTG[T/C]T CTCATTAAAGCCACAGTGGAATTGCCTCTATGGTTTCTCCTAAACTTTTGAATTTACCTTATA ACAAAGAAGTGGACTTTGAGCATCCCTGATTGTTTTTCAGTGTTAACTGCT |
| Chr18_42897855 (SEQ ID NO: 213) | T | C | T | TGTTGCTTTCCTGCACACAAGCAGTTGAACCAGAGTAGGGAGGAATCATTTTTAGGAATGTGT TATTATTATTTTTTAGGAATGCACAAAACCCATGCCAAAAAGCCCATCCACGTCTAA[T/C]G TCCTTGAACCTCTCCTTCACTGACAATTGTATTCTTTTATGTTCCCAATCAACTGGCTGGCCT GAAATAGATTTCTCCTACCAAGAAATGTAGATAAAAATATTTATTTCTGGAA |
| Chr18_45266899 (SEQ ID NO: 214) | G | G | G | GTCTCAGCCCTCTATTCCAGAAGGTAGGACTGGCCCTGGGCCTGTCTACGAGGTGGTGGCTGC GAGCCCTCAAGGCCTGGCATTGTCAAAGTTCTGACAACCTTCCCCACCTATGGCAGC[T/G]C AGTGTTAGACGTCCAGGCTGAGGGTTGATGCACACTTTTTCGGCTTCCAAAGTGTGGCCTTC TCCTCAGGGCTTCCCATGGGGTCCACAGGCTGGCAGCAACCTCTTGGAGAAA |
| Chr8_19298728 (SEQ ID NO: 215) | G | A | A | CAGCTGTGTCATGGAAATGGCACTTTAAAAATTCATATGAATCTTAACAGTAAAGCACAAGAC TTTGGAGATATTTCTCCTGTTGAATAGCTGCTTGGGGATGTGCCACAGATCTGTAGA[G/A]G TCAGCATTCACTCTAAGTTCCCGGGAACCATGAGAAGCAGCAGCAACCATGGCCACcacagcaac acagcaggtgcccataagcccattttacagatggagaaattgggtccagaga |
| Chr8_6295891 (SEQ ID NO: 216) | T | C | C | CCTCTGGCTCCCCAGAACCTCAGAGCTTAGGGGATGTAGTGGTTGTAATCCTGGATCCCTCTG TGGGGTGGCAGGTCTGGAGTGGTGAGCTACTGTGAGGGAACTGGGGTAACTGTGACC[T/C]G AGAAGAAAGGAGCGAGGGAGTGAGTGTGTGTCTGTGAAATATGCCTCTGTGTGTATAAACAGG GCTGGAGGGCTCAGTGCCCCCCACTCCCAAAGATCCACCTGTTACATCCCCG |
| Chr10_65089416 (SEQ ID NO: 217) | G | A | A | TtcttctcttgtgactggtcactaaagacagagatttcagGagagctgactttggtaggaatt ctcacccttttctggccTaggccTATAATTTTTATACCGACAGCTGGAGTCCCAGAT[G/A]G AAGAGACCTTAAACTCTTGGACATGAAGAACCTGTTTTTTCTCTCTCTCTCTTTTTTTTCC CCTTAAACAAAAATTTATTTTCCTCAGGCCTCatcctgtacccagtcttgt |
| Chr10_65142039 (SEQ ID NO: 218) | A | C | C | AGCTCCAATTTAGTCATATACTAAAGAATCAGGTCATACTCTAGGCAGACTCTAGGCAGTTAG CACATGAAACCAGTTCACATGCTTTATCATCATCCTTTTTGTTCTCAAAACAGCCAA[A/C]A ACAGTTCTGTATAAGATATTTCACATGTTTAATTCTTTCAGTTCTTCTAGCAAGCAGGAAGCT TAGAACAAGATTTTAGTATTTGGTTTAGATAACAATTGCAAATAGgagcacc |

TABLE 20-continued

Sequences of the SNPs (2$^{nd}$ SNPs) in Table 19

| SNP in Table 19 (2$^{nd}$ SNP) | base1 | base2 | High copper allele | Sequence |
|---|---|---|---|---|
| Chr22_3067105 (SEQ ID NO: 219) | G | A | G | GACTTTTCTAGAGAGACCATGGAAGATGCATGTGGGGCCTGCCCAGGCTGCCACAGGGGAAAG GAGCCGGGAGGAGGGAGCTGTCAGGCCACTTCCTCTGATGGCCCCTCAGCAGCAGGA[G/A]G AGAGCATTTCCTCACCAGATCCCACTCAACACTGGCCACGGTCCCCCTGTGGACTTCAGAACT GACTCAGAACTAACCTGACTGACTGCGTATGATTTGTCTTTTTAGGAGGACC |
| Chr22_3349188 (SEQ ID NO: 220) | G | A | G | CCCGCGCCAGGCCGGTCCTCTCCTCCCAGCTCCTCCTCTCCCGCTCGCAGTCAGGGCAGCCAG GGAGGGGAGAAATTCTCATCTCAAAACTAGTAAGACAAGGCCCCGCAGCGGGTCTGC[G/A]G CGCGGAGGCGGCTGCCTCTCCTGGTCCATACTGGACACAGCTGACCACATTTCAACAGGTAAG AATCATTTTAAATATTACCCTTAAACCAAAAAAAGTTCTTCTTTTGCTTCTA |
| Chr22_13256436 (SEQ ID NO: 221) | T | G | G | CAGTATTCCGATTCTTCTATTTGCTAATTTTAAAGTGCAGATCTAAGAGGACAACCTTATTAT TATTTCCATGGTCTTAGAGATCATCTTACTGTTGCCCCACAATGTCCATGCTTCCCG[T/G]G AAAGATGTGTGTATCCAGACTCAAAGTGAATCTAATAGGGAAGGAAGACTGAGAATTCTATTA GTAAGCAACCCGTATTTAACAACATGGCCCAGTTTGAAGATTTGCAGAAACA |
| Chr22_13202693 (SEQ ID NO: 222) | G | A | G | TCAGGAGTGAGCCTGTACGTTATCCTGACTACTGATTCCCTTGCACCAAAAAAGCAACGGGAG CATAAGGGCAAGATATGACCTTTAGCTAAAGGGTTGCAAGTTATATTACTAGTCGTC[G/A]C TGCTCAAACACCCAGCACCAGACCCTGCATAGAATACAGAAAAGAGTCCTCACCATCAAGCCA CTACCACCTGAAGCATGAAGGAGAGAACAAGGAGAGATCACCTCCTAAGTGT |
| Chr22_10985753 (SEQ ID NO: 223) | G | C | G | CtgacctctgCTCTAGTCAATTGCTCTGAAAGTACAGTCCTCTGATCCCTAGACTCGAACCCTC TCAAGCATAACAGTTCCATCTACTATTCACTAATCCATTTATTTAACTGGGAGTGTT[G/C]T ATGCTTTGGCTCTGGGATATGAAGGAAAGGACATTGTGCCCGAACATATAGGAAAGTTATTGT TTAAGGAGATATACAGGGAAATAATTTTAAAACACCATGGTAATCTTttcct |
| Chr22_10587732 (SEQ ID NO: 224) | A | G | A | CGTTTTCCTTATAAATTTTTagaaaacagaacaggaaaaaAaaaaaaAgaaagaaaacagaac agagaacaaaCCAACATGTCTTGATGCCTCCAGGAACCAGTTTTCTCATAGCCTTAG[A/G]G GAAACAATTTACAAAATATCTGAAAAGCCTGCAGATATCTTAGATCCAAGATTCCAAGGCATA AAAATGTAAGTGATCATGTACTACGTATTACTGAAATACAGAAAGCAACCAA |
| Chr22_14998527 (SEQ ID NO: 225) | G | A | G | AGCACCTTGAGAATGGTGTAGTGGAAAGAAAGTTGACTTTTAGTAACTATGCATTTGTCTCGT TAATGCAGTTTCTCACCTGCTTTGAGATAATGGGAAATGGAACTAACAGGTAGTGGT[G/A]A CACAGATGATGGACAATATAAAGATTTGAGATATATATAAAAAAAATTTGATCATTATATGTA CACTTTGCTAGTTTTGCTCTACATTTTTTATCCACACAAAAAGTAATTTGCA |
| Chr22_11895473 (SEQ ID NO: 226) | A | F | A | TAAGTAGCCTTTAGTGCAAGGAAAAGAAAAAGGCAGTAAGGATGAACCTTTGTTTCAAAGGTA TTAGGAGTCATTTAAGGAATTTCAAAAAAAAAAAAAGAAGTGACATGATTTTGAAC[A/G]A AGAAGTGACTGTCAGTACTATAAAGAGCACATTGCCTCAAGGAGAAACTGAAGTTAGAGAAGC CAAATTGGCTGATAAAAATCTAGGCCGGAGATGCAAACACCTAAATGAAAAC |

Model Generation

The mutations identified in Tables 17 to 20 can be used on their own to determine susceptibility to, or protection from, liver copper accumulation. However, a more accurate method of assessing susceptibility to, or protection from, liver copper accumulation may be achieved through the use of models involving combinations of mutations. The mutations in Tables 17 and 18 were used in model generation as described below.

Variables

The variables chosen were all the mutations identified in the Geneseek genotyping as well as gender coded as 0 for male 1 for female. Genotypes were coded in ordinal form as 0, 1 or 2 (count of second allele).

Two reporter variables were used, log 10-quantitative copper and histology score. Both of these appear to respond linearly to the genetics and approximately to each other and so make good candidates for linear modelling of this type.

Method

Due to the number of variables and the sample size available, not all genetic effects can be modelled together. To solve this a stepwise modelling technique was used. This technique determines which factors should be used in a model by inserting and removing them while observing the significance of the estimates of coefficients in the model. The precise method used is described below:

1. The data was mean-patched to allow for missing data.
2. A stepwise regression was carried out on the mean-patched data, using the MATLAB stepwise command. This uses a confidence interval around the coefficients of 0.9.
3. The selected variables and co-efficients were then recorded and residuals inspected for an appropriate variance distribution.
4. To explore appropriate cutoffs for a diagnostic, odds-ratios, prevalance-corrected positive predicted value and prevalance-corrected negative predicted value were generated for all potential cutoffs to generate a chart showing the trade-off between PPV and NPV at different cutoffs. For these purposes a positive was >2.5 on the histology scale and >600 mg/kg copper on the quantitative copper scale.

The key to the factors used in model determination is shown in Table 21:

TABLE 21

| Factor | Name |
|---|---|
| X1 | Chr32_38904515 (UBL5 ortholog) |
| X2 | Chr20_55461150 (STXB2) |
| X3 | Chr19_6078084 (microsomal glutathione S-transferase 2 (GST)) |

TABLE 21-continued

| Factor | Name |
|---|---|
| X4 | Chr3_86838677 (KRT18 (Indian childhood cirrhosis) |
| X5 | Chr14_39437543 (Interleukin-6 Precursor (IL-6)) |
| X6 | Chr8_4880518 |
| X7 | Chr8_4892743 |
| X8 | gender |
| X9 | Chr24_4011833 |
| X10 | Chr10_65209946 (COMMD1) |
| X11 | Chr22_3167534 (ATP7B) |
| X12 | Chr22_3135144 (ATP7B) |
| X13 | ChrX_63338063 (ATP7A) |
| X14 | Chr18_60812198 (ATOX1) |
| X15 | Chr15_62625024 (unknown gene) |
| X16 | Chr15_62625262 (unknown gene) |
| X17 | ChrX_120879711 (MTMR1) |

Results

Modelling using the stepwise tool produced the predictive functions shown in FIGS. 8 and 9. FIG. 8 illustrates stepwise modelling of the histology copper score. FIG. 9 illustrates stepwise modelling of the log-quantitative copper score.

What is claimed is:

1. A method of treating or breeding a dog, comprising:
   (a) genotyping a biological sample obtained from the dog to determine in a genome of the dog presence or absence of a polymorphism of Chr22_3167534 (position 101 of SEQ ID NO: 144; and
   (b) administering to the dog a low copper food stuff or a therapeutic amount of a copper chelator when the polymorphism is present; or
   breeding the dog when the polymorphism is absent.

2. The method of claim 1, further comprising genotyping the biological sample obtained from the dog to determine presence or absence of one or more polymorphisms selected from the group consisting of BICF2P506595 (position 61 of SEQ ID NO:1), BICF2P772765 (position 61 of SEQ ID NO:2), BICF2S2333187 (position 61 of SEQ ID NO:3), BICF2P1324008 (position 61 of SEQ ID NO: 4), BICF2P591872 (position 61 of SEQ ID NO:5), ATP7a_Reg4_F_9 (position 164 of SEQ ID NO: 131), UBL5_Reg1F_16 (position 97 of SEQ ID NO: 132), golga5_Reg1_24 (position 70 of SEQ ID NO: 133), golga5_26 (position 88 of SEQ ID NO: 134), golga5_27 (position 104 of SEQ ID NO: 135), golga5_28 (position 139 of SEQ ID NO: 136), golga5_29 (position 128 of SEQ ID NO: 137), golga5_30 (position 95 of SEQ ID NO: 138), golga5_31 (position 106 of SEQ ID NO: 139), atp7areg17_32 (position 95 of SEQ ID NO: 140), and atp7areg17_33 (position 90 of SEQ ID NO: 141).

3. The method of claim 1, further comprising genotyping the biological sample obtained from the dog to determine in the genome of the dog the presence or absence of one or more polymorphisms selected from the group consisting of Chr10_65209946 (position 101 of SEQ ID NO: 155), Chr22_3135144 (position 101 of SEQ ID NO: 145), Chr20_55461150 (position 101 of SEQ ID NO: 146), Chr19_6078084 (position 101 of SEQ ID NO: 148), Chr3_86838677 (position 101 of SEQ ID NO: 152), and ChrX_63338063 (position 102 of SEQ ID NO: 142).

4. The method of claim 1, wherein the dog has genetic inheritance of the Labrador Retriever breed.

5. The method of claim 1, further comprising genotyping the biological sample obtained from the dog to determine in the genome of the dog the presence or absence of one or more polymorphisms selected from the group consisting of Chr22_3135144 (position 101 of SEQ ID NO: 145), Chr20_55461150 (position 101 of SEQ ID NO: 146), ChrX 120879711 (position 101 of SEQ ID NO: 147), Chr19_6078084 (position 101 of SEQ ID NO: 148), Chr15_62625262 (position 101 of SEQ ID NO: 149), Chr14_39437543 (position 101 of SEQ ID NO: 150), Chr15 62625024 (position 101 of SEQ ID NO: 151), Chr3 86838677 (position 101 of SEQ ID NO: 152), Chr24_4011833 (position 101 of SEQ ID NO: 153), Chr18_60812198 (position 101 of SEQ ID NO: 154), CGCCCC repeat at chromosome location 22 starting at genomic location 3135287, Chr32_38904515 (position 101 of SEQ ID NO: 156), Chr8_4892743 (position 101 of SEQ ID NO: 157), Chr8_4880518 (position 101 of SEQ ID NO: 158), ChrX 63338063 (position 102 of SEQ ID NO: 142), BICF2P506595 (position 61 of SEQ ID NO: 1), BICF2P772765 (position 61 of SEQ ID NO:2), BICF2S2333187 (position 61 of SEQ ID NO: 3), BICF2P1324008 (position 61 of SEQ ID NO:4), BICF2P591872 (position 61 of SEQ ID NO: 5), ATP7a_Reg4_F_9 (position 164 of SEQ ID NO: 131), UBL5_Reg1F_16 (position 97 of SEQ ID NO: 132), golga5_Reg1_24 (position 70 of SEQ ID NO: 133), golga5_26 (position 88 of SEQ ID NO: 134), golga5_27 (position 104 of SEQ ID NO: 135), golga5_28 (position 139 of SEQ ID NO: 136), golga5_29 (position 128 of SEQ ID NO: 137), golga5_30 (position 95 of SEQ ID NO: 138), golga5_31 (position 106 of SEQ ID NO: 139), atp7areg17_32 (position 95 of SEQ ID NO: 140), and atp7areg17_33 (position 90 of SEQ ID NO: 141).

6. A method of treating or breeding a dog, comprising:
(a) inputting to a computer system genotyping data concerning presence or absence in a genome of the dog a polymorphism of Chr22_3167534 (position 101 of SEQ ID NO: 144);
(b) comparing the genotyping data to a computer database, wherein the computer database comprises information of the risk of dog liver copper accumulation associated with a polymorphism of Chr22_3167534 (position 101 of SEQ ID NO: 144);
(c) determining whether the dog is at risk of liver copper accumulation based on the comparison; and
(d) administering to the dog a low copper food stuff or a therapeutic amount of a copper chelator if the dog is determined to be at risk of liver copper accumulation, or
breeding the dog if the dog is determined to be not at risk of liver copper accumulation.

* * * * *